United States Patent [19]
Dickinson et al.

[11] Patent Number: 6,093,731
[45] Date of Patent: Jul. 25, 2000

[54] ISOQUINOLINES

[76] Inventors: Roger Peter Dickinson; Paul Vincent Fish; Christopher Gordon Barber, all of Pfizer Ltd., Ramsgate Road, Sandwich, Kent, United Kingdom

[21] Appl. No.: 09/359,439

[22] Filed: Jul. 22, 1999

[51] Int. Cl.[7] .................. A61K 31/472; C07D 217/22
[52] U.S. Cl. ................ 514/310; 546/143; 544/128; 544/363; 514/223.5; 514/253
[58] Field of Search ................ 514/310, 253, 514/233.5; 546/143; 544/128, 363

[56] References Cited

FOREIGN PATENT DOCUMENTS

| | | |
|---|---|---|
| 0568289 | 11/1993 | European Pat. Off. . |
| 9811089 | 3/1998 | WIPO . |
| 9905096 | 2/1999 | WIPO . |
| 9920608 | 4/1999 | WIPO . |

OTHER PUBLICATIONS

S. Rachlin, 1980, J. Med. Chem. 23:13–20, "Basic Anti–Inflammatory Compounds. N,N',N"–Trisubstituted Guanidines".

*Primary Examiner*—Charanjit S. Aulakh
*Attorney, Agent, or Firm*—Peter C. Richardson; Paul H. Ginsburg; Alan L. Koller

[57] ABSTRACT

Isoquinolinylguanidine compounds of formula (I):

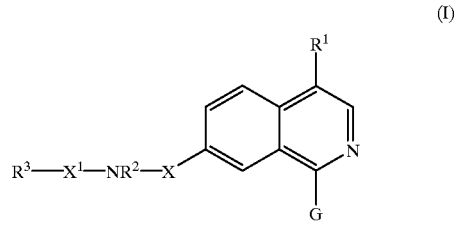

wherein the substituents are as defined herein, and salts thereof, are disclosed as urokinase inhibitors.

34 Claims, No Drawings

ISOQUINOLINES

This application claims priority from Great Britain Application No. GB 9816228.2, filed Jul. 24, 1998, and GB 9908829.6, filed Apr. 16, 1999.

This invention relates to certain isoquinolines useful as urokinase inhibitors, and in particular to isoquinolinylguanidines useful as urokinase inhibitors.

Urokinase (urinary-type plasminogen activator or uPA; International Union of Biochemistry classification number EC.3.4.21.31) is a serine protease produced by a large variety of cell types (smooth muscle cells, fibroblasts, endothelial cells, macrophages and tumour cells). It has been implicated as playing a key role in cellular invasion and tissue remodelling. A principal substrate for uPA is plasminogen which is converted by cell surface-bound uPA to yield the serine protease plasmin. Locally produced high plasmin concentrations mediate cell invasion by breaking down the extracellular matrix. Important processes involving cellular invasion and tissue remodelling include wound repair, bone remodelling, angiogenesis, tumour invasiveness and spread of metastases.

Beneficial effects of urokinase inhibitors have been reported using anti-urokinase monoclonal antibodies and certain other known urokinase inhibitors. For instance, anti-urokinase monoclonal antibodies have been reported to block tumour cell invasiveness in vitro (W. Hollas, et al, *Cancer Res.* 51:3690; A. Meissauer, et al, *Exp. Cell Res.* 192:453 (1991); tumour metastases and invasion in vivo (L. Ossowski, *J.Cell Biol.* 107:2437 (1988)); L. Ossowski, et al, *Cancer Res.* 51:274 (1991)) and angiogenesis in vivo (J. A. Jerdan et al, *J.Cell Biol.* 115[3 Pt 2]:402a (1991). Also, Amiloride™, a known urokinase inhibitor of only moderate potency, has been reported to inhibit tumour metastasis in vivo (J. A. Kellen et al, *Anticancer Res.,* 8:1373 (1988)) and angiogenesis/capillary network formation in vitro (M. A. Alliegro et al, *J.Cell Biol.* 115[3 Pt 2]:402a).

Conditions of particular interest for treatment by urokinase inhibitors include chronic dermal ulcers (including venous ulcers, diabetic ulcers and pressure sores), which are a major cause of morbidity in the ageing population and cause a significant economic burden on healthcare systems. Chronic dermal ulcers are characterised by excessive uncontrolled proteolytic degradation resulting in ulcer extension, loss of functional matrix molecules (e.g. fibronectin) and retardation of epithelisation and ulcer healing. A number of groups have investigated the enzymes responsible for the excessive degradation in the wound environment, and the role of plasminogen activators has been highlighted (M. C. Stacey et al., *Br. J. Surgery,* 80, 596; M. Palolahti et al., *Exp. Dermatol.,* 2, 29, 1993; A. A. Rogers et al., *Wound Repair and Regen.,* 3, 273, 1995). Urokinase activity has also been implicated as a factor in psoriasis: Jensen & Lavker (1996) Cell Growth Diff. 7, 1793–1804 Baker B S and Fry L (1992). Br J Dermatol, 126(1), 1–9.2; Spiers E M, et al (1994). J Invest Dermatol, 102(3), 333–338.3. Grondahl-Hansen J, et al (1987). J Invest Dermatol, 88(1), 28–32. Gissler H, et al (1993). Br J Dermatol, 128(6), 612–8; Venning V A, et al (1993). Clin Exp Dematol, 18(2), 119–23.

Normal human skin demonstrates low levels of plasminogen activators which are localised to blood vessels and identified as tissue type plasminogen activator (tPA). In marked contrast, chronic ulcers demonstrate high levels of urokinase type plasminogen activator (uPA) localised diffusely throughout the ulcer periphery and the lesion, and readily detectable in wound fluids. uPA could affect wound healing in several ways. Plasmin, produced by activation of plasminogen, can produce breakdown of extracellular matrix by both indirect (via activation of matrix metalloproteases) and direct means. Plasmin has been shown to degrade several extracellular matrix components, including gelatin, fibronectin, proteoglycan core proteins as well as its major substrate, fibrin. Whilst activation of matrix metalloproteases (MMPs) can be performed by a number of inflammatory cell proteases (e.g. elastase and cathepsin G), the uPA/plasmin cascade has been implicated in the activation of MMPs in situ, providing a broad capacity for degrading all components of the extracellular matrix. Furthermore, in addition to its effect on production of plasmin, uPA has been shown to catalyse direct cleavage of fibronectin yielding antiproliferative peptides. Thus, over-expression of uPA in the wound environment has the potential to promote uncontrolled matrix degradation and inhibition of tissue repair. Inhibitors of the enzyme thus have the potential to promote healing of chronic wounds.

Several related enzymes such as tPA, which also acts via production of plasmin, play a key role in the fibrinolytic cascade. Because of this it is important that an inhibitor has adequate potency and selectivity for uPA relative to both tPA and plasmin to avoid the possibility of anti-fibrinolytic side effects.

The utility of such potent and selective urokinase inhibitors is highlighted by the broad range of invasive biological processes and conditions mediated by urokinase. These processes and conditions include, but are not limited to, wound healing, angiogenesis-dependent conditions such as retinopathy, bone restructuring, embryo implantation in the uterus, infiltration of immune cells into inflammatory sites, ovulation, spermatogenesis, psoriasis, tissue remodelling during wound repair and organ differentiation, fibrosis, local invasion of tumours into adjacent areas, metastatic spread of tumour cells from primary to secondary sites, and tissue destruction in arthritis.

Various aromatic amidines have been reported to inhibit uPA (J. D. Geratz, M. C. -F. Cheng, Thromb. Diathes. haemorrh. (Stuttg.), 33, 230, 1975; J. Stürzebecher, F. Markwardt, Pharmazie, 33, 599, 1978; J. D. Geratz et al., Thromb. Res., 24, 73, 1981). The compounds reported in these publications are generally relatively weak and/or non-selective for uPA relative to other related serine proteases. EP 0 568 289 A2 discloses a series of benzo[b]thiophene-2-carboxamidines with significantly greater potency and selectivity with respect to tPA and plasmin (see also M. J. Towle et al., *Cancer Res.,* 53, 2553, 1993; A. J. Bridges et al., *Bioorg. Med. Chem.,* 1, 403, 1993).

There are few reports of guanidine derivatives as uPA inhibitors. Amiloride™ (see below) is a weak but selective inhibitor of uPA (J. -D. Vassalli, D. Belin, *FEBS Letters,* 214, 187, 1987), and various substituted phenylguanidines are reported to have a similar level of potency (H. Yang et al., *J. Med. Chem.,* 33, 2956, 1990).

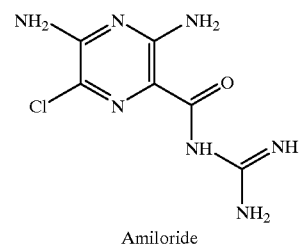

Amiloride

The compounds described herein are potent reversibly-competitive inhibitors of urokinase enzymatic activity, with selectivity for urokinase relative to certain other important proteases, including the fibrinolytic enzymes tissue-type plasminogen activator (tPA) and plasmin.

The selectivity of the instantly-claimed compounds for inhibition of urokinase over inhibition of other proteases such as tPA and plasmin, and the fact that they inhibit reversibly, prevents them from having thrombogenic properties.

Thus, according to the present invention, there are provided isoquinolinylguanidine compounds of formula (I):

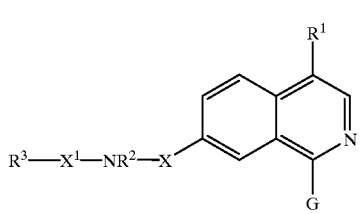

(I)

and the pharmaceutically acceptable salts thereof, wherein:
G is $N=C(NH_2)_2$ or $NHC(=NH)NH_2$;
$R^1$ is H or halo;
X is CO, $CH_2$ or $SO_2$;
$R^2$ is H, aryl, heteroaryl, $C_{3-7}$ cycloalkyl or $C_{1-6}$ alkyl each of which $C_{3-7}$ cycloalkyl and $C_{1-6}$ alkyl is optionally substituted by one or more substituents independently selected from halo, aryl, het, $C_{3-7}$ cycloalkyl, $C_{5-7}$ cycloalkenyl, OH, $C_{1-6}$ alkoxy, O-het$^1$, $C_{1-3}$ alkyl, $CO_2R^7$ and $NR^4R^5$;
$X^1$ is arylene, $C_{1-6}$ alkylene optionally substituted by one or more $R^6$ group, or cyclo($C_{4-7}$)alkylene optionally substituted by $R^6$, which cyclo($C_{4-7}$)alkylene ring can optionally contain a hetero moiety selected from O, $S(O)_p$ or $NR^7$;
or $R^2$ and $X^1$ can be taken together with the N atom to which they are attached to form an azetidine, pyrrolidine, piperidine or homopiperidine ring;
$R^3$ is $CO_2R^7$, $CH_2OH$, $CONR^8R^9$ or $CH_2NR^8R^9$;
or, when $X^1$ is taken independently from $R^2$ and is methylene optionally substituted by one or more $R^6$ group, or is a 1,1-cyclo($C_{4-7}$)alkylene optionally containing a hetero moiety selected from O, $S(O)_p$ or $NR^7$ and optionally substituted by $R^6$,
then $R^2$ and $R^3$ can be taken together with the N and $X^1$ groups to which they are attached, as a group of formula (IA) or (IB):

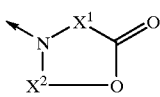

(IA)

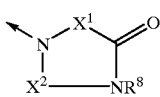

(IB)

wherein $X^2$ is ethylene, n-propylene or n-butylene;
$R^4$ and $R^5$ are each independently H, aryl or $C_{1-6}$ alkyl optionally substituted by aryl;
$R^6$ is halo, OH, $C_{1-6}$ alkoxy, $C_{1-6}$ alkylthio, $C_{3-7}$ cycloalkyl, SH, aryl, $CO_2R^7$, $CONHR^8$, or $C_{1-6}$ alkyl optionally substituted by aryl, $C_{1-6}$ alkoxy, $CO_2H$, OH, $CONR^8R^9$ or by $NR^8R^9$;

$R^7$ is H or $C_{1-6}$ alkyl;
$R^8$ and $R^9$ are either each independently H, or $C_{1-6}$ alkyl optionally substituted by OH, $CO_2R^7$, $C_{1-6}$ alkoxy or by $NR^4R^5$;
or $R^8$ and $R^9$ can be taken together with the N atom to which they are attached, to form a 4- to 7-membered ring optionally incorporating an additional hetero-group selected from O, S and $NR^7$;
p is 0, 1 or 2;
"aryl" is phenyl optionally substituted by one or more substituents independently selected from $C_{1-6}$ alkyl, $C_{1-6}$ alkoxy, or halo;
"het" is a saturated or partly or fully unsaturated 5- to 7-membered heterocycle containing up to 3 hetero-atoms independently selected from O, N and S, and which is optionally substituted by one or more substituents independently selected from $C_{1-6}$ alkyl, $C_{1-6}$ alkoxy, $CO_2R^7$ or halo;
"heteroaryl" is a fully unsaturated 5- to 7-membered heterocycle containing up to 3 hetero-atoms independently selected from O, N and S, and which is optionally substituted by one or more substituents independently selected from $C_{1-6}$ alkyl, $C_{1-6}$ alkoxy, $CO_2R^7$ or halo;
"het$^1$" is tetrahydropyran-2-yl (2-THP);
and "arylene" is phenylene optionally substituted by one or more substituents independently selected from $C_{1-6}$ alkyl, $C_{1-6}$ alkoxy, $CO_2R^7$ or halo.

"Alkyl" groups can be straight or branched chain. "Halo" in the definitions above refers to F, Cl or Br.

"Cycloalkylene" groups in the definition of the $X^1$ linker moiety which optionally contains a hetero moiety selected from O, $S(O)_p$ or $NR^7$ and is optionally substituted by $R^6$, can be linked via any available atoms. "1,1-Cycloalkylene" groups in the definition of the $X^1$ linker moiety which optionally contains a hetero moiety selected from O, $S(O)_p$ or $NR^7$ and is optionally substituted by $R^6$, means the linkage is via a common quaternary centre at one position in the ring, viz. for example: 1,1-cyclobutylene and 4,4-tetrahydropyranylene are to be regarded as both belonging to the same genus of "1,1-cycloalkylene" groups optionally containing a hetero moiety selected from O, $S(O)_p$ or $NR^7$ and optionally substituted by $R^6$.

The two definitions given for the "G" moiety in compounds of formula (I) are of course tautomeric. The skilled man will realise that in certain circumstances one tautomer will prevail, and in other circumstances a mixture of tautomers will be present. It is to be understood that the invention encompasses all tautomeric forms of the substances and mixtures thereof.

Pharmaceutically-acceptable salts are well know to those skilled in the art, and for example include those mentioned by Berge et al, in *J.Pharm.Sci.*, 66, 1–19 (1977). Suitable acid addition salts are formed from acids which form non-toxic salts and include the hydrochloride, hydrobromide, hydroiodide, nitrate, sulphate, bisulphate, phosphate, hydrogenphosphate, acetate, trifluoroacetate, gluconate, lactate, salicylate, citrate, tartrate, ascorbate, succinate, maleate, fumarate, gluconate, formate, benzoate, methanesulphonate, ethanesulphonate, benzenesulphonate and p-toluenesulphonate salts.

When one or more of the substituents on the compound of formula (I) contains an acidic moiety, suitable pharmaceutically acceptable base addition salts can be formed from bases which form non-toxic salts and include the aluminium, calcium, lithium, magnesium, potassium, sodium, zinc, and pharmaceutically-active amines such as diethanolamine, salts.

Certain of the compounds of formula (I) which have an acidic moiety can exist as one or more zwitterions. It is to be understood that all such zwitterions are included within the scope of the invention.

Certain of the compounds of the formula (I) may exist as geometric isomers. The compounds of the formula (I) may possess one or more asymmetric centres and so exist in two or more stereoisomeric forms. The present invention includes all the individual stereoisomers and geometric isomers of the compounds of formula (I) and mixtures thereof.

Another aspect of the invention is a pharmaceutical composition comprising a compound or salt according to the above definitions and a pharmaceutically-acceptable adjuvant, diluent or carrier.

Yet another aspect of the invention is a compound or salt according to the above definitions for use as a medicament.

A further aspect of the invention is the use of a compound or salt according to the above definitions for the manufacture of a medicament for the treatment of a condition or process mediated by uPA, such as angiogenesis (neo-vascularization), bone restructuring, embryo implantation in the uterus, infiltration of immune cells into inflammatory sites, ovulation, spermatogenesis, psoriasis, tissue remodelling during wound repair and organ differentiation, fibrosis, local invasion of tumours into adjacent areas, metastatic spread of tumour cells from primary to secondary sites, and tissue destruction in arthritis.

Yet another aspect of the invention is a method of treatment of a condition mediated by uPA, such as angiogenesis (neo-vascularization), bone restructuring, embryo implantation in the uterus, infiltration of immune cells into inflammatory sites, ovulation, spermatogenesis, psoriasis, tissue remodelling during wound repair and organ differentiation, fibrosis, local invasion of tumours into adjacent areas, metastatic spread of tumour cells from primary to secondary sites, and tissue destruction in arthritis, comprising administering a therapeutic amount of a compound or salt or composition according to the above definitions.

It is to be appreciated that reference to treatment includes prophylaxis as well as the alleviation of established symptoms of uPA-mediated conditions and processes.

Preferably G is $N=C(NH_2)_2$.

Preferably $R^1$ is halo.

More preferably $R^1$ is chloro or bromo.

Most preferably $R^1$ is chloro.

Preferably X is $SO_2$.

Preferably $R^2$ is H, $C_{3-7}$ cycloalkyl or $C_{1-6}$ alkyl each of which $C_{3-7}$ cycloalkyl and $C_{1-6}$ alkyl is optionally substituted by aryl, het, $C_{3-7}$ cycloalkyl, OH, Ohet$^1$, $C_{1-6}$ alkoxy, $CO_2H$, $CO_2(C_{1-6}$ alkyl) or by $NR^4R^5$, or $R^2$ and $X^1$ can be taken together with the N atom to which they are attached to form an azetidine, pyrrolidine, piperidine or homopiperidine ring.

More preferably $R^2$ is H, $C_{1-3}$ alkyl optionally substituted by aryl or by optionally substituted pyridyl or by $NR^4R^5$ or by HO or by Ohet$^1$, or $R^2$ and $X^1$ can be taken together with the N atom to which they are attached to form an azetidine, pyrrolidine, piperidine or homopiperidine ring.

Further more preferably $R^2$ is H, $CH_2CH_2N(CH_3)_2$, $CH_3$, $CH_2CH_2OH$, $CH_2CH_2O(2\text{-}THP)$, pyridinylmethyl, benzyl or methoxybenzyl, or $R^2$ and $X^1$ can be taken together with the N atom to which they are attached to form an azetidine, pyrrolidine, piperidine or homopiperidine ring linked to the $R^3$ moiety via the 2-position of said ring.

Most preferably $R^2$ is H, $CH_2CH_2N(CH_3)_2$, $CH_3$, $CH_2CH_2OH$, $CH_2CH_2O(2\text{-}THP)$ or $R^2$ and $X^1$ are taken together with the N atom to which they are attached to form a pyrrolidine ring linked to the $R^3$ moiety via the 2-position.

Preferably $X^1$ is phenylene optionally substituted by one or two substituents independently selected from methoxy and halo, or is $C_{1-3}$ alkylene optionally substituted by one or more group selected from aryl or ($C_{1-6}$ alkyl optionally substituted by aryl, $C_{1-6}$ alkoxy, $CO_2H$, OH, $NH_2$ or $CONH_2$), or is cyclo($C_{4-7}$)alkylene optionally contain a hetero moiety selected from O or $NR^7$, which ring is optionally substituted by $R^6$, or is taken together with $R^2$ and with the N atom to which they are attached to form an azetidine, pyrrolidine, piperidine or homopiperidine ring.

More preferably, $X^1$ is methylene optionally substituted by one or more group selected from aryl or ($C_{1-4}$ alkyl optionally substituted by OH, $NH_2$ or $CONH_2$), or is cyclobutylene, cyclopentylene, cyclohexylene, cycloheptylene, tetrahydropyranylene, piperidinylene substituted by $R^7$, or is taken together with $R^2$ and with the N atom to which they are attached to form an azetidine, pyrrolidine, piperidine or homopiperidine ring.

Yet more preferably $X^1$ is $C(CH_3)_2$, 1,1-cyclopentylene, 4,4-tetrahydropyranylene, N-methyl-4,4-piperidinylene, $CH_2$, $CH(CH(CH_3)_2)$, $CH(CH_2)_4NH_2$, $CH(CH_2)_3NH_2$, $CH(CH_2)CONH_2$, 1,1-cyclobutylene, 1,1-cyclopentylene, 1,1-cyclohexylene, 1,1-cycloheptylene, N-methyl-4,4-piperidinylene, 4,4-tetrahydropyranylene, or is taken together with $R^2$ and with the N atom to which they are attached to form an azetidine, pyrrolidine, piperidine or homopiperidine ring linked to the $R^3$ moiety via the 2-position.

Most preferably $X^1$ is $C(CH_3)_2$, 1,1-cyclopentylene, 4,4-tetrahydropyranylene, N-methyl-4,4-piperidinylene, or is taken together with $R^2$ and with the N atom to which they are attached to form an azetidine, pyrrolidine, piperidine ring linked to the $R^3$ moiety via the 2-position.

Preferably $R^3$ is $CO_2R^7$ or $CONR^8R^9$.

More preferably $R^3$ is $CO_2H$, $CONH_2$, $CON(CH_3)(CH_2)_2OH$, $CON(CH_3)(CH_2)_2NHCH_3$, $CO_2(C_{1-3}$ alkyl), $CONH(CH_2)_2OH$, $CONH(CH_2)_2OCH_3$, (morpholino)CO or (4-methylpiperazino)CO.

Most preferably $R^3$ is $CO_2H$.

A preferred group of substances (a) are the compounds where X is $SO_2$ in which the $R^3$-$X^1$-$NR^2$-moiety is, where $X^1$ is taken independently from $R^2$ and is methylene optionally substituted by one or more $R^6$ group, or is a 1,1-cyclo($C_{4-7}$)alkylene optionally containing a hetero moiety selected from O, $S(O)_p$ or $NR^7$ and optionally substituted by $R^6$, and $R^2$ and $R^3$ can be taken together with the N and $X^1$ groups to which they are attached, as a group of formula (IA) or (IB):

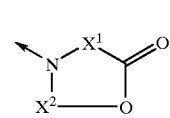

(IA)

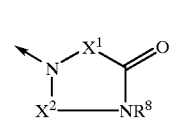

(IB)

wherein $X^2$ is ethylene, n-propylene or n-butylene.

In this group of substances (a) $X^1$ is preferably $C(CH_3)_2$, 1,1-cyclobutylene, 1,1-cyclopentylene, 1,1-cyclohexylene, 4,4-tetrahydropyranylene or N-methyl-4,4-piperidinylene, most preferably 1,1-cyclopentylene.

In this group of substances (a) $X^2$ is preferably ethylene.

A preferred group of substances are the compounds in which the substituent $R^1$ has the values as described by the Examples below, and the salts thereof.

A preferred group of substances are the compounds in which the substituent X has the values as described by the Examples below, and the salts thereof.

A preferred group of substances are the compounds in which the substituent $R^2$ has the values as described by the Examples below, and the salts thereof.

A preferred group of substances are the compounds in which the substituent $X^1$ has the values as described by the Examples below, and the salts thereof.

A preferred group of substances are the compounds in which the substituent $R^3$ has the values as described by the Examples below, and the salts thereof.

Another preferred group of substances are the compounds in which each of the substituents $R^1$, X, $R^2$ $X^1$ and $R^3$ have the values as described by the Examples below, and the salts thereof.

A preferred group of substances are the compounds where $R^1$ is chloro or bromo; X is $SO_2$; $R^2$ is H, $CH_2CH_2N(CH_3)_2$, $CH_3$, $CH_2CH_2OH$, $CH_2CH_2O$(2-THP), pyridinylmethyl, benzyl or methoxybenzyl, or $R^2$ and $X^1$ can be taken together with the N atom to which they are attached to form an azetidine, pyrrolidine, piperidine or homopiperidine ring linked to the $R^3$ moiety via the 2-position of said ring;

$X^1$ is $C(CH_3)_2$, 1,1-cyclopentylene, 4,4-tetrahydropyranylene, N-methyl-4,4-piperidinylene, $CH_2$, $CH(CH(CH_3)_2)$, $CH(CH_2)4NH_2$, $CH(CH_2)_3NH_2$, $CH(CH_2)CONH_2$, 1,1-cyclobutylene, 1,1-cyclopentylene, 1,1-cyclohexylene, 1,1-cycloheptylene, N-methyl-4,4-piperidinylene, 4,4-tetrahydropyranylene, or is taken together with $R^2$ and with the N atom to which they are attached to form an azetidine, pyrrolidine, piperidine or homopiperidine ring linked to the $R^3$ moiety via the 2-position.;

$R^3$ is $CO_2H$, $CONH_2$, $CON(CH_3)(CH_2)_2OH$, $CON(CH_3)(CH_2)_2NHCH_3$, $CO_2(C_{1-3}alkyl)$, $CONH(CH_2)_2OH$, $CONH(CH_2)_2OCH_3$, (morpholino)CO or (4-methylpiperazino)CO; and the salts thereof.

Another preferred group of substances are those in which $R^1$ is chloro; X is $SO_2$;

$R^2$ is H, $CH_2CH_2N(CH_3)_2$, $CH_3$, $CH_2CH_2OH$, $CH_2CH_2O$ (2-THP) or $R^2$ and $X^1$ are taken together with the N atom to which they are attached to form a pyrrolidine ring linked to the $R^3$ moiety via the 2-position;

$X^1$ is $C(CH_3)_2$, 1,1-cyclopentylene, 4,4-tetrahydropyranylene, N-methyl-4,4-piperidinylene, or is taken together with $R^2$ and with the N atom to which they are attached to form an azetidine, pyrrolidine, piperidine ring linked to the $R^3$ moiety via the 2-position;
and $R^3$ is $CO_2H$;
and the salts thereof.

Another preferred group of substances are the compounds of the Examples below and the salts thereof. More preferred within this group are the compounds of Examples 32(b), 34(b), 36(b), 37(b), 38, 39(a and b), 41(b), 43(b), 44(b), 71, 75, 76, 78, 79, 84(b), and 87(b and c) and the salts thereof.

The invention further provides Methods for the production of substances of the invention, which are described below and in the Examples. The skilled man will appreciate that the substances of the invention could be made by methods other than those herein described, by adaptation of the methods herein described in the sections below and/or adaptation thereof, and of methods known in the art.

In the Methods below, unless otherwise specified, the substituents are as defined above with reference to the compounds of formula (I) above.

Method 1

Compounds of formula (I) can be obtained from the corresponding 1-aminoisoquinoline derivative (II):

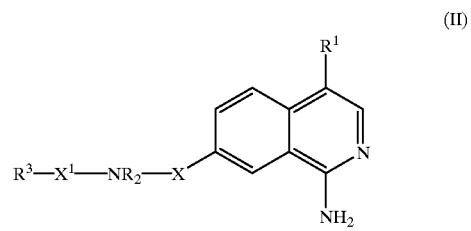

(II)

by reaction with cyanamide ($NH_2CN$) or a reagent which acts as a "$NHC^+=NH$" synthon such as carboxamidine derivatives, e.g. 1H-pyrazole-1-carboxamidine (M. S. Bernatowicz, Y. Wu, G. R. Matsueda, J. Org. Chem., 1992, 57, 2497), the 3,5-dimethylpyrazole analogue thereof (M. A. Brimble et al, J.Chem.Soc.Perkin Trans.I (1990)311), simple O-alkylthiouronium salts or S-alkylisothiouronium salts such as O-methylisothiourea (F. El-Fehail et al, J.Med.Chem.(1986), 29, 984), S-methylisothiouronium sulphate (S. Botros et al, J.Med.Chem.(1986)29,874; P. S. Chauhan et al, Ind. J. Chem., 1993, 32B, 858) or S-ethylisothiouronium bromide (M. L. Pedersen et al, J.Org.Chem.(1993) 58, 6966). Alternatively aminoiminomethanesulphinic acid, or aminoiminomethanesulphonic acid may be used (A. E. Miller et al, Synthesis (1986) 777; K. Kim et al, Tet.Lett.(1988) 29,3183).

Other methods for this transformation are known to those skilled in the art (see for example, "Comprehensive Organic Functional Group Transformations", 1995, Pergamon Press, Vol 6 p639, T. L. Gilchrist (Ed.); Patai's "Chemistry of Functional Groups", Vol. 2. "The Chemistry of Amidines and Imidates", 1991, 488).

Aminoisoquinolines (II) may be prepared by standard published methods (see for example, "The Chemistry of Heterocyclic Compounds" Vol. 38 Pt. 2 John Wiley & Sons, Ed. F. G. Kathawala, G. M. Coppolq, H. F. Schuster) including, for example, by rearrangement from the corresponding carboxy-derivative (Hoffmann, Curtius, Lossen, Schmidt-type rearrangements) and subsequent deprotection.

Aminoisoquinolines (II) may alternatively be prepared by direct displacement of a leaving group such as Cl or Br with a nitrogen nucleophile such as azide (followed by reduction), or by ammonia, or through Pd-catalysis with a suitable protected amine (such as benzylamine) followed by deprotection using standard conditions well-known in the art.

Haloisoquinolines are commercially available or can alternatively be prepared by various methods, for example those described in: Goldschmidt, Chem.Ber.(1895)28,1532; Brown and Plasz, J.Het.Chem.(1971)6,303; U.S. Pat. No. 3,930,837; Hall et al, Can.J.Chem.(1966)44,2473; White, J.Org.Chem.(1967)32,2689; and Ban, Chem.Pharm.Bull. (1964)12,1296.

1,4-(Dichloro- or dibromo)isoquinolines can be prepared by the method described by M. Robison et al in J.Org.Chem. (1958)23,1071, by reaction of the corresponding isocarbostyryl compound with $PCl_5$ or $PBr_5$.

Method 2

Compounds of formula (I) can be obtained from the corresponding aminoisoquinoline derivative (II) as defined in Method 1 above, via reaction with a reagent which acts as a protected amidine(2+) synthon (III),

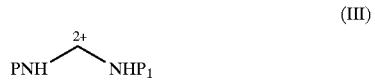

(III)

such as a compound PNHC(=X)NHP$_1$, PN=CXNHP$_1$ or PNHCX=NP$_1$, where X is a leaving group such as Cl, Br, I, mesylate, tosylate, alkyloxy, etc., and where P and P$_1$ may be the same or different and are N-protecting groups such as are well-known in the art, such as t-butoxycarbonyl, benzyloxycarbonyl, arylsulphonyl such as toluenesulphonyl, nitro, etc.

Examples of reagents that act as synthons (III) include N,N'-protected-S-alkylthiouronium derivatives such as N,N'-bis(t-butoxycarbonyl)-S-Me-isothiourea, N,N'-bis(benzyloxycarbonyl)-S-methylisothiourea, or sulphonic acid derivatives of these (J. Org. Chem. 1986, 51, 1882), or S-arylthiouronium derivatives such as N,N'-bis(t-butoxycarbonyl)-S-(2,4-dinitrobenzene) (S. G. Lammin, B. L. Pedgrift, A. J. Ratcliffe, Tet. Lett. 1996, 37, 6815), or mono-protected analogues such as [(4-methoxy-2,3,6-trimethylphenyl)sulphonyl]-carbamimidothioic acid methyl ester or the corresponding 2,2,5,7,8-pentamethylchroman-6-sulphonyl analogue (D. R. Kent, W. L. Cody, A. M. Doherty, Tet. Lett., 1996, 37, 8711), or S-methyl-N-nitroisothiourea (L. Fishbein et al, J.Am.Chem.Soc. (1954) 76, 1877) or various substituted thioureas such as N,N'-bis(t-butoxycarbonyl)thiourea (C. Levallet, J. Lerpiniere, S. Y. Ko, Tet. 1997, 53, 5291) with or without the presence of a promoter such as a Mukaiyama's reagent (Yong, Y. F.; Kowalski, J. A.; Lipton, M. A. J. Org. Chem., 1997, 62, 1540), or copper, mercury or silver salts, particularly with mercury (II) chloride. Suitably N-protected O-alkylisoureas may also be used such as O-methyl-N-nitroisourea (N. Heyboer et al, Rec.Chim.Trav.Pays-Bas (1962)81,69). Alternatively other guanylation agents known to those skilled in the art such as 1-H-pyrazole-1-[N,N'-bis(t-butoxycarbonyl)] carboxamidine, the corresponding bis-Cbz derivative (M. S. Bernatowicz, Y. Wu, G. R. Matsueda, Tet. Lett. 1993, 34, 3389) or monoBoc or mono-Cbz derivatives may be used (B. Drake. Synthesis, 1994, 579, M. S. Bernatowicz. Tet. Lett. 1993, 34, 3389). Similarly, 3,5-dimethyl-1-nitroguanylpyrazole may be used (T. Wakayima et al, Tet.Lett.(1986)29,2143).

The reaction can conveniently be carried out using a suitable solvent such as dichloromethane, N,N-dimethylformamide (DMF), methanol.

The reaction is also conveniently carried out by adding mercury (II) chloride to a mixture of the aminoisoquinoline (II) and a thiourea derivative of type (III) in a suitable base solvent mixture such as triethylamine/dichloromethane.

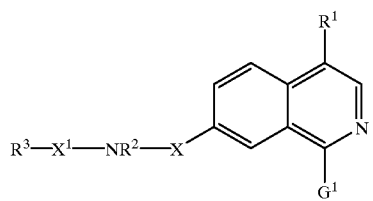

(IV)

The product of this reaction is the protected isoquinolinylguanidine (IV), where G$^1$ is a protected guanidine moiety N=C(NHP)(NHP$_1$) or tautomer thereof, where P and P$_1$ are nitrogen-protecting groups such as t-butoxycarbonyl ("Boc"), benzyl, benzyloxycarbonyl, etc., which can conveniently be deprotected to give (I) or a salt thereof.

For example, if the protecting group P and/or P$_1$ is t-butoxycarbonyl, conveniently the deprotection is carried out using an acid such as trifluoroacetic acid (TFA) or hydrochloric acid, in a suitable solvent such as dichloromethane, to give the bistrifluoroacetate salt of (I).

If P and/or P$_1$ is a hydrogenolysable group, such as benzyloxycarbonyl, the deprotection could be performed by hydrogenolysis.

Other protection/deprotection regimes include: nitro (K. Suzuki et al, Chem.Pharm.Bull. (1985)33,1528, Nencioni et al, J.Med.Chem.(1991)34,3373, B. T. Golding et al, J.C.S.Chem.Comm.(1994)2613; p-toluenesulphonyl (J. F. Callaghan et al, Tetrahedron (1993) 49 3479; mesitylsulphonyl (Shiori et al, Chem.Pharm.Bull.(1987)35,2698, ibid. (1987)35,2561, ibid., (1989)37,3432, ibid., (1987)35,3880, ibid., (1987)35,1076; 2-adamantoyloxycarbonyl (Iuchi et al, ibid., (1987) 35, 4307; and methylsulphonylethoxycarbonyl (Filippov et al, Syn.Lett.(1994)922).

It will be apparent to those skilled in the art that other protection and subsequent deprotection regimes during synthesis of a compound of the invention may be achieved by various other conventional techniques, for example as described in "Protective Groups in Organic Synthesis" by T W Greene and P G M Wuts, John Wiley and Sons Inc. (1991), and by P. J. Kocienski, in "Protecting Groups", Georg Thieme Verlag (1994).

Method 3

Compounds of the formula (I) can be obtained from compounds of formula (V)

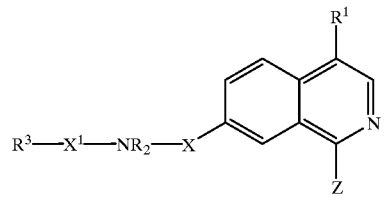

(V)

where Z is a suitable leaving group such as Cl, Br or OPh, by displacement of the leaving group by the free base of guanidine.

Compounds of formula (V) are available as mentioned above in the section on preparation of compounds of formula (II) in Method 1, and routine variation thereof.

The free base of guanidine may conveniently be generated in situ from a suitable salt, such as the hydrochloride, carbonate, nitrate, or sulphate with a suitable base such as sodium hydride, potassium hydride, or another alkali metal base, preferably in a dry non-protic solvent such as tetrahydrofuran (THF), DMSO, N,N-dimethylformamide (DMF), ethylene glycol dimethyl ether (DME), N,N-dimethyl acetamide (DMA), toluene or mixtures thereof. Alternatively it can be generated from a suitable salt using an alkoxide in an alcohol solvent such as potassium t-butoxide in t-butanol, or in a non-protic solvent as above.

The thus formed free guanidine can be combined with the 1-isoquinoline derivative (V), and the reaction to form compounds of formula (I) can be carried out at from room temperature to 200° C., preferably from about 50° C. to 150° C., preferably for between 4 hours and 6 days.

It will be clear to those skilled in the art, that some of the functionality in the R$^3$, R$^2$ and/or X$^1$ groups may need to be either protected and released subsequent to guanylation or added, or generated after the guanidine moiety had been added to the substrate.

For example, an acid group could be carried through the guanylation stage while protected as an ester and subsequently hydrolyseded. Base-catalysed hydrolysis of an ethyl ester and acid-catalysed hydrolysis of a t-butyl ester are two such suitable examples of this. In another example, an alcohol may be protected with groups well documented in the literature such as a 2-tetrahydropyranyl ether (2-THP) and subsequently removed by treatment with acid.

The addition of new functionality after the guanidine moiety has been installed is also encompassed by the invention. For example, alkylation of the sulphonamido NH (i.e. "X-NR$^2$" is SO$_2$NH) with an alkyl halide may be performed in the presence of a base such as potassium carbonate and optionally in the presence of a promoter such as KI. In another example, an acid group may be converted to an amide through a range of coupling conditions known to those skilled in the art, or conveniently though the acid chloride while in the presence of a free or protected guanidine. Alternatively an ester group can be directly reacted with an amine to generate an amide; if this occurs in an intramolecular process, a lactam may be formed. Using similar methodology esters and lactones may be prepared. Additional functionality could have been present in a protected form at this stage and subsequently revealed—such as an amino group which could be protected by groups well documented in the literature, e.g. a Boc group and subsequently removed under standard conditions, such as treatment with a strong base such as HCl or TFA.

Method 4

Compounds of the invention where one or more substituent is or contains a carboxylic acid group or carbamoyl group can be made from the corresponding compound where the corresponding substituent is a nitrile by full or partial hydrolysis. Compounds of the invention where one or more substituent is or contains a carboxylic acid group can be made from the corresponding compound where the corresponding substituent is a carbamoyl moiety, by hydrolysis.

The hydrolysis can be carried out by methods well-known in the art, for example those mentioned in "Advanced Organic Chemistry" by J. March, 3rd edition (Wiley-Interscience) chapter 6-5, and references therein. Conveniently the hydrolysis is carried out using concentrated hydrochloric acid, at elevated temperatures, and the product forms the hydrochloride salt.

Method 5

Where desired or necessary the compound of formula (I) is converted into a pharmaceutically acceptable salt thereof. A pharmaceutically acceptable salt of a compound of formula (I) may be conveniently be prepared by mixing together solutions of a compound of formula (I) and the desired acid or base, as appropriate. The salt may be precipitated from solution and collected by filtration, or may be collected by other means such as by evaporation of the solvent.

Other Methods

Compounds of the formula (I) where one or more substituent is or contains Cl or Br may be dehalogenated to give the corresponding hydrido compounds of formula (I) by hydrogenolysis, suitably using a palladium on charcoal catalyst, in a suitable solvent such as ethanol at about 20° C. and at elevated pressure.

Compounds of formula (I) where one or more substituent is or contains a carboxy group may be prepared from a compound with a group hydrolysable to give a carboxy moiety, for example a corresponding nitrile or ester, by hydrolysis, for example by acidic hydrolysis with e.g. conc. aq. HCl at reflux. Other hydrolysis methods are well known in the art.

Compounds of formula (I) in which one or more substituent is or contains an amide moiety may be made via reaction of an optionally protected corresponding carboxy compund, either by direct coupling with the amine of choice, or via initial formation of the corresponding acid chloride or mixed anhydride, and subsequent reaction with the amine, followed by deprotection if appropriate. Such transformations are well-known in the art.

Certain of the compounds of formula (I) which have an electrophilic group attached to an aromatic ring can be made by reaction of the corresponding hydrido compound with an electrophilic reagent. For example sulphonylation of the aromatic ring using standard reagents and methods, such as fuming sulphuric acid, gives a corresponding sulphonic acid. This can then be optionally converted into the corresponding sulphonamide by methods known in the art, for example by firstly converting to the acid chloride followed by reaction with an amine.

Certain of the compounds of the invention can be made by cross-coupling techniques such as by reaction of a compound containing a bromo-substituent attached to e.g. an aromatic ring, with e.g. a boronic acid derivative, an olefin or a tin derivative by methods well-known in the art, for example by the methods described in certain of the Preparations below.

Certain of the compounds of the invention having an electrophilic substituent can be made via halogen/metal exchange followed be reaction with an electrophilic reagent. For example a bromo-substituent may react with a lithiating reagent such as n-butyllithium and subsequently an electrophilic reagent such as $CO_2$, an aldehyde or ketone, to give respectively an acid or an alcohol.

Compounds of the invention are available by either the methods described herein in the Methods and Examples or suitable adaptation thereof using methods known in the art. It is to be understood that the synthetic transformation methods mentioned herein may be carried out in various different sequences in order that the desired compounds can be efficiently assembled. The skilled chemist will exercise his judgement and skill as to the most efficient sequence of reactions for synthesis of a given target compound.

It will be apparent to those skilled in the art that sensitive functional groups may need to be protected and deprotected during synthesis of a compound of the invention. This may be achieved by conventional techniques, for example as described in "Protective Groups in Organic Synthesis" by T W Greene and P G M Wuts, John Wiley and Sons Inc. (1991), and by P. J. Kocienski, in "Protecting Groups", Georg Thieme Verlag (1994).

It is possible during some of the reactions described herein that any stereocentres present could, under certain conditions, be racemised, for example if a base is used in a reaction with a substrate having an having an optical centre comprising a base-sensitive group. This is possible during e.g. a guanylation step. It should be possible to circumvent potential problems such as this by choice of reaction sequence, conditions, reagents, protection/deprotection regimes, etc. as is well-known in the art.

The compounds and salts of the invention may be separated and purified by conventional methods.

Separation of diastereomers may be achieved by conventional techniques, e.g. by fractional crystallisation, chromatography or H.P.L.C. of a stereoisomeric mixture of a compound of formula (I) or a suitable salt or derivative thereof. An individual enantiomer of a compound of formula (I) may also be prepared from a corresponding optically pure intermediate or by resolution, such as by H.P.L.C. of the corresponding racemate using a suitable chiral support or by fractional crystallisation of the diastereomeric salts formed by reaction of the corresponding racemate with a suitably optically active acid or base.

For human use, the compounds of formula (I) or their salts can be administered alone, but will generally be administered in admixture with a pharmaceutically acceptable diluent or carrier selected with regard to the intended route of administration and standard pharmaceutical practice. For example, they can be administered orally, including sublingually, in the form of tablets containing such excipients as starch or lactose, or in capsules or ovules either alone or in admixture with excipients, or in the form of elixirs, solutions or suspensions containing flavouring or colouring agents. They can be injected parenterally, for example, intravenously, intramuscularly or subcutaneously. For parenteral administration, they are best used in the form of a sterile aqueous solution or suspension which may contain other substances, for example, enough salt or glucose to make the solution isotonic with blood. They can be administered topically, in the form of sterile creams, gels, suspensions, lotions, ointments, dusting powders, sprays, drug-incorporated dressings or via a skin patch. For example they can be incorporated into a cream consisting of an aqueous or oily emulsion of polyethylene glycols or liquid paraffin, or they can be incorporated into an ointment consisting of a white wax soft paraffin base, or as hydrogel with cellulose or polyacrylate derivatives or other viscosity modifiers, or as a dry powder or liquid spray or aerosol with butane/propane, HFA or CFC propellants, or as a drug-incorporated dressing either as a tulle dressing, with white soft paraffin or polyethylene glycols impregnated gauze dressings or with hydrogel, hydrocolloid, alginate or film dressings. The compound or salt could also be administered intraocularly as an eye drop with appropriate buffers, viscosity modifiers (e.g. cellulose derivatives), preservatives (e.g. benzalkonium chloride (BZK)) and agents to adjust tenicity (e.g. sodium chloride).

All such formulations may also contain appropriate stabilisers and preservatives.

For oral and parenteral administration to human patients, the daily dosage level of the compounds of formula (I) or their salts will be from 0.001 to 20, preferably from 0.01 to 20, more preferably from 0.1 to 10, and most preferably from 0.5 to 5 mg/kg (in single or divided doses). Thus tablets or capsules of the compounds will contain from 0.1 to 500, preferably from 50 to 200, mg of active compound for administration singly or two or more at a time as appropriate.

The physician in any event will determine the actual dosage which will be most suitable for an individual patient and it will vary with the age, weight and response of the particular patient. the above dosages are exemplary of the average case; there can of course be individual instances where higher or lower dosage ranges are merited, and such are within the scope of this invention.

It is to be appreciated that reference to treatment includes prophylaxis as well as the alleviation of established symptoms of the condition to be treated.

Test Methods

Compounds were tested for their ability to inhibit human urokinase, human tPA and human plasmin, using substantially the same methods as described by Yang, et al, J.Med.Chem.,(1990)33,2961. The urokinase assay was carried out using S-2444 (Quadratech 820357) as substrate and the urokinase used was HMWT Human Urokinase (Calbiochem 672081). The tPA assay was carried out using S-2288 (Quadratech 820832) tPA substrate, Quadratech 321116 as tPA stimulator, and the tPA used was Human tPA (Quadratech 881157). The plasmin assay was carried out using human plasmin (Quadratech 810665) acting on Chromozym-PL (Boehringer 378461) as substrate.

The compounds of Examples 32(b), 34(b), 36(b), 37(b), 38, 39(a and b), 41(b), 43(b), 44(b), 71, 75, 76, 78, 79, 84(b), and 87(b and c) all had $K_i$ values of 20 nM or less vs. urokinase.

The invention is illustrated by the following Examples.

EXPERIMENTAL SECTION

General Details

Melting points (mp) were determined using either Gallenkamp or Electrothermal melting point apparatus and are uncorrected. Proton nuclear magnetic resonance ($^1$H NMR) data were obtained using a Varian Unity 300 or a Varian Inova 400. Low resolution mass spectral (LRMS) data were recorded on a Fisons Instruments Trio 1000 (thermaspray) or a Finnigan Mat. TSQ 7000 (APCl). Elemental combustion analyses (Anal.) were determined by Exeter Analytical UK. Ltd.

Column chromatography was performed using Merck silica gel 60 (0.040–0.063 mm). Reverse phase column chromatography was performed using Mitsubishi MCl gel (CHP 20P).

The following abbreviations were used: ammonia solution sp. gr. 0.880 (0.880NH$_3$); diethyl azodicarboxylate (DEAD); 1,2-dimethoxyethane (DME); N,N-dimethylacetamide (DMA); N,N-dimethylformamide (DMF); dimethylsulphoxide (DMSO); tetrahydrofuran (THF); trifluoroacetic acid (TFA); toluene (PhMe); methanol (MeOH); ethyl acetate (EtOAc) propanol (PrOH). Other abbreviations are used according to standard chemical practice.

Some nomenclature has been allocated using the IUPAC NamePro software available from Advanced Chemical Development Inc. It was noted following some preparations involving guanylation of intermediates containing a quaternary centre adjacent to a base-sensitive group e.g. an ester, that some racemisation had occurred, so in such cases there may be a mixture of enantiomers produced.

EXAMPLES

Example 1

(a) tert-Butyl 2-{[(4-chloro-1-guanidino-7-isoquinolinyl) sulphonyl]amino}benzoate (b) 2-{[(4-Chloro-1-guanidino-7-isoquinolinyl)sulphonyl] amino}benzoic acid hydrochloride

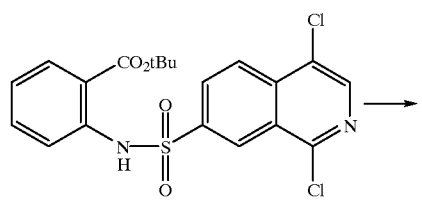

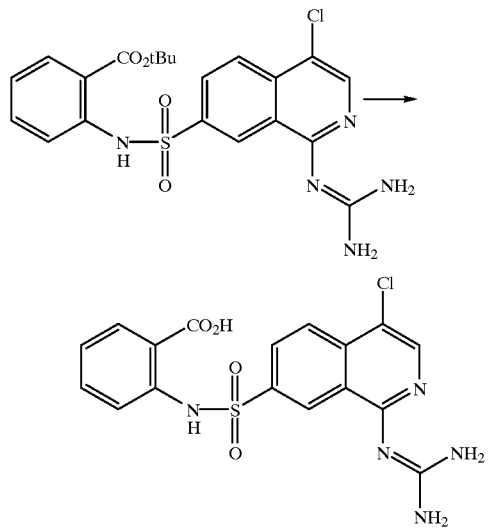

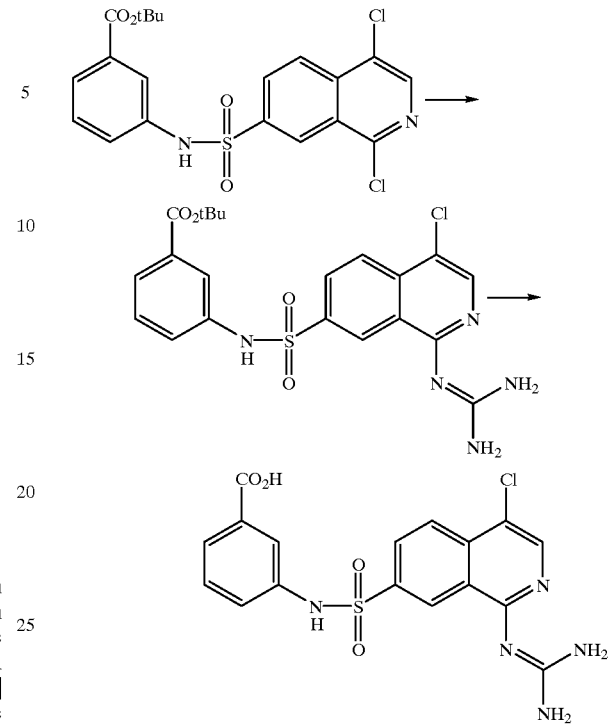

Guanidine hydrochloride (60 mg, 0.63 mmol) was added in one portion to a suspension of NaH (18 mg, 80% dispersion by wt in mineral oil, 0.6 mmol) in DMSO (3.0 mL) and the mixture was heated at 60° C. under $N_2$ for 30 min. tert-Butyl 2-{[(1,4-dichloro-7-isoquinolinyl)sulphonyl]amino}benzoate (110 mg, 0.24 mmol) was added and the mixture heated at 100° C. for 24 h. The cooled mixture was poured into water and extracted with EtOAc (×3) and the combined organic phase was then washed with brine and evaporated in vacuo. The residue was purified by column chromatography upon silica gel using $CH_2Cl_2$-MeOH-$0.880NH_3$ (97:3:0.3 to 95:5:0.5) as eluant to give a yellow resin (36 mg). This resin was suspended in water and extracted with ether (×3). The combined organic phase was washed with brine and evaporated in vacuo to give tert-butyl 2-{[(4-chloro-1-guanidino-7-isoquinolinyl)sulphonyl]amino}benzoate (30 mg, 0.063 mmol) as a brown solid.

TLC $R_f$ 0.60 ($CH_2Cl_2$-MeOH-$0.880NH_3$, 90:10:1).

$^1$H (CD$_3$OD, 400 MHz) δ 1.4 (9H, s), 7.1 (1H, dd), 7.5 (1H, dd), 7.7 (1H, d), 7.8 (1H, d), 7.9 (1H, d), 8.0 (1H, d), 8.1 (1H, s), 9.1 (1H, s) ppm.

LRMS 475 (MH$^+$).

The silica gel column was then eluted with MeOH and the combined washings were concentrated in vacuo to give an off-white solid. This was dissolved in a solution of EtOH saturated with HCl gas and the mixture stirred at room temperature. The solvents were evaporated in vacuo and the residue was then dissolved in EtOAc-MeOH, filtered and again evaporated in vacuo. The solid was triturated with water and then dried to give 2-{[(4-chloro-1-guanidino-7-isoquinolinyl)sulphonyl]amino}benzoic acid hydrochloride (11.8 mg, 0.02 mmol) as a pale yellow solid.

mp>280° C. (dec).

$^1$H (CD$_3$OD, 400 MHz) δ 7.0 (1H, dd), 7.3 (1H, dd), 7.65 (1H, d), 7.8 (1H, d), 8.1 (1H, d), 8.2 (1H, d), 8.3 (1H, s), 8.9 (1H, s) ppm.

LRMS 420, 422 (M$^+$), 421 (MH$^+$).

Anal. Found: C, 43.58; H, 3.37; N, 14.65. Calc for $C_{17}H_{14}ClN_5O_4S.1.0HCl.0.7H_2O$: C, 43.54; H, 3.53; N, 14.94.

Example 2
(a) tert-Butyl 3-{[(4-chloro-1-guanidino-7-isoquinolinyl)sulphonyl]amino}benzoate
(b) 3-{[(4-Chloro-1-guanidino-7-isoquinolinyl)sulphonyl]amino}benzoic acid trifluoroacetate Guanidine hydrochloride (140 mg, 1.47 mmol) was added in one portion to a suspension of NaH (44 mg, 80% dispersion by wt in mineral oil, 1.47 mmol) in DMSO (4.0 mL) and the mixture was heated at 60° C. under $N_2$ for 30 min. A solution of tert-butyl 3-{[(1,4-dichloro-7-isoquinolinyl)-sulphonyl]amino}benzoate (280 mg, 0.59 mmol) in DMSO (2.0 mL) was added and the mixture heated at 90° C. for 18 h. The cooled mixture was poured into water (50 mL), extracted with EtOAc (×3) and the combined organic phase was then evaporated in vacuo. The residue was purified by column chromatography upon silica gel using $CH_2Cl_2$-MeOH-$0.880NH_3$ (97:3:0.3 to 95:5:0.5) as eluant to give tert-butyl 3-{[(4-chloro-1-guanidino-7-isoquinolinyl)sulphonyl]amino}benzoate (64 mg, 0.13 mmol) as a tan solid.

mp>142° C. (dec).

$^1$H (CD$_3$OD, 400 MHz) δ 1.5 (9H, s), 7.25–7.35 (2H, m), 7.65–7.7 (2H, m), 7.95 (1H, d), 8.05 (1H, d), 8.1 (1H, s), 9.1 (1H, s) ppm.

LRMS 475 (MH$^+$).

Anal. Found: C, 51.07; H, 4.55; N, 13.94. Calc for $C_{21}H_{22}ClN_5O_4S.0.23CH_2Cl_2$: C, 51.46; H, 4.57; N, 14.13.

tert-Butyl 3-{[(4-chloro-1-guanidino-7-isoquinolinyl)sulphonyl]amino}benzoate (30 mg, 0.063 mmol) was dissolved in $CF_3CO_2H$ (1.0 mL) and the mixture stirred at room temperature for 1 h. The mixture was diluted with PhMe and the solvents were evaporated in vacuo. The residue was triturated with $Et_2O$ and then azeotroped with $CH_2Cl_2$ to give 3-{[(4-chloro-1-guanidino-7-isoquinolinyl)sulphonyl]amino}-benzoic acid trifluoroacetate (29 mg, 0.055 mmol) as an off-white solid.

mp>180° C. (dec).

$^1$H (CD$_3$OD, 400 MHz) δ 7.2–7.35 (2H, m), 7.55 (1H, d), 7.65 (1H, s), 8.15 (1H, d), 8.3 (1H, d), 8.35 (1H, s), 8.85 (1H, s) ppm.

LRMS 419,421 (MH$^+$).

Anal. Found: C, 42.51; H, 3.07; N, 13.19. Calc for $C_{17}H_{14}ClN_5O_4S.1.0CF_3CO_2H$: C, 42.75; H, 2.83; N, 13.12.

Example 3

(a) Methyl 3-{[(4-chloro-1-guanidino-7-isoquinolinyl)sulphonyl]amino}-4-methoxybenzoate (b) 3-{[(4-Chloro-1-guanidino-7-isoquinolinyl)sulphonyl]amino}-4-methoxybenzoic acid hydrochloride

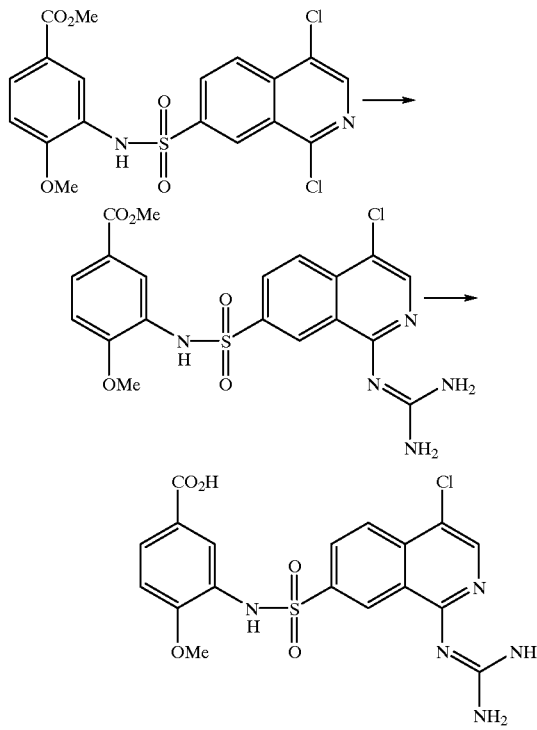

Guanidine hydrochloride (179.8 mg, 1.88 mmol) was added in one portion to a suspension of NaH (54.9 mg, 80% dispersion by wt in mineral oil, 1.83 mmol) in DMSO (10 mL) and the mixture was heated at 60° C. under $N_2$ for 20 min. Methyl 3-{[(1,4-dichloro-7-isoquinolinyl)sulphonyl]amino}-4-methoxybenzoate (238.6 mg, 0.541 mmol) was added and the mixture heated at 90° C. for 24 h. The solvents were evaporated in vacuo and the residue was purified by column chromatography upon silica gel using $CH_2Cl_2$-MeOH-0.880$NH_3$ (97:3:0.3 to 90:10:1) as eluant to give methyl 3-{[(4-chloro-1-guanidino-7-isoquinolinyl)sulphonyl]amino}-4-methoxybenzoate (203.2 mg, 0.43 mmol) as a pale yellow solid.

mp 134–137° C. (dec).

$^1$H (DMSO-$d_6$, 300 MHz) δ 3.45 (3H, s), 3.8 (3H, s), 6.95 (1H, d), 7.05–7.4 (4H, br s), 7.7 (1H, d), 7.8 (1H, s), 8.0 (2H, s), 8.1 (1H, s), 9.05 (1H, s), 9.9 (1H, br s) ppm.

LRMS 464, 466 (MH$^+$).

Anal. Found: C, 48.37; H, 3.81; N, 14.75. Calc for $C_{19}H_{18}ClN_5O_5S.0.15CH_2Cl_2$: C, 48.26; H, 3.87; N, 14.69.

An aqueous solution of NaOH (0.7 mL, 1.0 M, 0.7 mmol) was added slowly to a stirred solution of methyl 3-{[(4-chloro-1-guanidino-7-isoquinolinyl)sulphonyl]amino}-4-methoxybenzoate (52.2 mg, 0.113 mmol) in dioxane (2.5 mL) and the mixture stirred at room temperature for 1.5 h, and then at 70° C. for 3 h. The mixture was cooled to room temperature, dilute HCl (2 mL, 2 N) was added, the solvents were evaporated in vacuo and the residue was dried by azeotroping with i-PrOH (×3). The solid was extracted with hot i-PrOH (×4), the combined organic extracts were filtered, and the solvents were evaporated in vacuo. The residue was triturated with Et$_2$O to give 3-{[(4-chloro-1-guanidino-7-isoquinolinyl)sulphonyl]amino}-4-methoxybenzoic acid hydrochloride (29 mg, 0.055 mmol) as a solid.

mp 258° C. (dec).

$^1$H (DMSO-$d_6$, 300 MHz) δ 3.45 (3H, s), 6.95 (1H, d), 7.7 (1H, d), 7.8 (1H, s), 8.3–8.7 (4H, br s), 8.3 (1H, d), 8.4 (1H, d), 8.45 (1H, s), 8.9 (1H, s), 10.05 (1H, br s), 10.9 (1H, br s), 12.75 (1H, br s) ppm.

LRMS 450 (MH$^+$).

Anal. Found: C, 44.50; H, 4.60; N, 12.17. Calc for $C_{18}H_{16}ClN_5O_5S.1.0HCl.1.0(CH_3)_2CHOH.1.0H_2O$: C, 44.69; H, 4.82; N, 12.41.

Example 4

(a) N-[(4-chloro-1-guanidino-7-isoquinolinyl)sulphonyl]glycine t-butyl ester hydrochloride N-[(-Chloro-1-guanidino-7-isoquinolinyl)sulphonyl]glycine trifluoroacetate

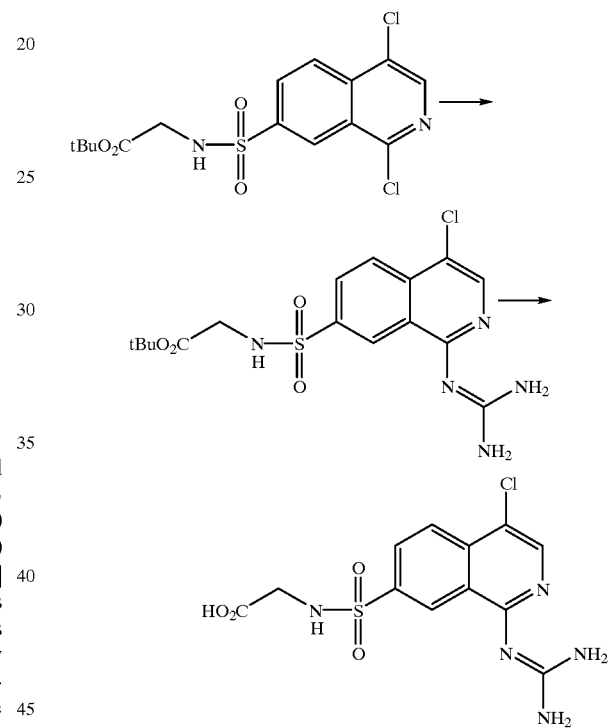

NaH (29 mg, 80% dispersion by wt in mineral oil, 0.97 mmol) was added in one portion to a stirred solution of guanidine hydrochloride (146 mg, 1.52 mmol) in DMSO (2.0 mL) and the mixture was heated at 60° C. under $N_2$ for 30 min. N-[(1,4-Dichloro-7-isoquinolinyl)sulphonyl]glycine t-butyl ester (150 mg, 0.38 mmol) was added and the mixture heated at 90° C. for 9 h. The cooled mixture was diluted with water (30 mL), extracted with EtOAc (4×20 mL) and the combined organic extracts were washed with water, brine, dried (Na$_2$SO$_4$) and evaporated in vacuo. The residue was dissolved in Et$_2$O and a solution of HCl in Et$_2$O (1 M) was added to give a sticky precipitate. The Et$_2$O was decanted and the residue triturated with EtOAc to give a white solid. Filtration with EtOAc and Et$_2$O washing gave N-[(4-chloro-1-guanidino-7-isoquinolinyl)sulphonyl]glycine t-butyl ester hydrochloride (68 mg, 0.14 mmol).

mp 172–175° C.

$^1$H (DMSO-$d_6$, 300 MHz) δ 1.2 (9H, s), 3.75 (2H, s), 8.3 (1H, d), 8.35–8.4 (2H, m), 8.5 (1H, s), 8.5–8.9 (4H, br), 9.1 (1H, s), 11.3 (1H, br s) ppm.

LRMS 414,416 (MH+).

Anal. Found: C, 42.45; H, 4.92; N, 14.76. Calc for $C_{16}H_{20}ClN_5O_4S.1.0HCl.0.33H_2O.0.2EtOAc$: C, 42.58; H, 4.95; N, 14.78.

N-[(4-Chloro-1-guanidino-7-isoquinolinyl)sulphonyl]glycine t-butyl ester hydrochloride (50 mg, 0.11 mmol) was dissolved in $CF_3CO_2H$ (1.0 mL) and the mixture stirred at room temperature for 1.5 h. The mixture was diluted with PhMe and the solvents were evaporated in vacuo. The residue was triturated with $Et_2O$ and EtOAc to give N-[(4-chloro-1-guanidino-7-isoquinolinyl)sulphonyl]glycine trifluoroacetate (36 mg, 0.073 mmol) as a white powder.

$^1H$ ($CF_3CO_2D$, 400 MHz) δ 4.1 (2H, s), 8.25 (1H, d), 8.3 (1H, s), 8.55 (1H, d), 9.0 (1H, s) ppm.

LRMS 358 (MH+), 715 ($M_2H^+$).

Anal. Found: C, 36.25; H, 2.86; N, 14.28. Calc for $C_{12}H_{12}ClN_5O_4S.1.0CF_3CO_2H.0.2EtOAc$: C, 36.32; H, 3.01; N, 14.31.

Example 5

(a) N-[(4-chloro-1-guanidino-7-isoquinolinyl)sulphonyl]-β-alanine t-butyl ester
(b) N-[(4-Chloro-1-guanidino-7-isoquinolinyl)sulphonyl]-β-alanine trifluoroacetate

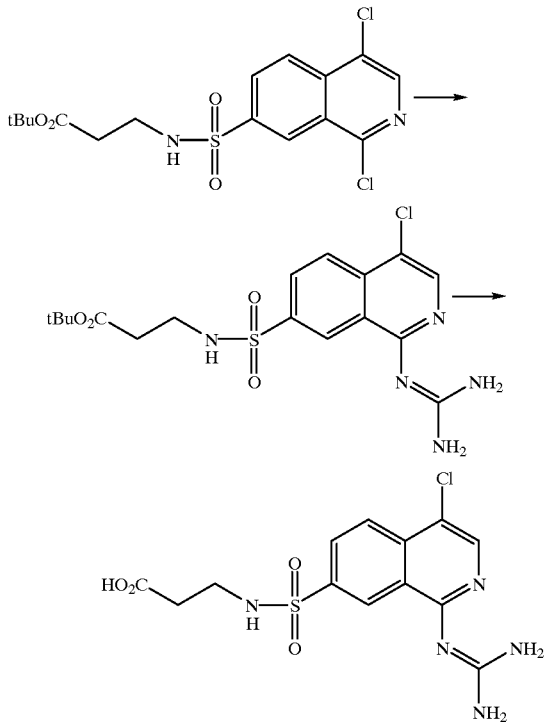

Guanidine hydrochloride (140 mg, 1.46 mmol was added in one portion to a stirred suspension of NaH (35 mg, 80% dispersion by wt in mineral oil, 1.17 mmol) in DME (8.0 mL) and the mixture was heated at 30° C. under $N_2$ for 30 min. N-[(1,4-Dichloro-7-isoquinolinyl)sulphonyl]-β-alanine t-butyl ester (150 mg, 0.37 mmol) was added and the mixture heated at 90° C. for 18 h. The cooled mixture was diluted with EtOAc, washed with water, brine, dried ($MgSO_4$) and evaporated in vacuo. The residue was purified by column chromatography upon silica gel using $CH_2Cl_2$-MeOH-0.880$NH_3$ (97:3:0.3 to 95:5:0.5) as eluant to give N-[(4-chloro-1-guanidino-7-isoquinolinyl)sulphonyl]-β-alanine t-butyl ester (75 mg, 0.175 mmol) as a yellow foam mp>180° C. (dec).

$^1H$ (DMSO-$d_6$, 300 MHz) δ 1.35 (9H, s), 2.3 (2H, t), 2.9 (2H, dt), 7.1–7.4 (4H, br), 7.8 (1H, br t), 8.05 (2H, s), 8.1 (1H, s), 9.1 (1H, s) ppm.

LRMS 428 (MH+).

Anal. Found: C, 47.32; H, 5.24; N, 16.02. Calc for $C_{17}H_{22}ClN_5O_4S.0.2H_2O$: C, 47.32; H, 5.23; N, 16.23.

N-[(4-Chloro-1-guanidino-7-isoquinolinyl)sulphonyl]-β-alanine t-butyl ester (30 mg, 0.07 mmol) was dissolved in $CF_3CO_2H$ (1.0 mL) and the mixture stirred at room temperature for 1 h. The mixture was evaporated in vacuo, azeotroping with PhMe, MeOH and then $CH_2Cl_2$, to give N-[(4-chloro-1-guanidino-7-isoquinolinyl)sulphonyl]-β-alanine trifluoroacetate (32 mg, 0.066 mmol) as a white solid.

mp>200° C. (dec).

$^1H$ (DMSO-$d_6$+$D_2O$, 400 MHz) δ 2.35 (2H, t), 3.0 (2H, t), 8.2 (1H, d),8.3 (1H, d), 8.4 (1H, s), 9.1 (1H, s) ppm.

LRMS 372 (MH+).

Anal. Found: C, 37.38; H, 3.1 1; N, 14.52. Calc for $C_{13}H_{14}ClN_5O_4S.1.0CF_3CO_2H$: C, 37.08; H, 3.11; N, 14.42.

Example 6

(a) N-[(4-chloro-1-guanidino-7-isoquinolinyl)sulphonyl]-N-methylglycine t-butyl ester
(b) N-[(4-Chloro-1-guanidino-7-isoquinolinyl)sulphonyl]-N-methylglycine bis(trifluoroacetate)

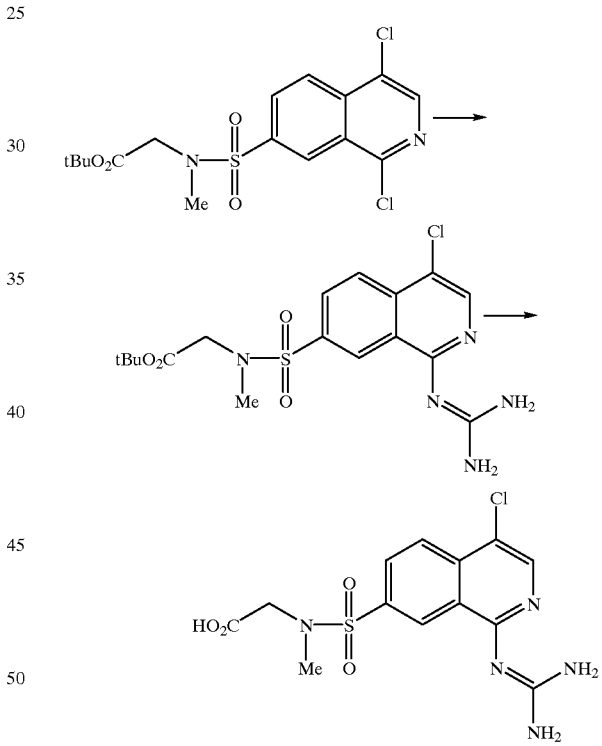

Guanidine hydrochloride (286 mg, 2.99 mmol was added in one portion to a stirred suspension of NaH (77.5 mg, 80% dispersion by wt in mineral oil, 2.58 mmol) in DME (2.0 mL) and the mixture was heated at 50° C. under $N_2$ for 20 min. A solution of N-[(1,4-dichloro-7-isoquinolinyl)sulphonyl]-N-methylglycine t-butyl ester (393 mg, 0.97 mmol) in DME (10 mL) was added and the mixture heated at 90° C. for 2 h. The solvents were evaporated in vacuo and the residue was purified by column chromatography upon silica gel using $CH_2Cl_2$-MeOH-0.880$NH_3$ (97:3:0.3) as eluant to give N-[(4-chloro-1-guanidino-7-isoquinolinyl)sulphonyl]-N-methylglycine t-butyl ester (260 mg, 0.607 mmol) as an off-white foam
mp 84° C.

¹H (DMSO-d₆, 300 MHz) δ 1.3 (9H, s), 2.85 (3H, s), 3.95 (2H, s), 7.0–7.5 (4H, br), 8.0 (1H, d), 8.05 (1H, d), 8.1 (1H, s), 9.05 (1H, s) ppm.

LRMS 427 (MH⁺), 855 (M₂H⁺).

Anal. Found: C, 47.92; H, 5.38; N, 15.07. Calc for C₁₇H₂₂ClN₅O₄S: C, 47.72; H, 5.18; N, 16.37.

N-[(4-Chloro-1-guanidino-7-isoquinolinyl)sulphonyl]-N-methylglycine t-butyl ester (255 mg, 5.96 mmol) was dissolved in CF₃CO₂H (4.0 mL) and CH₂Cl₂ (2.0 mL), and the mixture stirred at room temperature for 1 h. The mixture was diluted with PhMe and the solvents were evaporated in vacuo to give N-[(4-chloro-1-guanidino-7-isoquinolinyl)sulphonyl]-N-methylglycine bis(trifluoroacetate) (349 mg, 0.56 mmol) as a white powder.

mp 240–242° C. (dec).

¹H (DMSO-d₆, 300 MHz) δ 2.9 (3H, s), 4.05 (2H, s), 8.3 (1H, d), 8.4 (1H, d), 8.4–8.7 (4H, br), 8.5 (1H, s), 8.9 (1H, s) ppm.

LRMS 372, 374 (MH⁺), 744 (M₂H⁺).

Anal. Found: C, 36.26; H, 3.10; N, 11.04. Calc for C₁₃H₁₄ClN₅O₄S.2.0CF₃CO₂H.0.3PhMe: C, 36.56; H, 2.96; N, 11.16.

Example 7
(a) N-[(4-chloro-1-guanidino-7-isoquinolinyl)sulphonyl]-N-phenylglycine t-butyl ester
(b) N-[(4-Chloro-1-guanidino-7-isoquinolinyl)sulphonyl]-N-phenylglycine trifluoroacetate

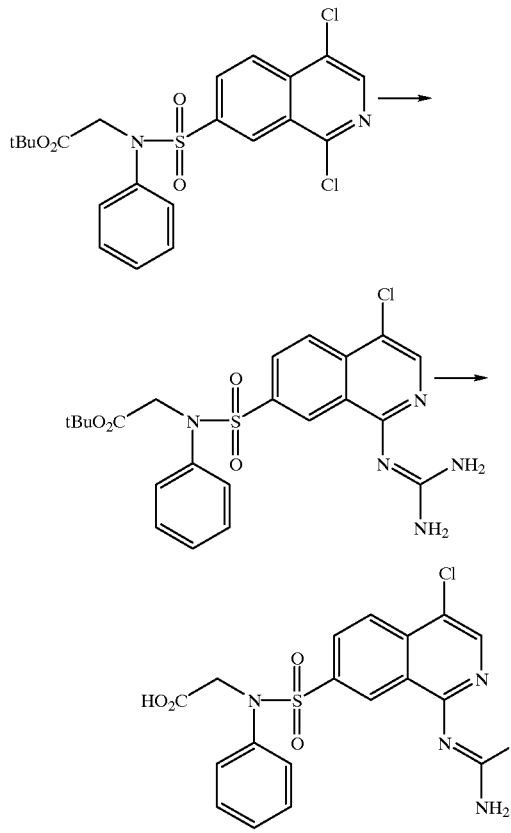

NaH (32 mg, 80% dispersion by wt in mineral oil, 1.07 mmol) was added in one portion to a stirred suspension of guanidine hydrochloride (164 mg, 1.71 mmol) in DME (5.0 mL) and the mixture was heated at 60° C. under N₂ for 30 min. N-[(1,4-Dichloro-7-isoquinolinyl)sulphonyl]-N-phenylglycine t-butyl ester (200 mg, 0.43 mmol) was added and the mixture heated at 95° C. for 6 h. The solvents were evaporated in vacuo and the residue was purified by column chromatography upon silica gel using CH₂Cl₂-MeOH-0.880N₃ (97:3:0.3 to 95:5:0.5) as eluant to give N-[(4-chloro-1-guanidino-7-isoquinolinyl)sulphonyl]-N-phenylglycine t-butyl ester (28 mg, 0.057 mmol) as a yellow resin.

¹H (DMSO-d₆, 300 MHz) δ 1.3 (9H, s), 4.45 (2H, s), 7.2–7.3 (2H, m), 7.2–7.4 (4H, br), 7.3–7.4 (3H, m), 7.9 (1H, d), 8.0 (1H, d), 8.1 (1H, s), 8.95 (1H, s) ppm.

LRMS 490, 492 (MH⁺), 981 (M₂H⁺).

N-[(4-Chloro-1-guanidino-7-isoquinolinyl)sulphonyl]-N-phenylglycine t-butyl ester (25 mg, 0.05 mmol) was dissolved in CF₃CO₂H (1.0 mL) and the mixture stirred at room temperature for 2 h. The mixture was concentrated in vacuo, azeotroping with PhMe, and the residue triturated with Et₂O to give N-[(4-chloro-1-guanidino-7-isoquinolinyl)sulphonyl]-N-phenylglycine trifluoroacetate (13 mg, 0.23 mmol) as a pale yellow powder.

mp 218–223° C.

¹H (DMSO-d₆, 300 MHz) δ 4.5 (2H, s), 7.1–7.2 (2H, d), 7.25–7.4 (3H, m), 7.8–8.4 (4H, br), 8.0 (1H, d), 8.2 (1H, d), 8.35 (1H, s), 8.9 (1H, s) ppm.

LRMS 434, 436 (MH⁺), 744 (M₂H⁺).

Anal. Found: C, 42.55; H, 3.39; N, 11.90. Calc for C₁₈H₁₆ClN₅O₄S.1.0CF₃CO₂H.H₂O.0.2Et₂O: C, 42.74; H, 3.52; N, 12.22.

Example 8
(a) N-[(4-chloro-1-guanidino-7-isoquinolinyl)sulphonyl-N-(cyclopentylmethyl)-glycine t-butyl ester
(b) N-[(4-Chloro-1-guanidino-7-isoquinolinyl)sulphonyl]-N-(cyclopentylmethyl)glycine

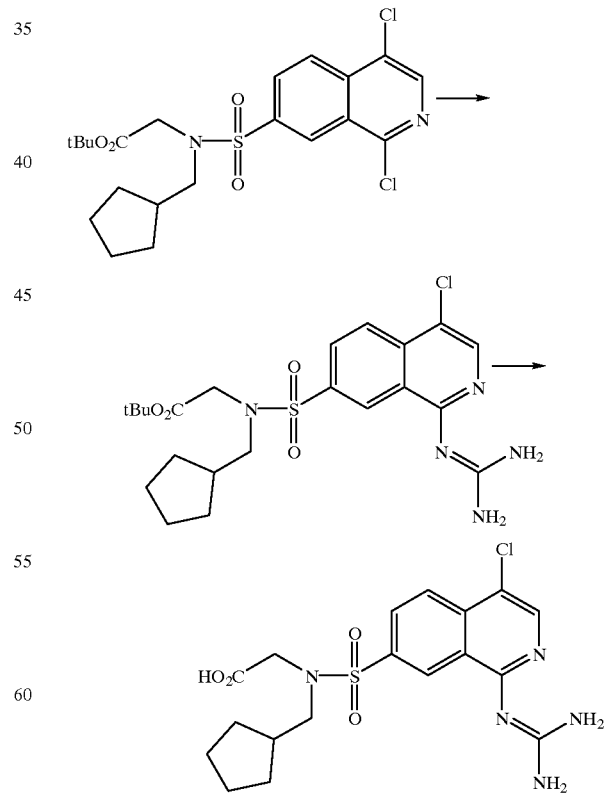

Guanidine hydrochloride (96 mg, 1.00 mmol was added in one portion to a stirred suspension of NaH (19 mg, 80% dispersion by wt in mineral oil, 0.63 mmol) in DME (5.0 mL) and the mixture was heated at 60° C. under $N_2$ for 30 min. A solution of N-[(1,4-dichloro-7-isoquinolinyl)sulphonyl]-N-(cyclopentylmethyl)glycine t-butyl ester (120 mg, 0.25 mmol) in DME (5.0 mL) was added and the mixture heated at 90° C. for 3 h. The solvents were evaporated in vacuo, the residue was dissolved with EtOAc (200 mL), and washed with aqueous $NH_4Cl$ (150 mL), dried ($MgSO_4$) and evaporated in vacuo. The residue was purified by column chromatography upon silica gel using pentane-EtOAc (100:0 to 40:60) as eluant to give N-[(4-chloro-1-guanidino-7-isoquinolinyl)sulphonyl]-N-(cyclopentylmethyl)-glycine t-butyl ester (60 mg, 0.12 mmol).

$^1$H ($CDCl_3$, 400 MHz) δ 1.1–1.25 (2H, m), 1.35 (9H, s), 1.45–1.7 (4H, m), 1.7–1.8 (2H, m), 2.1 (1H, m), 3.25 (2H, d), 4.0 (2H, s), 8.05 (1H, d), 8.1 (1H, d), 8.15 (1H, s), 9.2 (1H, s) ppm.

LRMS 496 (MH$^+$).

Anal. Found: C, 52.99; H, 6.07; N, 13.82. Calc for $C_{22}H_{30}ClN_5O_4S$: C, 53.38; H, 5.90; N, 14.15.

A solution of HCl (2 mL, 2 M, 4 mmol) was added to a solution of N-[(4-chloro-1-guanidino-7-isoquinolinyl)sulphonyl]-N-(cyclopentylmethyl)glycine t-butyl ester (50 mg, 0.10 mmol) in dioxane (4.0 mL) and the mixture was heated at 60° C. for 24 h. The solvents were evaporated in vacuo, and the residue triturated with dichloromethane to give N-[(4-chloro-1-guanidino-7-isoquinolinyl)sulphonyl]-N-(cyclopentylmethyl)glycine hydrochloride (40 mg, 0.080 mmol) as a white solid.

mp 139–142° C.

$^1$H ($CD_3OD$, 400 MHz) δ 1.2–1.3 (2H, m), 1.5–1.7 (4H, m), 1.7–1.8 (2H, m), 2.2 (1H, m), 3.65 (2H, d), 4.2 (2H, s), 8.35 (1H, d), 8.45 (1H, s), 8.45 (1H, d), 8.9 (1H, s) ppm.

LRMS 440 (MH$^+$).

Anal. Found: C, 43.48; H, 5.32; N, 12.91. Calc for $C_{18}H_{22}ClN_5O_4S.1.0HCl.1.0H_2O.0.05CH_2Cl_2.0.05$ dioxane: C, 43.17; H, 5.11; N, 13.92.

Example 9

(a) N-[(4-chloro-1-guanidino-7-isoquinolinyl)sulphonyl]-N-(cyclohexylmethyl)glycine t-butyl ester (b) N-[(4-Chloro-1-guanidino-7-isoquinolinyl)sulphonyl]-N-(cyclohexylmethyl)glycine hydrochloride

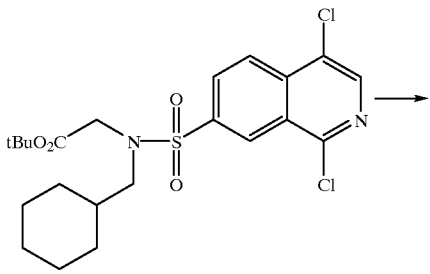

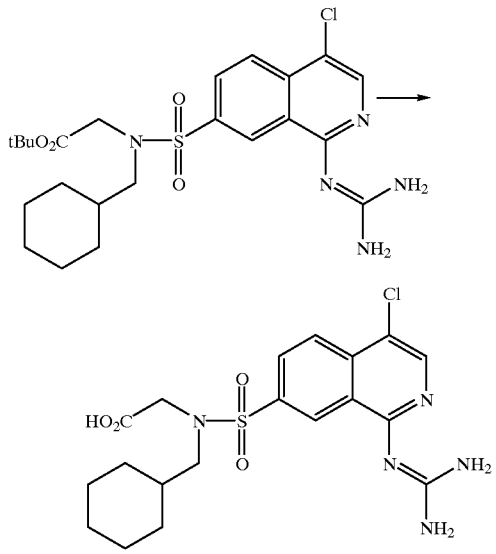

Guanidine hydrochloride (125 mg, 1.31 mmol was added in one portion to a stirred suspension of NaH (25 mg, 80% dispersion by wt in mineral oil, 0.82 mmol) in DME (10 mL) and the mixture was heated at 60° C. under $N_2$ for 30 min. N-[(1,4-Dichloro-7-isoquinolinyl)sulphonyl]-N-(cyclohexylmethyl)-glycine t-butyl ester (160 mg, 0.33 mmol) was added and the mixture heated at 80–90° C. for 2.5 h. The solvents were evaporated in vacuo, the residue was dissolved with EtOAc (200 mL), and washed with aqueous $NH_4Cl$ (150 mL), dried ($MgSO_4$) and evaporated in vacuo. The residue was purified by column chromatography upon silica gel using pentane-EtOAc (100:0 to 40:60) as eluant to give N-[(4-chloro-1-guanidino-7-isoquinolinyl)sulphonyl]-N-(cyclohexylmethyl)glycine t-butyl ester (65 mg, 0.127 mmol) as an off-white foam.

$^1$H ($CDCl_3$, 400 MHz) δ 0.8–0.95 (2H, m), 1.1–1.25 (3H, m), 1.3 (9H, s), 1.6–1.8 (6H, m), 3.1 (2H, d), 4.0 (2H, s), 8.0 (1H, d), 8.1 (1H, d), 8.15 (1H, s), 9.2 (1H, s) ppm.

LRMS 510 (MH$^+$).

Anal. Found: C, 54.21; H, 6.46; N, 13.46. Calc for $C_{23}H_{32}ClN_5O_4S$: C, 54.16; H, 6.32; N, 13.73.

A solution of HCl (2 mL, 2 M, 4 mmol) was added to a solution of N-[(4-chloro-1-guanidino-7-isoquinolinyl)sulphonyl]-N-(cyclohexylmethyl)glycine t-butyl ester (53 mg, 0.10 mmol) in dioxane (4.0 mL). The mixture was stirred at 23° C. for 18 h and then heated at 50–60° C. for 16 h. On cooling, a white precipitate crashed out of solution. The solid was collected by filtration, triturated with EtOAc and then dried under vacuum to give N-[(4-chloro-1-guanidino-7-isoquinolinyl)sulphonyl]-N-(cyclohexylmethyl)glycine hydrochloride (26 mg, 0.057 mmol).

$^1$H ($CDCl_3$, 400 MHz) δ 0.8–1.0 (2H, m), 1.1–1.3 (3H, m), 1.55–1.8 (6H, m), 3.2 (2H, d), 4.15 (2H, s), 8.3 (1H, d), 8.45 (1H, d), 8.45 (1H, s), 8.9 (1H, s) ppm.

LRMS 454, 456 (MH$^+$).

Anal. Found: C, 44.70; H, 5.15; N, 13.56. Calc for $C_{23}H_{32}ClN_5O_4S.HCl.H_2O$: C, 44.89; H, 5.36; N, 13.77.

Example 10

(a) N-[(4-chloro-1-guanidino-7-isoquinolinyl)sulphonyl]-N-benzylglycine t-butyl ester (b) N-[(4-Chloro-1-guanidino-7-isoquinolinyl)sulphonyl]-N-benzylglycine trifluoroacetate

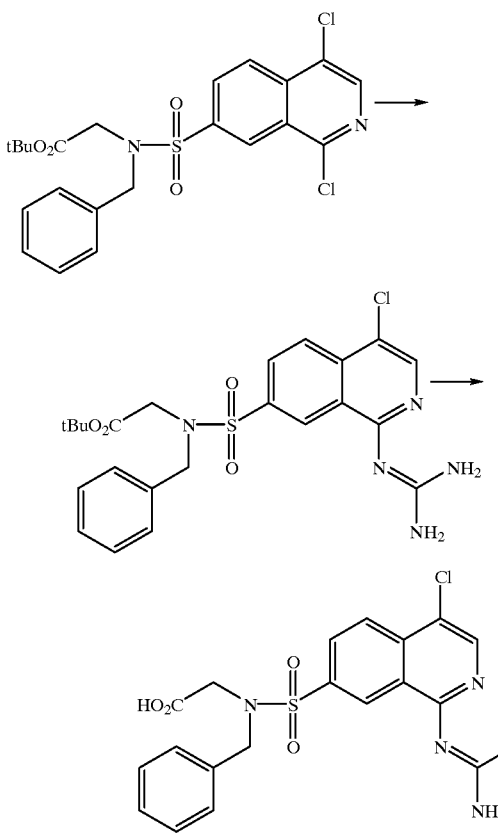

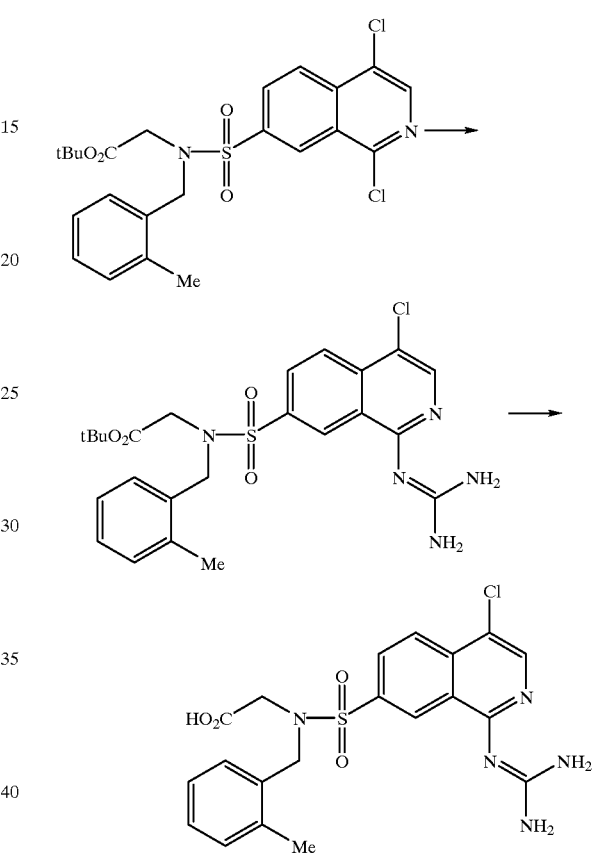

Guanidine hydrochloride (180 mg, 1.88 mmol) was added in one portion to a suspension of NaH (45 mg, 80% dispersion by wt in mineral oil, 1.5 mmol) in DME (11 mL) and the mixture was heated at 60° C. under $N_2$ for 30 min. N-[(1, 4-Dichloro-7-isoquinolinyl)sulphonyl]-N-benzylglycine t-butyl ester (225 mg, 0.467 mmol) was added and the mixture heated at 90° C. for 18 h. The cooled mixture was poured into water, extracted with EtOAc (×3) and the combined organic phase was then washed with water, dried ($Na_2SO_4$) and evaporated in vacuo. The residue was purified by column chromatography upon silica gel using $CH_2Cl_2$-MeOH-0.880$NH_3$ (97:3:0.3) as eluant to give N-[(4-chloro-1-guanidino-7-isoquinolinyl)sulphonyl]-N-benzylglycine t-butyl ester (172 mg, 0.34 mmol) as a yellow foam.

mp>150° C. (dec).

$^1$H (DMSO-$d_6$, 400 MHz) δ 1.2 (9H, s), 3.8 (2H, s), 4.45 (2H, s), 7.1–7.4 (4H, br), 7.2–7.35 (5H, m), 8.0 (1H, d), 8.1 (1H, d), 8.1 (s, 1H), 9.1 (1H, s) ppm.

LRMS 504, 506 (MH$^+$).

Anal. Found: C, 55.19; H, 5.55; N, 13.23. Calc for $C_{23}H_{26}ClN_5O_4S.0.1C_6H_{14}$: C, 55.30; H, 5.39; N, 13.66.

N-[(4-Chloro-1-guanidino-7-isoquinolinyl)sulphonyl]-N-benzylglycine t-butyl ester (50 mg, 0.10 mmol) was dissolved in $CF_3CO_2H$ (1.0 mL) and the mixture stirred at room temperature for 1 h. The mixture was diluted with PhMe and the solvents were evaporated in vacuo. The residue was azeotroped with PhMe and then $CH_2Cl_2$ to give N-[(4-chloro-1-guanidino-7-isoquinolinyl)sulphonyl]-N-benzylglycine trifluoroacetate (52 mg, 0.10 mmol) as a white solid.

mp 274° C. (dec).

$^1$H (DMSO-$d_6$, 400 MHz) δ 3.95 (2H, s), 4.5 (2H, s), 7.2–7.35 (5H, m), 8.3 (1H, d), 8.35 (1H, d), 8.4–8.6 (4H, br), 8.45 (1H, s), 8.9 (1H, s), 10.6 (1H, br), 12.7 (1H, br) ppm.

LRMS 448, 450 (MH$^+$), 497 (M$_2$H$^+$).

Anal. Found: C, 43.96; H, 3.39; N, 11.87. Calc for $C_{19}H_{18}ClN_5O_4S.1.0CF_3CO_2H.0.5H_2O$: C, 44.18; H, 3.53; N, 12.27.

Example 11

(a) N-[(4-chloro-1-guanidino-7-isoquinolinyl)sulphonyl]-N-(2-methylbenzyl)glycine t-butyl ester (b) N-[(4-Chloro-1-guanidino-7-isoquinolinyl)sulphonyl]-N-(2-methylbenzyl)glycine trifluoroacetate Guanidine hydrochloride (120 mg, 1.26 mmol) was added in one portion to a suspension of NaH (32 mg, 80% dispersion by wt in mineral oil, 1.06 mmol) in DME (10 mL) and the mixture was heated at 60° C. under $N_2$ for 30 min. N-[(1, 4-Dichloro-7-isoquinolinyl)sulphonyl]-N-(2-methylbenzyl) glycine t-butyl ester (200 mg, 0.405 mmol) was added and the mixture heated at 90° C. for 2 h. The cooled mixture was diluted with EtOAc, washed with water, brine, dried ($Na_2SO_4$) and evaporated in vacuo. The residue was purified by column chromatography upon silica gel using pentane-$CH_2Cl_2$ (50:50), then $CH_2Cl_2$, and finally $CH_2Cl_2$-MeOH-0.880$NH_3$ (95:5:0.5) as eluant to give N-[(4-chloro-1-guanidino-7-isoquinolinyl)sulphonyl]-N-(2-methylbenzyl) glycine t-butyl ester (94 mg, 0.18 mmol) as an off-white solid.

mp>1 10° C. (dec).

$^1$H (CDCl$_3$, 400 MHz) δ 1.25 (9H, s), 2.3 (3H, s), 3.8 (2H, s), 4.6 (2H, s), 7.1–7.2 (4H, m), 8.05 (1H, d), 8.1 (1H, d), 8.15 (s, 1H), 9.3 (1H, s) ppm.

LRMS 518, 520 (MH$^+$).

Anal. Found: C, 56.21; H, 5.83; N, 12.57. Calc for $C_{24}H_{28}ClN_5O_4S.0.3H_2O.0.25C_6H_{14}$: C, 56.20; H, 5.94; N, 12.85.

N-[(4-Chloro-1-guanidino-7-isoquinolinyl)sulphonyl]-N-(2-methylbenzyl)glycine t-butyl ester (30 mg, 0.058 mmol) was dissolved in $CF_3CO_2H$ (1.0 mL) and the mixture stirred at room temperature for 1 h. The mixture was diluted with PhMe and the solvents were evaporated in vacuo. The residue was azeotroped with PhMe and then $Et_2O$ to give N-[(4-chloro-1-guanidino-7-isoquinolinyl)sulphonyl]-N-(2-methylbenzyl)glycine trifluoroacetate (29 mg, 0.05 mmol) as an off-white solid.

mp>150° C. (dec).

$^1H$ ($CD_3OD$, 400 MHz) δ 2.3 (3H, s), 3.95 (2H, s), 4.7 (2H, s), 7.05–7.2 (4H, m), 8.35 (1H, d), 8.45 (1H, s), 8.45 (1H, d), 8.9 (1H, s) ppm.

LRMS 462, 464 ($MH^+$).

Anal. Found: C, 45.51; H, 3.95; N, 11.36. Calc for $C_{20}H_{20}ClN_5O_4S.1.0CF_3CO_2H.1.0H_2O.0.1PhMe$: C, 45.20; H, 3.98; N, 11.61.

Example 12

(a) N-[(4-chloro-1-guanidino-7-isoquinolinyl)sulphonyl]-N-(2-methoxybenzyl)glycine t-butyl ester trifluoroacetate
(b) N-[(4-Chloro-1-guanidino-7-isoquinolinyl)sulphonyl]-N-(2-methoxybenzyl)glycine trifluoroacetate

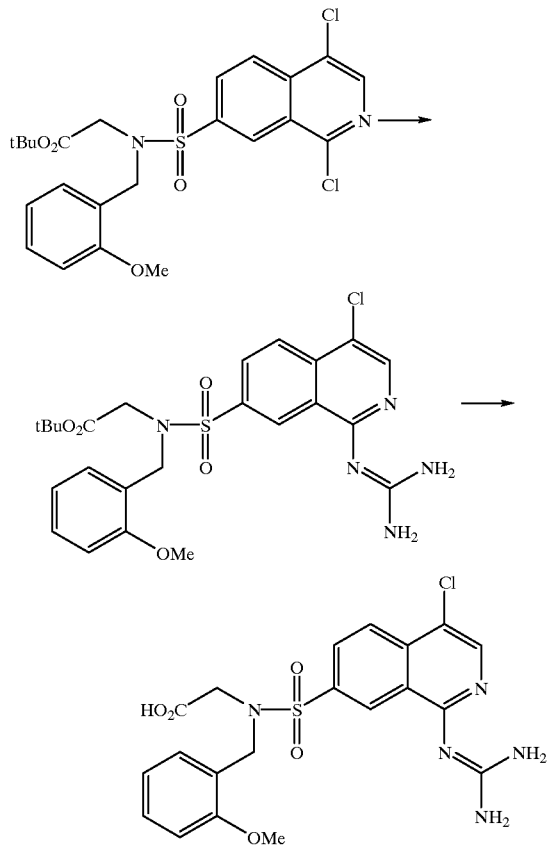

Guanidine hydrochloride (225 mg, 2.36 mmol) was added in one portion to a stirred suspension of NaH (44 mg, 80% dispersion by wt in mineral oil, 1.47 mmol) in DME (20 mL) and the mixture was heated at 60° C. under $N_2$ for 30 min. N-[(1,4-Dichloro-7-isoquinolinyl)sulphonyl]-N-(2-methoxybenzyl)glycine t-butyl ester (300 mg, 0.59 mmol) was added and the mixture heated at 90° C. for 2 h. The cooled mixture was poured into water and extracted with EtOAc (×3). The combined organic extracts were then washed with water, brine, dried ($Na_2SO_4$) and evaporated in vacuo. The residue was purified by column chromatography upon silica gel using hexane-EtOAc (80:20), and then $CH_2Cl_2$-MeOH-$0.880NH_3$ (95:5:0.5 to 90:10:1) as eluant to give the product as a yellow semi-solid. This semi-solid was dissolved in EtOAc, a solution of TFA (35 µL) in EtOAc (25 mL) was added and the solvents were evaporated in vacuo, azeotroping with PhMe. The residue was triturated with i-$Pr_2O$, the resulting white solid was collected by filtration, and then dried to give N-[(4-chloro-1-guanidino-7-isoquinolinyl)sulphonyl]-N-(2-methoxybenzyl)glycine t-butyl ester trifluoroacetate (219 mg, 0.338 mmol).

mp>197° C. (dec).

$^1H$ (DMSO-$d_6$, 400 MHz) δ 1.25 (9H, s), 3.6 (3H, s), 4.0 (2H, s), 4.45 (2H, s), 6.8–6.9 (2H, m), 7.1–7.2 (2H, m), 8.3 (2H, s), 8.4–8.6 (4H, br s), 8.5 (s, 1H), 8.8 (1H, s) ppm.

LRMS 534, 536 ($MH^+$).

Anal. Found: C, 48.33; H, 4.55; N, 10.52. Calc for $C_{24}H_{28}ClN_5O_5S.1.0CF_3CO_2H$: C, 48.18; H, 4.51; N, 10.81.

N-[(4-chloro-1-guanidino-7-isoquinolinyl)sulphonyl]-N-(2-methoxybenzyl)glycine t-butyl ester trifluoroacetate (150 mg, 0.231 mmol) was dissolved in $CF_3CO_2H$ (1.0 mL) and the mixture stirred at room temperature for 40 min. The mixture was diluted with PhMe, concentrated in vacuo, azeotroping with PhMe, and the residue triturated with i-$Pr_2O$ to give N-[(4-chloro-1-guanidino-7-isoquinolinyl)sulphonyl]-N-(2-methoxybenzyl)glycine trifluoroacetate (122 mg, 0.206 mmol) as a white solid.

mp>165° C. (dec).

$^1H$ (DMSO-$d_6$, 400 MHz) δ 3.6 (3H, s), 4.0 (2H, s), 4.5 (2H, s), 6.8 (1H, d), 6.85 (1H, dd), 7.1–7.2 (2H, m), 8.3 (2H, s), 8.35–8.5 (4H, br s), 8.5 (s, 1H), 8.8 (1H, s) ppm.

LRMS 478, 480 ($MH^+$).

Anal. Found: C, 44.64; H, 3.58; N, 11.83. Calc for $C_{20}H_{20}ClN_5O_5S.1.0CF_3CO_2H$: C, 44.69; H, 3.68; N, 11.63.

Example 13

(a) N-[(4-chloro-1-guanidino-7-isoquinolinyl)sulphonyl]-N-(3-methoxybenzyl)glycine t-butyl ester hydrochloride
(b) N-[(4-Chloro-1-guanidino-7-isoquinolinyl)sulphonyl]-N-(3-methoxybenzyl)glycine

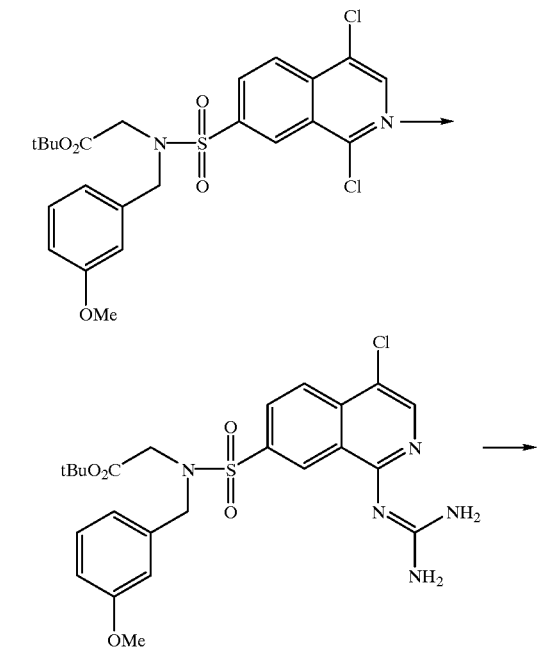

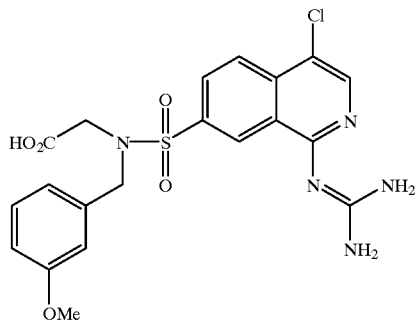

Guanidine hydrochloride (149 mg, 1.55 mmol) was added in one portion to a suspension of NaH (35 mg, 80% dispersion by wt in mineral oil, 1.16 mmol) in DME (10 mL) and the mixture was heated at 60° C. under $N_2$ for 30 min. N-[(1,4-Dichloro-7-isoquinolinyl)sulphonyl]-N-(3-methoxybenzyl)glycine t-butyl ester (200 mg, 0.39 mmol) was added and the mixture heated at 90° C. for 2 h. The cooled mixture was poured into water, extracted with EtOAc (×3), and the combined organic extracts were washed with brine, dried ($Na_2SO_4$) and evaporated in vacuo. The residue was dissolved in $Et_2O$-EtOAc and a solution of HCl in $Et_2O$ (0.5 M) was added to give a precipitate. The solid was collected by filtration, triturated with EtOAc and then dried to give N-[(4-chloro-1-guanidino-7-isoquinolinyl)sulphonyl]-N-(3-methoxybenzyl)glycine t-butyl ester hydrochloride (124 mg, 0.21 mmol) as a white solid.

mp 203–205° C.

$^1$H (DMSO-$d_6$, 300 MHz) δ 1.2 (9H, s), 3.65 (3H, s), 4.05 (2H, s), 4.5 (2H, s), 6.7 (1H, s), 6.75–6.85 (2H, m), 7.2 (1H, dd), 8.3 (1H, d), 8.35 (1H, d), 8.5 (s, 1H), 9.3 (1H, s), 11.6 (1H, br s) ppm.

LRMS 534, 536 (MH$^+$), 1069 ($M_2H^+$).

Anal. Found: C, 50.22; H, 5.1 1; N, 12.23. Calc for $C_{24}H_{28}ClN_5O_5S \cdot 1.0HCl$: C, 56.52; H, 5.12; N, 12.28.

N-[(4-Chloro-1-guanidino-7-isoquinolinyl)sulphonyl]-N-(3-methoxybenzyl)glycine t-butyl ester hydrochloride (95 mg, 0.167 mmol) was dissolved in $CF_3CO_2H$ (1.0 mL) and the mixture stirred at room temperature for 1 h. The mixture was diluted with PhMe and the solvents were evaporated in vacuo. The residue was dissolved in EtOAc and stirred at room temperature for 1 h. The resulting precipitate was collected by filtration, washed with $Et_2O$ and dried to give N-[(4-chloro-1-guanidino-7-isoquinolinyl)sulphonyl]-N-(3-methoxybenzyl)glycine (65 mg, 0.128 mmol) as a white powder.

mp 290° C. (dec).

$^1$H ($CF_3CO_2D$, 400 MHz) δ 3.9 (3H, s), 4.3 (2H, s), 4.6 (2H, s), 6.9–7.0 (3H, m), 7.3 (1H, dd), 8.35 (1H, d), 8.45 (1H, s), 8.6 (1H, d), 8.95 (1H, s) ppm.

LRMS 477, 479 (MH$^+$), 955 ($M_2H^+$).

Anal. Found: C, 48.67; H, 4.09; N, 13.88. Calc for $C_{20}H_{20}ClN_5O_5S \cdot 0.25CF_3CO_2H$: C, 48.62; H, 4.03; N, 13.83.

Example 14

(a) N-[(4-chloro-1-guanidino-7-isoquinolinyl)sulphonyl]-N-(3-chlorobenzyl)glycine t-butyl ester hydrochloride
(b) N-[(4-Chloro-1-guanidino-7-isoquinolinyl)sulphonyl]-N-(3-chlorobenzyl)glycine trifluoroacetate

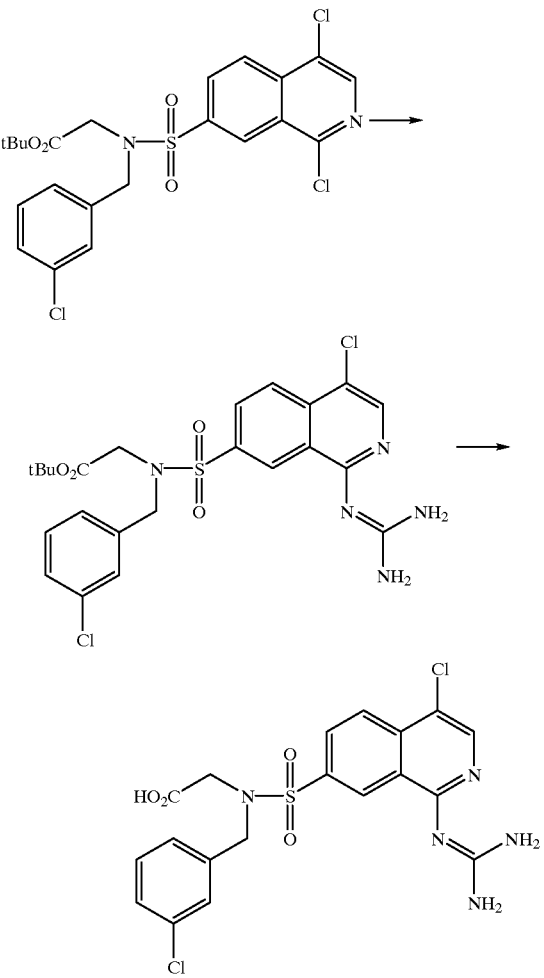

NaH (35 mg, 80% dispersion by wt in mineral oil, 1.16 mmol) was added in one portion to a suspension of guanidine hydrochloride (150 mg, 1.55 mmol) in DME (10 mL) and the mixture was heated at 60° C. under $N_2$ for 30 min. N-[(1,4-Dichloro-7-isoquinolinyl)sulphonyl]-N-(3-chlorobenzyl)glycine t-butyl ester (185 mg, 0.36 mmol) was added and the mixture heated at 90° C. for 5 h. The cooled mixture was diluted with $Et_2O$, washed with water, dried ($Na_2SO_4$) and evaporated in vacuo. The residue was dissolved in $Et_2O$ and a solution of HCl in $Et_2O$ (1 M) was added to give a precipitate. The solvents were evaporated in vacuo, and the white solid triturated with EtOAc and then dried to give N-[(4-chloro-1-guanidino-7-isoquinolinyl)sulphonyl]-N-(3-chlorobenzyl)glycine t-butyl ester hydrochloride (85 mg, 0.145 mmol).

mp 203–205° C.

$^1$H (DMSO-$d_6$, 300 MHz) δ 1.2 (9H, s), 4.1 (2H, s), 4.55 (2H, s), 7.2–7.35 (4H, m), 8.3 (1H, d), 8.35 (1H, d), 8.5 (s, 1H), 9.3 (1H, s), 11.55 (1H, br s) ppm.

LRMS 538, 540 (MH$^+$), 1076 ($M_2H^+$).

Anal. Found: C, 47.04; H, 4.53; N, 11.82. Calc for $C_{23}H_{25}Cl_2N_5O_4S \cdot 1.0HCl \cdot 0.5H_2O$: C, 47.31; H, 4.66; N, 11.99.

N-[(4-Chloro-1-guanidino-7-isoquinolinyl)sulphonyl]-N-(3-chlorobenzyl)glycine t-butyl ester hydrochloride (60 mg, 0.104 mmol) was dissolved in $CF_3CO_2H$ (0.5 mL) and the mixture stirred at room temperature for 1 h. The mixture was diluted with PhMe and the solvents were evaporated in vacuo. The residue was dissolved in Et$_2$O and stirred at room temperature for 1 h. The resulting precipitate was collected by filtration, washed with Et$_2$O and dried to give N-[(4-chloro-1-guanidino-7-isoquinolinyl)sulphonyl]-N-(3-chlorobenzyl)glycine trifluoroacetate (31 mg, 0.052 mmol) as a white solid.

mp 306–308° C.

$^1$H (CF$_3$CO$_2$D, 400 MHz) δ 4.3 (2H, s), 4.55 (2H, s), 7.0–7.1 (2H, m), 7.1–7.15 (2H, m), 8.25 (1H, d), 8.4 (1H, s), 8.5 (1H, d), 8.8 (1H, s) ppm.

LRMS 482,484 (MH$^+$), 496, 498 (MH$^+$of corresponding methyl ester).

Anal. Found: C, 42.60; H, 3.04; N, 12.03. Calc for C$_{19}$H$_{17}$Cl$_2$N$_5$O$_4$S.1.0CF$_3$CO$_2$H: C, 42.29; H, 3.04; N, 11.74.

Example 15
(a) N-[(4-chloro-1-guanidino-7-isoquinolinyl)sulphonyl]-N-(4-methoxybenzyl)glycine t-butyl ester hydrochloride
(b) N-[(4-Chloro-1-guanidino-7-isoquinolinyl)sulphonyl]-N-(4-methoxybenzyl)glycine

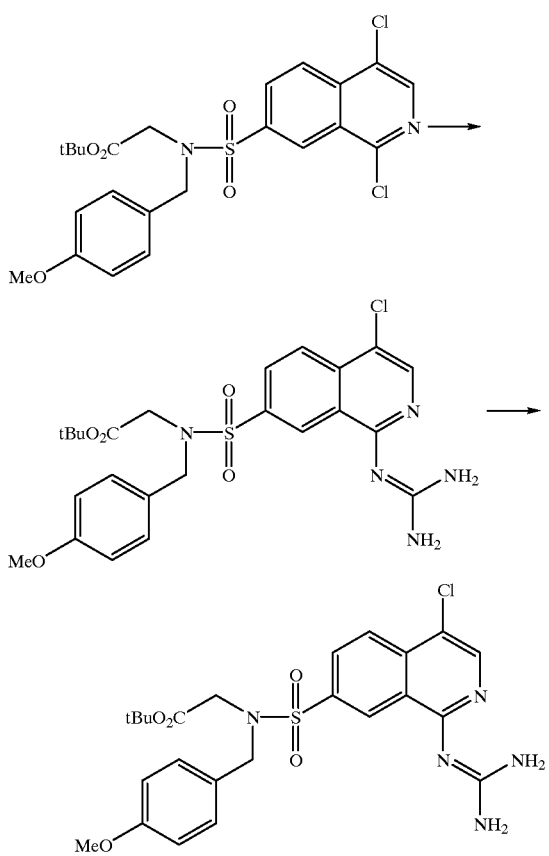

Guanidine hydrochloride (118 mg, 1.24 mmol) was added in one portion to a stirred suspension of NaH (23 mg, 80% dispersion by wt in mineral oil, 0.78 mmol) in DME (10 mL) and the mixture was heated at 60° C. under N$_2$ for 30 min. N-[(1,4-Dichloro-7-isoquinolinyl)sulphonyl]-N-(4-methoxybenzyl)glycine t-butyl ester (155 mg, 0.31 mmol) was added and the mixture heated at 90° C. for 1 h. The cooled mixture was poured into water and extracted with EtOAc (×3). The combined organic extracts were then washed with water, brine, dried (Na$_2$SO$_4$) and evaporated in vacuo. The residue was purified by column chromatography upon silica gel using hexane-EtOAc (80:20), and then CH$_2$Cl$_2$-MeOH-0.880NH$_3$ (95:5:0.5 to 90:10:1) as eluant to give a yellow gum. Trituration with i-Pr$_2$O gave N-[(4-chloro-1-guanidino-7-isoquinolinyl)sulphonyl]-N-(4-methoxybenzyl)glycine t-butyl ester (80 mg, 0.15 mmol) as a sticky yellow solid. A small sample (10–15 mg) was dissolved in EtOAc, a solution of HCl in Et$_2$O was added and the solvents were evaporated in vacuo, to give N-[(4-chloro-1-guanidino-7-isoquinolinyl)sulphonyl]-N-(4-methoxybenzyl)glycine t-butyl ester hydrochloride (18 mg) as a solid. (All characterisation data is for the HCl salt).

mp>192° C. (dec).

$^1$H (DMSO-d$_6$, 400 MHz) δ 1.2 (9H, s), 3.7 (3H, s), 4.0 (2H, s), 4.4 (2H, s), 6.8 (2H, d), 7.1 (2H, d), 8.3 (1H, d), 8.3 (1H, d), 8.4–8.9 (4H, br s), 8.5 (s, 1H), 8.2 (1H, s) ppm.

LRMS 534, 536 (MH$^+$).

Anal. Found: C, 51.36; H, 5.53; N, 11.23. Calc for C$_{24}$H$_{28}$ClN$_5$O$_5$S.1.0HCl.0.28i-Pr$_2$O: C, 51.48; H, 5.54; N, 11.69.

N-[(4-chloro-1-guanidino-7-isoquinolinyl)sulphonyl]-N-(4-methoxybenzyl)glycine t-butyl ester (65 mg, 0.122 mmol) was dissolved in CF$_3$CO$_2$H (1.0 mL) and the mixture stirred at room temperature for 40 min. The mixture was diluted with PhMe, concentrated in vacuo, and the residue purified by column chromatography upon silica gel using CH$_2$Cl$_2$-MeOH-0.880NH$_3$ (83:15:3) as eluant to give N-[(4-chloro-1-guanidino-7-isoquinolinyl)sulphonyl]-N-(4-methoxybenzyl)glycine (11 mg, 0.023 mmol) as a white solid.

mp>293° C. (dec).

$^1$H (DMSO-d$_6$, 400 MHz) δ 3.7 (3H, s), 3.8 (2H, s), 4.4 (2H, s), 6.85 (2H, d), 7.15 (2H, d), 7.2–7.5 (4H, br s), 8.0 (1H, d), 8.1 (1H, d), 8.15 (s, 1H), 9.1 (1H, s) ppm.

Anal. Found: C, 48.44; H, 4.47; N, 14.12. Calc for C$_{20}$H$_{20}$ClN$_5$O$_5$S.1.0H$_2$O: C, 48.34; H, 4.27; N, 14.28.

Example 16
(a) N-[(4-chloro-1-guanidino-7-isoquinolinyl)sulphonyl]-N-(2-pyridylmethyl)glycine t-butyl ester
(b) N-[(4-Chloro-1-guanidino-7-isoquinolinyl)sulphonyl]-N-(2-pyridylmethyl)glycine dihydrochloride

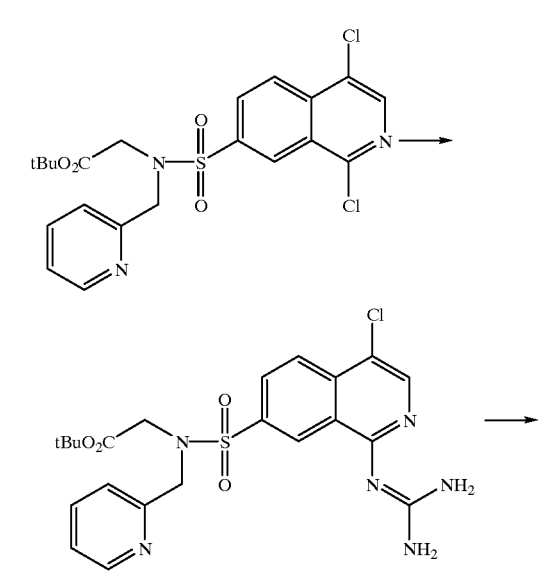

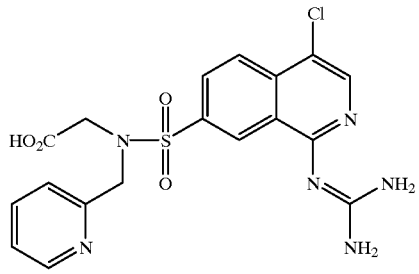

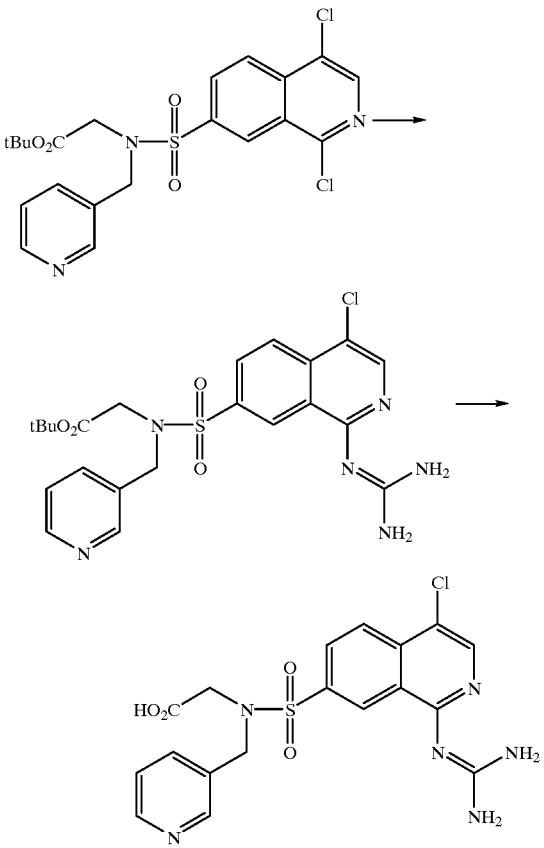

Guanidine hydrochloride (293 mg, 3.07 mmol was added in one portion to a stirred suspension of NaH (57 mg, 80% dispersion by wt in mineral oil, 1.92 mmol) in DME (10 mL) and the mixture was heated at 60° C. under $N_2$ for 30 min. A solution of N-[(1,4-dichloro-7-isoquinolinyl)sulphonyl]-N-(2-pyridylmethyl)glycine t-butyl ester (370 mg, 0.78 mmol) in DME (10 mL) was added and the mixture heated at 90° C. for 1 h. The solvents were evaporated in vacuo, the residue was dissolved with EtOAc (200 mL), and washed with aqueous $NH_4Cl$ (150 mL), dried ($MgSO_4$) and evaporated in vacuo. The residue was purified by column chromatography upon silica gel using pentane-EtOAc (100:0 to 20:80) as eluant to give N-[(4-chloro-1-guanidino-7-isoquinolinyl)sulphonyl]-N-(2-pyridylmethyl)glycine t-butyl ester (120 mg, 0.24 mmol) as a pale yellow foam.

$^1$H (CDCl$_3$, 400 MHz) δ 1.3 (9H, s), 4.1 (2H, s), 4.65 (2H, s), 7.2 (1H, m), 7.5 (1H, d), 7.65 (1H, dd), 8.05 (1H, d), 8.1 (1H, d), 8.1 (1H, s), 8.45 (1H, d), 9.25 (1H, s) ppm.

LRMS 505 (MH$^+$).

Anal. Found: C, 51.93; H, 5.03; N, 15.45. Calc for $C_{22}H_{25}ClN_6O_4S.0.1H_2O.0.2EtOAc$: C, 52.24; H, 5.18; N, 15.89.

A solution of HCl (3 mL, 2 M, 6 mmol) was added to a solution of N-[(4-chloro-1-guanidino-7-isoquinolinyl)sulphonyl]-N-(2-pyridylmethyl)glycine t-butyl ester (115 mg, 0.23 mmol) in dioxane (5.0 mL) and the mixture was heated at 60° C. for 18 h. The solvents were evaporated in vacuo and the residue triturated with hot EtOAc to give N-[(4-chloro-1-guanidino-7-isoquinolinyl)sulphonyl]-N-(2-pyridylmethyl)glycine dihydrochloride (95 mg, 0.167 mmol) as an off-white solid.

mp 216–220° C.

$^1$H (CD$_3$OD, 400 MHz) δ 4.4 (2H, s), 5.1 (2H, s), 8.05 (1H, m), 8.3 (1H, d), 8.4 (1H, d), 8.5 (1H, s), 8.5 (1H, d), 8.6 (1H, dd), 8.85 (1H, d), 9.3 (1H, s) ppm.

Anal. Found: C, 39.01; H, 4.01; N, 14.14. Calc for $C_{18}H_{17}ClN_6O_4S.2.0HCl.2.0H_2O.0.12dioxane$: C, 39.05; H, 4.25; N, 14.78.

Example 17

(a) N-1(4-chloro-1-guanidino-7-isoquinolinyl)sulphonyl]-N-(3-pyridylmethyl)glycine t-butyl ester (b) N-[(4-Chloro-1-guanidino-7-isoquinolinyl)sulphonyl]-N-(3-pyridylmethyl)glycine dihydrochloride Guanidine hydrochloride (317 mg, 3.32 mmol was added in one portion to a stirred suspension of NaH (62.3 mg, 80% dispersion by wt in mineral oil, 2.08 mmol) in DME (10 mL) and the mixture was heated at 60° C. under $N_2$ for 30 min. A solution of N-[(1,4-dichloro-7-isoquinolinyl)sulphonyl]-N-(3-pyridylmethyl)glycine t-butyl ester (400 mg, 0.83 mmol) in DME (10 mL) was added and the mixture heated at 80° C. for 4 h. The solvents were evaporated in vacuo, the residue was dissolved with EtOAc (200 mL), and washed with aqueous $NH_4Cl$ (200 mL), dried ($MgSO_4$) and evaporated in vacuo. The residue was purified by column chromatography upon silica gel using (i) pentane-EtOAc (70:30 to 50:50) and then (ii) $CH_2Cl_2$-MeOH-0.880NH$_3$ (95:5:0.5 to 90:10:1) as eluant to give N-[(4-chloro-1-guanidino-7-isoquinolinyl)sulphonyl]-N-(3-pyridylmethyl)glycine t-butyl ester (104 mg, 0.21 mmol) as a pale yellow solid.

$^1$H (CDCl$_3$, 400 MHz) δ 1.3 (9H, s), 3.8 (2H, s), 4.5 (2H, s), 6.4–6.8 (4H, br), 7.2 (1H, m), 7.6 (1H, d), 8.0 (1H, d), 8.05 (1H, s), 8.05 (1H, d), 8.4 (1H, s), 8.5 (1H, d), 9.3 (1H, s) ppm.

LRMS 505, 507 (MH$^+$).

Anal. Found: C, 51.95; H, 5.02; N, 16.25. Calc for $C_{22}H_2$,ClN$_6$O$_4$S: C, 52.33; H, 4.99; N, 16.64.

CF$_3$CO$_2$H (1.0 mL) was added to a stirred solution of N-[(4-chloro-1-guanidino-7-isoquinolinyl)sulphonyl]-N-(3-pyridylmethyl)glycine t-butyl ester (100 mg, 0.20 mmol) in CH$_2$Cl$_2$ (1.0 mL) and the mixture was stirred at 23° C. for 3.5 h. The solvents were evaporated in vacuo, azeotroping with PhMe and CH$_2$Cl$_2$. The oily residue was dissolved in EtOAc and a solution of EtOAc saturated with HCl (3.0 mL) was added which gave a precipitate. The white solid was collected by filtration and dried to give N-[(4-chloro-1-guanidino-7-isoquinolinyl)sulphonyl]-N-(3-pyridylmethyl) glycine dihydrochloride (48 mg, 0.086 mmol).

¹H (CD₃OD, 400 MHz) δ 4.25 (2H, s), 4.9 (2H, s), 8.05 (1H, dd), 8.4 (1H, d), 8.45 (1H, s), 8.5 (1H, d), 8.7 (1H, d), 8.8 (1H, d), 9.0 (1H, s), 9.2 (1H, s) ppm.

Anal. Found: C, 39.32; H, 4.07; N, 15.07. Calc for C₁₈H₁₇ClN₆O₄S.2.0HCl.1.5H₂O.0.05EtOAc.0.05 CH₂Cl₂: C, 39.19; H, 3.72; N, 14.64.

Example 18
(a) N-[(4-chloro-1-guanidino-7-isoquinolinyl)sulphonyl]-N-(4-pyridylmethyl)glycine t-butyl ester
(b) N-[(4-Chloro-)-guanidino-7-isoquinolinyl)sulphonyl]-N-(4-pyridylmethyl)glycine dihydrochloride

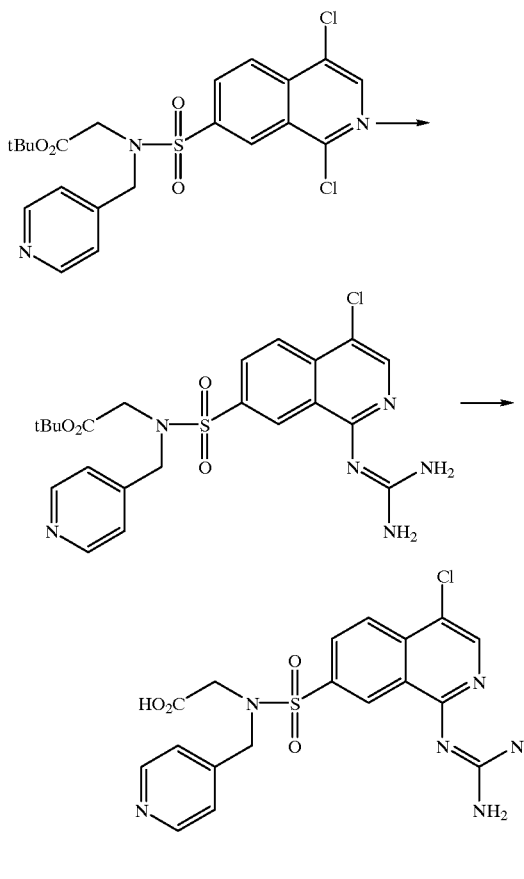

Guanidine hydrochloride (300 mg, 3.14 mmol was added in one portion to a stirred suspension of NaH (59 mg, 80% dispersion by wt in mineral oil, 1.97 mmol) in DME (10 mL) and the mixture was heated at 60° C. under N₂ for 30 min. A solution of N-[(1,4-dichloro-7-isoquinolinyl)sulphonyl]-N-(4-pyridylmethyl)glycine t-butyl ester (379 mg, 0.79 mmol) in DME (10 mL) was added and the mixture heated at 80° C. for 4 h. The solvents were evaporated in vacuo, the residue was dissolved with EtOAc (200 mL), and washed with aqueous NH₄Cl (150 mL), dried (MgSO₄) and evaporated in vacuo. The residue was purified by repeated column chromatography upon silica gel using (i) pentane-EtOAc (70:30 to 50:50) and then with (ii) CH₂Cl₂-MeOH-0.880NH₃ (95:5:0.5 to 90:10:1) as eluant to give N-[(4-chloro-1-guanidino-7-isoquinolinyl)sulphonyl]-N-(4-pyridylmethyl)glycine t-butyl ester (96 mg, 0.19 mmol).

¹H (CDCl₃, 400 MHz) δ 1.3 (9H, s), 3.9 (2H, s), 4.55 (2H, s), 7.25 (2H, d), 8.05 (1H, d), 8.1 (1H, d), 8.15 (1H, s), 8.6 (2H, d), 9.3 (1H, s) ppm.

LRMS 505, 507 (MH⁺).

Anal. Found: C, 52.63; H, 5.09; N, 16.18. Calc for C₂₂H₂₅ClN₆O₄S: C, 52.33; H, 4.99; N, 16.64.

CF₃CO₂H (1.0 mL) was added to a stirred solution of N-[(4-chloro-1-guanidino-7-isoquinolinyl)sulphonyl]-N-(4-pyridylmethyl)glycine t-butyl ester (88 mg, 0.17 mmol) in CH₂Cl₂ (1.0 mL) and the mixture was stirred at 23° C. for 3.5 h. The solvents were evaporated in vacuo, azeotroping with CH₂Cl₂. The oily residue was dissolved in CH₂Cl₂-MeOH (1.0 mL, 9:1) and a solution of EtOAc saturated with HCl (3.0 mL) was added which gave a precipitate. The white solid was collected by filtration and dried to give N-[(4-chloro-1-guanidino-7-isoquinolinyl)sulphonyl]-N-(4-pyridylmethyl)glycine dihydrochloride (18 mg, 0.033 mmol).

¹H (CD₃OD, 400 MHz) δ 4.3 (2H, s), 5.0 (2H, s), 8.2 (2H, d), 8.4 (1H, d), 8.5 (1H, s), 8.55 (1H, d), 8.8 (2H, d), 9.1 (1H, s) ppm.

Anal. Found: C, 39.57; H, 4.12; N, 14.85. Calc for C₁₈H₁₇ClN₆O₄S.2.0HCl.1.5H₂O: C, 39.39; H, 4.04; N, 15.39.

Example 19
(a) N-[(4-chloro-1-guanidino-7-isoquinolinyl)sulphonyl]-N-[(1R)-1-phenylethyl]glycine t-butyl ester
(b) N-[(4-Chloro-1-guanidino-7-isoquinolinyl)sulphonyl]-N-[(1R)-1-phenylethyl]glycine hydrochloride

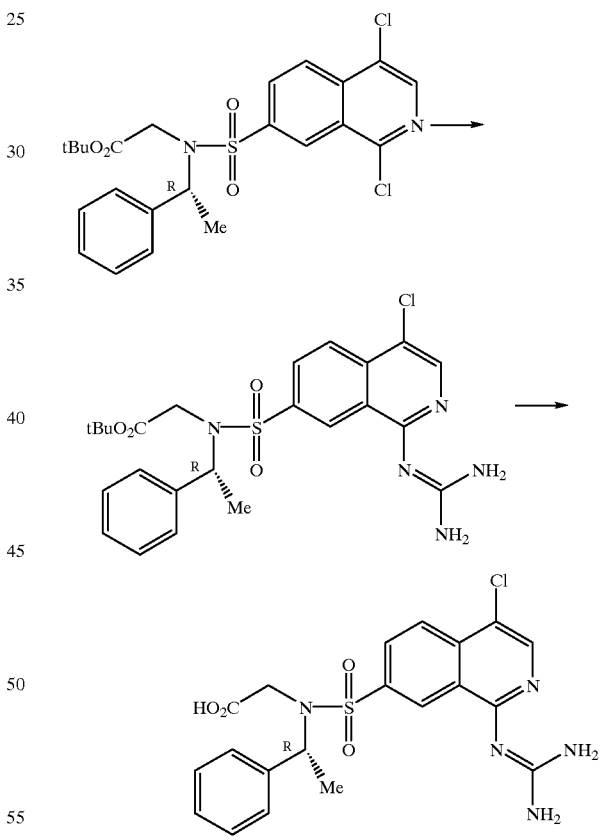

NaH (30 mg, 80% dispersion by wt in mineral oil, 1.01 mmol) was added in one portion to a stirred suspension of guanidine hydrochloride (154 mg, 1.61 mmol) in DME (6.0 mL) and the mixture was heated at 60° C. under N₂ for 30 min. A solution of N-[(1,4-dichloro-7-isoquinolinyl)sulphonyl]-N-[(1R)-1-phenylethyl]glycine t-butyl ester (200 mg, 0.40 mmol) in DME (3.0 mL) was added and the mixture heated at 95° C. for 5 h. The solvents were evaporated in vacuo and the residue was purified by column chromatography upon silica gel using pentane-EtOAc (50:50 to 33:66) as eluant to give N-[(4-chloro-1-guanidino-7-isoquinolinyl)sulphonyl]-N-[(1R)-1-phenylethyl]glycine t-butyl ester (125 mg, 0.23 mmol) as pale yellow foam after repeated evaporation from CH₂Cl₂.

mp 106–111° C.

¹H (DMSO-d₆, 300 MHz) δ 1.2 (9H, s), 1.3 (3H, d), 3.7 (1H, d), 3.95 (1H, d), 5.05 (1H, q), 7.1–7.4 (4H, br), 7.2–7.3 (5H, m), 8.0 (1H, d), 8.1 (1H, s), 8.2 (1H, d), 9.15 (1H, s) ppm.

LRMS 518, 520 (MH⁺), 1035 (M₂H⁺).

Anal. Found: C, 55.15; H, 5.55; N, 12.84. Calc for C₂₄H₂₈ClN₅O₄S.0.2EtOAc.0.1CH₂Cl₂: C, 54.96; H, 5.52; N, 12.87.

N-[(4-Chloro-1-guanidino-7-isoquinolinyl)sulphonyl]-N-[(1R)-1-phenylethyl]glycine t-butyl ester (100 mg, 0.19 mmol) was dissolved in a solution of EtOAc saturated with HCl (7.0 mL) and the mixture stirred at room temperature for 4 h. The mixture was concentrated in vacuo and the residue triturated with EtOAc to give N-[(4-Chloro-1-guanidino-7-isoquinolinyl)sulphonyl]-N-[(1R)-1-phenylethyl]glycine hydrochloride (75 mg, 0.14 mmol) as a white powder.

mp 185–190° C.

¹H (DMSO-d₆, 300 MHz) δ 1.35 (3H, d), 3.85 (1H, d), 4.15 (1H, d), 5.3 (1H, q), 7.15 (5H, br s), 8.3 (1H, d), 8.4–8.8 (4H, br), 8.4 (1H, d), 8.5 (1H, s), 9.1 (1H, s), 11.3 (1H, br), 12.5 (1H, br) ppm.

Anal. Found: C, 47.42; H, 4.40; N, 13.54. Calc for C₂₀H₂₀ClN₅O₄S.1.0HCl.0.5H₂O.0.2EtOAc: C, 47.59; H, 4.53; N, 13.34.

Example 20

(a) N-[(4-chloro-1-guanidino-7-isoquinolinyl)sulphonyl]-N-[(1S)-1-phenylethyl]glycine t-butyl ester (b) N-[(4-Chloro-1-guanidino-7-isoquinolinyl)sulphonyl]-N-[(1S)-1-phenylethyl]glycine hydrochloride

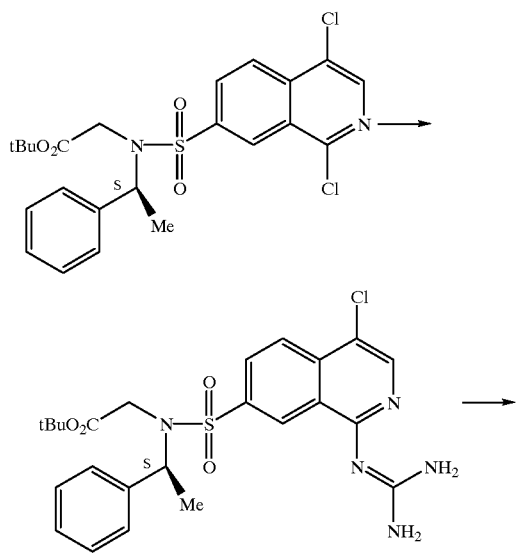

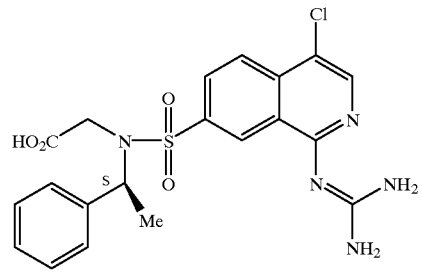

NaH (30 mg, 80% dispersion by wt in mineral oil, 1.01 mmol) was added in one portion to a stirred suspension of guanidine hydrochloride (154 mg, 1.61 mmol) in DME (6.0 mL) and the mixture was heated at 60° C. under N₂ for 30 min. A solution of N-[(1,4-dichloro-7-isoquinolinyl)sulphonyl]-N-[(1S)-1-phenylethyl]glycine t-butyl ester (200 mg, 0.40 mmol) in DME (3.0 mL) was added and the mixture heated at 95° C. for 5 h. The solvents were evaporated in vacuo and the residue was purified by column chromatography upon silica gel using pentane-EtOAc (50:50 to 33:66) as eluant to give N-[(4-chloro-1-guanidino-7-isoquinolinyl)sulphonyl]-N-[(1S)-1-phenylethyl]glycine t-butyl ester (128 mg, 0.23 mmol) as pale yellow foam after repeated evaporation from CH₂Cl₂.

mp 109–115° C.

¹H (DMSO-d₆, 300 MHz) δ 1.2 (9H, s), 1.3 (3H, d), 3.7 (1H, d), 3.95 (1H, d), 5.05 (1H, q), 7.1–7.45 (4H, br), 7.2–7.3 (5H, m), 8.0 (1H, d), 8.1 (1H, s), 8.2 (1H, d), 9.15 (1H, s) ppm.

LRMS 518, 520 (MH⁺), 1035 (M₂H⁺).

Anal. Found: C, 55.26; H, 5.56; N, 12.86. Calc for C₂₄H₂₈ClN₅O₄S.0.1EtOAc.0.05CH₂Cl₂: C, 55.28; H, 5.54; N, 12.97.

N-[(4-Chloro-1-guanidino-7-isoquinolinyl)sulphonyl]-N-[(1S)-1-phenylethyl]glycine t-butyl ester (100 mg, 0.19 mmol) was dissolved in a solution of EtOAc saturated with HCl (4.0 mL) and the mixture stirred at room temperature for 4 h. The mixture was concentrated in vacuo and the residue triturated with EtOAc to give N-[(4-Chloro-1-guanidino-7-isoquinolinyl)sulphonyl]-N-[(1S)-1-phenylethyl]glycine hydrochloride (72 mg, 0.14 mmol) as a white powder.

mp 196–200° C.

¹H (DMSO-d₆, 300 MHz) δ 1.35 (3H, d), 3.85 (1H, d), 4.15 (1H, d), 5.3 (1H, q), 7.15 (5H, br s), 8.3 (1H, d), 8.4–8.8 (4H, br), 8.4 (1H, d), 8.5 (1H, s), 9.1 (1H, s), 11.3 (1H, br), 12.4 (1H, br) ppm.

Anal. Found: C, 47.42; H, 4.30; N, 13.51. Calc for C₂₀H₂₀ClN₅O₄S.1.0HCl.1.0H₂O.0.1EtOAc: C, 47.47; H, 4.45; N, 13.57.

Example 21

(a) N-benzyl-N-[(4-chloro-1-guanidino-7-isoquinolinyl)sulphonyl]-L-alanine t-butyl ester (b) N-Benzyl-N-[(4-chloro-1-guanidino-7-isoquinolinyl)sulphonyl]-L-alanine hydrochloride

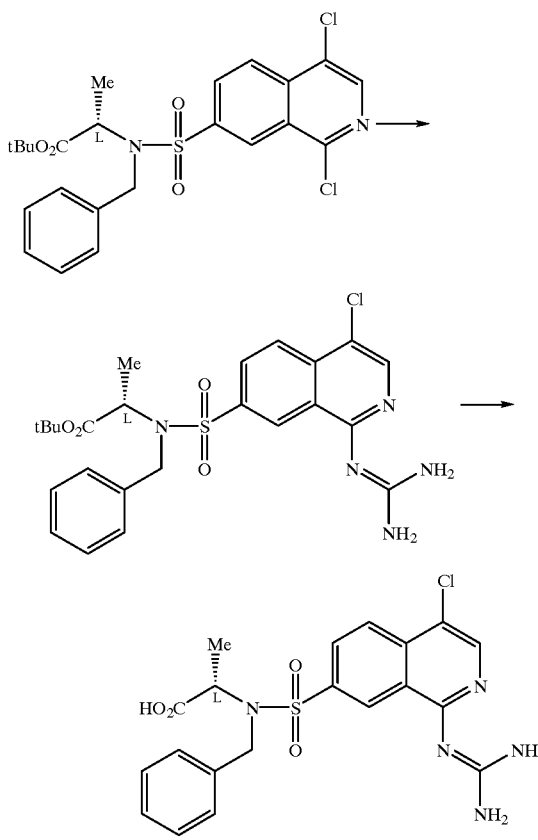

NaH (30 mg, 80% dispersion by wt in mineral oil, 1.01 mmol) was added in one portion to a stirred suspension of guanidine hydrochloride (154 mg, 1.61 mmol) in DME (5.0 mL) and the mixture was heated at 60° C. under $N_2$ for 45 min. A solution of N-benzyl-N-[(1,4-dichloro-7-isoquinolinyl)sulphonyl]-L-alanine t-butyl ester (200 mg, 0.40 mmol) in DME (2.0 mL) was added and the mixture heated at 95° C. for 4 h. The solvents were evaporated in vacuo and the residue was purified by column chromatography upon silica gel using pentane-EtOAc (50:50 to 20:80) as eluant to give N-benzyl-N-[(4-chloro-1-guanidino-7-isoquinolinyl)sulphonyl]-L-alanine t-butyl ester (120 mg, 0.225 mmol) as pale yellow foam after repeated evaporation from $CH_2Cl_2$.

$^1$H (DMSO-$d_6$, 300 MHz) δ 1.1 (9H, s), 1.15 (3H, d), 4.35 (1H, d), 4.5 (1H, q), 4.7 (1H, d), 7.1–7.45 (4H, br), 7.2–7.4 (5H, m), 8.0 (1H, d), 8.1 (1H, d), 8.15 (1H, s), 9.1 (1H, s) ppm.

LRMS 518,520 (MH$^+$).

Anal. Found: C, 55.33; H, 5.55; N, 12.82. Calc for $C_{24}H_{28}ClN_5O_4S.0.1EtOAc.0.05CH_2Cl_2$: C, 55.30; H, 5.48; N, 13.19.

N-Benzyl-N-[(4-chloro-1-guanidino-7-isoquinolinyl) sulphonyl]-L-alanine t-butyl ester (100 mg, 0.19 mmol) was dissolved in a solution of EtOAc saturated with HCl (5.0 mL) and the mixture stirred at room temperature for 18 h. The mixture was concentrated in vacuo, azeotroping with EtOAc, to give N-benzyl-N-[(4-chloro-1-guanidino-7-isoquinolinyl)sulphonyl]-L-alanine hydrochloride (77 mg, 0.15 mmol) as a white powder.

mp 256–262° C.

$^1$H (DMSO-$d_6$, 300 MHz) δ 1.2 (3H, d), 4.35 (1H, d), 4.7 (1H, q), 4.8 (1H, d), 7.1–7.4 (5H, m), 8.3 (2H, s), 8.4–8.7 (4H, br), 8.5 (1H, s), 9.05 (1H, s), 11.2 (1H, br), 12.7 (1H, br) ppm.

LRMS 461, 463 (MH$^+$).

Anal. Found: C, 48.02; H, 4.38; N, 13.33. Calc for $C_{20}H_{20}ClN_5O_4S.1.0HCl.0.25H_2O.0.1EtOAc$: C, 47.88; H, 4.39; N, 13.69.

Example 22

(a) N-(t-butoxycarbonylmethyl)-N-[(4-chloro-1-guanidino-7-isoquinolinyl)sulphonyl]glycine t-butyl ester
(b) N-(Carboxymethyl)-N-[(4-chloro-1-guanidino-7-isoquinolinyl)sulphonyl]glycine hydrochloride

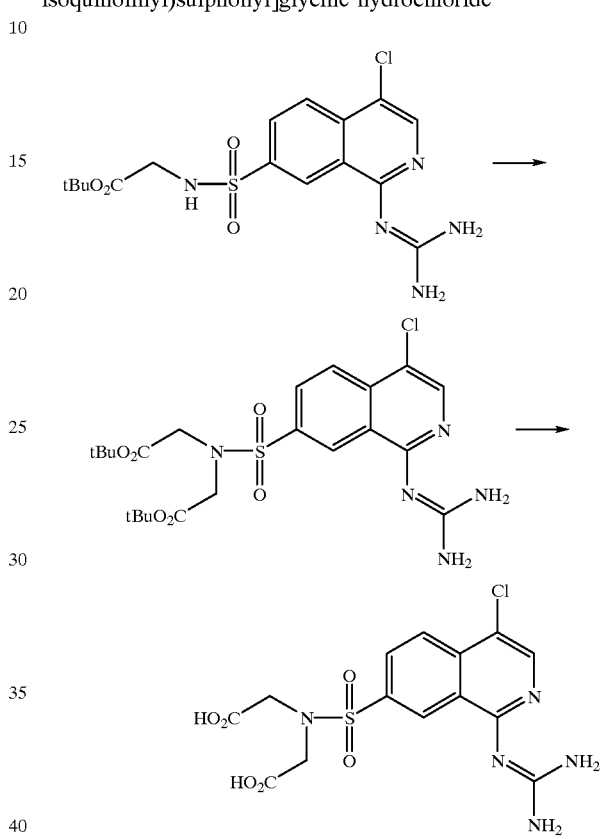

Anhydrous $K_2CO_3$ (88 mg, 0.64 mmol) and then t-butyl bromoacetate (56 μL, 0.38 mmol) were added to a stirred solution of N-[(4-chloro-1-guanidino-7-isoquinolinyl) sulphonyl]glycine t-butyl ester (132 mg, 0.33 mmol) in DMF (2.0 mL) and the mixture was stirred at 23° C. for 18 h. The mixture was diluted with EtOAc (300 mL), washed with brine (150 mL), water (200 mL), dried (MgSO$_4$) and evaporated in vacuo. The residue was purified by column chromatography upon silica gel using pentane-EtOAc (80:20 to 50:50) as eluant to give N-(t-butoxycarbonylmethyl)-N-[(4-chloro-1-guanidino-7-isoquinolinyl)sulphonyl]glycine t-butyl ester (101 mg, 0.19 mmol) as a pale yellow foam.

$^1$H (CDCl$_3$, 400 MHz) δ 1.4 (18H, s), 4.1 (4H, s), 8.0 (1H, d), 8.1 (1H, d), 8.15 (1H, s), 9.25 (1H, s) ppm.

LRMS 528 (MH$^+$).

Anal. Found: C, 49.57; H, 5.78; N, 12.73. Calc for $C_{22}H_{30}ClN_5O_6S.0.1H_2O.0.1EtOAc$: C, 49.95; H, 5.80; N, 13.00.

A solution of HCl (3 mL, 2 M, 6 mmol) was added to a solution of N-[(4-chloro-1-guanidino-7-isoquinolinyl) sulphonyl]-N-(t-butoxycarbonylmethyl)glycine t-butyl ester (90 mg, 0.17 mmol) in dioxane (4.0 mL). The mixture was stirred at 23° C. for 18 h and then heated at 70° C. The solvents were evaporated in vacuo and the residue dried to give N-(carboxymethyl)-N-[(4-chloro-1-guanidino-7-isoquinolinyl)sulphonyl]glycine hydrochloride (61 mg, 0.127 mmol) as a white solid.

mp 296–300° C. (dec).

$^1$H (DMSO-d$_6$, 400 MHz) δ 4.05 (4H, s), 7.9–8.3 (4H, br), 8.2 (1H, d), 8.25 (1H, d), 8.35 (1H, s), 9.0 (1H, s) ppm.

Anal. Found: C, 38.29; H, 3.58; N, 14.13. Calc for C$_{14}$H$_{14}$ClN$_5$O$_6$S.1.0HCl.0.1H$_2$O.0.3dioxane: C, 37.99; H, 3.69; N, 14.57.

Example 23
(a) N-[(4-chloro-1-guanidino-7-isoquinolinyl)sulphonyl]-L-alanine t-butyl ester
(b) N-[(4-Chloro-1-guanidino-7-isoquinolinyl)sulphonyl]-L-alanine trifluoroacetate

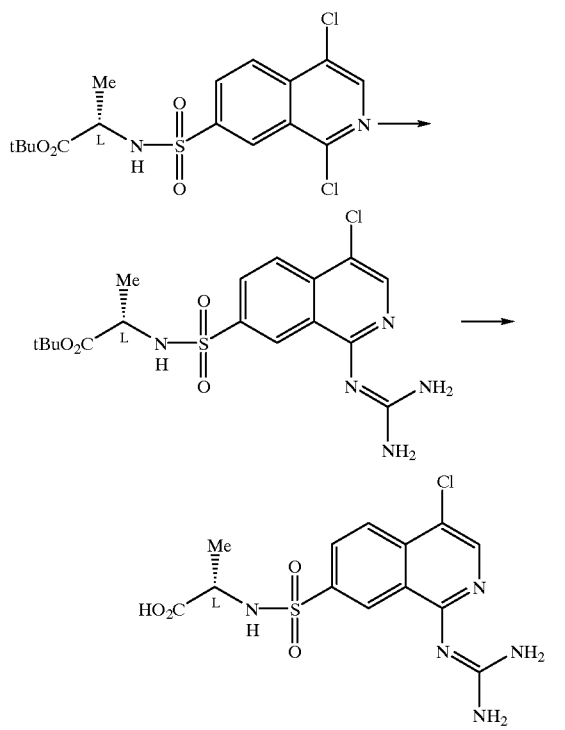

NaH (37 mg, 80% dispersion by wt in mineral oil, 1.23 mmol) was added in one portion to a stirred solution of guanidine hydrochloride (189 mg, 1.97 mmol) in DME (6 mL) and the mixture was heated at 60° C. under N$_2$ for 30 min. 1-{[(1,4-Dichloro-7-isoquinolinyl)sulphonyl]amino}-L-alanine t-butyl ester (200 mg, 0.49 mmol) was added and the mixture heated at 90° C. for 7 h. The cooled mixture was concentrated in vacuo, the residue suspended in water and extracted with EtOAc (3×30 mL). The combined organic extracts were dried (MgSO$_4$) and the solvents evaporated in vacuo. The residue was purified by column chromatography upon silica gel using CH$_2$Cl$_2$-MeOH-0.880NH$_3$ (95:5:0.5) as eluant to give N-[(4-chloro-1-guanidino-7-isoquinolinyl)sulphonyl]-L-alanine t-butyl ester (160 mg, 0.37 mmol) as a white powder.

$^1$H (DMSO-d$_6$, 300 MHz) δ 1.1 (9H, s), 1.15 (3H, d), 3.8 (1H, dq), 7.1–7.4 (4H, br), 8.0 (1H, d), 8.05 (1H, d), 8.1(1H, s), 8.3 (1H, d), 9.05 (1H, s) ppm.

CF$_3$CO$_2$H (1.0 mL) was added to a stirred solution of N-[(4-chloro-1-guanidino-7-isoquinolinyl)sulphonyl]-L-alanine t-butyl ester (ca. 150 mg, 0.35 mmol) in CH$_2$Cl$_2$ (3.0 mL) and the mixture stirred at room temperature for 2 h. The mixture was evaporated in vacuo, azeotroping with PhMe and CH$_2$Cl$_2$, and then triturated with Et$_2$O to give N-[(4-chloro-1-guanidino-7-isoquinolinyl)sulphonyl]-L-alanine trifluoroacetate (62 mg, 0.126 mmol) as a white powder.

mp>250° C.

$^1$H (CD$_3$OD +TFA-d, 300 MHz) δ 1.35 (3H, d), 4.05 (1H, q), 8.3 (1H, d), 8.4 (1H, s), 8.45 (1H, d), 8.9 (1H, s) ppm.

LRMS 389, 391 (MNH$_4^+$).

Anal. Found: C, 36.66; H, 3.11; N, 14.00. Calc for C$_{13}$H$_{14}$ClN$_5$O$_4$S.1.0CF$_3$CO$_2$H.0.3H$_2$O: C, 36.64; H, 3.21; N, 14.24.

Example 24
(a) N-[(4-chloro-1-guanidino-7-isoquinolinyl)sulphonyl]-D-alanine methyl ester
(b) N-[(4-chloro-1-guanidino-7-isoquinolinyl)sulphonyl]-D-alanine hydrochloride

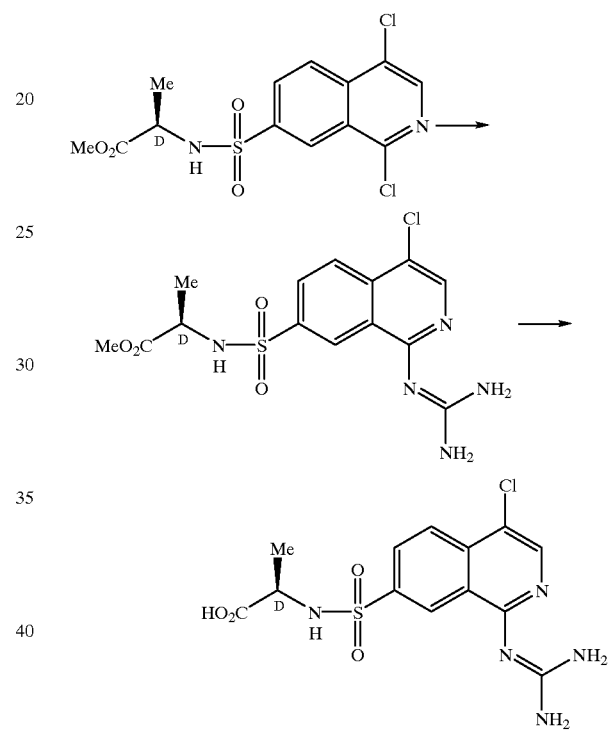

NaH (35 mg, 80% dispersion by wt in mineral oil, 1.17 mmol) was added in one portion to a stirred solution of guanidine hydrochloride (179 mg, 1.87 mmol) in DMSO (5 mL) and the mixture was heated at 60° C. under N$_2$ for 45 min. 1-{[(1,4-Dichloro-7-isoquinolinyl)sulphonyl]amino}-D-alanine methyl ester (170 mg, 0.47 mmol) was added and the mixture heated at 90° C. for 4 h. The cooled mixture was poured into water and extracted with EtOAc (3×30 mL). The combined organic extracts were dried (MgSO$_4$) and the solvents evaporated in vacuo. The residue was purified by column chromatography upon silica gel using pentane-EtOAc (66:33 to 0:100) as eluant to give N-[(4-chloro-1-guanidino-7-isoquinolinyl)sulphonyl]-D-alanine methyl ester (22 mg, 0.057 mmol) as a yellow foam/oil.

$^{11}$H (CD$_3$OD, 300 MHz) δ 1.3 (3H, d), 3.4 (3H, s), 4.1 (1H, q), 8.1 (1H, d), 8.1 (1H, d), 8.15 (1H, s), 9.1 (1H, s) ppm.

LRMS 386, 388 (MH$^+$).

A solution of NaOH (1 mL, 2 M, 2 mmol) was added to a solution of N-[(4-chloro-1-guanidino-7-isoquinolinyl)sulphonyl]-D-alanine methyl ester (17 mg, 0.044 mmol) in MeOH (3 mL) and the mixture was heated at 60° C. for 18 h. The cooled mixture was neutralised with dilute HCl (2 M), the MeOH was evaporated in vacuo, and the residue triturated with water (10 mL). The solid was collected by filtration, with water washing, and dried under high vacuum to give N-[(4-chloro-1-guanidino-7-isoquinolinyl) sulphonyl]-D-alanine hydrochloride (9 mg, 0.021 mmol) as an off-white powder.

$^1$H (DMSO-d$_6$, 300 MHz) δ 1.2 (3H, d), 3.8 (1H, dq), 7.2–7.6 (4H, br), 8.05 (1H, d), 8.1 (1H, d), 8.15 (1H, s), 8.2 (1H, m), 9.1 (1H, s) ppm.

Anal. Found: C, 37.56; H, 3.98; N, 15.74. Calc for C$_{13}$H$_{14}$ClN$_5$O$_4$S.1.0HCl.0.5H$_2$O: C, 37.42; H, 3.86; N, 16.78.

Example 25

(a) 1-{[(4-chloro-1-guanidino-7-isoquinolinyl)sulphonyl] amino}-L-valine t-butyl ester (b) N-[(4-Chloro-1-guanidino-7-isoquinolinyl)sulphonyl]-L-valine trifluoroacetate

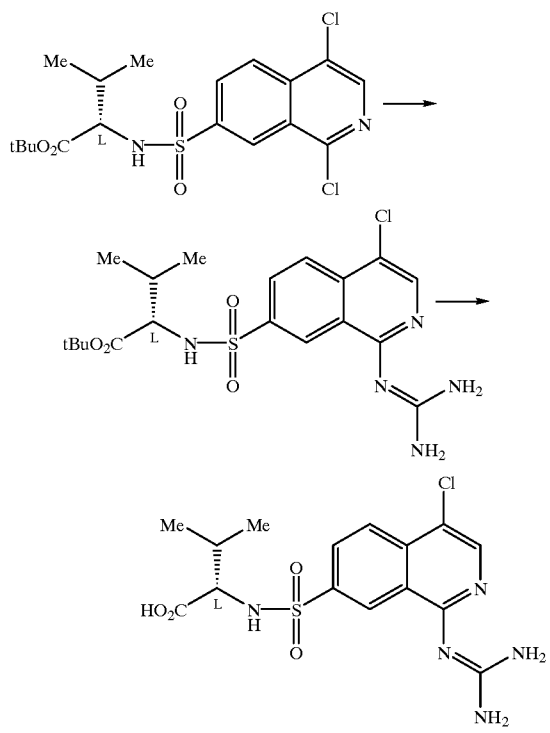

NaH (35 mg, 80% dispersion by wt in mineral oil, 1.17 mmol) was added in one portion to a stirred solution of guanidine hydrochloride (176 mg, 1.84 mmol) in DMA (4 mL) under N$_2$ and the mixture was heated at 60° C. for 30 min. 1-{[(1,4-Dichloro-7-isoquinolinyl)sulphonyl]amino}-L-valine t-butyl ester (161 mg, 0.43 mmol) was added in one portion and the mixture heated at 80° C. for 18 h. The cooled mixture was poured into water (50 mL), extracted with EtOAc (2×20 mL) and the combined organic extracts were washed with brine, dried (Na$_2$SO$_4$) and evaporated in vacuo. The residue was dissolved Et$_2$O and a solution of HCl in Et$_2$O (1 M) was added which gave a white precipitate. The Et$_2$O was decanted and the solid residue dissolved in MeCN and the solution cooled to ca. 0° C. which gave a precipate. This solid was collected by filtration and then dried to give 1-{[(4-chloro-1-guanidino-7-isoquinolinyl)sulphonyl] amino}-L-valine t-butyl ester hydrochloride (36 mg, 0.072 mmol) as a white solid. Evaporation of the combined organic mother liquors gave a gum which was purified by column chromatography upon silica gel using CH$_2$Cl$_2$-MeOH-0.880NH$_3$ (90:10:1) as eluant to give 1-{[(4-chloro-1-guanidino-7-isoquinolinyl)sulphonyl]amino}-L-valine t-butyl ester (104 mg, 0.228 mmol). (The sample was characterised as the hydrochloride salt.)

mp 192–194° C. (dec).

$^1$H (DMSO-d$_6$, 300 MHz) δ 0.8 (3H, d), 0.85 (3H, d), 1.05 (9H, s), 2.0 (1H, sept), 3.7 (1H, dd), 8.3 (1H, d), 8.4 (1H, d), 8.4 (1H, d), 8.45 (1H, s), 8.5–8.7 (4H, br), 9.05 (1H, s), 11.3 (1H, br), ppm.

LRMS 456, 458 (MH$^+$).

Anal. Found: C, 45.67; H, 5.54; N, 13.97. Calc for C$_{19}$H$_{26}$ClN$_5$O$_4$S.1.0HCl.0.5H$_2$O: C, 45.51; H, 5.63; N, 13.97.

1-{[(4-Chloro-1-guanidino-7-isoquinolinyl)sulphonyl] amino}-L-valine t-butyl ester (104 mg, 0.228 mmol) was dissolved in CF$_3$CO$_2$H (1.0 mL) and the mixture stirred at room temperature for 1 h. The mixture was diluted with PhMe (25 mL) and concentrated in vacuo. The residue was crystallised with Et$_2$O containing a small amount of EtOAc to give a white solid. This solid was then triturated with water and dried to give 1-{[(4-chloro-1-guanidino-7-isoquinolinyl)sulphonyl]amino}-L-valine trifluoroacetate (39 mg, 0.084 mmol).

mp>300° C.

$^1$H (TFA-d, 400 MHz) δ 0.95 (3H, d), 1.0 (3H, d), 2.25 (1H, sept), 4.0 (1H, d), 8.3 (1H, d), 8.4 (1H, s), 8.55 (1H, d), 9.0 (1H, s) ppm.

LRMS 400, 402 (MH$^+$).

Anal. Found: C, 41.29; H, 4.37; N, 14.99. Calc for C$_{15}$H$_{18}$ClN$_5$O$_4$S.0.5CF$_3$CO$_2$H.0.3H$_2$O: C, 41.57; H, 4.16; N, 15.15.

Example 26

(a) 1-{[(4-chloro-1-guanidino-7-isoquinolinyl)sulphonyl] amino}-D-valine t-butyl ester hydrochloride (b) N-[(4-Chloro-1-guanidino-7-isoquinolinyl)sulphonyl]-D-valine hydrochloride

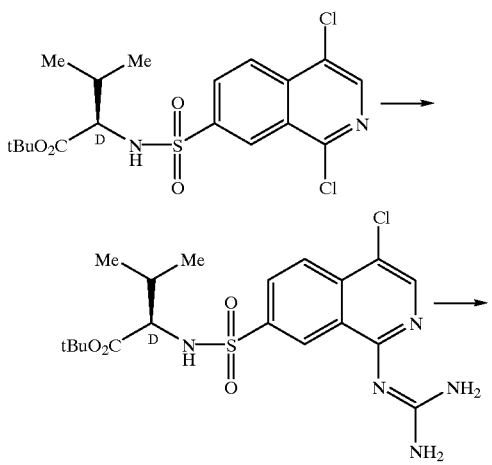

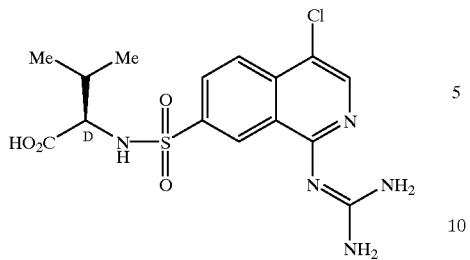

NaH (35 mg, 80% dispersion by wt in mineral oil, 1.17 mmol) was added in one portion to a stirred solution of guanidine hydrochloride (176 mg, 1.84 mmol) in DMSO (2.5 mL) under $N_2$ and the mixture was heated at 23° C. for 30 min. 1-{[(1,4-Dichloro-7-isoquinolinyl)sulphonyl]amino}-D-valine t-butyl ester (200 mg, 0.46 mmol) was added in one portion and the mixture heated at 90° C. for 3 h. The cooled mixture was poured into water, extracted with EtOAc and the combined organic extracts were washed with brine, dried ($MgSO_4$) and evaporated in vacuo. The residue was dissolved $Et_2O$ and a solution of HCl in $Et_2O$ (0.5 mL, 1 M) was added which gave a white precipitate. Purification by column chromatography upon silica gel using $CH_2Cl_2$-MeOH-$0.880NH_3$ (95:5:0.5) as eluant furnished the product which was again treated with a solution of HCl in $Et_2O$ (1 M) to give 1-{[(4-chloro-1-guanidino-7-isoquinolinyl)sulphonyl]amino}-D-valine t-butyl ester hydrochloride (76.6 mg, 0.151 mmol).

mp 124–125° C. (dec).

$^1$H (DMSO-$d_6$, 300 MHz) δ 0.8 (3H, d), 0.85 (3H, d), 1.05 (9H, s), 2.0 (1H, sept), 3.7 (1H, dd), 8.3 (1H, d), 8.4 (1H, d), 8.4 (1H, d), 8.45 (1H, s), 8.4–8.8 (4H, br), 9.05 (1H, s), 11.2 (1H, br) ppm.

LRMS 456, 458 (MH$^+$), 478, 480 MNa$^+$).

Anal. Found: C, 46.07; H, 5.67; N, 13.50. Calc for $C_{19}H_{26}ClN_5O_4S.1.0HCl.0.5MeOH$: C, 46.07; H, 5.75; N, 13.77.

1-{[(4-Chloro-1-guanidino-7-isoquinolinyl)sulphonyl]amino}-D-valine t-butyl ester hydrochloride (61 mg, 0.12 mmol) was dissolved in a solution of EtOAc saturated with HCl (10 mL) at 0° C., and the mixture stirred at room temperature for 4 h. The mixture was concentrated in vacuo, the residue extracted with hot EtOAc, and the organic solution was then concentrated in vacuo and dried to give 1-{[(4-chloro-1-guanidino-7-isoquinolinyl)sulphonyl]amino}-D-valine hydrochloride (24.3 mg, 0.050 mmol) as a pale yellow solid.

mp>190° C. (dec).

$^1$H (TFA-d, 400 MHz) δ 0.95 (3H, br s), 1.0 (3H, br s), 2.3 (1H, br s), 4.05 (1H, br s), 8.35 (1H, br s), 8.4 (1H, br s), 8.55 (1H, br s), 9.1 (1H, br s) ppm.

LRMS 400 (MH$^+$), 417 (MNH$_4^+$).

Anal. Found: C, 41.29; H, 4.76; N, 14.16. Calc for $C_{15}H_{18}ClN_5O_4S.1.0HCl.0.7H_2O.0.4EtOAc$: C, 41.18; H, 4.91; N, 14.46.

Example 27

(a) 1-{[(4-chloro-1-guanidino-7-isoquinolinyl)sulphonyl]amino}-D-tert-leucine t-butyl ester hydrochloride (b) N-[(4-Chloro-1-guanidino-7-isoquinolinyl)sulphonyl]-D-tert-leucine hydrochloride

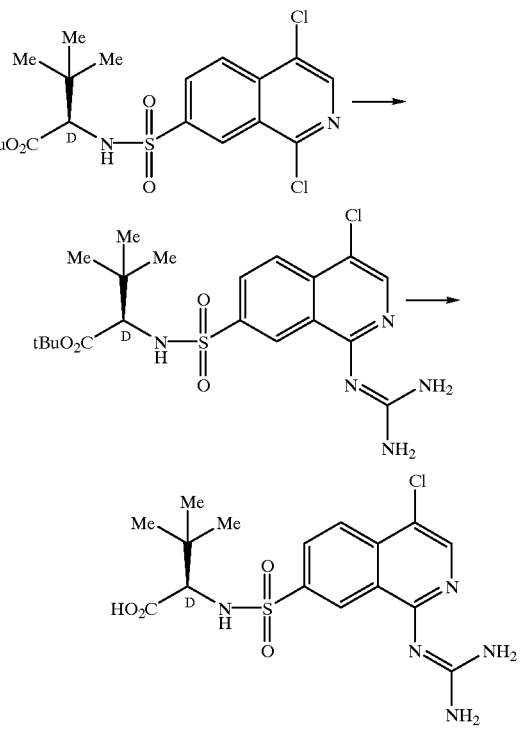

NaH (58 mg, 80% dispersion by wt in mineral oil, 1.27 mmol) was added in one portion to a stirred solution of guanidine hydrochloride (191 mg, 2.0 mmol) in DMSO (5.0 mL) under $N_2$ and the mixture was heated at 23° C. for 30 min. A solution of 1-{[(1,4-dichloro-7-isoquinolinyl)sulphonyl]amino}-D-tert-leucine t-butyl ester (225 mg, 0.50 mmol) in DMSO (3.0 mL) was added in one portion and the mixture heated at 90° C. for 9 h. A second portion of guanidine (0.67 mmol) [prepared from guanidine hydrochloride (100 mg) and NaH (20 mg)] in DMSO (1.0 mL) was added and the mixture heated at 90° C. for an additional 8 h. The cooled mixture was poured into water, extracted with EtOAc and the combined organic extracts were washed with water, brine, dried ($MgSO_4$) and evaporated in vacuo. The residue was dissolved $Et_2O$ and a solution of HCl in $Et_2O$ (1.5 mL, 1 M) was added which gave a white precipitate. The solvents were evaporated in vacuo and the residue triturated with $Et_2O$ to give 1-{[(4-chloro-1-guanidino-7-isoquinolinyl)sulphonyl]amino}-D-tert-leucine t-butyl ester hydrochloride (222 mg, 0.43 mmol).

mp 187–189° C.

$^1$H (DMSO-$d_6$, 400 MHz) δ 0.9 (9H, s), 0.95 (9H, s), 3.6 (1H, d), 8.3 (1H, d), 8.4 (1H, d), 8.4–8.8 (4H, br), 8.5 (1H, s), 9.0 (1H, s), 11.15 (1H, br) ppm.

LRMS 470, 472 (MH$^+$).

Anal. Found: C, 46.55; H, 5.78; N, 13.46. Calc for $C_{20}H_{28}ClN_5O_4S.1.0HCl.0.5H_2O$: C, 46.60; H, 5.87; N, 13.59.

1-{[(4-Chloro-1-guanidino-7-isoquinolinyl)sulphonyl]amino}-D-tert-leucine t-butyl ester hydrochloride (188 mg, 0.36 mmol) was dissolved in a solution of EtOAc saturated with HCl (30 mL) and the mixture stirred at room temperature for 5 h. The mixture was concentrated in vacuo and the residue heated with EtOAc to give a white solid. The hot organic solution was decanted and the solid dried in vacuo to give 1-{[(4-chloro-1-guanidino-7-isoquinolinyl)sulphonyl]amino}-D-tert-leucine hydrochloride (109.3 mg, 0.24 mmol) as a white solid.

mp 234–236° C. (dec).
$^1$H (TFA-d, 400 MHz) δ 1.1 (9H, s), 3.9 (1H, s), 8.35 (1H, d), 8.5 (1H, s), 8.6 (1H, d), 9.1 (1H, s) ppm.
LRMS 414,416 (MH$^+$).
Anal. Found: C, 41.70; H, 4.86; N, 15.01. Calc for $C_{16}H_{20}ClN_5O_4S.1.0HCl.0.5H_2O$: C, 41.84; H, 4.83; N, 15.25.

Example 28
(a) N-[(4-chloro-1-guanidino-7-isoquinolinyl)sulphonyl]-L-phenylalanine t-butyl ester
(b) N-[(4-Chloro-1-guanidino-7-isoquinolinyl)sulphonyl]-L-phenylalanine trifluoroacetate

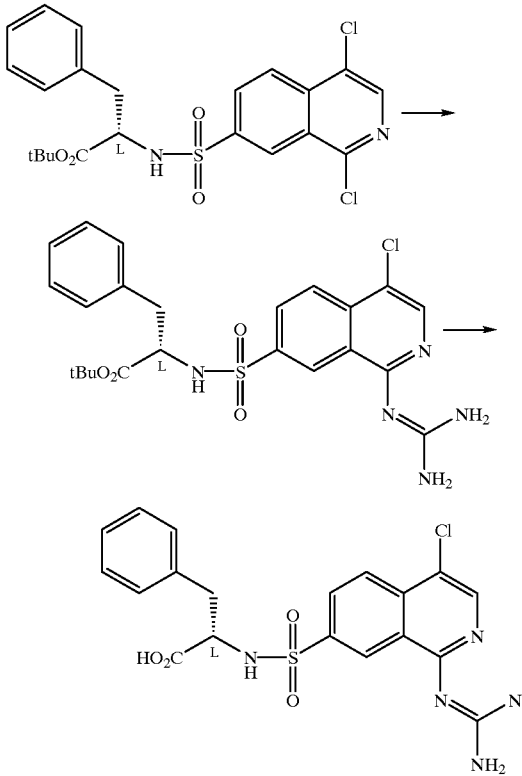

NaH (22 mg, 80% dispersion by wt in mineral oil, 0.73 mmol) was added in one portion to a stirred suspension of guanidine hydrochloride (76.7 mg, 0.80 mmol) in DMSO (5.0 mL) and the mixture was heated at 60° C. under $N_2$ for 20 min. N-[(1,4-Dichloro-7-isoquinolinyl)sulphonyl]-L-phenylalanine t-butyl ester (103 mg, 0.21 mmol) was added and the mixture heated at 95° C. for 17 h. The solvents were evaporated in vacuo and the residue was purified by column chromatography upon silica gel using $CH_2Cl_2$-MeOH-0.880NH$_3$ (95:5:0.5 to 80:20:2) as eluant to give N-[(4-chloro-1-guanidino-7-isoquinolinyl)sulphonyl]-L-phenylalanine t-butyl ester (34.7 mg, 0.069 mmol) as a yellow resin.
$^1$H (DMSO-d$_6$, 300 MHz) δ 1.0 (9H, s), 2.7 (1H, dd), 2.8 (1H, dd), 3.9 (1H, dd), 7.1–7.2 (5H, m), 7.1–7.3 (4H, br s), 7.9 (1H, d), 7.95 (1H, d), 8.1 (s, 1H), 8.5 (1H, br d), 8.95 (1H, s) ppm.
LRMS 504, 506 (MH$^+$).

N-[(4-Chloro-1-guanidino-7-isoquinolinyl)sulphonyl]-L-phenylalanine t-butyl ester (30 mg, 0.060 mmol) was dissolved in $CF_3CO_2H$ (2.5 mL) and the mixture stirred at room temperature for 2.5 h. The mixture was diluted with $CH_2Cl_2$ and PhMe, concentrated in vacuo, azeotroping with PhMe, and the residue triturated with $Et_2O$ to give N-[(4-chloro-1-guanidino-7-isoquinolinyl)sulphonyl]-L-phenylalanine trifluoroacetate (24.4 mg, 0.42 mmol) as a white solid.
mp 306° C. (dec).
$^1$H (DMSO-d$_6$, 300 MHz) δ 2.7 (1H, dd), 3.0 (1H, dd), 3.95 (1H, m), 6.9–7.1 (5H, m), 7.8–8.4 (4H, br), 7.9 (1H, d), 8.05 (1H, d), 8.3 (s, 1H), 8.6 (1H, br s), 8.8 (1H, s) ppm.
LRMS 448 (MH$^+$).
Anal. Found: C, 44.35; H, 3.78; N, 11.38. Calc for $C_{19}H_{18}ClN_5O_4S.1.0CF_3CO_2H.0.5H_2O.0.12Et_2O$: C, 44.50; H, 3.69; N, 12.08.

Example 29
(a) 1-{[(4-chloro-1-guanidino-7-isoquinolinyl)sulphonyl]amino}-O-methyl-D-serine t-butyl ester hydrochloride
(b) N-[(4-Chloro-1-guanidino-7-isoquinolinyl)sulphonyl]-O-methyl-D-serine hydrochloride

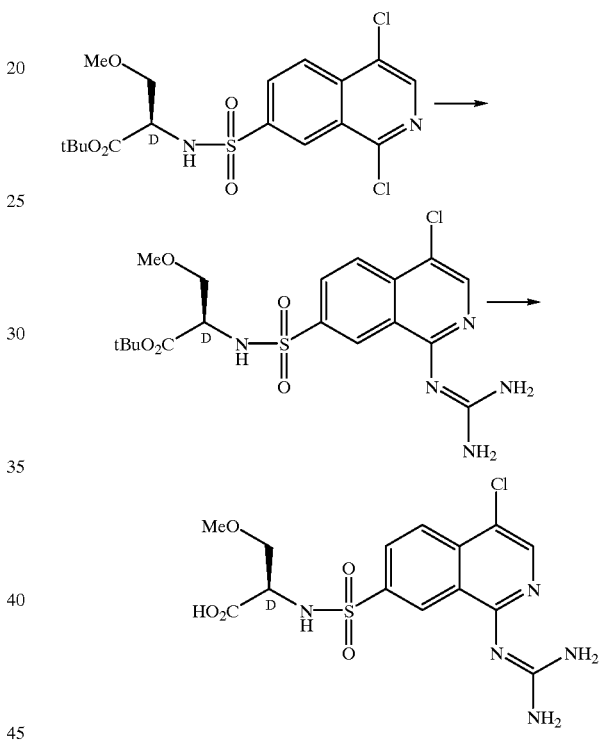

NaH (50 mg, 80% dispersion by wt in mineral oil, 1.66 mmol) was added in one portion to a stirred solution of guanidine hydrochloride (260 mg, 2.72 mmol) in DMSO (4 mL) under $N_2$ and the mixture was heated at 50° C. for 30 min. 1-{[(1,4-Dichloro-7-isoquinolinyl)sulphonyl]amino}-O-methyl-D-serine t-butyl ester (300 mg, 0.689 mmol) was added in one portion and the mixture heated at 90° C. for 8 h. The cooled mixture was poured into water (50 mL), the aqueous solution was extracted with EtOAc (×2) and the combined organic extracts were washed with water, brine, dried (MgSO$_4$). The solvents were evaporated in vacuo and the residue purified by column chromatography upon silica gel using $CH_2Cl_2$-MeOH-0.880NH$_3$ (90:10:1) as eluant to give the desired product. This material was treated with a solution of HCl in $Et_2O$ (1.0 mL, 1 M), the solvents evaporated in vacuo, and the residue triturated with $Et_2O$ (×2) to give 1-{[(4-chloro-1-guanidino-7-isoquinolinyl)sulphonyl]amino}-O-methyl-D-serine 1-butyl ester hydrochloride (18 mg, 0.036 mmol) as a white solid.
$^1$H (d4-MeOH, 300 MHz) δ 1.2 (9H,s), 3.2 (3H,s), 3.5–3.6 (1H,m), 3.6–3.7 (1H,m), 4.1–4.2 (1H,m), 8.35–8.5 (3H,m), 8.9 (1H,s) ppm.

LRMS 458 (MH).

1-{[(4-Chloro-1-guanidino-7-isoquinolinyl)sulphonyl] amino}-O-methyl-D-serine t-butyl ester hydrochloride (18 mg, 0.036 mmol) was dissolved in a solution of EtOAc saturated with HCl (5 mL) and the mixture stirred at room temperature for 3 h. The mixture was concentrated in vacuo and the residue triturated with EtOAc (×3) to give 1-{[(4-chloro-1-guanidino-7-isoquinolinyl)sulphonyl]amino}-L-tert-leucine hydrochloride (9 mg, 0.02 mmol) as an off-white solid.

$^1$H (d-TFA, 400 MHz) 3.6 (3H,s), 4.0–4.2 (2H,m), 4.65 (1H, br s), 8.4 (1H,d), 8.5 (1H,s), 8.65 (1H,d), 9.1 (1H,s) ppm.

LRMS 402 (MH).

Example 30

(a) N-[(4-chloro-1-guanidino-7-isoquinolinyl)sulphonyl]-D-aspartic acid di-t-butyl ester (b) N-[(4-Chloro-1-guanidino-7-isoquinolinyl)sulphonyl]-D-aspartic acid hydrochloride

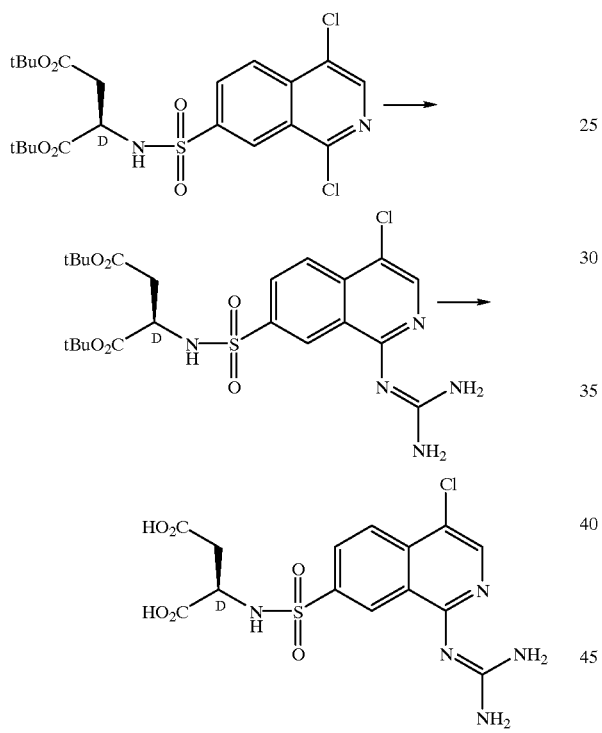

Guanidine hydrochloride (190 mg, 2.0 mmol) was added in one portion to a stirred suspension of NaH (47 mg, 80% dispersion by wt in mineral oil, 1.57 mmol) in DME (7 mL) and the mixture was heated at 60° C. under $N_2$ for 30 min. 1-{[(1,4-Dichloro-7-isoquinolinyl)sulphonyl]amino}-D-aspartic acid di-t-butyl ester (250 mg, 0.50 mmol) was added and the mixture heated at reflux for 18 h. The cooled mixture was diluted with EtOAc, washed with water, brine, dried (MgSO$_4$) and the solvents evaporated in vacuo. The residue was purified by column chromatography upon silica gel using CH$_2$Cl$_2$-MeOH-0.880NH$_3$ (97:3:0.3) as eluant to give N-[(4-chloro-1-guanidino-7-isoquinolinyl)sulphonyl]-D-aspartic acid di-t-butyl ester (50 mg, 0.095 mmol) as a yellow solid.

$^1$H (CDCl$_3$, 400 MHz) δ 1.2 (9H, s), 1.4 (9H, s), 2.7 (1H, dd), 2.8 (1H, dd), 4.1 (1H, br t), 8.05 (1H, d), 8.1 (1H, d), 8.15 (1H, s), 9.3 (1H, s) ppm.

LRMS 528, 530 (MH$^+$).

N-[(4-chloro-1-guanidino-7-isoquinolinyl)sulphonyl]-D-aspartic acid di-t-butyl ester (50 mg, 0.095 mmol) was dissolved in a solution of EtOAc saturated with HCl (10 mL) and the mixture stirred at room temperature for 4 h. The mixture was concentrated in vacuo and the residue triturated with PhMe and then Et$_2$O to give N-[(4-chloro-1-guanidino-7-isoquinolinyl)sulphonyl]-D-aspartic acid hydrochloride (29 mg, 0.062 mmol) as an off-white solid.

$^1$H (CD$_3$OD, 400 MHz) δ 2.7 (1H, dd), 2.8 (1H, dd), 4.4 (1H, br t), 8.35 (1H, d), 8.45 (1H, s), 8.45 (1H, d), 8.9 (1H, s) ppm.

LRMS 415 (M$^+$)

Anal. Found: C, 36.05; H, 3.72; N, 13.62. Calc for C$_{14}$H$_{14}$ClN$_5$O$_6$S.1.0HCl.0.8H$_2$O: C, 36.03; H, 3.59; N, 15.01.

Example 31

(a) N-[(4-chloro-1-guanidino-7-isoquinolinyl)sulphonyl]-L-proline t-butyl ester (b) N-[(4-Chloro-1-guanidino-7-isoquinolinyl)sulphonyl]-L-proline hydrochloride

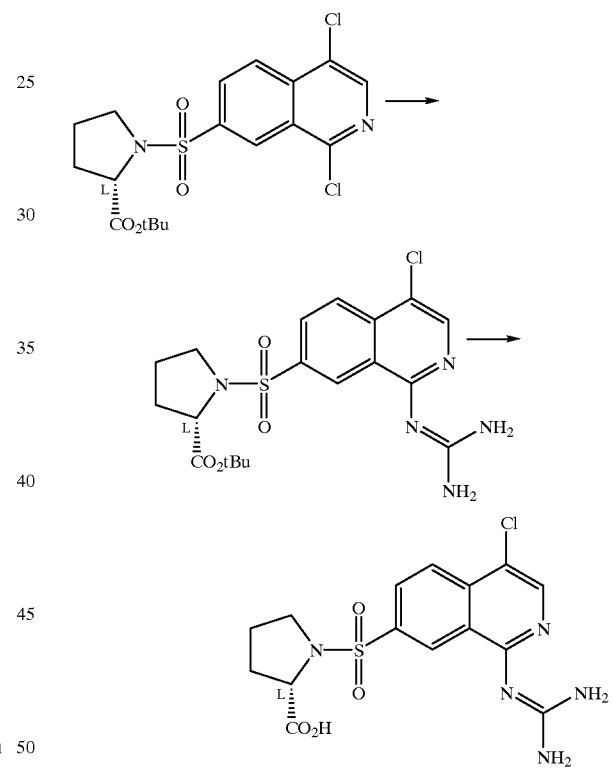

NaH (35 mg, 80% dispersion by wt in mineral oil, 1.16 mmol) was added in one portion to a stirred solution of guanidine hydrochloride (177 mg, 1.85 mmol) in DME (5 mL) and the mixture was heated at 60° C. under $N_2$ for 45 min. A solution of 1-{[(1,4-dichloro-7-isoquinolinyl) sulphonyl]amino}-L-proline t-butyl ester (200 mg, 0.46 mmol) in DME (2 mL) was added and the mixture heated at 95° C. for 4 h. The solvents were evaporated in vacuo and the residue was purified by column chromatography upon silica gel using pentane-EtOAc (80:20 to 0:100) as eluant, followed by azeotroping with CH$_2$Cl$_2$, to give N-[(4-chloro-1-guanidino-7-isoquinolinyl)sulphonyl]-L-proline t-butyl ester (153 mg, 0.32 mmol) as a pale yellow foam.

$^1$H (DMSO-d$_6$, 300 MHz) δ 1.35 (9H, s), 1.6–1.7 (1H, in), 1.7–1.9 (2H, in), 1.9–2.0 (1H, m), 3.15–3.25 (1H, m), 3.35–3.5 (1H, in), 4.1 (1H, dd), 7.15–7.4 (4H, br), 8.05 (1H, d), 8.1 (1H, d), 8.1 (1H, s), 9.05 (1H, s) ppm.

LRMS 454, 456 (MH⁺), 907 (M₂H⁺).

Anal. Found: C, 50.02; H, 5.41; N, 14.84. Calc for $C_{19}H_{24}ClN_5O_4S.0.1EtOAc.0.05CH_2Cl_2$: C, 50.02; H, 5.37; N, 15.00.

N-[(4-Chloro-1-guanidino-7-isoquinolinyl)sulphonyl]-L-proline t-butyl ester (60 mg, 0.13 mmol) was dissolved in a solution of EtOAc saturated with HCl (5.0 mL) and the mixture stirred at room temperature for 1 h. The mixture was concentrated in vacuo, azeotroping with EtOAc, and the residue triturated with $CH_2Cl_2$ to give N-[(4-chloro-1-guanidino-7-isoquinolinyl)sulphonyl]-L-proline hydrochloride (44 mg, 0.095 mmol) as a white powder.

mp 185–189° C.

¹H (DMSO-d₆, 300 MHz) δ 1.5–1.7 (1H, m), 1.7–2.0 (3H, m), 3.2–3.5 (2H, m), 4.2 (1H, dd), 8.3–8.8 (4H, br), 8.2 (2H, s), 8.5 (1H, s), 8.1 (1H, s), 9.05 (1H, s), 11.2 (1H, br) ppm.

Anal. Found: C, 39.89; H, 4.06; N, 14.93. Calc for $C_{15}H_{16}ClN_5O_4S.1.0HCl.1.0H_2O.0.1EtOAc$: C, 40.11; H, 4.33; N, 15.19.

Example 32
(a) N-[(4-chloro-1-guanidino-7-isoquinolinyl)sulphonyl]-D-proline t-butyl ester
(b) N-[(4-Chloro-1-guanidino-7-isoquinolinyl)sulphonyl]-D-proline hydrochloride

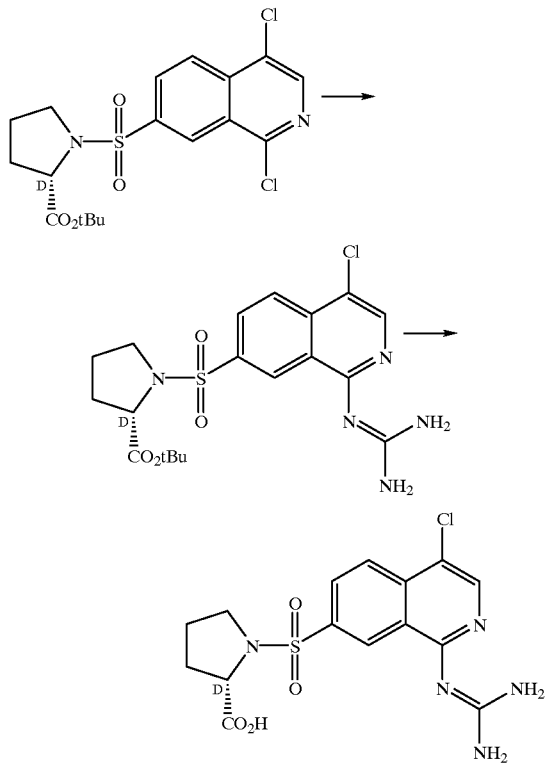

Guanidine hydrochloride (220 mg, 2.3 mmol) was added in one portion to a stirred suspension of NaH (55 mg, 80% dispersion by wt in mineral oil, 1.83 mmol) in DME (8 mL) and the mixture was heated at 60° C. under N₂ for 30 min. 1-{[(1,4-Dichloro-7-isoquinolinyl)sulphonyl]amino}-D-proline t-butyl ester (250 mg, 0.58 mmol) was added and the mixture heated at reflux for 5 h. The cooled mixture was diluted with EtOAc, washed with water, brine, dried (MgSO₄) and the solvents evaporated in vacuo. The residue was purified by column chromatography upon silica gel using $CH_2Cl_2$-MeOH-0.880NH₃ (97:3:0.3) as eluant to give N-[(4-chloro-1-guanidino-7-isoquinolinyl)sulphonyl]-D-proline t-butyl ester (200 mg, 0.44 mmol) as a yellow solid.

mp>170° C. (dec).

¹H (CDCl₃, 400 MHz) δ 1.45 (9H, s), 1.7–1.8 (1H, m), 1.8–2.05 (3H, m), 3.3–3.45 (1H, m), 3.5–3.6 (1H, m), 4.3 (1H, dd), 6.3–6.6 (4H, br), 8.05 (1H, d), 8.1 (1H, d), 8.1 (1H, s), 9.2 (1H, s) ppm.

LRMS 454, 456 (MH⁺).

Anal. Found: C, 49.57; H, 5.27; N, 14.95. Calc for $C_{19}H_{24}ClN_5O_4S.0.2H_2O.0.04CH_2Cl_2$: C, 49.61; H, 5.35; N, 15.19.

N-[(4-Chloro-1-guanidino-7-isoquinolinyl)sulphonyl]-D-proline t-butyl ester (50 mg, 0.11 mmol) was dissolved in a solution of EtOAc saturated with HCl (10 mL) and the mixture stirred at room temperature for 2.5 h. The mixture was concentrated in vacuo, azeotroping with $CH_2Cl_2$, to give N-[(4-chloro-1-guanidino-7-isoquinolinyl)sulphonyl]-D-proline hydrochloride (40 mg, 0.092 mmol) as a white powder.

mp>200° C. (dec).

¹H (CD₃OD, 400 MHz) δ 1.7–1.85 (1H, m), 1.9–2.2 (3H, m), 3.4–3.5 (1H, m), 3.5–3.6 (1H, m), 4.4 (1H, dd), 8.4 (1H, d), 8.45 (1H, s), 8.5 (1H, d), 8.9 (1H, s) ppm.

LRMS 397, 399 (MH⁺)

Anal. Found: C, 40.22; H, 3.92; N, 14.88. Calc for $C_{15}H_{16}ClN_5O_4S.1.0HCl.0.2H_2O.0.25CH_2Cl_2$: C, 39.89; H, 3.93; N, 15.25.

It was noted that some racemisation had occurred during repetition of the above preparation in some conditions. An alternative route to Example 32(b) was developed, reversing the guanylation/hydrolysis sequence, as exemplified below:
1. Hydrolysis

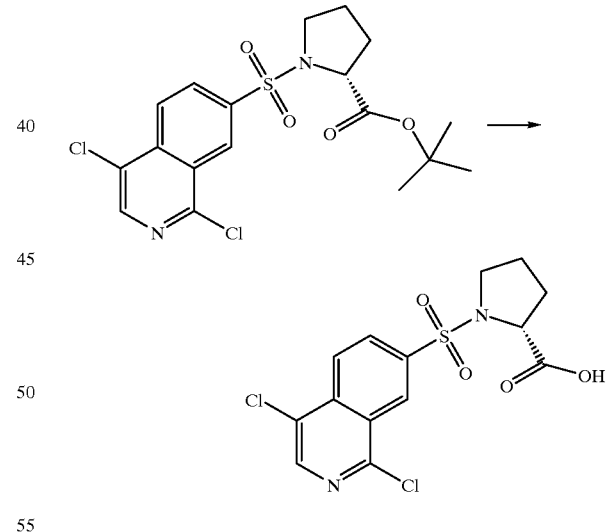

tert-Butyl (2S)-1-[(1,4-dichloro-7-isoquinolinyl)sulfonyl]-2-pyrrolidinecarboxylate (50.0 g, 0.116 mol) was dissolved in conc. HCl (12 M, 200 ml) and stirred for 3.5 h. Water (200 ml) was added over 30 minutes and the resultant white precipitate stirred for a further 0.5 h, filtered and washed with water (3×100 ml). Drying under vacuum gave (2S)-1-[(1,4-dichloro-7-isoquinolinyl)sulfonyl]-2-pyrrolidinecarboxylic acid as a white solid (42.9 g, 0.114 mol).

¹H (d₆-DMSO, 300 MHz) δ 1.6–1.95 (3H, m), 1.95–2.1 (1H, m), 3.25–3.35 (1H, m), 3.35–3.45 (1H, m), 4.3 (1H, dd), 8.35 (2H, s), 8.6 (1H, s), 8.65 (1H, s) ppm.

Chiral analysis was performed using capillary electrophoresis, showing an enantiomeric purity of 97.41%.

2. Guanylation of free acid

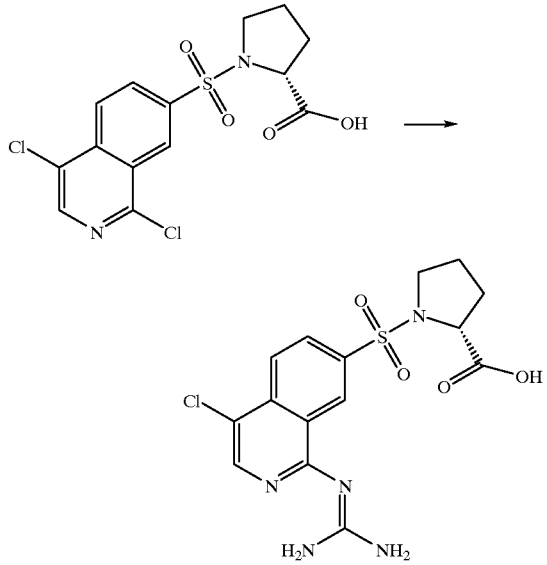

Potassium t-butoxide (49.0 g, 0.0437 mol) and guanidine-.HCl (42.8 g, 0.448 mol) in DME (210 ml) was heated to reflux under nitrogen for 20 min. (2S)-1-[(1,4-dichloro-7-isoquinolinyl)sulfonyl]-2-pyrrolidinecarboxylic acid (42.0 g, 0.112 mol) was added and heating continued at reflux for 5.5 h. Water (420 ml) was added and the mixture acidified with c. HCl to pH=5 giving a solid which was removed by filtration, washed with aq. DME (1:1, 2×75 ml) and water (2×75 ml) and dried to yield the title compound (b) as a yellow solid (40.71 g, 0.102 mol).

$^1$H (d$_6$-DMSO, 300 MHz) δ 1.5–1.65 (1H, m), 1.7–2.0 (3H, m), 3.1–3.25 (1H, m), 3.35–4.05 (1H, m), 4.2 (1H, dd), 7.2–7.7 (4H, br s), 8.0 (1H, d), 8.1–8.2 (2H, m), 9.05 (1H,d).

Chiral analysis was performed using capillary electrophoresis, showing an enantiomeric purity of 99.76% (n=2).

Example 33

4-Chloro-1-guanidino-7-{[(2R)-(hydroxymethyl)-1-pyrrolidinyl]sulphonyl}isoquinoline hydrochloride

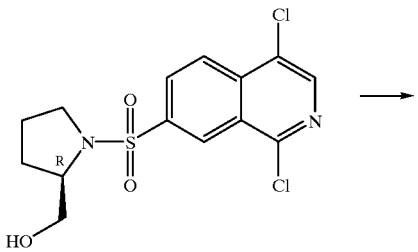

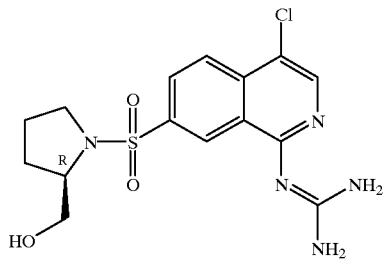

NaH (26 mg, 80% dispersion by wt in mineral oil, 0.87 mmol) was added in one portion to a stirred solution of guanidine hydrochloride (126 mg, 1.32 mmol) in DMSO (2 mL) and the mixture was heated at 50° C. under N$_2$ for 20 min. A solution of 1,4-dichloro-7-{[(2R)-(hydroxymethyl)-1-pyrrolidinyl]sulphonyl}isoquinoline (120 mg, 0.33 mmol) in DMSO (3 mL) was added in one portion and the mixture heated at 80–90° C. for 1 h. The cooled mixture was poured into water, extracted with EtOAc (2×) and the combined organic extracts were then washed with water (×3), brine, dried (MgSO$_4$) and evaporated in vacuo. The residue was purified by column chromatography upon silica gel using CH$_2$Cl$_2$-MeOH-0.880NH$_3$ (95:5:0.5 to 80:20:5) as eluant to give the desired product as an off-white, sticky solid. This material was dissolved in MeOH, a solution of HCl in Et$_2$O (1 M) was added and the solvents were evaporated in vacuo. The residue was recrystallised from MeOH to give 4-chloro-1-guanidino-7-{[(2R)-(hydroxymethyl)-1-pyrrolidinyl]sulphonyl}isoquinoline hydrochloride (43 mg, 0.10 mmol) as a white solid.

mp 275–276.5° C.

$^1$H (CD$_3$OD, 400 MHz) δ 1.5–1.65 (2H, m), 1.8–1.95 (2H, m), 3.25 –3.35 (2H, m), 3.45–3.55 (1H, m), 3.6–3.65 (1H, m), 3.7–3.85 (2H, m), 8.4 (1H, d), 8.45 (1H, s), 8.5 (1H, d), 8.9 (1H, s) ppm.

LRMS 383 (MH$^+$), 405 (MNa$^+$), 767 (M$_2$H$^+$).

Anal. Found: C, 42.36; H, 4.54; N, 16.14. Calc for C$_{15}$H$_{18}$ClN$_5$O$_3$S.1.0HCl.0.25H$_2$O: C, 42.41; H, 4.63; N, 16.49.

Example 34

(a) 1-{[(4-chloro-1-guanidino-7-isoquinolinyl)sulphonyl]amino}isobutyric acid methyl ester (b) 2-{[(4-Chloro-1-guanidino-7-isoquinolinyl)sulphonyl]amino}isobutyric acid hydrochloride

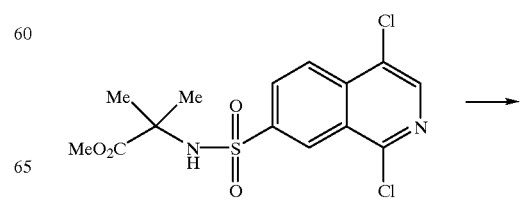

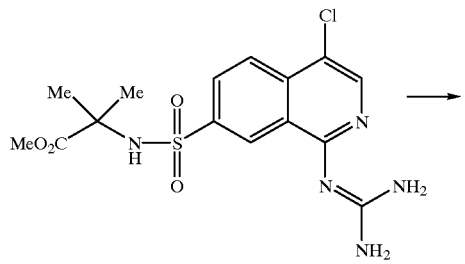

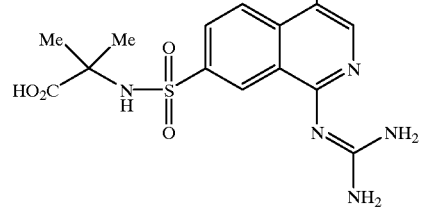

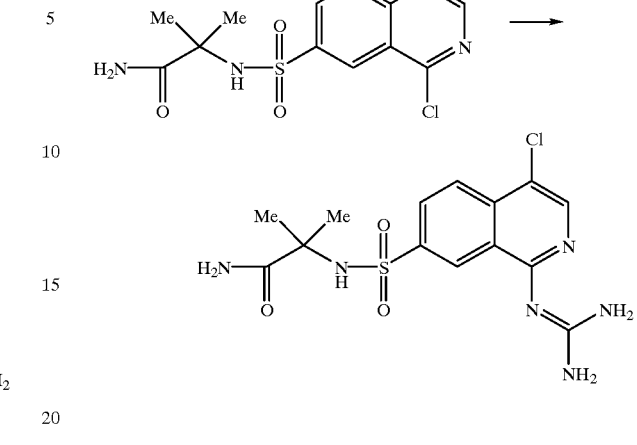

NaH (32 mg, 80% dispersion by wt in mineral oil, 1.07 mmol) was added in one portion to a stirred solution of guanidine hydrochloride (167 mg, 1.7 mmol) in DMSO (5 mL) and the mixture was heated at 50° C. under $N_2$ for 20 min. 1-{[(1,4-Dichloro-7-isoquinolinyl)sulphonyl]amino}isobutyric acid methyl ester (161 mg, 0.43 mmol) was added in one portion and the mixture heated at 80° C. for 6.5 h. The cooled mixture was poured into water (50 mL), extracted with EtOAc (2×100, 2×25 mL) and the combined organic extracts were washed with water, brine, dried ($Na_2SO_4$) and evaporated in vacuo. The residue was purified by repeated column chromatography upon silica gel using (i) $CH_2Cl_2$-MeOH-0.880$NH_3$ (95:5:0.5), (ii) hexane-EtOAc (70:30), and then (iii) $CH_2Cl_2$-MeOH-0.880$NH_3$ (90:10:01), as eluant to give the product as a yellow oil. Trituration with $Et_2O$ gave 1-{[(4-chloro-1-guanidino-7-isoquinolinyl)sulphonyl]amino}isobutyric acid methyl ester (23 mg, 0.054 mmol) as yellow solid.

mp>170° C. (dec).

$^1H$ ($CD_3OD$, 300 MHz) δ 1.4 (6H, s), 3.5 (3H, s), 8.15–8.25 (3H, m), 9.1 (1H, s) ppm.

LRMS 400, 402 (MH$^+$).

Anal. Found: C, 44.02; H, 4.65; N, 16.29. Calc for $C_{15}H_{18}ClN_5O_4S.0.9H_2O.0.1i$-$Pr_2O$: C, 43.95; H, 5.01; N, 16.43.

A solution of NaOH (1 mL, 2 M, 2 mmol) was added to a solution of 1-{[(4-chloro-1-guanidino-7-isoquinolinyl)sulphonyl]amino}isobutyric acid methyl ester (16.5 mg, 0.041 mmol) in MeOH (0.5 mL) and the mixture was heated at 40–50° C. for 16 h. The cooled mixture was neutrilised with dilute HCl (0.5 mL, 2 M) to give a precipitate. The solid was collected by filtration, with copious water washing, and then dissolved in conc. HCl. The solvents were evaporated in vacuo azeptroping with PhMe, and then dried under high vacuum to give 1-{[(4-chloro-1-guanidino-7-isoquinolinyl)sulphonyl]-amino}isobutyric acid hydrochloride (12 mg, 0.026 mmol) as a pale cream solid.

mp 258° C. (dec)

$^1H$ ($CD_3OD$, 400 MHz) δ 1.45 (6H, s), 8.4 (1H, d), 8.4 (1H, s), 8.45 (1H, d), 8.9 (1H, s) ppm.

LRMS 386, 388 (MH$^+$).

Anal. Found: C, 37.89; H, 4.33; N, 15.18. Calc for $C_{14}H_{16}ClN_5O_4S.1.0HCl.1.5H_2O.0.05Et_2O$: C, 37.65; H, 4.56; N, 15.46.

Example 35
2-{[(4-Chloro-1-guanidino-7-isoquinolinyl)sulphonyl]amino}-2-methylpropanamide hydrochloride NaH (41 mg, 80% dispersion by wt in mineral oil, 1.36 mmol) was added in one portion to a stirred solution of guanidine hydrochloride (210 mg, 2.2 mmol) in DMSO (10 mL) under $N_2$ and the mixture was heated at 23° C. for 30 min. 2-{[(1,4-Dichloro-7-isoquinolinyl)sulphonyl]amino}-2-methylpropanamide (225 mg, 0.50 mmol) was added in one portion and the mixture heated at 90° C. for 8 h. The cooled mixture was partially concentrated in vacuo and the residue poured into water. The aqueous solution was extracted with EtOAc (×4) and the combined organic extracts were washed with water, brine, dried ($MgSO_4$). The solvents were evaporated in vacuo and the residue purified by column chromatography upon silica gel using $CH_2Cl_2$-MeOH-0.880$NH_3$ (90:10:1) as eluant to give the desired product. This material was dissolved in MeOH and treated with a solution of HCl in $Et_2O$ (1.0 mL, 1 M) to furnish 2-{[(4-chloro-1-guanidino-7-isoquinolinyl)sulphonyl]amino}-2-methylpropanamide hydrochloride (86 mg, 0.188 mmol) as an off-white powder.

mp 279–281° C.

$^1H$ (TFA-d, 400 MHz) δ 1.6 (6H, s), 8.35 (1H, br s), 8.4 (1H, s), 8.55 (1H, s), 9.1 (1H, br s) ppm.

LRMS 385, 387 (MH$^+$).

Anal. Found: C, 39.68; H, 4.81; N, 18.18. Calc for $C_{14}H_{17}ClN_6O_3S.1.0HCl.1.2$ MeOH: C, 39.71; H, 5.00; N, 18.28.

Example 36

(a) Ethyl 1-{[(4-chloro-1-guanidino-7-isoquinolinyl)sulphonyl]amino}cyclobutanecarboxylate (b) 1-{[(4-Chloro-1-guanidino-7-isoquinolinyl)sulphonyl]amino}cyclobutanecarboxylic acid hydrochloride

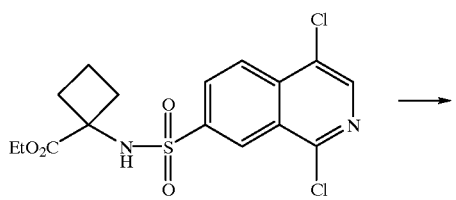

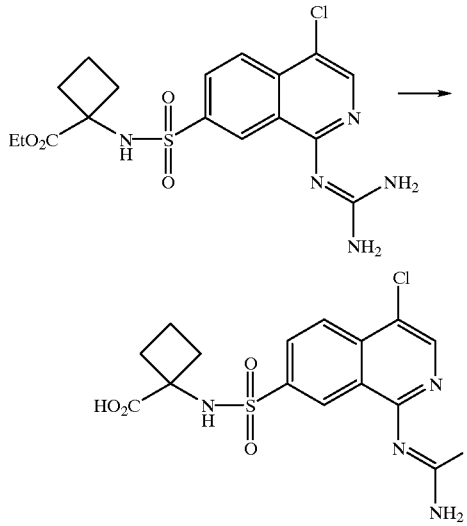

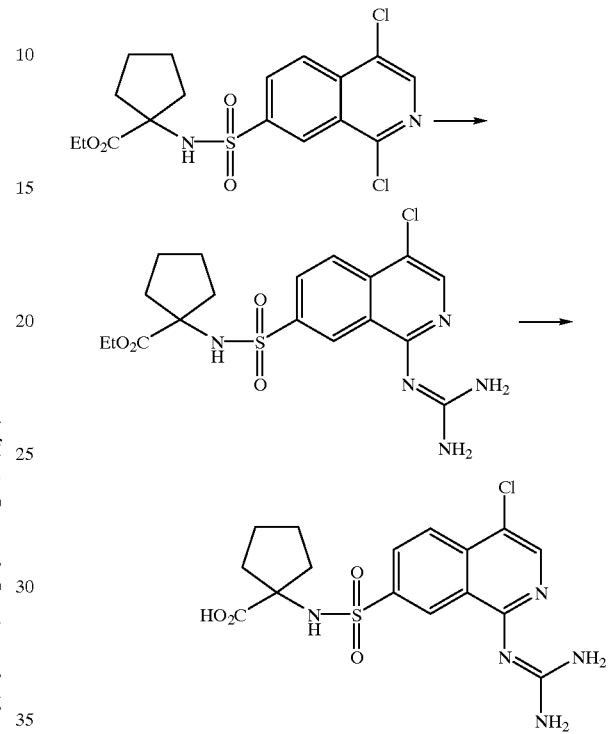

NaH (37 mg, 80% dispersion by wt in mineral oil, 1.24 mmol) was added in one portion to a stirred solution of guanidine hydrochloride (189 mg, 1.98 mmol) in DMSO (6 mL) and the mixture was heated at 60° C. under $N_2$ for 30 min. Ethyl 1-{[(1,4-dichloro-7-isoquinolinyl)sulphonyl] amino)-cyclobutanecarboxylate (200 mg, 0.50 mmol) was added in one portion and the mixture heated at 80° C. for 10 h. The cooled mixture was poured into water, extracted with EtOAc (2×50 mL) and the combined organic extracts were dried ($MgSO_4$) and evaporated in vacuo. The residue was purified by column chromatography upon silica gel using pentane-EtOAc (50:50 to 0:100) as eluant to give ethyl 1-{[(4-chloro-1-guanidino-7-isoquinolinyl)sulphonyl] amino)cyclobutanecarboxylate (150 mg, 0.34 mmol) as a yellow powder.

mp 165–169° C.

$^1$H (DMSO-$d_6$, 300 MHz) δ 1.0 (3H, t), 1.6–1.8 (2H, m), 2.05–2.2 (2H, m), 2.25–2.4 (2H, m), 3.8 (2H, q), 7.0–7.4 (4H, br), 8.05 (2H, s), 8.1 (1H, s), 8.6 (1H, s), 9.05 (1H, s) ppm.

LRMS 426, 428 ($MH^+$).

Anal. Found: C, 46.62; H, 4.62; N, 15.82. Calc for $C_{17}H_{20}ClN_5O_4S.0.25CH_2Cl_2$: C, 46.45; H, 4.63; N, 15.70.

A solution of NaOH (5 mL, 2 M, 10 mmol) was added to a solution of ethyl 1-{[(4-chloro-1-guanidino-7-isoquinolinyl)sulphonyl]amino)cyclobutanecarboxylate (100 mg, 0.23 mmol) in MeOH (5 mL) and the mixture was heated at 55° C. for 6 h. The cooled mixture was neutrilised with dilute HCl (5 mL, 2 M) to give a precipitate and the MeOH was evaporated in vacuo. The solid was collected by filtration, with copious water washing, and dried under high vacuum to give 1-{[(4-chloro-1-guanidino-7-isoquinolinyl) sulphonyl]amino}cyclobutanecarboxylic acid hydrochloride (15 mg, 0.033 mmol).

$^1$H (DMSO-$d_6$, 400 MHz) δ 1.65–1.8 (2H, m), 2.05–2.2 (2H, m), 2.25–2.4 (2H, m), 8.3 (1H, d), 8.35–8.7 (4H, br), 8.4 (1H, d), 8.5 (1H, s), 8.7 (1H, s), 8.95 (1H, s), 11.0 (1H, br), 12.5 (1H, br) ppm.

Anal. Found: C, 40.06; H, 4.34; N, 15.09. Calc for $C_{15}H_{16}ClN_5O_4S.1.0HCl.1.0H_2O$: C, 39.83; H, 4.23; N, 15.48.

Example 37

(a) N-[(4-chloro-1-guanidino-7-isoquinolinyl)sulphonyl] cyclo-leucine ethyl ester
(b) N-[(4-Chloro-1-guanidino-7-isoquinolinyl)sulphonyl] cycloleucine
(c) N-[(4-chloro-1-guanidino-7-isoquinolinyl)sulphonyl] cycloleucine trifluoroacetate NaH (1.12 g, 80% dispersion by wt in mineral oil, 37.3 mmol) was added portionwise to a stirred suspension of guanidine hydrochloride (5.85 g, 59.4 mmol) in DMSO (320 mL) and the mixture was heated at 30–50° C. under $N_2$ for 30 min. N-[(1,4-Dichloro-1-guanidino-7-isoquinolinyl) sulphonyl]-cycloleucine ethyl ester (6.2 g, 14.9 mmol) was added in one portion and the mixture heated at 80° C. for 8 h. The cooled mixture concentrated in vacuo to ca. 160 mL and poured into water (800 mL). The aqueous mixture was extracted with EtOAc (4×150 mL) and the combined organic extracts were then washed with water, brine, dried ($MgSO_4$) and evaporated in vacuo. The residue was purified by column chromatography upon silica gel using $CH_2Cl_2$-MeOH-0.880$NH_3$ (95:5:0.5 to 90:10:1) as eluant and then recrystallised from EtOAc to give N-[(4-chloro-1-guanidino-7-isoquinolinyl)sulphonyl]cyclo-leucine ethyl ester (1.43 g, 3.25 mmol) as a yellow solid.

mp 225–226° C.

$^1$H (DMSO-$d_6$, 300 MHz) δ 1.1 (3H, t), 1.35–1.45 (2H, m), 1.45–1.5 (2H, m), 1.85–1.95 (4H, br), 3.9 (2H, q), 7.1–7.35 (4H, br), 8.0 (1H, d), 8.05 (1H, d), 8.1 (1H, s), 9.1 (1H, s) ppm.

LRMS 440, 442 ($MH^+$).

Anal. Found: C, 49.02; H, 4.97; N, 15.61. Calc for $C_{18}H_{22}ClN_5O_4S$: C, 49.14; H, 5.04; N, 15.92.

A solution of NaOH (75 mL, 2 M, 150 mmol) was added to a solution of N-[(4-chloro-1-guanidino-7-isoquinolinyl) sulphonyl]cycloleucine ethyl ester (1.39 g, 3.16 mmol) in MeOH (75 mL) and the mixture heated at 40–50° C. for 24 h. The cooled mixture was neutrilised with dilute HCl (75 mL, 2 M) to give a precipitate and the MeOH was evaporated in vacuo. The solid was collected by filtration, with copious water washing, and dried under high vacuum to give N-[(4-chloro-1-guanidino-7-isoquinolinyl)sulphonyl]
cycloleucine (1.27 g, 3.08 mmol) as a white powder.

Anal. Found: C, 46.40; H, 4.39; N, 16.66. Calc for
$C_{16}H_{18}ClN_5O_4S$: C, 46.66; H, 4.41; N, 17.00.

N-[(4-Chloro-1-guanidino-7-isoquinolinyl)sulphonyl]
cycloleucine (8 mg) was dissolved in $CF_3CO_2H$ (ca. 1.0 mL)
and the mixture was evaporated in vacuo, azeotroping with
PhMe. The residue was triturated with i-$Pr_2O$ and $Et_2O$ to
give a white solid. The solid was dissolved in MeOH,
filtered and the filtrate evaporated in vacuo to give N-[(4-
chloro-1-guanidino-7-isoquinolinyl)sulphonyl]cycloleucine
trifluoroacetate (12 mg).

mp>178° C. (dec).

$^1H$ (DMSO-$d_6$, 400 MHz) δ 1.3–1.45 (2H, m), 1.45–1.55
(2H, m), 1.85–1.95 (4H, br), 8.25–8.6 (4H, br), 8.3 (1H, d),
8.4 (1H, d), 8.5 (1H, s), 8.85 (1H, s), 10.8 (1H, br), 12.4 (1H,
br) ppm.

LRMS 412,414 (MH$^+$).

Anal. Found: C, 39.50; H, 3.62; N, 11.50. Calc for
$C_{16}H_{18}ClN_5O_4S.1.0CF_3CO_2H.1.0H_2O$: C, 39.75; H, 3.89;
N, 12.88.

Example 38

1-{[(4-Chloro-1-guanidino-7-isoquinolinyl)sulphonyl]
amino}-N-(2-hydroxyethyl)cyclopentanecarboxamine
hydrochloride

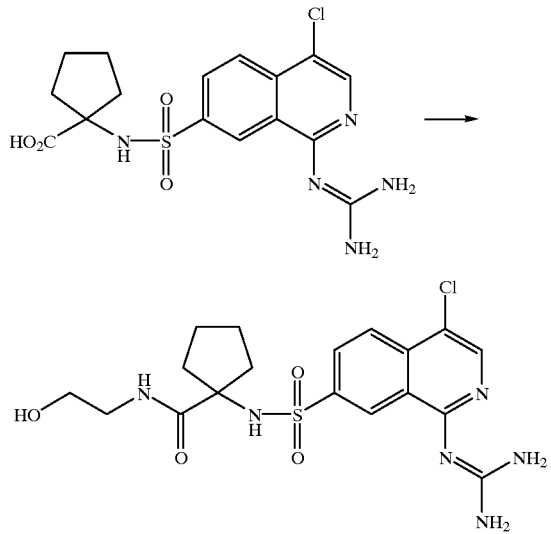

(COCl)$_2$ (60 μL, 0.67 mmol) and then DMF (3 drops) were
added to a stirred suspension of N-[(4-chloro-1-guanidino-
7-isoquinolinyl)sulphonyl]cycloleucine hydrochloride (150
mg, 0.334 mmol) in $CH_2Cl_2$ (15 mL) and the mixture was
stirred at 23° C. for 30 min. The solvents were evaporated
in vacuo, azeotroping with PhMe, to give the corresponding
acid chloride. This material was redissolved in $CH_2Cl_2$ (15
mL) and added to a stirred solution of 2-hydroxyethylamine
(400 μL) in $CH_2Cl_2$ (15 mL) and the mixture stirred for 1 h.
The solvents were evaporated in vacuo and the residue was
purified by column chromatography upon silica gel using
$CH_2Cl_2$-MeOH-0.880NH$_3$ (90:10:1) as eluant to give 1-{
[(4-chloro-1-guanidino-7-isoquinolinyl)sulphonyl]amino}-
N-(2-hydroxyethyl)cyclopentanecarboxamine. This mate-
rial was dissolved in EtOAc-EtOH and a solution of HCl in
$Et_2O$ (1 M) was added which gave a precipitate. The
solvents were decanted and the solid was triturated with
$Et_2O$, collected by filtration and dried to give 1-{[(4-chloro-
1-guanidino-7-isoquinolinyl)sulphonyl]amino}-N-(2-
hydroxyethyl)cyclopentanecarboxamine hydrochloride (77
mg, 0.155 mmol) as a white solid.

mp 244–246° C.

$^1H$ (CD$_3$OD, 300 MHz) δ 1.35–1.5 (2H, m), 1.5–1.65
(2H, m), 1.85–2.0 (2H, m), 2.0–2.15 (2H, m), 3.1–3.2 (2H,
m), 3.5–3.65 (2H, m), 8.4 (1H, d), 8.45 (1H, s), 8.5 (1H, d),
8.95 (1H, s) ppm.

LRMS 455 (MH$^+$), 477 (MNa$^+$).

Anal. Found: C, 43.63; H, 5.03; N, 16.65. Calc for
$C_{18}H_{23}ClN_6O_4S.1.0HCl.0.25H_2O$: C, 43.60; H, 4.98; N,
16.95.

Example 39

(a) 1-{[(4-Chloro-1-guanidino-7-isoquinolinyl)sulphonyl]
amino}-N-[2-(dimethylamino)ethyl]
cyclopentanecarboxamine (b)1-{[(4-Chloro-1-guanidino-7-isoquinolinyl)sulphonyl]
amino}-N-[2-(dimethylamino)ethyl]
cyclopentanecarboxamine dihydrochloride

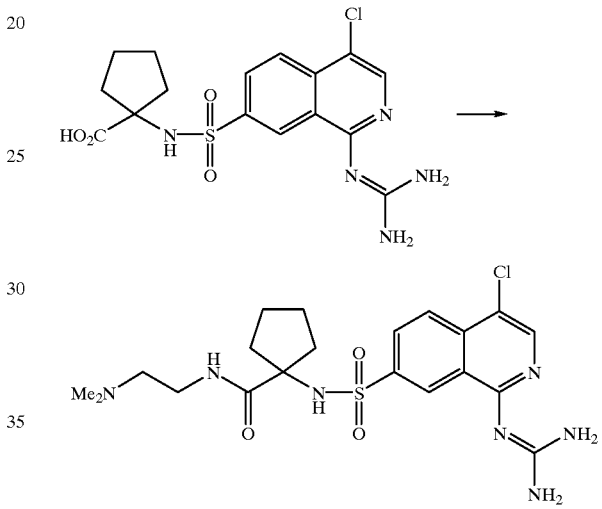

A solution HCl in $Et_2O$ (0.5 mL, 1 M) was added to a stirred
solution of N-[(4-chloro-1-guanidino-7-isoquinolinyl)
sulphonyl]cycloleucine (100 mg, 0.243 mmol) in MeOH.
The solvents were evaporated in vacuo and the residue
azeotroped with PhMe to give the corresponding hydrochlo-
ride salt.

(COCl)$_2$ (42 μL, 0.48 mmol) and then DMF (2 drops)
were added to a stirred solution of N-[(4-chloro-1-
guanidino-7-isoquinolinyl)sulphonyl]cycloleucine hydro-
chloride (0.243 mmol) in $CH_2Cl_2$ (5 mL) and the mixture
was stirred at 23° C. for 18 h. The solvents were evaporated
in vacuo, the residue redissolved in $CH_2Cl_2$ (5 mL), and
2-(dimethylamino)ethylamine (60 μL, 0.48 mmol) was
added and the mixture stirred for 3 h. The solvents were
evaporated in vacuo and the residue partioned between
EtOAc and aqueous NaHCO$_3$ (10%). The organic phase was
dried and evaporated. The residue was purified by column
chromatography upon silica gel using $CH_2Cl_2$-MeOH-
0.880NH$_3$ (95:5:0.5 to 90:10:1) as eluant to give 1-{[(4-
chloro-1-guanidino-7-isoquinolinyl)sulphonyl]amino}-N-
[2-(dimethylamino)ethyl]cyclopentanecarboxamine.

LRMS 482 (MH$^+$).

This material was dissolved in EtOAc, a solution of HCl
in $Et_2O$ (1 M) was added and the solvents were evaporated
in vacuo to give 1-{[(4-chloro-1-guanidino-7-isoquinolinyl)
sulphonyl]amino}-N-[2-(dimethylamino)ethyl]
cyclopentanecarboxamine dihydrochloride (28 mg, 0.048
mmol) as a white solid.

¹H (TFA-d, 400 MHz) δ 1.5 (2H, br s), 1.7 (2H, br s), 2.1 (4H, br s), 3.2 (6H, s), 3.7 (2H, br s), 4.0 (2H, br s), 7.8 (1H, br s), 8.45 (1H, d), 8.5 (1H, s), 8.6 (1H, d), 9.5 (1H, s) ppm.
LRMS 482 (MH⁺).

Anal. Found: C, 41.25; H, 5.63; N, 16.59. Calc for $C_{20}H_{28}ClN_7O_3S.2.0HCl.1.5H_2O$: C, 41.28; H, 5.72; N, 16.85.

Example 40
4-Chloro-1-guanidino-N-[1-(hydroxymethyl)cyclopentyl]-7-isoquinolinesulphonamide hydrochloride

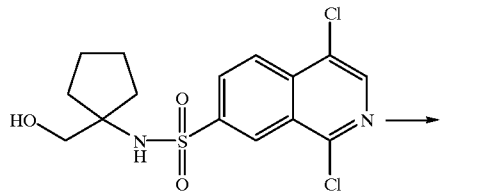

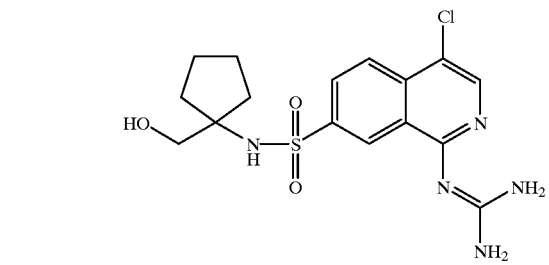

NaH (30 mg, 80% dispersion by wt in mineral oil, 1.0 mmol) was added in one portion to a stirred solution of guanidine hydrochloride (157 mg, 1.6 mmol) in DMSO (5 mL) and the mixture was heated at 60° C. under N₂ for 20 min. 1,4-Dichloro-N-[1-(hydroxymethyl)cyclopentyl]-7-isoquinolinesulphonamide (150 mg, 0.40 mmol) was added in one portion and the mixture heated at 80° C. for 4 h. A second portion of guanidine (0.40 mmol)[prepared from guanidine hydrochloride (38 mg) and NaH (12 mg)] in DMSO (1 mL) was added and the mixture heated at 80° C. for an additional 6 h. The cooled mixture was poured into water (80 mL), extracted with EtOAc (2×50 mL) and the combined organic extracts were then washed with brine, dried (MgSO₄) and evaporated in vacuo. The residue was purified by column chromatography upon silica gel using $CH_2Cl_2$-MeOH-0.880NH₃ (97.5:2.5:0.25 to 80:20:5) as eluant to give the partially purified product (90 mg). This material was converted to the corresponding hydrochloride salt by treatment with a solution of HCl in Et₂O (1 M) and then recrystallised from EtOH to give 4-chloro-1-guanidino-N-[1-(hydroxymethyl)cyclopentyl]-7-isoquinolinesulphonamide hydrochloride (16 mg, 0.040 mmol) as a white solid.
mp 245–247° C.
¹H (CD₃OD, 400 MHz) δ 1.4–1.55 (4H, m), 1.55–1.7 (2H, m), 1.8–1.9 (2H, m), 3.5 (2H, s), 8.4 1H, d), 8.45 (1H, s), 8.45 (1H, d), 8.9 (1H, s) ppm.
LRMS 398, 400 (MH⁺).

Anal. Found: C, 44.17; H, 4.84; N, 15.88. Calc for $C_{16}H_{26}ClN_5O_3S.1.0HCl$: C, 44.24; H, 4.87; N, 16.12.

Example 41
(a) N-[(4-chloro-1-guanidino-7-isoquinolinyl)sulphonyl]-N-[2-(dimethylamino)ethyl]cycloleucine ethyl ester dihydrochloride
(b) N-[(4-Chloro-1-guanidino-7-isoquinolinyl)sulphonyl]-N-[2-(dimethylamino)ethyl]cycloleucine dihydrochloride

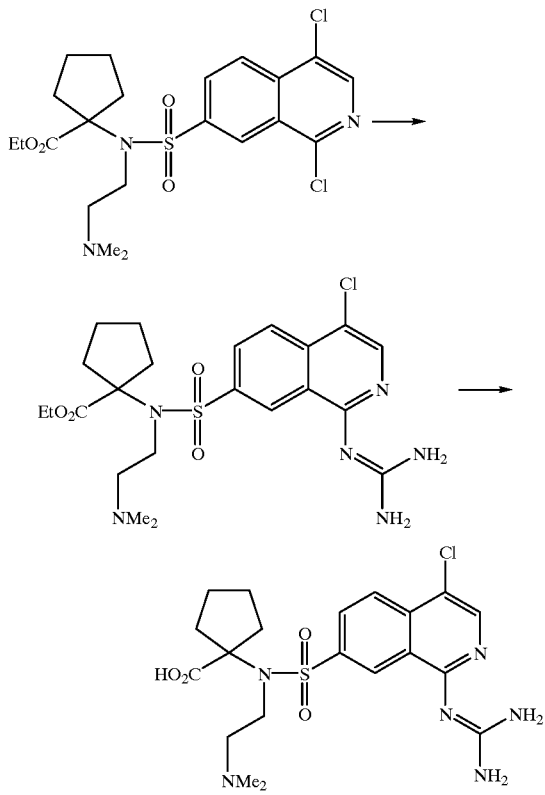

NaH (32 mg, 80% dispersion by wt in mineral oil, 1.05 mmol) was added in one portion to a stirred solution of guanidine hydrochloride (145 mg, 1.52 mmol) in DMSO (4 mL) and the mixture was heated at 50° C. under N₂ for 20 min. N-[(1,4-Dichloro-7-isoquinolinyl)sulphonyl]-N-[2-(dimethylamino)ethyl]cycloleucine ethyl ester hydrochloride (160 mg, 0.305 mmol) was added in one portion and the mixture heated at 90° C. for 1 h. The cooled mixture was poured into water, extracted with EtOAc (2×20 mL) and the combined organic extracts were then washed with brine, dried (Na₂SO₄) and evaporated in vacuo. The residue was dissolved in Et₂O, filtered, and a solution of HCl in Et₂O (1 M) was added which gave a precipitate. The solvents were evaporated in vacuo and the residue recrystallised from hot EtOH to give N-[(4-chloro-1-guanidino-7-isoquinolinyl)sulphonyl]-N-[2-(dimethylamino)ethyl]cycloleucine ethyl ester dihydrochloride (123 mg, 0.20 mmol) as a pale yellow solid.
mp 228–230° C.
¹H (TFA-d, 400 MHz) δ 1.45 (3H, t), 1.7 (2H, br s), 1.9 (2H, br s), 2.2 (2H, br s), 2.5 (2H, br ), 3.3 (6H, s), 3.75 (2H, br s), 4.3 (2H, br s), 4.4 (2H, q), 8.15 (1H, br s), 8.4 (1H, d), 8.5 (1H, s), 8.65 (1H, d), 9.35 (1H, s) ppm.
LRMS 511, 513 (MH⁺).

Anal. Found: C, 43.74; H, 5.88; N, 13.75. Calc for $C_{22}H_{31}ClN_6O_4S.2.0HCl.1.0H_2O$: C, 43.90; H, 5.86; N, 13.96.

A solution of NaOH (5 mL, 5 M) was added to a solution of N-[(4-chloro-1-guanidino-7-isoquinolinyl)sulphonyl]-N-[2-(dimethylamino)ethyl]cycloleucine ethyl ester dihydrochloride (75 mg, 0.128 mmol) in dioxane (5 mL) and the mixture was heated at 80° C. for 30 h. The cooled mixture was diluted with water (20 mL), the dioxane was evaporated in vacuo, and the aqueous residue neutralised with dilute HCl (2 M) to pH 6. The precipitate was collected by filtration with water washing, and then dissolved in MeOH, filtered and evaporated in vacuo. The residue was purified by column chromatography upon silica gel using $CH_2Cl_2$-MeOH-$0.880NH_3$ (90:10:1 to 80:20:5) as eluant to give to give the desired product. This material was dissolved in MeOH-EtOAc, a solution of HCl in $Et_2O$ (1 M) was added and the solvents were evaporated in vacuo. The residue was triturated with EtOAc to give N-[(4-chloro-1-guanidino-7-isoquinolinyl)sulphonyl]-N-[2-(dimethylamino)ethyl]cycloleucine dihydrochloride (15.4 mg, 0.025 mmol).

$^1$H (TFA-d, 400 MHz) δ 1.7 (2H, br s), 1.9 (2H, br s), 2.2 (2H, br s), 2.6 (2H, br s), 3.25 (6H, s), 3.8 (2H, br s), 4.3 (2H, br s), 8.1(1H, br s), 8.4 (1H, d), 8.5 (1H, s), 8.65 (1H, d), 9.4 (1H, s) ppm.

LRMS 483 (MH$^+$).

Anal. Found: C, 39.03; H, 5.60; N, 14.02. Calc for $C_{20}H_{27}ClN_6O_4S.2HCl.3H_2O$: C, 39.38; H, 5.78; N, 13.78.

Example 42
N-(t-Butoxycarbonylmethyl)-N-[(4-chloro-1-guanidino-7-isoquinolinyl)sulphonyl]cycloleucine ethyl ester

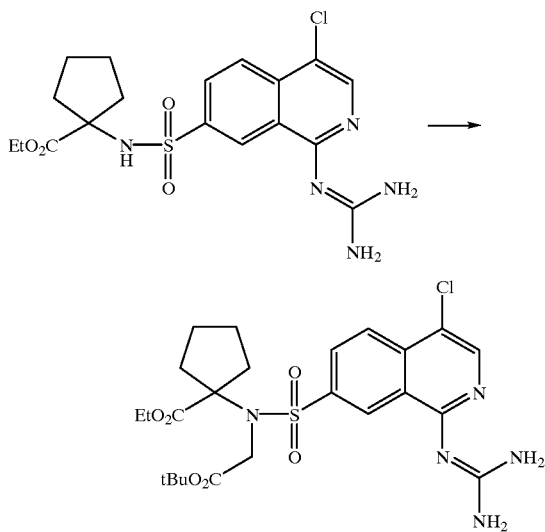

Anhydrous $K_2CO_3$ (34 mg, 0.25 mmol) and t-butyl bromoacetate (44 μL, 0.30 mmol) were added to a stirred solution of N-[(4-chloro-1-guanidino-7-isoquinolinyl)sulphonyl]cycloleucine ethyl ester (110 mg, 0.25 mmol) in DMF (1.0 mL) and the mixture was stirred at 23° C. for 18 h. The mixture was diluted with EtOAc (60 mL), washed with water (3×100 mL), dried (MgSO$_4$) and evaporated in vacuo. The residue was purified by column chromatography upon silica gel using pentane-EtOAc (100:0 to 20:80) as eluant to give N-(t-butoxycarbonylmethyl)-N-[(4-chloro-1-guanidino-7-isoquinolinyl)sulphonyl]cycloleucine ethyl ester (95 mg, 0.17 mmol) as a white solid.

$^1$H (CDCl$_3$, 400 MHz) δ 1.3 (3H, t), 1.45 (9H, s), 1.6–1.7 (4H, m), 1.85–1.95 (2H, br), 2.25–2.35 (2H, m), 4.2 (2H, q), 4.5 (2H, s), 8.1 (1H, d), 8.15 (1H, s), 8.3 (1H, dd), 9.3 (1H, d) ppm.

LRMS 554 (MH$^+$).

Anal. Found: C, 52.31; H, 5.94; N, 13.33. Calc for $C_{24}H_{32}ClN_5O_6S$: C, 52.03; H, 5.82; N, 12.64.

Example 43
(a) Methyl 1-{[(4-chloro-1-guanidino-7-isoquinolinyl)sulphonyl]amino}cyclohexanecarboxylate
(b) 1-{[(4-Chloro-1-guanidino-7-isoquinolinyl)sulphonyl]amino}cyclohexanecarboxylic acid hydrochloride

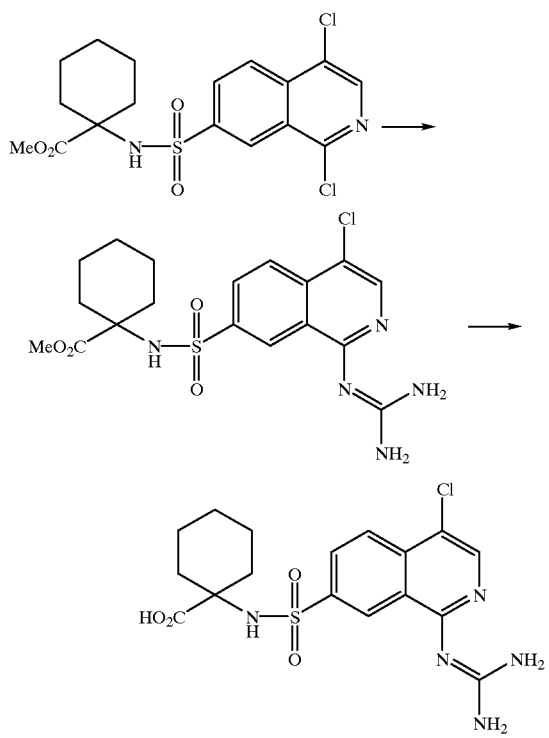

NaH (22.3 mg, 80% dispersion by wt in mineral oil, 0.743 mmol) was added in one portion to a stirred solution of guanidine hydrochloride (117 mg, 1.98 mmol) in DMSO (5 mL) and the mixture was heated at 50–70° C. under N$_2$ for 25 min. Methyl 1-{[(1,4-dichloro-7-isoquinolinyl)sulphonyl]amino}-cyclohexanecarboxylate (124 mg, 0.30 mmol) was added in one portion and the mixture heated at 80° C. for 8 h. The cooled mixture was poured into water (50 mL), extracted with EtOAc (2×50 mL) and the combined organic extracts were washed with water, brine, dried (MgSO$_4$) and evaporated in vacuo. The residue was crystallised from a minimum of hot EtOAc to give methyl 1-{[(4-chloro-1-guanidino-7-isoquinolinyl)sulphonyl]amino}cyclohexanecarboxylate (12 mg, 0.043 mmol) as yellow solid. Evaporation of the mother liquors and trituration of the residue with Et$_2$O gave a second crop (7 mg).

mp>220° C. (dec).

$^1$H (DMSO-d$_6$, 400 MHz) δ 1.1–1.35 (6H, m), 1.65–1.75 (2H, m), 1.75–1.85 (2H, m), 3.35 (3H, s), 7.1–7.4 (4H, br), 8.0 (1H, d), 8.05 (1H, d), 8.1 (1H, s), 8.15 (1H, s), 9.0 (1H, s) ppm.

LRMS 440, 442 (MH$^+$).

Anal. Found: C, 48.55; H, 5.12; N, 15.73. Calc for $C_{18}H_{22}ClN_5O_4S.0.3H_2O$: C, 49.14; H, 5.04; N, 15.92.

A solution of NaOH (1 mL, 2 M, 2 mmol) was added to a solution of methyl 1-{[(4-chloro-1-guanidino-7-isoquinolinyl)sulphonyl]amino}cyclohexanecarboxylate (12 mg, 0.027 mmol) in MeOH (4 mL) and the mixture was heated at 50–60° C. for 4 d. The cooled mixture was neutrilised with dilute HCl (1 mL, 2 M) to give a precipitate. The solid was collected by filtration, with copious water washing, and then triturated with EtOAc. The solid was dissolved in conc. HCl, the solvents were evaporated in vacuo azeptroping with PhMe, and then dried under high vacuum to give 1-{[(4-chloro-1-guanidino-7-isoquinolinyl)sulphonyl]amino}cyclohexanecarboxylic acid hydrochloride (11 mg, 0.021 mmol).

mp 194° C. (dec)

¹H (DMSO-d₆, 400 MHz) δ 1.1–1.4 (6H, m), 1.6–1.8 (2H, m), 1.8–1.95 (2H, m), 8.15–8.7 (4H, br), 8.2 (1H, s), 8.3 (1H, d), 8.4 (1H, d), 8.45 (1H, s), 8.9 (1H, s), 10.9 (1H, br), 12.4 (1H, br) ppm.

LRMS 426 (MH⁺).

Anal. Found: C, 39.87; H, 5.05; N, 13.16. Calc for $C_{17}H_{20}ClN_5O_4S.1.0HCl.3.0H_2O$: C, 39.54; H, 5.27; N, 13.56.

Example 44

(a) Methyl 4-{[(4-chloro-1-guanidino-7-isoquinolinyl)sulphonyl]amino}tetrahydro-2H-pyran-4-carboxylate (b) 4-{[(4-Chloro-1-guanidino-7-isoquinolinyl)sulphonyl]amino}tetrahydro-2H-pyran-4-carboxylic acid hydrochloride

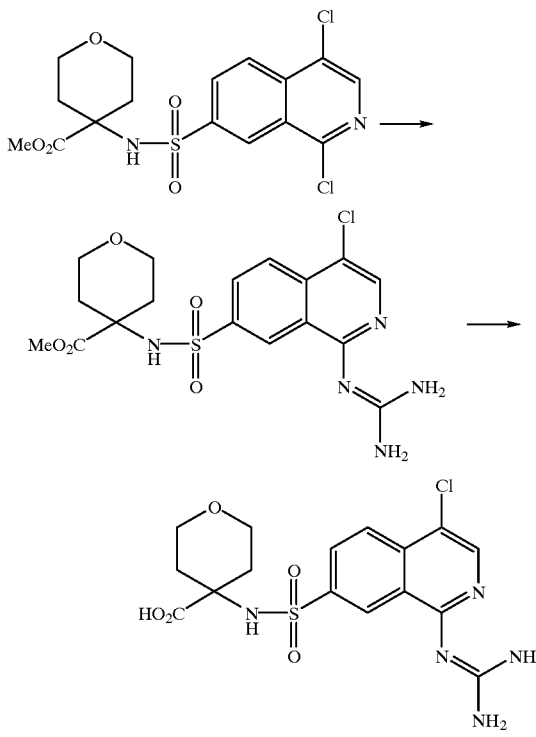

NaH (33.5 mg, 80% dispersion by wt in mineral oil, 1.12 mmol) was added in one portion to a stirred solution of guanidine hydrochloride (176 mg, 1.84 mmol) in DMSO (3.0 mL) under N₂ and the mixture was heated at 50° C. for 15 min. Methyl 4-{[(1,4-dichloro-7-isoquinolinyl)sulphonyl]amino}tetrahydro-2H-pyran-4-carboxylate (187 mg, 0.446 mmol) was added in one portion and the mixture heated at 80° C. for 8 h. A second portion of guanidine (0.45 mmol) [prepared from guanidine hydrochloride and NaH] in DMSO (1.0 mL) was added and the mixture heated at 90° C. for an additional 4 h. The cooled mixture was poured into water (100 mL), extracted with EtOAc (3×50 mL) and the combined organic extracts were washed with brine, dried (Na₂SO₄). The solvents were evaporated in vacuo and the residue purified by column chromatography upon silica gel using CH₂Cl₂-MeOH-0.880NH₃ (95:5:0.5) as eluant, and then crystallised with EtOAc, to give to give methyl 4-{[(4-chloro-1-guanidino-7-isoquinolinyl)sulphonyl]amino}tetrahydro-2H-pyran-4-carboxylate (83 mg, 0.186 mmol) as a yellow solid.

mp 245–247° C.

¹H (CDCl₃, 400 MHz) δ 3.3 (3H, s), 3.35–3.45 (8H, m), 7.1–7.4 (4H, br), 8.05 (2H, s), 8.1 (1H, s), 8.4 (1H, s), 9.0 (1H, s) ppm.

LRMS 442, 444 (MH⁺).

Anal. Found: C, 46.18; H, 4.56; N, 15.32. Calc for $C_{17}H_{20}ClN_5O_5S.0.2H_2O$: C, 45.83; H, 4.62; N, 15.72.

A solution of NaOH (1 mL, 2 M, 2 mmol) was added to a solution of methyl 4-([(4-chloro-1-guanidino-7-isoquinolinyl)sulphonyl]amino}tetrahydro-2H-pyran-4-carboxylate (68 mg, 0.153 mmol) in MeOH (12 mL) and the mixture was heated at reflux for 30 h. The cooled mixture was neutralised with dilute HCl (1 mL, 2 M), partially concentrated by evaporation in vacuo to give a precipitate which was collected by filtration, with water washing. The solid was extracted with warm conc. HCl, the solution decanted from insoluble material and the solvents were evaporated in vacuo. The solid residue was azeptroped with PhMe and then dried under high vacuum to give 4-{[(4-chloro-1-guanidino-7-isoquinolinyl)sulphonyl]amino}tetrahydro-2H-pyran-4-carboxylate acid hydrochloride (30 mg, 0.062 mmol) as a white solid.

mp 190–210° C. (dec).

¹H (DMSO-d₆, 400 MHz) δ 3.2–3.5 (8H, m), 8.2–8.7 (4H, br), 8.3 (1H, d), 8.4 (1H, d), 8.45 (1H, s), 8.95 (1H, s), 11.0 (1H, br s), 12.6 (1H, br s) ppm.

Anal. Found: C, 39.76; H, 4.33; N, 14.12. Calc for $C_{16}H_{18}ClN_5O_5S.1.0HCl.1.1H_2O$: C, 39.69; H, 4.41; N, 14.47.

Example 45

(a) t-Butyl (±)-cis-2-{[(4-chloro-1-guanidino-7-isoquinolinyl)sulphonyl]amino}-cyclohexanecarboxylate (b) (±)-cis-2-{[(4-Chloro-1-guanidino-7-isoquinolinyl)sulphonyl]amino}cyclohexanecarboxylic acid hydrochloride

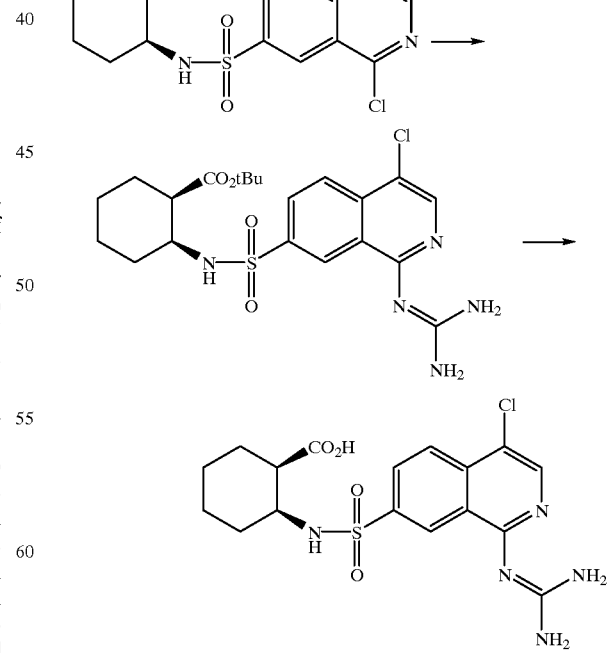

Guanidine hydrochloride (325 mg, 3.4 mmol) was added in one portion to a stirred suspension of NaH (89 mg, 80% dispersion by wt in mineral oil, 2.97 mmol) in DME (5 mL) and the mixture was heated at 60° C. under $N_2$ for 30 min. A solution of t-butyl (±)-cis-2-{[(1,4-dichloro-7-isoquinolinyl)sulphonyl]amino}cyclohexanecarboxylate (391 mg, 0.85 mmol) in DME (5 mL) was added and the mixture heated at 90° C. for 6 h. The solvents were evaporated in vacuo, the residue was dissolved with EtOAc, washed with aqueous $NH_4Cl$, dried ($MgSO_4$) and evaporated in vacuo. The residue was purified by column chromatography upon silica gel using using toluene-i-PrOH-0.880$NH_3$ (100:0:0 to 90:10:0.05) as eluant to give t-butyl (±)-cis-2-{[(4-chloro-1-guanidino-7-isoquinolinyl)sulphonyl]amino}cyclohexanecarboxylate (75 mg, 0.15 mmol) as a white solid.

$^1$H (CDCl$_3$, 400 MHz) δ 1.1–1.8 (7H, mm), 1.4 (9H, s), 1.95 (1H, m), 2.55 (1H, dd), 3.45 (1H, br s), 5.9 (1H, d), 6.0–6.5 (4H, br), 8.05 (1H, d), 8.1 (1H, d), 8.15 (1H, s), 9.3(1H, s) ppm.

LRMS 482, 484 (MH$^+$).

CF$_3$CO$_2$H (3.0 mL) was added to a stirred solution of t-butyl (±)-cis-2-{[(4-chloro-1-guanidino-7-isoquinolinyl)sulphonyl]amino}cyclohexanecarboxylate (66 mg, 0.14 mmol) in CH$_2$Cl$_2$ (3.0 mL) and the mixture was stirred at 23° C. for 6 h. The solvents were evaporated in vacuo, azeotroping CH$_2$Cl$_2$ (×3). The residue was dissolved in EtOAc and a solution of HCl in Et$_2$O (200 μL, 1.0 M) was added which gave a precipitate. The white solid was collected by filtration and dried to give (±)-cis-2-{[(4-chloro-1-guanidino-7-isoquinolinyl)sulphonyl]amino}cyclohexanecarboxylic acid hydrochloride (35 mg, 0.069 25 mmol).

mp 220–223° C. (dec).

$^1$H (DMSO-d$_6$, 400 MHz) δ 1.1–1.3 (3H, m), 1.4–1.6 (4H, m), 1.7–1.8 (1H, m), 2.5 (1H, m), 30 3.75 (1H, br s), 8.0 (1H, d), 8.25–8.6 (4H, br), 8.35 (2H, s), 8.45 (1H, s), 8.95 (1H, s) ppm.

Anal. Found: C, 42.95; H. 4.96; N, 13.79. Calc for C$_{17}$H$_{20}$ClN$_5$O$_4$S.1.0HCl.1.25H$_2$O.0.3Et$_2$O: C, 43.11; H, 5.27; N, 13.81.

Example 46
Ethyl (±)-trans-2-{[(4-chloro-1-guanidino-7-isoquinolinyl)sulphonyl]amino}cyclohexanecarboxylate

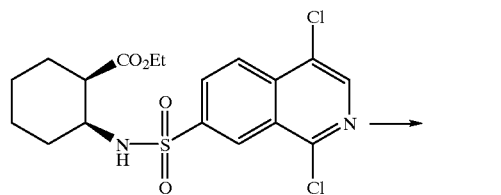

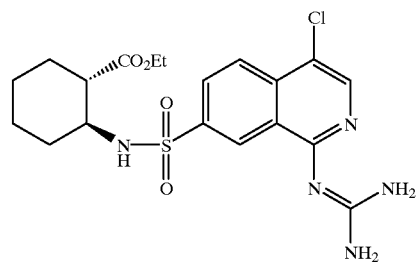

Guanidine hydrochloride (458 mg, 4.8 mmol) was added in one portion to a stirred suspension of NaH (90 mg, 80% dispersion by wt in mineral oil, 2.97 mmol) in DME (10 mL) and the mixture was heated at 60° C. under $N_2$ for 30 min. A solution of ethyl (±)-cis-2-{[(1,4-dichloro-7-isoquinolinyl)sulphonyl]amino}cyclohexanecarboxylate (377 mg, 0.87 mmol) in DMA (5 mL) was added and the mixture heated at 90° C. for 4 h. The solvents were evaporated in vacuo, the residue was dissolved with EtOAc (200 mL), washed with aqueous NH$_4$Cl (20 mL), then with water (500 mL), and the combined aqueous washings were extracted with EtOAc (2×50 mL). The combined EtOAc extracts were washed with water (4×100 mL), dried (MgSO$_4$) and evaporated in vacuo. The residue was purified by column chromatography upon silica gel using using toluene-i-PrOH-0.880NH$_3$ (100:0:0 to 90:10:0.05) as eluant to give ethyl (±)-trans-2-{[(4-chloro-1-guanidino-7-isoquinolinyl)sulphonyl]amino}cyclohexanecarboxylate (65 mg, 0.14 mmol) as a white solid. [A small amount of ethyl (±)-cis-2-{[(4-chloro-1-guanidino-7-isoquinolinyl)sulphonyl]amino}cyclohexanecarboxylate (<20 mg) was also isolated.)

$^1$H (CDCl$_3$, 400 MHz) δ 1.1–1.8 (6H, mm), 1.1 (3H, t), 1.9 (1H, m), 2.0 (1H, m), 2.25 (1H, td), 3.45 (1H, m), 3.8–4.0 (2H, m), 8.05 (1H, d), 8.1 (1H, d), 8.15 (1H, s), 9.3 (1H, s) ppm.

LRMS 454, 456 (MH$^+$).

Example 47
(a) t-Butyl cis-4-{[(4-chloro-1-guanidino-7-isoquinolinyl)sulphonyl]amino}cyclohexane-carboxylate
(b) t-butyl trans-4-{[(4-chloro-1-guanidino-7-isoquinolinyl)sulphonyl]amino}cyclohexane-carboxylate
(c) cis-4-{[(4-Chloro-1-guanidino-7-isoquinolinyl)sulphonyl]amino}cyclohexanecarboxylic acid hydrochloride

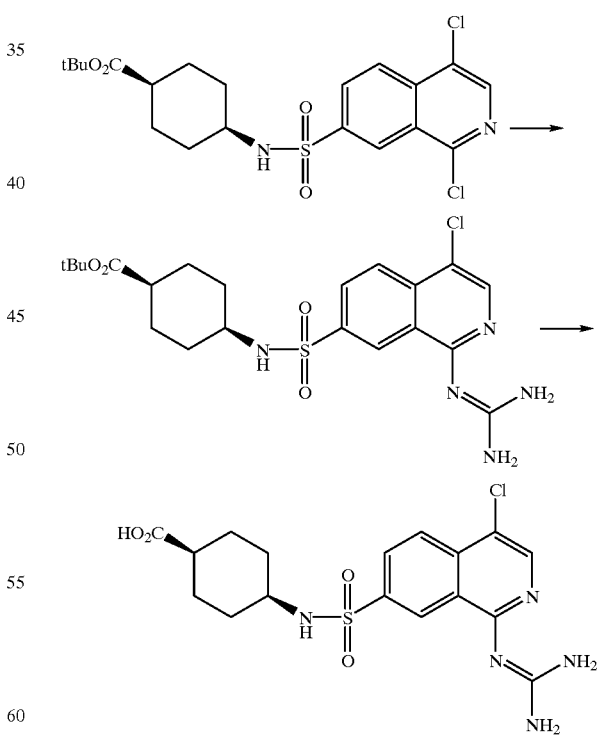

Guanidine hydrochloride (286 mg, 3.0 mmol) was added in one portion to a stirred suspension of NaH (56 mg, 80% dispersion by wt in mineral oil, 1.82 mmol) in DME (5 mL) and the mixture was heated at 60° C. under $N_2$ for 30 min. A solution of t-butyl cis-4-{[(1,4-dichloro-7-isoquinolinyl)

sulphonyl]amino}cyclohexanecarboxylate (346 mg, 0.75 mmol) in DME (15 mL) was added and the mixture heated at 90° C. for 2 h. A second portion of guanidine (0.75 mmol)[prepared from guanidine hydrochloride (72 mg) and NaH (22 mg)] in DME (5 mL) was added and the mixture heated at 90° C. for 1 h. DMA (10 mL) was then added to the heterogeneous reaction mixture and the now homogeneous mixture heated for an additional 6 h. The solvents were evaporated in vacuo, the residue was quenched aqueous $NH_4Cl$ (10 mL), diluted with water (150 mL) and extracted with EtOAc (2×150 mL). The combined organic extracts were washed with water (100 mL), dried ($MgSO_4$) and evaporated in vacuo. The residue was purified by repeated column chromatography upon silica gel using (i), pentane-EtOAc (100:0 to 25:75) and then (ii), PhMe-EtOAc (50:50 to 0:100) as eluant to give t-butyl cis-4-{[(4-chloro-1-guanidino-7-isoquinolinyl)sulphonyl] amino}cyclohexanecarboxylate (247 mg, 0.51 mmol). [A small amount of t-butyl trans-4-{[(4-chloro-1-guanidino-7-isoquinolinyl)sulphonyllamino}cyclohexanecarboxylate (20 mg) was also isolated.]

$^1H$ ($CDCl_3$, 400 MHz) δ 1.4 (9H, s), 1.5–1.8 (8H, mm), 2.3 (1H, m), 3.4 (1H, m), 4.8–4.9 (1H, br), 6.1–6.55 (4H, br), 8.05 (1H, d), 8.1 (1H, d), 8.15 (1H, s), 9.3 (1H, s) ppm.

LRMS 482 ($MH^+$), 963 ($M_2H^+$).

Anal. Found: C, 52.14; H, 5.92; N, 14.19. Calc for $C_{21}H_{28}ClN_5O_4S$: C, 52.33; H, 5.86; N, 14.53.

t-Butyl cis-4-{[(4-chloro-1-guanidino-7-isoquinolinyl) sulphonyl]amino}cyclohexanecarboxylate (55 mg, 0.121 mmol) was suspended in a solution of EtOAc saturated with HCl (50 mL) and the mixture heated at reflux. The mixture was cooled, the white solid was collected by filtration, with EtOAc washing, and then dried to give cis-4-{[(4-chloro-1-guanidino-7-isoquinolinyl)sulphonyl]amino}-cyclohexanecarboxylic acid hydrochloride (110 mg, 0.236 mmol).

mp 287–289° C.

$^1H$ ($CDCl_3$, 400 MHz) δ 1.5–1.6 (6H, m), 1.8–1.9 (2H, m), 2.35 (1H, m), 3.4 (1H, m), 8.35 (1H, d), 8.45 (1H, s), 8.5 (1H, d), 8.9 (1H, s) ppm Anal. Found: C, 43.88; H, 4.61; N, 14.69. Calc for $C_{17}H_{20}ClN_5O_4S \cdot 1.0HCl \cdot 0.2H_2O$: C, 43.82; H, 4.63; N, 15.03.

Example 48

(a) Ethyl trans-4-{[(4-chloro-1-guanidino-7-isoquinolinyl) sulphonyl]amino}cyclohexane-carboxylate (b) trans-4-{[(4-Chloro-1-guanidino-7-isoquinolinyl) sulphonyl]amino}cyclohexanecarboxylic acid hydrochloride

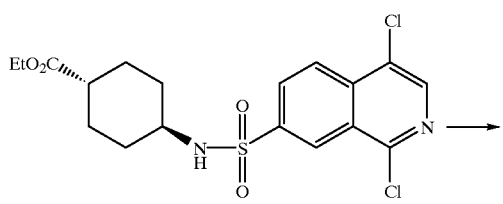

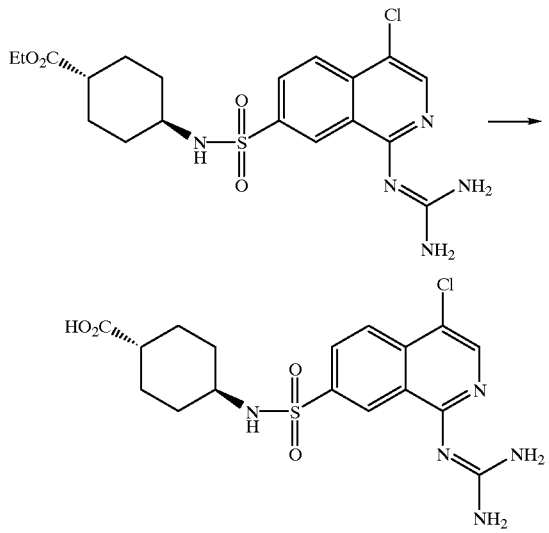

Guanidine hydrochloride (273 mg, 2.86 mmol) was added in one portion to a stirred suspension of NaH (55 mg, 80% dispersion by wt in mineral oil, 1.82 mmol) in DME (10 mL) and the mixture was heated at 60° C. under $N_2$ for 30 min. A solution of ethyl trans-4-{[(1,4-dichloro-7-isoquinolinyl) sulphonyl]amino}cyclohexanecarboxylate (370 mg, 0.78 mmol) in DMA (10 mL) was added and the mixture heated at 90° C. for 3 h. The solvents were evaporated in vacuo, the residue was partitioned between $Et_2O$ (100 mL), aqueous $NH_4Cl$ (10 mL), and water (150 mL). The separated aqueous phase was extracted with $Et_2O$ (3×100 mL) and the combined organic extracts were dried ($MgSO_4$) and evaporated in vacuo. The residue was purified by column chromatography upon silica gel using toluene-i-PrOH-0.880$NH_3$ (100:0:0 to 90:10:0.05) as eluant to give ethyl trans-4-{[(4-chloro-1-guanidino-7-isoquinolinyl)sulphonyl] amino}cyclohexanecarboxylate (70 mg, 0.15 mmol).

$^1H$ ($CDCl_3$, 400 MHz) δ 1.1 (3H, s), 1.1–1.3 (4H, mm), 1.6 (2H, br d), 1.8 (2H, br d), 2.1 (1H, m), 2.9 (1H, m), 3.95 (2H, q), 7.1–7.4 (4H, br), 7.8 (1H, d), 8.0 (114, d), 8.1 (1H, d), 8.1 (1H, s),9.1 (1H,s)ppm.

LRMS 454, 456 ($MH^+$).

Anal. Found: C, 50.27; H, 5.56; N, 14.92. Calc for $C_{19}H_{24}ClN_5O_4S$: C, 50.27; H, 5.32; N, 15.43.

A solution of HCl (5 mL, 2 M, 10 mmol) was added to a solution of ethyl trans-4-{[(4-chloro-1-guanidino-7-isoquinolinyl)sulphonyl]amino}cyclohexanecarboxylate (55 mg, 0.121 mmol) in dioxane (5.0 mL) and the mixture was heated at reflux for 2 h. The solvents were evaporated in vacuo and the residue was purified by column chromatography upon MCI gel (CHP 20P) using water-MeOH (100:0 to 20:80) as eluant to give trans-4-{[(4-chloro-1-guanidino-7-isoquinolinyl)sulphonyl]amino}-cyclohexanecarboxylic acid. This material was dissolved in dilute HCl (20 mL, 0.1 M), the solvents were evaporated in vacuo, and the residue triturated with $Et_2O$ to give trans-4-{[(4-chloro-1-guanidino-7-isoquinolinyl)sulphonyl] amino}cyclohexanecarboxylic acid hydrochloride (35 mg, 0.067 mmol) as a white solid.

mp>205° C. (dec).

$^1H$ ($CD_3OD$, 400 MHz) δ 1.2–1.4 (4H, mm), 1.8 (2H, br d), 1.9 (2H, br d), 2.1 (1H, m), 3.1 (1H, m), 8.3 (1H, d), 8.45 (1H, s), 8.5 (1H, d), 8.9 (1H, s) ppm.

Anal. Found: C, 42.75; H, 5.04; N, 13.35. Calc for $C_{17}H_{20}ClN_5O_4S \cdot 1.0HCl \cdot 1.5H_2O \cdot 0.4Et_2O$: C, 43.04; H, 5.44; N, 13.49.

Example 49

(a) N-[(4-chloro-1-guanidino-7-isoquinolinyl)carbonyl]glycine t-butyl ester (b) N-[(4-Chloro-1-guanidino-7-isoquinolinyl)carbonyl]glycine trifluoroacetate

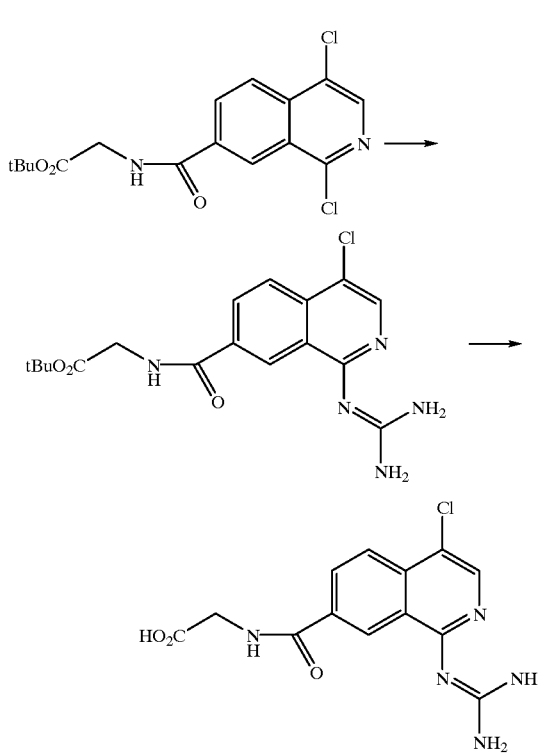

NaH (34 mg, 60% dispersion in mineral oil, 0.85 mmol) was added to a stirred solution of guandine hydrochloride (80 mg, 0.84 mmol) in DMSO (2 mL) at 23° C. After 30 min, N-[(1,4-dichloro-7-isoquinolinyl)carbonyl]glycine t-butyl ester (120 mg, 0.34 mmol) was added and the resultant solution heated at 90° C. for 21 h. After cooling, the mixture was poured into water (30 mL), extracted with EtOAc, and then with $CH_2Cl_2$, and the combined organic extracts were dried ($Na_2SO_4$) and evaporated in vacuo. The residue was purified by column chromatography on silica gel using $CH_2Cl_2$-MeOH-0.880$NH_3$ (90:10:1) as eluant to give N-[(4-chloro-1-guanidino-7-isoquinolinyl)carbonyl]glycine t-butyl ester (25 mg, 0.07 mmol) as a yellow gum.

LRMS 378 ($MH^+$), 756 ($M_2H^+$).

A solution of N-[(4-chloro-1-guanidino-7-isoquinolinyl)carbonyl]glycine t-butyl ester (24 mg, 0.06 mmol) in $CF_3CO_2H$ (0.5 ml) was stirred at 0° C. for 1.5 h. The reaction mixture was diluted with PhMe, evaporated in vacuo, azeotroping with PhMe, and the residue triturated with $Et_2O$ to give N-[(4-chloro-1-guanidino-7-isoquinolinyl)carbonyl]glycine trifluoroacetate (21 mg, 0.05 mmol) as a white solid.

mp>300° C.

$^1$H (TFA-d, 400 MHz) δ 4.6 (2H, s), 8.4 (1H, d), 8.45 (1H, s), 8.6 (1H, d), 9.3 (1H, s) ppm.

LRMS 322 ($MH^+$).

Anal. Found: C, 40.60; H, 2.91; N, 15.47. Calc for $C_{13}H_{12}ClN_5O_3.CF_3CO_2H$: C, 40.58; H, 2.93; N, 15.46.

Example 50

(a) N-[(4-chloro-1-guanidino-7-isoquinolinyl)carbonyl]-β-alanine t-butyl ester (b) N-[(4-Chloro-1-guanidino-7-isoquinolinyl)carbonyl]-β-alanine

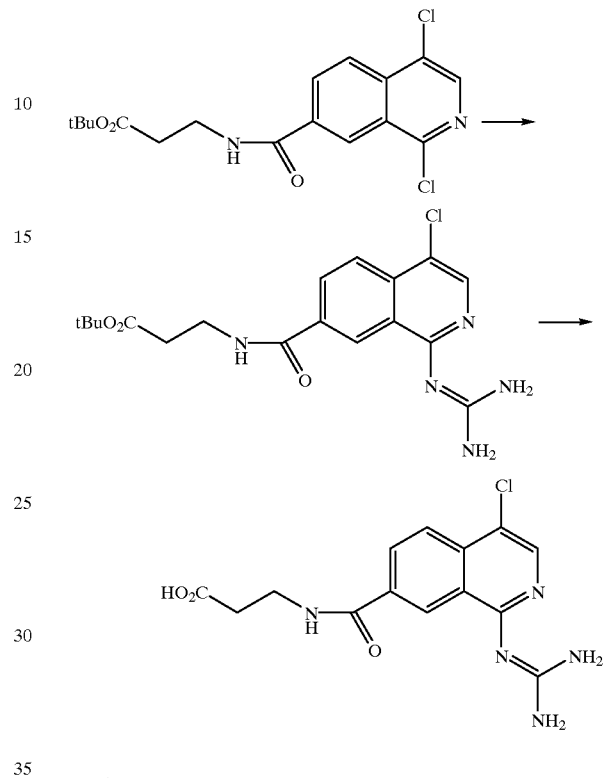

NaH (114 mg, 60% dispersion in mineral oil, 2.85 mmol) was added portionwise to a stirred solution of guanidine hydrochloride (272 mg, 2.85 mmol) in DMSO (8 mL) and the solution was heated at 80° C. for 20 min. N-[(1,4-Dichloro-7-isoquinolinyl)carbonyl]-P-alanine t-butyl ester (420 mg, 1.14 mmol) was added and the mixture heated at 90° C. overnight. The cooled mixture was poured into water, extracted with EtOAc, and the combined organic extracts were washed with water, saturated brine, dried ($Na_2SO_4$) and evaporated in vacuo. The residue was crystallised from i-$Pr_2O$-$CH_2Cl_2$ to give N-[(4-chloro-1-guanidino-7-isoquinolinyl)carbonyl]-β-alanine t-butyl ester (190 mg, 0.48 mmol).

mp 224–226° C.

$^1$H (DMSO-$d_6$, 400 MHz) δ 1.4 (9H, s), 2.55–2.5 (2H, m), 3.5 (2H, dt), 7.0–7.3 (4H, br s), 7.85 (1H, d), 8.0 (1H, s), 8.1 (1H, d), 8.65 (1H, t), 9.1 (1H, s) ppm.

LRMS 392 ($MH^+$), 783 ($M_2H^+$).

Anal. Found: C, 54.89; H, 5.68; N, 17.94. Calc for $C_{18}H_{22}ClN_5O_3$: C, 55.17; H, 5.66; N, 17.87.

A solution of N-[(4-chloro-1-guanidino-7-isoquinolinyl)carbonyl]-β-alanine t-butyl ester (145 mg, 0.37 mmol) in $CF_3CO_2H$ (1.5 mL) was stirred at 0° C. for 30 min, and then at room temperature for 1 h. PhMe (15 mL) was added, the mixture evaporated in vacuo, and the residue triturated with EtOAc and $Et_2O$ to give N-[(4-Chloro-1-guanidino-7-isoquinolinyl)carbonyl]-β-alanine (117 mg, 0.26 mmol) as a white solid.

mp 235–236° C.

$^1$H (DMSO-$d_6$, 300 MHz) δ 2.6 (2H, t), 3.55 (2H, dt), 8.25 (1H, d), 8.35–8.4 (2H, m), 8.5 (4H, br s), 8.8–8.9 (2H, m) ppm.

LRMS 336 ($MH^+$).

Anal. Found: C, 42.72; H, 3.56; N, 14.55. Calc for $C_{14}H_{14}ClN_5O_2.0.25EtOAc$: C, 42.75; H, 3.57; N, 14.49.

Example 51
(a) N-[(4-chloro-1-guanidino-7-isoquinolinyl)carbonyl] cycloleucine ethyl ester
(b) N-[(4-Chloro-1-guanidino-7-isoquinolinyl)carbonyl] cycloleucine

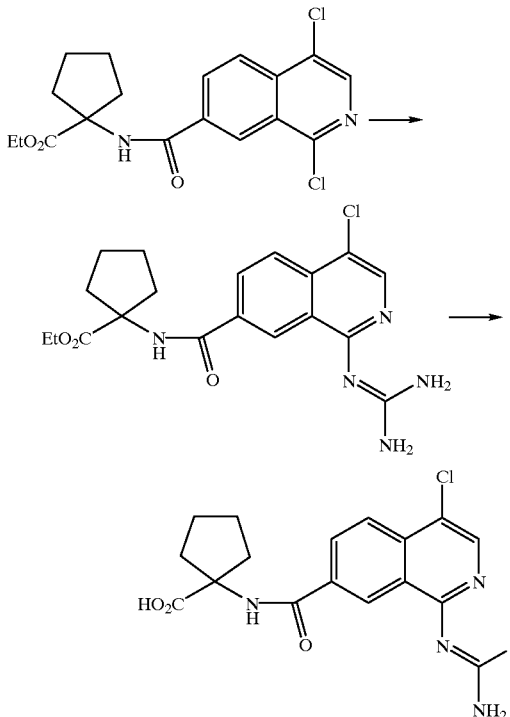

NaH (45 mg, 60% dispersion in mineral oil, 1.13 mmol) was added to t-BuOH and the mixture heated at 50° C. for 15 min. Guanidine hydrochloride (105 mg, 1.10 mmol) was added and the mixture heated at 50° C. for an additional 15 min. N-[(1,4-Dichloro-7-isoquinolinyl)carbonyl] cycloleucine ethyl ester (350 mg, 0.92 mmol) was added and the mixture heated at reflux for 17 h. The solvents were evaporated in vacuo and the residue purified by column chromatography on silica gel using $CH_2Cl_2$-MeOH-0.880$NH_3$ (90:10:1) as eluant, followed by trituration with $CH_2Cl_2$-i-$Pr_2O$, to give N-[(4-chloro-1-guanidino-7-isoquinolinyl)carbonyl]cycloleucine ethyl ester (55 mg, 0.14 mmol) as a pale yellow powder.

$^1$H (CDCl$_3$, 300 MHz) δ 1.0 (3H, t), 1.5–1.65 (4H, m), 1.8–2.0 (2H, m), 2.0–2.15 (2H, m), 3.9 (2H, q), 6.7 (4H, br s), 7.5 (1H, s), 7.7 (1H, d), 7.8 (1H, s), 7.9 (1H, d), 8.95 (1H, s) ppm.

LRMS 404 (MH$^+$).

Anal. Found: C, 55.94; H, 5.42; N, 16.94. Calc for $C_{19}H_{22}ClN_5O_3.0.25H_2O$: C, 55.87; H, 5.55; N, 17.14.

A partly heterogeneous solution of N-[(4-chloro-1-guanidino-7-isoquinolinyl)carbonyl]cycloleucine ethyl ester (45 mg, 0.11 mmol) in dioxane (1.5 mL) was stirred with aqueous NaOH (1 mL, 2 M) for 2.5 h at 23° C. Dilute HCl (1 mL, 2 M) was added to give a cream suspension. The solid was collected by filtration and dried in vacuo to yield N-[(4-chloro-1-guanidino-7-isoquinolinyl)carbonyl] cycloleucine (40 mg, 0.11 mmol).

mp>275° C.

$^1$H (TFA-d, 400 MHz) δ 1.9–2.1 (4H, m), 2.2–2.4 (2H, m), 2.5–2.7 (2H, m), 8.3 (1H, d), 8.35 (1H, s), 8.45 (1H, d), 9.25 (1H, s) ppm.

LRMS 376 (MH$^+$), 751 (M$_2$H$^+$).

Anal. Found: C, 51.67; H, 4.92; N, 17.39. Calc for $C_{17}H_{18}ClN_5O_3.H_2O$: C, 51.84; H, 5.1 1; N, 17.78.

Example 52
(a) N-[(4-chloro-1-guanidino-7-isoquinolinyl)carbonyl]-DL-phenylglycine t-butyl ester
(b) N-[(4-Chloro-1-guanidino-7-isoquinolinyl)carbonyl]-DL-phenylglycine trifluoroacetate

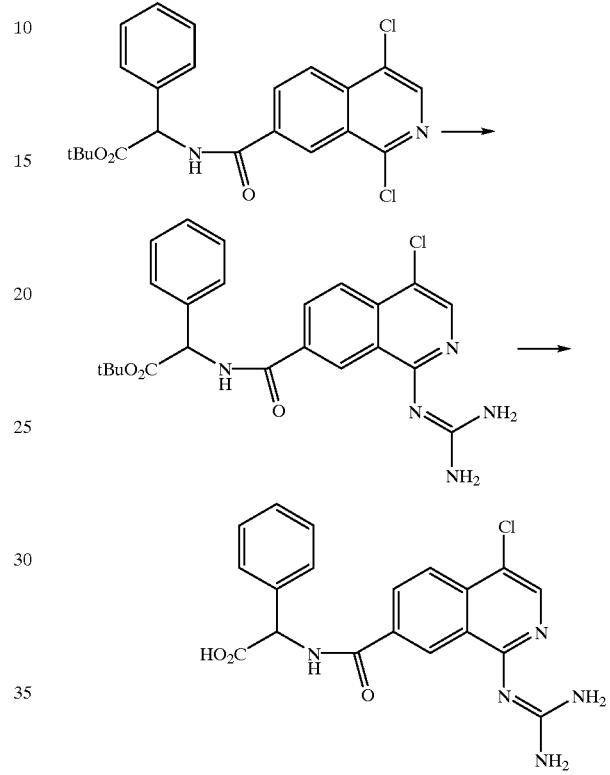

A mixture of guanidine hydrochloride (326 mg, 3.41 mmol) and NaH (137 mg, 60% dispersion in oil, 3.43 mmol) in DMSO (5 mL) was heated to 70° C., a solution of N-[(1,4-dichloro-7-isoquinolinyl)carbonyl]-DL-phenylglycine t-butyl ester (590 mg, 1.37 mmol) in DMSO (3 mL) was added, and the mixture heated at 80–90° C. overnight. After cooling, the reaction mixture was poured into water (50 mL) and extracted with EtOAc (3×30 mL). The combined organic extracts were washed with water, dried (Na$_2$SO$_4$), and evaporated in vacuo. Purification of the residue by column chromatography on silica gel using $CH_2Cl_2$-MeOH-0.880$NH_3$ (90:10:1) as eluant, followed by crystallisation from i-Pr$_2$O, gave N-[(4-chloro-1-guanidino-7-isoquinolinyl)carbonyl]-DL-phenylglycine t-butyl ester (110 mg, 0.24 mmol) as a pale yellow solid.

mp 158° C. (foam), 170° C. (dec).

$^1$H (CDCl$_3$, 300 MHz) δ 1.4 (9H, s), 5.7 (1H, d), 6.5 (4H, br s), 7.25–7.4 (3H, m), 7.4–7;5 (3H, m), 8.05 (1H, d), 8.10 (1H, s), 8.15 (1H, d), 9.2 (1H, d) ppm.

LRMS 454 (MH$^+$).

Anal. Found: C, 61.53; H, 5.96; N, 14.27. Calc for $C_{23}H_{24}ClN_5O_3.0.3i$-Pr$_2$O: C, 61.53; H, 5.92; N, 14.27.

A solution of N-[(4-chloro-1-guanidino-7-isoquinolinyl) carbonyl]-DL-phenylglycine t-butyl ester (100 mg, 0.22 mmol) in $CF_3CO_2H$ (1.5 mL) was stirred at 0° C. for 30 min, and then at 23° C. for 1 h. The reaction mixture was diluted with PhMe (15 mL) and evaporated in vacuo. The residual gum was triturated with EtOAc, and then Et$_2$O, and the resulting white solid was dried in vacuo to give N-[(4-chloro-1-guanidino-7-isoquinolinyl)carbonyl]-DL-phenylglycine trifluoroacetate (50 mg, 0.10 mmol).

$^1$H (DMSO-d$_6$, 300 MHz) δ 5.6 (1H, d), 7.3–7.45 (3H, m), 7.55 (2H, d), 8.2 (1H, d), 8.2–8.4 (5H, m), 8.45 (1H, d), 8.95 (1H, s), 9.4 (1H, d) ppm.

LRMS 398 (MH$^+$).

Anal. Found: C, 49.72; H, 3.68; N, 14.04. Calc for C$_{19}$H$_{16}$ClN$_5$O$_3$.0.95CF$_3$CO$_2$H: C, 49.27; H, 3.35; N, 13.68.

Example 53
(a) N-[(4-chloro-1-guanidino-7-isoquinolinyl)carbonyl]-L-phenylglycine t-butyl ester
(b) N-[(4-Chloro-1-guanidino-7-isoquinolinyl)carbonyl]-L-phenylglycine trifluoroacetate

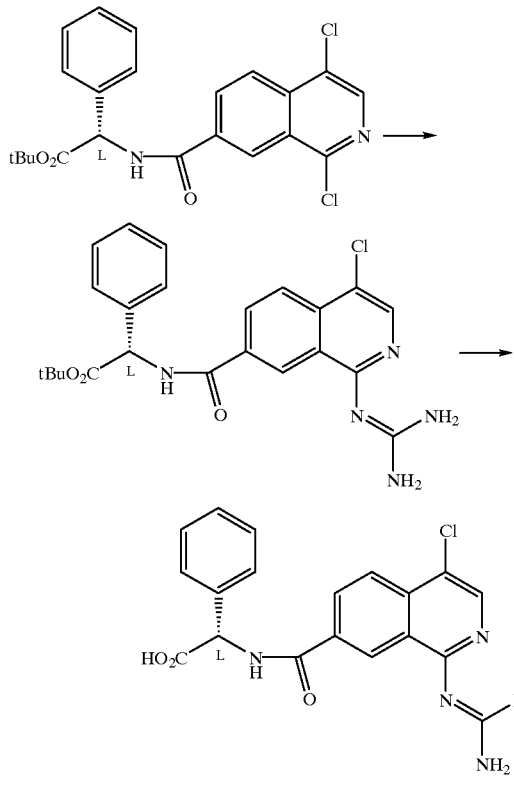

NaH (38 mg, 80% dispersion in mineral oil, 1.27 mmol) was added to a stirred solution of guanidine hydrochloride (121 mg, 1.27 mmol) in DMSO (4 mL) at 23° C., and the mixture heated at 80–85° C. for 15 min. N-[(1,4-Dichloro-7-isoquinolinyl)carbonyl]-L-phenylglycine t-butyl ester (218 mg, 0.51 mmol) was added and the mixture heated at 85° C. for 4 h. The cooled solution was poured into water and extracted with EtOAc (×3). The combined organics were washed with saturated brine, dried (Na$_2$SO$_4$) and evaporated in vacuo. The residue was crystallised with i-Pr$_2$O to give N-[(4-chloro-1-guanidino-7-isoquinolinyl)carbonyl]-L-phenylglycine 1-butyl ester (55 mg, 0.12 mmol) as a pale yellow solid.

mp 147° C. (dec).

$^1$H (CDCl$_3$, 400 MHz) δ 1.4 (9H, s), 5.7 (1H, d), 6.2–6.8 (4H, br s), 7.3–7.4 (3H, m), 7.45–7.5 (3H, m), 8.0–8.1 (2H, m), 8.15–8.2 (1H, d), 9.2 (1H, s) ppm.

LRMS 454 (MH$^+$), 907 (M$_2$H$^+$).

Anal. Found: C, 61.22; H, 6.01; N, 13.91. Calc for C$_{23}$H$_{24}$ClN$_5$O$_3$.0.4i-Pr$_2$O: C, 61.21; H, 6.07; N, 14.05.

A solution of N-[(4-chloro-1-guanidino-7-isoquinolinyl)carbonyl]-L-phenylglycine t-butyl ester (40 mg, 0.09 mmol) in CF$_3$CO$_2$H (1 mL) was stirred at room temperature for 1 h. The reaction mixture was diluted with PhMe, evaporated in vacuo, and the residue triturated with EtOAc to give N-[(4-chloro-1-guanidino-7-isoquinolinyl)carbonyl]-L-phenylglycine trifluoroacetate (32 mg, 0.06 mmol) as a white powder.

mp 163° C. (shrinks), >200° C. (dec).

$^1$H (TFA-d, 400 MHz) δ 5.85 (1H, s), 7.35–7.4 (3H, m), 7.4–7.45 (2H, m), 8.25 (1H, d), 8.3 (1H, s), 8.4 (1H, d), 9.15 (1H, s) ppm.

LRMS 398 (MH$^+$), 795 (M$_2$H$^+$).

Anal. Found: C, 48.28; H, 3.74; N, 13.57. Calc for C$_{19}$H$_{16}$ClN$_5$O$_3$.CF$_3$CO$_2$H.0.5H$_2$O: C, 48.43; H, 3.48; N, 13.45.

Example 54
(a) N-[(4-chloro-1-guanidino-7-isoquinolinyl)carbonyl]-D-phenylglycine t-butyl ester
(b) N-1(4-Chloro-1-guanidino-7-isoquinolinyl)carbonyl]-D-phenylglycine trifluoroacetate

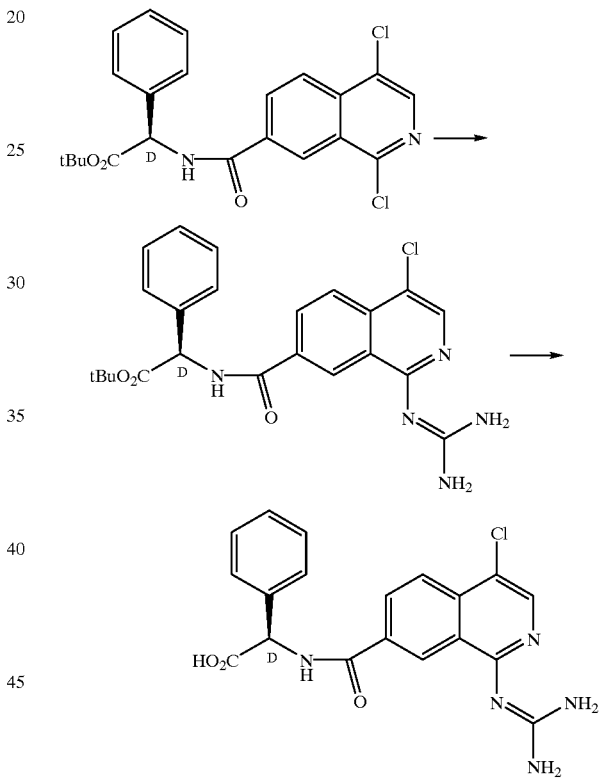

NaH (30 mg, 80% dispersion in mineral oil, 1.0 mmol) was added to a solution of guanidine hydrochloride (97 mg, 1.0 mmol) in DMSO (3 mL) and the solution heated to 80° C. for 30 min. N-[(1,4-Dichloro-7-isoquinolinyl)carbonyl]-D-phenylglycine t-butyl ester (175 mg, 0.41 mmol) was added, the mixture heated at 85° C. for 3.5 h, and then at 23° C. overnight. The mixture was poured into water (25 mL), extracted with EtOAc (3×20 mL), and the combined organics washed with brine, dried (MgSO$_4$), and evaporated in vacuo. The reside was purified by column chromatography on silica gel using CH$_2$Cl$_2$-MeOH-0.880NH$_3$ (95:5:0.5) as eluant, followed by crystallisation from CH$_2$Cl$_2$-i-Pr$_2$O, to give N-[(4-chloro-1-guanidino-7-isoquinolinyl)carbonyl]-D-phenylglycine t-butyl ester (37 mg, 0.08 mmol) as a solid.

mp 154–156° C. (dec).

$^1$H (CDCl$_3$, 400 MHz) δ 1.4 (9H, s), 5.7 (1H, d), 7.3–7.4 (3H, m), 7.4–7.5 (3H, m), 8.05 (1H, d), 8.05 (1H, s), 8.15 (1H, d), 9.2 (1H, s) ppm.

LRMS 454 (MH⁺), 907 (M₂H⁺).

Anal. Found: C, 61.15; H, 6.00; N, 13.87. Calc for C₂₃H₂₄ClN₅O₃.0.45i-Pr₂O.0.2H₂O: C, 61.31; H, 6.15; N, 13.91.

A solution of N-[(4-chloro-1-guanidino-7-isoquinolinyl) carbonyl]-D-phenylglycine t-butyl ester (40 mg, 0.09 mmol) in CF₃CO₂H (0.5 mL) was stirred at room temperature for 1 h. The solution was diluted with PhMe, evaporated in vacuo, and the residue was triturated with Et₂O to give N-[(4-chloro-1-guanidino-7-isoquinolinyl)carbonyl]-D-phenylglycine trifluoroacetate (21 mg, 0.04 mmol) as a white powder.

mp 222° C. (dec).

¹H (TFA-d, 400 MHz) δ 5.9 (1H, s), 7.4–7.5 (3H, m), 7.5–7.55 (2H, m), 8.3 (1H, d), 8.35 (1H, s), 8.4 (1H, d), 9.2 (1H, s) ppm.

LRMS 398 (MH⁺), 795 (M₂H⁺).

Anal. Found: C, 49.02; H, 3.42; N, 13.26. Calc for C₁₉H₁₆ClN₅O₃.CF₃CO₂H.0.25H₂O: C, 48.85; H, 3.42; N, 13.56.

Example 55
(a) N-[(4-chloro-1-guanidino-7-isoquinolinyl)carbonyl]-DL-valine t-butyl ester
(b) N-[(4-Chloro-1-guanidino-7-isoquinolinyl)carbonyl]-DL-valine trifluoroacetate

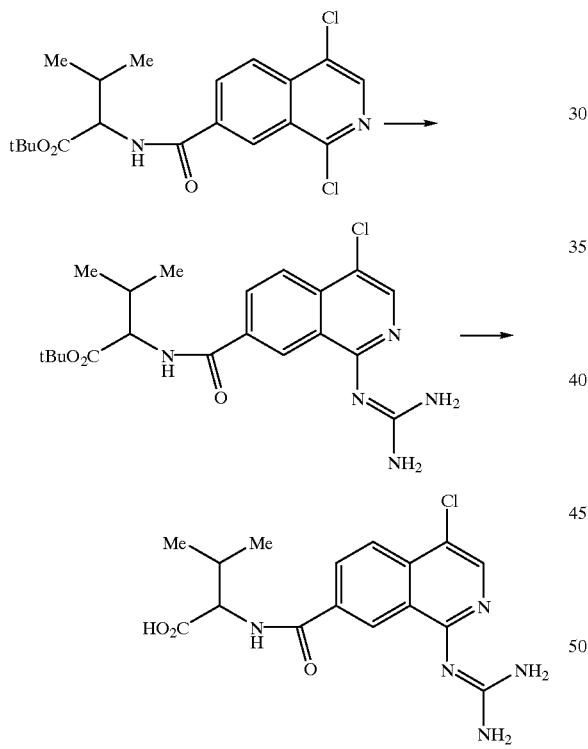

NaH (88 mg, 60% dispersion in mineral oil, 2.2 mmol) was added to a stirred solution of guanidine hydrochloride (210 mg, 2.2 mmol) in DMSO (5 mL) at 70° C. and the solution stirred for 30 min. N-[(1,4-Dichloro-7-isoquinolinyl) carbonyl]-DL-valine t-butyl ester (350 mg, 0.88 mmol) was added and the solution heated at 80–90° C. overnight. The cooled mixture was poured into water, extracted with EtOAc (3×20 mL), and the combined organic extracts were dried (MgSO₄) and evaporated in vacuo. The residue was crystallised with CH₂Cl₂-i-Pr₂O to give N-[(4-chloro-1-guanidino-7-isoquinolinyl)carbonyl]-DL-valine t-butyl ester (285 mg, 0.68 mmol) as a yellow solid.

mp 178–180° C. (dec).

¹H (CDCl₃, 300 MHz) shows 1:1 mixture of rotamers, δ 1.0 (½ of 6H, d), 1.05 (½ of 6H, d), 1.5 (9H, s), 2.2–2.4 (1H, m), 4.7 (½ of 1H, d), 4.75 (½ of 1H, d), 6.2–6.8 (4H, br s), 6.9 (1H, d), 8.05 (1H, d), 8.1 (1H, s), 8.15 (1H, d), 9.1 (1H, s) ppm.

LRMS 420 (MH⁺), 839 (M₂H⁺).

Anal. Found: C, 56.00; H, 6.35; N, 16.33. Calc for C₂₀H₂₆ClN₅O₃.0.5H₂O: C, 55.71; H, 6.36; N, 16.32.

A solution of N-[(4-Chloro-1-guanidino-7-isoquinolinyl) carbonyl]-DL-valine t-butyl ester (200 mg, 0.48 mmol) in CF₃CO₂H (1.5 mL) was stirred at 0° C. for 30 min, and at 23° C. for 1 h. The reaction mixture was diluted with PhMe, evaporated in vacuo, and the residue triturated with EtOAc to give N-[(4-chloro-1-guanidino-7-isoquinolinyl) carbonyl]-DL-valine trifluoroacetate (170 mg, 0.36 mmol) as a white solid.

mp 243–245° C. (dec).

¹H (DMSO-d₆, 300 MHz) shows a 1:1 mixture of rotamers, δ 0.95 (½ of 6H, d), 1.0 (½ of 6H, d), 2.15–2.3 (1H, m), 4.35 (1H, t), 8.25 (1H, d), 8.4 (1H, s), 8.45 (1H, d), 8.4–8.6 (4H, br s), 8.85 (1H, d), 8.9 (1H, s) ppm.

LRMS 364 (MH⁺).

Anal. Found: C, 44.96; H, 3.95; N, 14.56. Calc for C₁₆H₁₈ClN₅O₃.CF₃CO₂H: C, 45.24; H, 4.01; N, 14.65.

Example 56
(a) N-[(4-chloro-1-guanidino-7-isoquinolinyl)carbonyl]-DL-proline t-butyl ester
(b) N-1(4-Chloro-1-guanidino-7-isoquinolinyl)carbonyl]-DL-proline trifluoroacetate

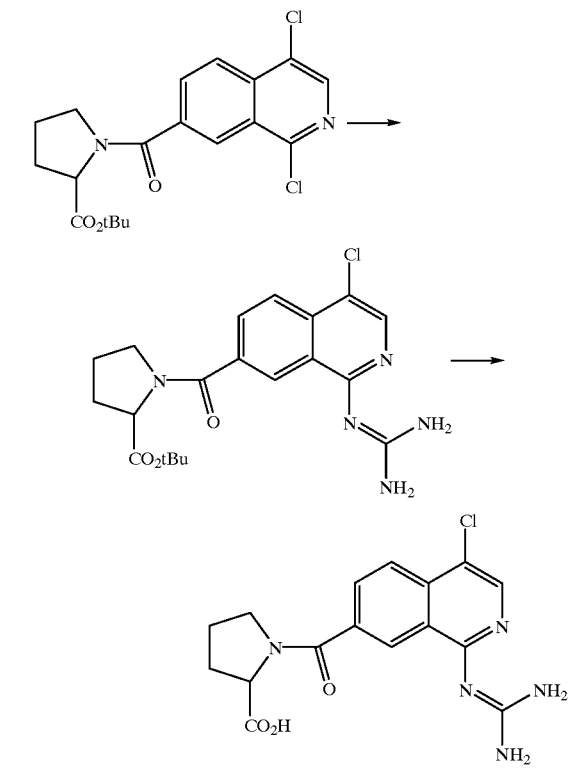

NaH (65 mg, 60% dispersion in mineral oil, 1.63 mmol) was added to a stirred solution of guanidine hydrochloride (154 mg, 1.61 mmol) in DMSO (5 mL) at 50° C. and the solution stirred for 15 min. N-[(1,4-Dichloro-7-isoquinolinyl) carbonyl]-DL-proline t-butyl ester (253 mg, 0.64 mmol) was added and the mixture was heated at 80° C. overnight. The mixture was poured into water (20 mL) and extracted with EtOAc (×2). The combined organic extracts were washed with water, brine, dried over (MgSO$_4$), and evaporated in vacuo. The residue was crystallised with CH$_2$Cl$_2$-i-Pr$_2$O to give N-[(4-chloro-1-guanidino-7-isoquinolinyl)carbonyl]-DL-proline t-butyl ester (241 mg, 0.58 mmol).

mp 147–149° C. (dec).

$^1$H (CDCl$_3$, 300 MHz) shows 1:3 mixture of rotamers, δ 1.55 (9H, s), 1.8–2.1 (3H, m), 2.15–2.45 (1H, m), 3.55–3.65 (1H, m), 3.75–3.85 (1H, m), 4.35–4.45 (1H, m), 6.5–7.2 (4H, br m), 7.7 (¼ of 1H, d), 7.85 (¾ of 1H, d), 7.9–8.1 (2H, m), 8.85 (¼ of 1H, s), 8.95 (¾ of 1H, s) ppm.

LRMS 418 (MH$^+$), 835 (M$_2$H$^+$).

Anal. Found: C, 58.46; H, 6.49; N, 14.95. Calc for C$_{20}$H$_{24}$ClN$_5$O$_3$.0.4i-Pr$_2$O: C, 58.65; H, 6.50; N, 15.27.

A solution of N-[(4-Chloro-1-guanidino-7-isoquinolinyl) carbonyl]-DL-proline t-butyl ester (175 mg, 0.42 mmol) in CF$_3$CO$_2$H (1 mL) was stirred at room temperature for 1 h. The solution was diluted with PhMe, evaporated in vacuo, and the residue was triturated with Et$_2$O to give N-[(4-chloro-1-guanidino-7-isoquinolinyl)carbonyl]-DL-proline trifluoroacetate (156 mg, 0.33 mmol) as a white solid.

mp 185° C. (dec).

$^1$H (DMSO-d$_6$+1 drop TFA-d, 300 MHz) δ 1.8–2.1 (3H, m), 2.25–2.4 (1H, m), 3.45–3.7 (2H, m), 4.4–4.5 (1H, m), 8.0–8.6 (4H, m) ppm.

LRMS 362 (MH$^+$).

Anal. Found: C, 45.65; H, 3.84; N, 14.43. Calc for C$_{16}$H$_{16}$ClN$_5$O$_3$.CF$_3$CO$_2$H: C, 45.43; H, 3.60; N, 14.72.

Example 57

(a) N-[(4-chloro-1-guanidino-7-isoquinolinyl)carbonyl]-DL-phenylalanine 1-butyl ester (b) N-[(4-Chloro-1-guanidino-7-isoquinolinyl)carbonyl]-DL-phenylalanine trifluoroacetate

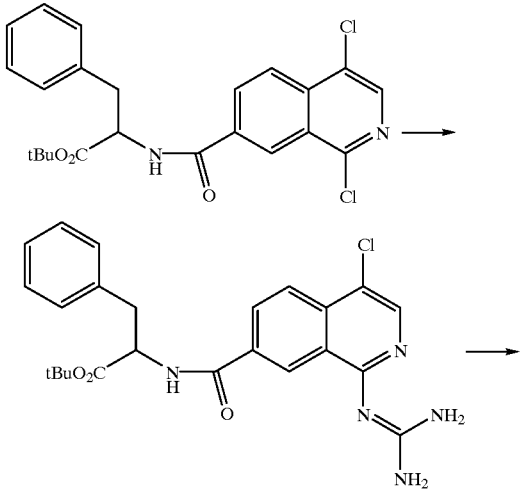

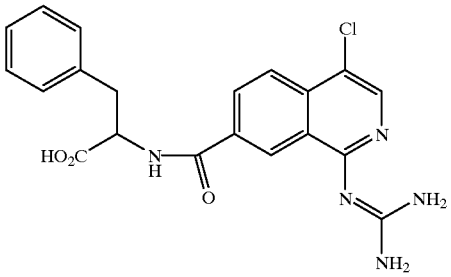

NaH (78 mg, 60% dispersion in mineral oil, 1.95 mmol) was added to a solution of guanidine hydrochloride (188 mg, 1.97 mmol) in DMSO (6 mL) at 50° C. and the solution was stirred for 15 min. N-[(1,4-Dichloro-7-isoquinolinyl) carbonyl]-DL-phenylalanine t-butyl ester (350 mg, 0.79 mmol) was added and the mixture heated at 80° C. overnight. The cooled mixture was poured into water (50 mL) and extracted with EtOAc (2×25 mL). The combined organics were washed with brine, dried (Na$_2$SO$_4$) and evaporated in vacuo. The residue was crystallised with CH$_2$Cl$_2$-i-Pr$_2$O to give N-[(4-chloro-1-guanidino-7-isoquinolinyl) carbonyl]-DL-phenylalanine t-butyl ester (172 mg, 0.37 mmol) as a cream coloured solid.

mp 201–203° C. (dec).

$^1$H (CDCl$_3$, 300 MHz) δ 1.45 (9H, s), 1.5–1.8 (1H, br m), 3.25 (2H, d), 5.0 (1H, dt), 6.0–6.8 (3H, br s), 6.9 (1H, d), 7.15–7.35 (5H, m), 8.0–8.1 (3H, m), 9.1 (1H, s) ppm.

LRMS 468 (MH$^+$), 935 (M$_2$H$^+$).

Anal. Found: C, 61.60; H, 5.60; N, 14.97. Calc for C$_{24}$H$_{26}$ClN$_5$O$_3$: C, 61.60; H, 5.76; N, 14.68.

A solution of N-[(4-Chloro-1-guanidino-7-isoquinolinyl) carbonyl]-DL-phenylalanine t-butyl ester (210 mg, 0.48 mmol) in CF$_3$CO$_2$H (1 mL) was stirred at room temperature for 1 h. The solution was diluted with PhMe, evaporated in vacuo, and the residue was triturated with Et$_2$O to give N-[(4-chloro-1-guanidino-7-isoquinolinyl)carbonyl]-DL-phenylalanine trifluoroacetate (196 mg, 0.37 mmol).

mp 192° C. (dec).

$^1$H (DMSO-d$_6$+1 drop TFA-d, 300 MHz) δ 3.1 (1H, dd), 3.25 (1H, dd), 4.7 (1H, dd), 7.1–7.35 (5H, m), 8.25 (1H, d), 8.35 (1H, s), 8.35 (1H, d), 8.9 (1H, s), 9.15 (½H, d partially exchanged amide NH) ppm.

LRMS 412 (MH$^+$).

Anal. Found: C, 50.92; H, 3.81; N, 13.57. Calc for C$_{20}$H$_{18}$ClN$_5$O$_3$.0.9CF$_3$CO$_2$H: C, 50.90; H, 3.70; N, 13.61.

Example 58

(a) N-[(4-chloro-1-guanidino-7-isoquinolinyl)carbonyl]-DL-leucine t-butyl ester (b) N-[(4-Chloro-1-guanidino-7-isoquinolinyl)carbonyl]-DL-leucine trifluoroacetate

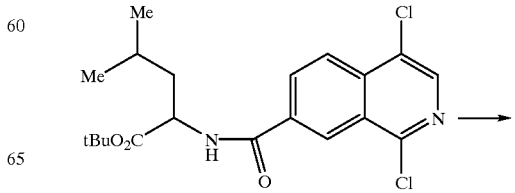

-continued

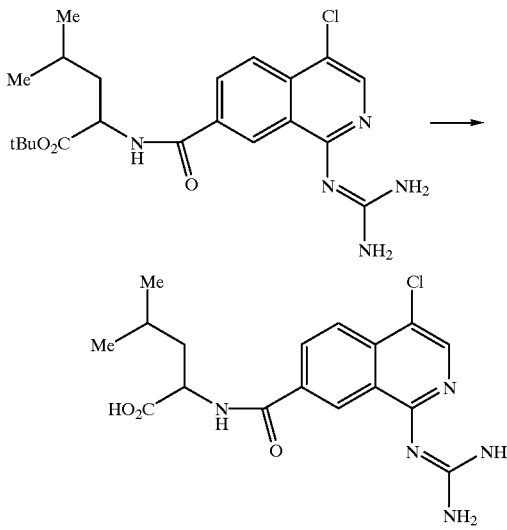

NaH (73 mg, 60% dispersion in mineral oil, 1.83 mmol) was added to a stirred solution of guanidine hydrochloride (174 mg, 1.82 mmol) in DMSO (6 mL) at 50° C. and the solution stirred for 15 min. N-[(1,4-Dichloro-7-isoquinolinyl) carbonyl]-DL-leucine t-butyl ester (300 mg, 0.73 mmol) was added and the solution heated at 80° C. overnight. The cooled mixture was poured into water (50 mL), extracted with EtOAc (2×25 mL) and the combined organic extracts were washed with brine, dried ($Na_2SO_4$) and evaporated in vacuo. The residue was crystallised with $CH_2Cl_2$-i-$Pr_2O$ to give N-[(4-chloro-1-guanidino-7-isoquinolinyl)carbonyl]-DL-leucine t-butyl ester (185 mg, 0.43 mmol).

mp 210–212° C. (dec).

$^1$H (CDCl$_3$, 300 MHz) δ 0.9–1.0 (6H, m), 1.5 (9H, s), 1.6–1.8 (3H, m), 4.7–4.8 (1H, m), 6.4–7.0 (4H, br s), 6.85 (1H, d), 8.05 (1H, d), 8.05 (1H, s), 8.15 (1H, d), 9.15 (1H, s) ppm.

LRMS 434 (MH$^+$), 866 ($M_2H^+$).

Anal. Found: C, 58.35; H, 6.75; N, 15.51. Calc for $C_2$,$H_2$,ClN$_5$O$_3$.0.15i-$Pr_2$O: C, 58.55; H, 6.75; N, 15.59.

A solution of N-[(4-chloro-1-guanidino-7-isoquinolinyl) carbonyl]-DL-leucine t-butyl ester (184 mg, 0.57 mmol) in $CF_3CO_2H$ (1 mL) was stirred at room temperature for 1 h. The solution was diluted with PhMe, evaporated in vacuo, and the residue was triturated with $Et_2O$ to give N-[(4-chloro-1-guanidino-7-isoquinolinyl)carbonyl]-DL-leucine trifluoroacetate (183 mg, 0.37 mmol).

mp 249° C.

$^1$H (DMSO-d$_6$, 300 MHz) 1:1 mixture of rotamers, δ 0.9 (½ of 6H, d), 0.95 (½ of 6H, d), 1.6–1.8 (3H, m), 4.45–4.5 (1H, m), 8.35 (1H, d), 8.4 (1H, s), 8.4 (1H, d), 8.3–8.6 (4H, br s), 8.95 (1H, s), 9.0 (1H, d) ppm.

LRMS 378 (MH$^+$).

Anal. Found: C, 46.3 1; H, 4.27; N, 14.08. Calc for $C_{17}H_{20}ClN_5O_3.CF_3CO_2H$: C, 46.39; H, 4.30; N, 14.24.

Example 59

(a) t-butyl DL-3-{[(4-chloro-1-guanidino-7-isoquinolinyl) carbonyl]amino}-3-phenylpropanoate (b) DL-3-{[(4-Chloro-1-guanidino-7-isoquinolinyl) carbonyl]amino}-3-phenylpropanoic acid trifluoroacetate

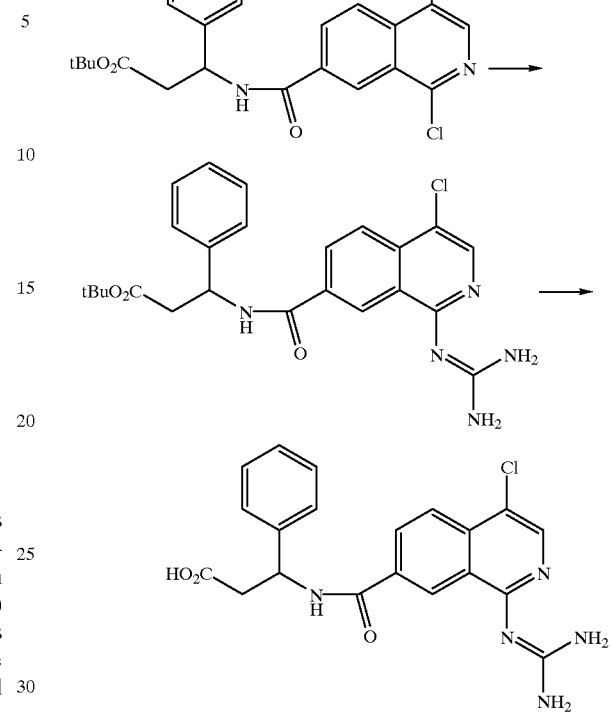

NaH (67 mg, 60% dispersion in oil, 1.68 mmol) was added to a solution of guanidine hydrochloride (161 mg, 1.69 mmol) in DMSO (6 mL) and the solution was heated to 50° C. for 15 mins. t-Butyl DL-3-[(1,4-dichloro-7-isoquinolinyl) carbonyl]amino}-3-phenylpropanoate (300 mg, 0.67 mmol) was added and the mixture heated at 80° C. overnight. The cooled mixture was poured into water (50 mL) and extracted with EtOAc (2×25 mL). The combined organic extracts were washed with brine, dried ($Na_2SO_4$) and evaporated in vacuo. The residue was crystallised with i-$Pr_2$O to give t-butyl DL-3-{[(4-chloro-1-guanidino-7-isoquinolinyl) carbonyl]amino}-3-phenylpropanoate (55 mg, 0.12 mmol) as a yellow solid.

mp 227° C. (dec).

$^1$H (CDCl$_3$+drop of DMSO-d$_6$, 300 MHz) δ 1.25 (9H, s), 2.75 (1H, dd), 2.85 (1H, dd), 5.5 (1H, ddd), 6.4–6.8 (4H, br s), 7.1–7.35 (5H, m), 7.8 (1H, d), 7.9 (1H, d), 7.95 (1H, s), 8.05 (1H, d), 9.05 (1H, s) ppm.

LRMS 468 (MH$^+$).

Anal. Found: C, 61.48; H, 5.62; N, 14.70. Calc for $C_{24}H_{26}ClN_5O_3$: C, 61.60; H, 5.60; N, 14.97.

A solution of t-butyl DL-3-{[(4-chloro-1-guanidino-7-isoquinolinyl)carbonyl]amino}-3-phenylpropanoate (153 mg, 0.33 mmol) in $CF_3CO_2H$ (1 mL) was stirred at room temperature for 1 h. The solution was diluted with PhMe, evaporated in vacuo, and the residue was triturated with $Et_2O$ to give DL-3-{[(4-chloro-1-guanidino-7-isoquinolinyl)carbonyl]amino}-3-phenylpropanoic acid trifluoroacetate (132 mg, 0.25 mmol).

mp 241–244° C.

$^1$H (DMSO-d$_6$+1 drop TFA-d, 300 MHz) δ 2.8 (1H, dd), 2.95 (1H, dd), 5.5–5.6 (1H, m), 7.2–7.35 (3H, m), 7.4 (2H, d), 8.25 (1H, d), 8.35 (1H, s), 8.4 (1H, d), 8.9 (1H, s) ppm.

LRMS 412 (MH$^+$).

Anal. Found: C, 49.95; H, 3.64; N, 13.03. Calc for $C_{20}H_{18}ClN_5O_3.CF_3CO_2H$: C, 50.25; H, 3.45; N, 13.32.

Example 60
(a) N-[(4-chloro-1-guanidino-7-isoquinolinyl)carbonyl]-DL-aspartic acid α,β-di-t-butyl ester
(b) N-[(4-Chloro-1-guanidino-7-isoquinolinyl)carbonyl]-DL-aspartic acid trifluoroacetate

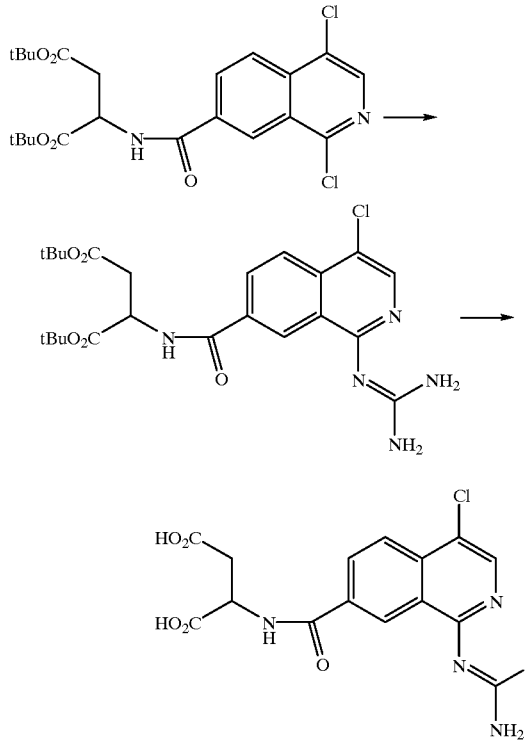

NaH (53 mg, 80% dispersion in mineral oil, 1.77 mmol) was added to a solution of guanidine hydrochloride (168 mg, 1.76 mmol) in DMSO (6 mL) and the solution ws heated to 50° C. for 30 min. N-[(1,4-Dichloro-7-isoquinolinyl)carbonyl]-DL-aspartic acid a,,-di-t-butyl ester (330 mg, 0.70 mmol) was added and the mixture heated at 80–90° C. overnight. The cooled mixture was poured into water (50 mL) and extracted with EtOAc extract (5×20 mL). The combined organic extracts were washed with water, brine, dried ($Na_2SO_4$) and evaporated in vacuo. The residue was purified by (i), trituration with i-$Pr_2O$ (ii), column chromatography on silica gel using $CH_2Cl_2$-MeOH-$0.880NH_3$ (95:5:0.5) as eluant, and (iii), crystallisation from i-$Pr_2O$, to give N-[(4-chloro-1-guanidino-7-isoquinolinyl)carbonyl]-DL-aspartic acid at,-di-t-butyl ester (145 mg, 0.29 mmol) as a yellow solid.

mp 165–167° C.

$^1$H ($CDCl_3$, 300 MHz) δ 1.45 (9H, s), 1.5 (9H, s), 2.9 (1H, dd), 3.0 (1H, dd), 4.95–5.0 (1H, m), 7.5 (1H, d), 7.95 (1H, s), 8.0 (1H, d), 8.15 (1H, d), 9.2 (1H, s) ppm.

LRMS 492 ($MH^+$), 983 ($M_2H^+$).

Anal. Found: C, 56.06; H, 6.28; N, 13.92. Calc for $C_{23}H_{20}ClN_5O_5$: C, 56.15; H, 6.15; N, 14.24.

A solution of N-[(4-chloro-1-guanidino-7-isoquinolinyl)carbonyl]-DL-aspartic acid α,β-di-t-butyl ester (120 mg, 0.24 mmol) in $CF_3CO_2H$ (1 mL) was stirred at room temperature for 1 h. The solution was diluted with PhMe, evaporated in vacuo, and the residue was triturated with $Et_2O$ to give N-[(4-chloro-1-guanidino-7-isoquinolinyl)carbonyl]-DL-aspartic acid trifluoroacetate (60 mg, 0.12 mmol).

mp 125° C. (dec).

$^1$H (TFA-d, 400 MHz) 5 3.3–3.4 (2H, m), 5.35–5.4 (1H, m), 8.25 (1H, d), 8.3 (1H, s), 8.45 (1H, d), 9.2 (1H, s) ppm.

LRMS 380 ($MH^+$), 758 ($M_2H^+$).

Anal. Found: C, 43.22; H, 3.75; N, 14.31. Calc for $C_{15}H_{14}ClN_5O_5.0.8CF_3CO_2H.0.25Et_2O$: C, 43.19; H. 3.56; N, 14.31.

Example 61
(a) O-i-butyl-N-[(4-chloro-1-guanidino-7-isoquinolinyl)carbonyl]-DL-serine t-butyl ester
(b) N-[(4-Chloro-1-guanidino-7-isoquinolinyl)carbonyl]-DL-serine trifluoroacetate

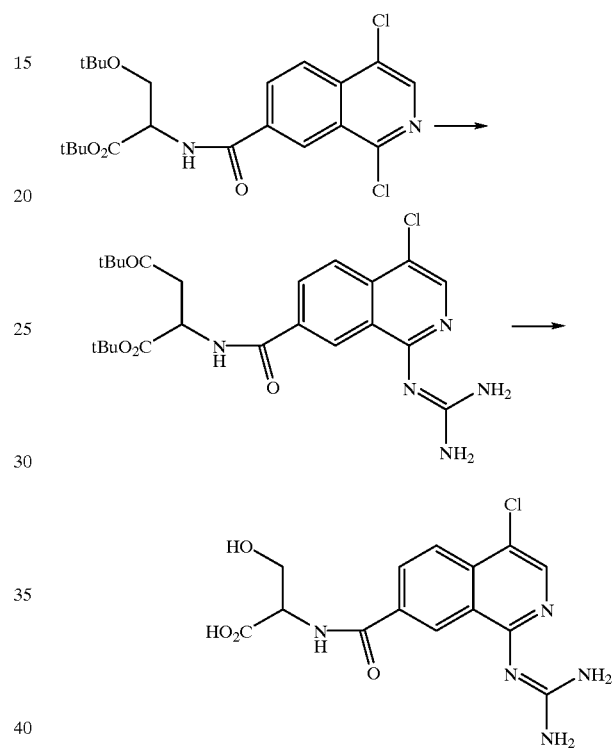

NaH (54 mg, 80% dispersion in mineral oil, 1.80 mmol) was added to a solution of guanidine hydrochloride (173 mg, 1.81 mmol) in DMSO (6 mL) and the solution was heated to 80° C. for 30 min. O-t-Butyl-N-[(1,4-dichloro-7-isoquinolinyl)carbonyl]-DL-serine t-butyl ester (330 mg, 0.70 mmol) was added and the mixture heated at 80° C. for 3 h. The cooled mixture was poured into water (50 mL) and extracted with EtOAc. The combined organic extracts were washed with water, brine, dried ($Na_2SO_4$) and evaporated in vacuo. The residue was crystallised with i-$Pr_2O$ to give O-t-butyl-N-[(4-chloro-1-guanidino-7-isoquinolinyl)carbonyl]-DL-serine t-butyl ester (138 mg, 0.30 mmol) as a yellow solid.

mp 215–219° C.

$^1$H ($CDCl_3$, 300 MHz) δ 1.2 (9H, s), 1.5 (9H, s), 1.5–1.7 (1H, br s), 3.75 (1H, dd), 3.95 (1H, dd), 4.8–4.9 (1H, m), 6.2–6.8 (3H, br s), 7.25–7.3 (1H, m), 8.0 (1H, s), 8.05 (1H, d), 8.15 (1H, d), 9.2 (1H, s) ppm.

LRMS 464 ($MH^+$), 927 ($M_2H^+$).

Anal. Found: C, 56.88; H, 6.65; N, 15.10. Calc for $C_{22}H_{30}ClN_5O_4.0.25H_2O.0.2i-Pr_2O$: C, 57.00; H, 6.87; N, 14.32.

A solution of O-t-butyl-N-[(4-chloro-1-guanidino-7-isoquinolinyl)carbonyl]-DL-serine t-butyl ester in $CF_3CO_2H$ (1 mL) was stirred at room temperature for 1 h.

The solution was diluted with PhMe, evaporated in vacuo, and the residue was recystallised twice from MeOH-EtOAc to give N-[(4-chloro-1-guanidino-7-isoquinolinyl)carbonyl]-DL-serine trifluoroacetate (68 mg, 0.19 mmol) as a white solid.

mp 203° C. (dec).

$^1$H (TFA-d, 400 MHz) δ 4.4 (1H, dd), 4.5 (1H, dd), 5.2–5.25 (1H, m), 8.35 (1H, s), 8.4 (1H, d), 8.5 (1H, d), 9.2 (1H, s) ppm.

LRMS 352 (MH$^+$), 703 (M$_2$H$^+$).

Anal. Found: C, 42.48; H, 3.69; N, 14.21. Calc for $C_{14}H_{14}ClN_5O_4.CF_3CO_2H.0.4EtOAc$: C, 42.19; H, 3.66; N, 13.98.

Example 62
(a) N-[(4-chloro-1-guanidino-7-isoquinolinyl)carbonyl]-DL-α-cyclopentylglycine t-butyl ester
(b) N-[(4-Chloro-1-guanidino-7-isoquinolinyl)carbonyl]-DL-α-cyclopentylglycine trifluoroacetate

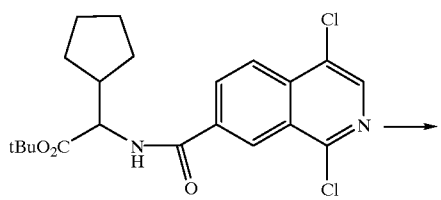

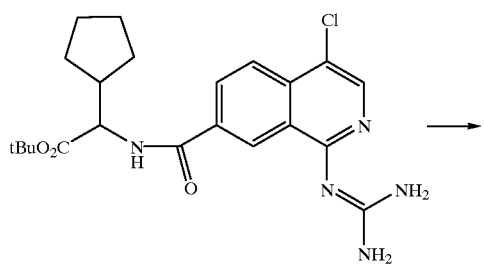

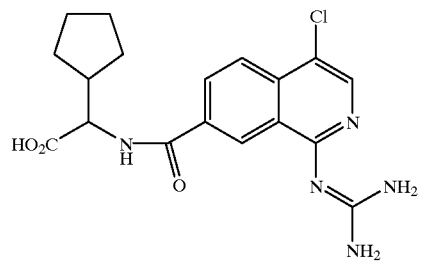

NaH (30 mg, 80% dispersion in mineral oil, 1.00 mmol) was added to a solution of guanidine hydrochloride (96 mg, 1.01 mmol) in DMSO (3 mL) and the solution was heated at 75–80° C. N-[(1,4-Dichloro-7-isoquinolinyl)carbonyl]-α-cyclopentylglycine t-butyl ester (170 mg, 0.40 mmol) was added and the mixture heated at 80° C. for 4.5 h. The cooled mixture was poured into water (25 mL) and extracted with EtOAc (3×20 mL). The combined organic extracts were washed with water, brine, dried (Na$_2$SO$_4$) and evaporated in vacuo to give N-[(4-chloro-1-guanidino-7-isoquinolinyl)carbonyl]-DL-α-cyclopentylglycine t-butyl ester (105 mg, 0.23 mmol) as a yellow solid.

An analytical sample was prepared as follows: this yellow solid was extracted with hot i-Pr$_2$O (3×20 mL), the hot solution was filtered, and on cooling gave the title compound as a pale yellow solid (40 mg) which was collected by filtration and dried in vacuo.

mp 219–221° C. (dec).

$^1$H (CDCl$_3$, 300 MHz) δ 1.4–1.8 (18H, m), 2.25–2.4 (1H, m), 4.7 (1H, dd), 6.2–6.9 (3H, br s), 6.95 (1H, d), 8.05 (1H, d), 8.1 (1H, s), 8.15 (1H, d), 9.15 (1H, s) ppm.

LRMS 446 (MH$^+$), 891 (M$_2$H$^+$).

Anal. Found: C, 58.83; H, 6.39; N, 15.34. Calc for $C_{22}H_{28}ClN_5O_3.0.2H_2O$: C, 58.78; H, 6.37; N, 15.30.

A solution of N-[(4-chloro-1-guanidino-7-isoquinolinyl)carbonyl]-DL-α-cyclopentylglycine t-butyl ester (65 mg, 0.15 mmol) in CF$_3$CO$_2$H (0.5 mL) was stirred at room temperature for 1 h. The solution was diluted with PhMe, evaporated in vacuo, and the residue was crystallised with EtOAc. This solid was then triturated with Et$_2$O to give N-[(4-chloro-1-guanidino-7-isoquinolinyl)carbonyl]-DL-α-cyclopentylglycine trifluoroacetate (52 mg, 0.10 mmol) as white powder.

mp 235° C. (dec).

$^1$H (TFA-d, 400 MHz) δ 1.4–1.8 (6H, m), 1.85–2.0 (2H, m), 2.4–2.55 (1H, m), 4.8 (1H, d), 8.25 (1H, d), 8.35 (1H, s), 8.45 (1H, d), 9.15 (1H, s) ppm.

LRMS 390 (MH$^+$), 779 (M$_2$H$^+$).

Anal. Found: C, 47.34; H, 4.36; N, 13.60. Calc for $C_{18}H_{20}ClN_5O_3.CF_3CO_2H$: C, 47.67; H, 4.20; N, 13.90.

Example 63
(a) N-Benzyl-N-[(4-chloro-1-guanidino-7-isoquinolinyl)carbonyl]glycine hydrochloride
(b) N-Benzyl-N-[(4-chloro-1-guanidino-7-isoquinolinyl)carbonyl]glycine hydrochloride

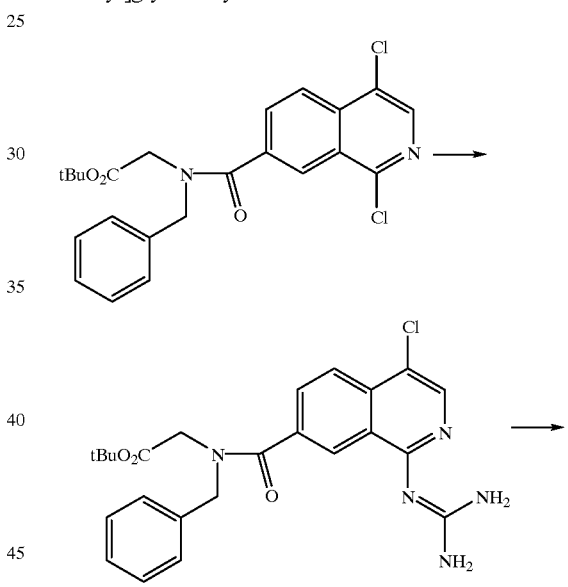

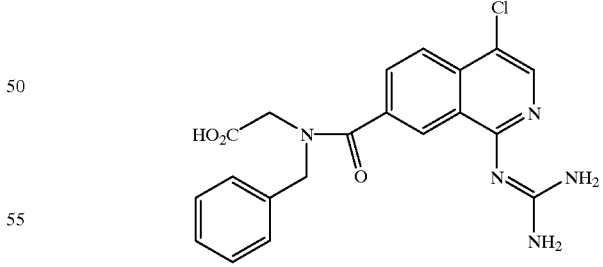

NaH (16 mg, 80% dispersion in mineral oil, 0.53 mmol) was added to a solution of guanidine hydrochloride (82 mg, 0.86 mmol) in DME (4 mL) and the mixture was heated at 60° C. for 30 min. A solution of N-benzyl-N-[(1,4-dichloro-7-isoquinolinyl)carbonyl]glycine t-butyl ester (95 mg, 0.21 mmol) in DME (2 mL) was added and the mixture was heated at 90° C. for 4 h. The cooled mixture was partioned between Et$_2$O and water, and the combined organic extracts were dried and evaporated in vacuo. The residue was dissolved in Et$_2$O and a solution of HCl in Et$_2$O (1M) was added to give a precipitate of N-benyl-N-[(4-chloro-1-guanidino-7-isoquinolinyl)carbonyl]glycine hydrochloride. Evaporation of the ethereal mother liquors gave recovered, unreacted N-benzyl-N-[(1,4-dichloro-7-isoquinolinyl) carbonyl]glycine t-butyl ester which was again reacted with guanidine (as above) to give a second batch. Total yield: 70 mg, 0.15 mmol.

mp 130° C. (dec).

$^1$H (DMSO-d$_6$, 400 MHz) 5:6 mixture of rotamers, δ 1.2 (⁶/₁₁ of 9H, s), 1.4 (⁵/₁₁ of 9H, s), 4.0 (⁶/₁₁ of 2H, s), 4.05 (⁵/₁₁ of 2H, s), 4.5 (⁵/₁₁ of 2H, s), 4.75 (⁶/₁₁ of 2H, s), 7.2–7.5 (5H,, m), 7.9–8.0 (1H, m), 8.2–8.3 (1H, m), 8.35 (1H, s), 8.75 (⁵/₁₁ of 1H, s), 8.85 (⁶/₁₁ of 1H, s) ppm.

LRMS 468 (MH$^+$), 934 (M$_2$H$^+$).

Anal. Found: C, 56.98; H, 5.71; N, 13.01. Calc for C$_{24}$H$_{26}$ClN$_5$O$_3$.HCl.0.5H$_2$O.0.2i-Pr$_2$O: C, 56.70; H, 5.82; N, 13.12.

A solution of N-benzyl-N-[(4-chloro-1-guanidino-7-isoquinolinyl)carbonyl]glycine hydrochloride (50 mg, 0.10 mmol) in CF$_3$CO$_2$H (1 mL) was stirred at room temperature for 1 h. The solution was diluted with PhMe, evaporated in vacuo, and the residue was triturated with Et$_2$O to afford a white solid (41 mg). This solid was dissolved in EtOAc and a solution of HCl in Et$_2$O was added which gave a precipitate. The mother liquors were decanted and the solid triturated with MeCN to give N-benyl-N-[(4-chloro-1-guanidino-7-isoquinolinyl)carbonyl]glycine hydrochloride (16 mg, 0.04 mmol) as an off-white powder.

$^1$H (TFA-d, 400 MHz) 1:4 mixture of rotamers, δ 4.2 (⅕ of 2H, s), 4.45 (⅘ of 2H, s), 4.7 (⅘ of 2H, s), 4.95 (115 of 2H, s), 7.2 (2H, d), 7.3–7.4 (3H, m), 8.15 (⅕ of 1H, d), 8.2 (⅘ of 1H, d), 8.4 (1H, s), 8.45 (⅕ of 1H, d), 8.5 (⅕ of 1H, d), 8.7 (⅕ of 1H, s), 8.8 (⅘ of 1H, s) ppm.

LRMS 412 (MH$^+$), 823 (M$_2$H$^+$), 845 (M$_2$Na$^+$).

Anal. Found: C, 52.55; H, 4.33; N, 15.10. Calc for C$_{20}$H$_{18}$ClN$_5$O$_3$.HCl.0.5H$_2$O: C, 52.52; H, 4.41; N, 15.32.

Example 64

(a) N-[(4-chloro-1-guanidino-7-isoquinolinyl)methyl]-N-methyl-DL-phenylglycine t-butyl ester
(b) N-[(4-chloro-1-guanidino-7-isoquinolinyl)methyl]-N-methyl-DL-phenylglycine t-butyl ester dihydrochloride
(c) N-[(4-Chloro-1-guanidino-7-isoquinolinyl)methyl]-N-methyl-DL-phenylglycine trifluoroacetate

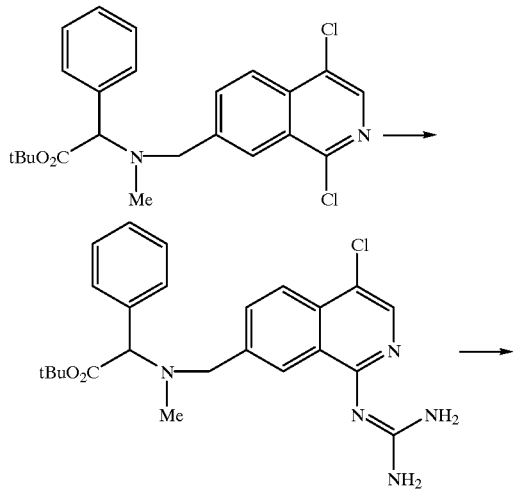

-continued

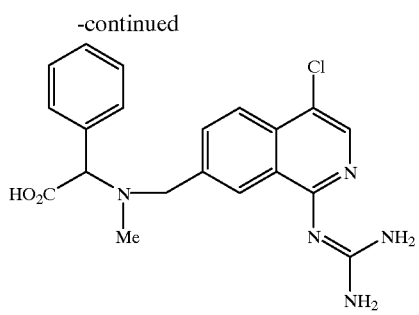

NaH (21 mg, 80% dispersion in mineral oil, 0.7 mmol) was added to t-BuOH (2.5 ml) and heated at 50° C. for 15 min. Guanidine hydrochloride (68 mg, 0.71 mmol) was added and heated at 50° C. for an additional 15 min. N-[(1,4-Dichloro-7-isoquinolinyl)methyl]-N-methyl-DL-phenylglycine t-butyl ester (102 mg, 0.24 mmol) was added and the mixture heated at 95° C. for 9.5 h. The cooled mixture was evaporated in vacuo and the residue was purified by column chromatography on silica gel using hexane-EtOAc (9:1), and then CH$_2$Cl$_2$-MeOH-0.880NH$_3$ (90:10:1) as eluant to give N-[(4-chloro-1-guanidino-7-isoquinolinyl)methyl]-N-methyl-DL-phenylglycine t-butyl ester (26 mg, 0.06 mmol) as a yellow gum. A portion of this material was dissolved in Et$_2$O, a solution of HCl in Et$_2$O was added and the resultant precipitate was triturated with hexane and then i-Pr$_2$O to give the corresponding dihydrochloride salt.

$^1$H (CD$_3$OD, 400 MHz) free base, δ 1.4 (9H, s), 2.2 (3H, s), 3.7 (1H, d), 3.8 (1H, d), 4.2 (1H, s), 7.3–7.4 (3H, m), 7.5 (2H, d), 7.9 (1H, d), 8.05 (1H, d), 8.05 (1H, s), 8.35 (1H, s) ppm.

LRMS 454 (MH$^+$).

Anal. Found: C, 51.89; H, 6.01; N, 12.42. Calc for C$_{24}$H$_{28}$ClN$_5$O$_2$.2HCl.1.5H$_2$O: C, 52.04; H, 6.01; N, 12.64.

A solution of N-[(4-chloro-1-guanidino-7-isoquinolinyl)methyl]-N-methyl-DL-phenylglycine 1-butyl ester (20 mg, 0.44 mmol) in CH$_2$Cl$_2$ (2 mL) was stirred with CF$_3$CO$_2$H (2 mL) at room temperature for 4 h. The solvents were evaporated in vacuo, and the residue was triturated with Et$_2$O and then EtOAc to give N-[(4-chloro-1-guanidino-7-isoquinolinyl)methyl]-N-methyl-DL-phenylglycine trifluoroacetate (6.5 mg, 0.02 mmol) as a white solid.

mp 180–182° C.

$^1$H (TFA-d, 400 MHz) 3:5 mixture of rotamers,δ 2.7 (⅝ of 3H, s), 3.05 (⅜ of 3H, s), 3.95–4.05 (⅜ of 1H, m), 4.55–4.7 (⅝ of 1H, m), 4.95–5.1 (1H, m), 5.35 (⅝ of 1H, s), 5.45 (⅜ of 1H, s), 7.4–7.7 (5H, m), 7.95 (⅜ of 1H, d), 8.1 (⅝ of 1H, d), 8.35 (1H, s), 8.4–8.65 (2H, m) ppm.

LRMS 400 (MH$^+$).

Anal. Found: C, 50.1 0; H, 4.27; N, 12.90. Calc for C$_{20}$H$_{21}$ClN$_5$O$_2$.CF$_3$CO$_2$H.H$_2$O: C, 49.87; H, 4.37; N, 13.22.

Example 65

(a) N-benzyl-N-[(4-chloro-1-guanidino-7-isoquinolinyl) methyl]glycine t-butyl ester
(b) N-Benzyl-N-[(4-chloro-1-guanidino-7-isoquinolinyl) methyl]glycine bistrifluoroacetate

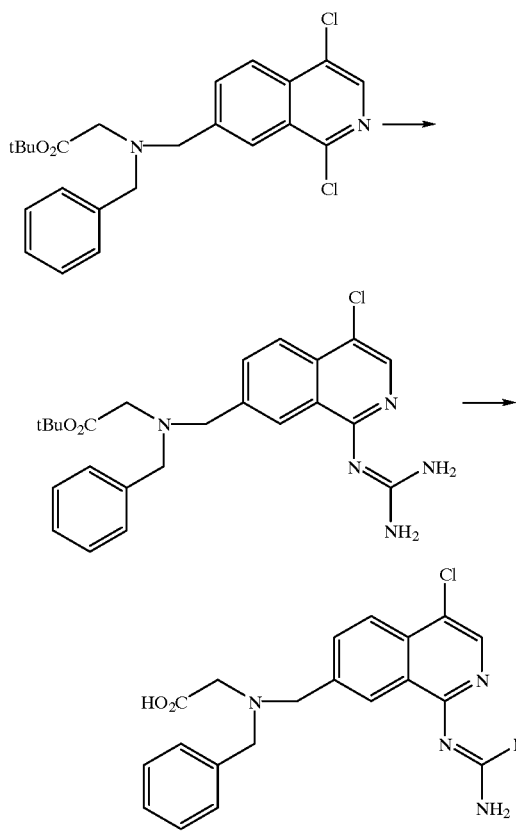

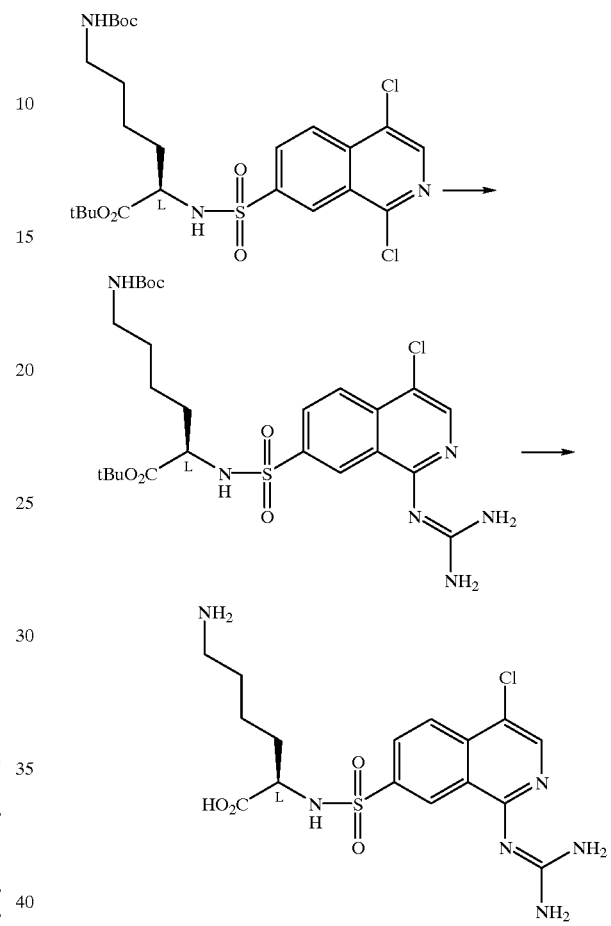

Example 66

(a) Nα-[(4-chloro-1-guanidino-7-isoquinolinyl)sulphonyl]-Nε-tert-butyloxycarbonyl-L-lysine tert-butyl ester (b) Nα-[(4-Chloro-1-guanidino-7-isoquinolinyl)sulphonyl]-L-lysine dihydrochloride.

NaH (48.6 mg, 80% dispersion in mineral oil, 1.62 mmol) was added to t-BuOH (5 mL) and heated to 50° C. for 15 min. Guanidine hydrocloride (155 mg, 1.62 mmol) was added and heated at 50° C. for an additional 20 min. N-Benzyl-N-[(1,4-dichloro-7-isoquinolinyl)methyl]glycine t-butyl ester (40 mg, 0.09 mmol) added and the mixture was then heated at 95° C. for 20 h. The cooled mixture was evaporated in vacuo and the residue purified by column chromatography on silica gel using $CH_2Cl_2$-MeOH-0.880$NH_3$ (95:5:0.5), followed by trituration with hexane and crystallisation with i-$Pr_2O$, to give N-benzyl-N-[(4-chloro-1-guanidino-7-isoquinolinyl)methyl]glycine t-butyl ester (5 mg, 0.01 mmol) as a white solid.

$^1$H (CD$_3$OD, 400 MHz) δ 1.45 (9H, s), 3.15 (2H, s), 3.8 (2H, s), 3.95 (2H, s), 7.2–7.4 (5H, m), 7.85–7.95 (1H, m), 8.0–8.1 (2H, m), 8.5–8.55 (1H, m) ppm.

LRMS 454 (MH$^+$), 907 (M$_2$H$^+$).

Anal. Found: C, 62.57; H, 6.13; N, 15.17. Calc for $C_{24}H_{27}ClN_5O_2.0.4H_2O$: C, 62.51; H, 6.29; N, 15.19.

A solution of N-benzyl-N-[(4-chloro-1-guanidino-7-isoquinolinyl)methyl]glycine t-butyl ester (16 mg, 0.04 mmol) in $CF_3CO_2H$ (1 mL) was stirred for at room temperature 1.5 h. The solution was diluted with PhMe, evaporated in vacuo, and the residue was triturated with $Et_2O$ to give N-benzyl-N-[(4-chloro-1-guanidino-7-isoquinolinyl)methyl]glycine bistrifluoroacetate (6 mg, 0.02 mmol) as a white solid.

mp 199° C. dec.

$^1$H (TFA-d, 400 MHz) δ 4.2 (2H, s), 4.6 (1H, d), 4.75 (1H, d), 4.85 (1H, d), 4.95 (1H, d), 7.3–7.5 (5H, m), 8.0 (1H, d), 8.3 (1H, s), 8.45 (1H, d), 8.55 (1H, s) ppm.

LRMS 398 (MH$^+$).

Anal. Found: C, 44.50; H, 3.81; N, 10.80. Calc for $C_{20}H_{20}ClN_5O_2.2CF_3CO_2H.1.2H_2O$: C, 44.52; H, 3.80; N, 10.82.

NaH (44 mg, 80% dispersion in mineral oil, 1.47 mmol) was added in a single portion to a solution of guanidine hydrochloride (224 mg, 2.35 mmol) in DMSO (5 ml) and stirred at room temperature until solution occurred. Na-[(1,4-dichloro-7-isoquinolinyl)sulphonyl]-Nε-tert-butyloxycarbonyl-L-lysine-tert-butyl ester (330 mg, 0.59 mmol) was added and the solution stirred at 100° C. for 6 h. After cooling, the reaction mixture was quenched with water (30 ml), extracted with EtOAc (3×20 ml) and the combined organic extracts washed with water and brine. The organic solution was evaporated in vacuo and the residue purified by column chromatography upon silica gel using $CH_2Cl_2$-MeOH-0.880 $NH_3$ (90:10:1) as eluant to give Nα-[(4-chloro-1-guanidino-7-isoquinolinyl)sulphonyl]-NE-tert-butyloxycarbonyl-L-lysine tert-butyl ester (152 mg, 0.26 mmol). An analytical sample was obtained by crystallisation from i-$Pr_2O$.

$^1$H (CDCl$_3$, 300 MHz) δ 1.15 (9H, s), 1.3–1.5 (13H, m), 1.5–1.8 (2H, m), 3.0–3.1 (2H, m), 3.8–3.9 (1H, m), 4.5–4.6 (1H, m), 5.2–5.4 (1H, m), 6.25–6.6 (3H, m), 8.0 (1H, d), 8.05 (1H, d), 8.1 (1H, s), 9.1 (1H, s) ppm.

LRMS 585 (MH$^+$).

Anal. Found: C, 51.02; H, 6.32; N, 14.12. Calc for $C_{25}H_{37}ClN_6O_6S$: C, 51.32; H, 6.37; N, 14.36.

Nα-[(4-Chloro-1-guanidino-7-isoquinolinyl) sulphonyl]-Nε-tert-butyloxycarbonyl-L-lysine tert-butyl ester (119 mg, 0.20 mmol) was dissolved in EtOAc (10 ml) and saturated with gaseous HCl. After 20 min, the resultant white precipitate was obtained by filtration and recrystallised from EtOH to give Nα-[(4-chloro-1-guanidino-7-isoquinolinyl)sulphonyl]-L-lysine (13 mg, 0.03 mmol).

$^1$H (DMSO-d$_6$+CF$_3$CO$_2$D, 300 MHz) δ 1.1–1.7 (6H, m), 2.65–2.75 (2H, m), 3.75–3.80 (1H, m), 8.25 (1H, d), 8.35 (1H, d), 8.25 (1H, s), 8.9 (1H, s) ppm.

LRMS 429 (MH$^+$).

Anal. Found: C, 37.00; H, 4.93; N, 15.72. Calc for C$_{16}$H$_{21}$ClN$_6$O$_4$S.2HCl. H$_2$O.0.15 EtOH: C, 37.15; H. 4.95; N, 15.97.

Example 67
Nα-[(4-Chloro-1-guanidino-7-isoquinolinyl)sulphonyl]-D-lysine dihydrochloride

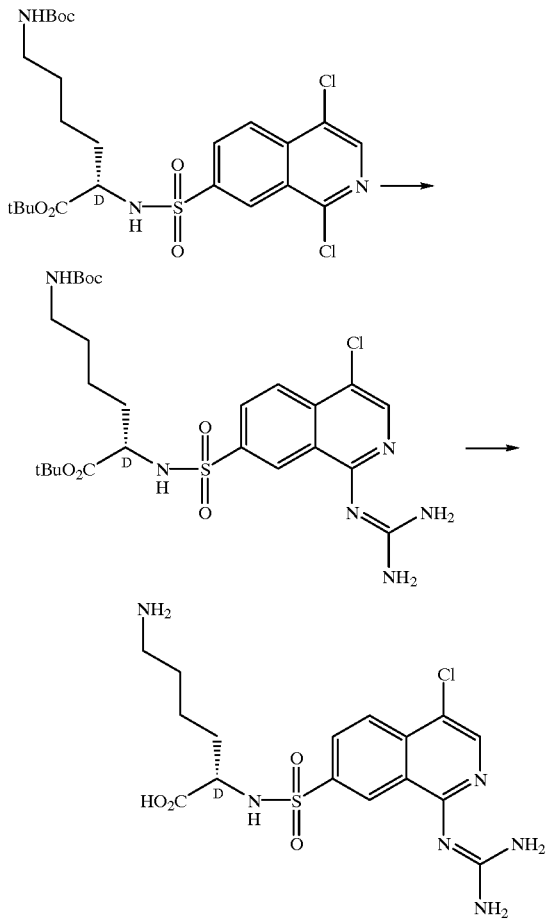

NaH (33 mg, 80% dispersion in mineral oil, 1.1 mmol) was added to a stirred solution of guanidine hydrochloride (170 mg, 1.78 mmol) in DMSO (3 ml) at 50° C. After 30 min, Nα-[(1,4-dichloro-7-isoquinolinyl)sulphonyl]-Nε-tert-butyloxycarbonyl-D-lysine tert-butyl ester (250 mg, 0.44 mmol) was added and the solution stirred at 90° C. for 8 h. The cooled mixture was poured into water and the precipitate extracted into Et$_2$O (4×15 ml). The combined organic extracts were washed with brine, dried (Na$_2$SO$_4$) and treated with 1N ethereal HCl. The solution was concentrated in vacuo, and the residue triturated with Et$_2$O and then EtOAc-EtOH to give Nα-[(4-chloro-1-guanidino-7-isoquinolinyl)sulphonyl]-D-lysine dihydrochloride (90 mg, 0.18 mmol).

$^1$H (DMSO-d$_6$, 400 MHz) δ 1.2–1.4 (2H, m), 1.4–1.7 (4H, m), 2.6–2.75 (2H, m), 3.9–4.0 (1H, m), 7.75–7.85 (3H, br s), 8.3 (1H, d), 8.35 (1H, d), 8.4 (1H, d), 8.4 (1H, s), 8.2–9.0 (3H, br m), 9.1 (1H, s) ppm.

LRMS 429 (MH$^+$).

Anal. Found: C, 36.15; H, 5.10; N, 15.06. Calc for C$_{16}$H$_2$,ClN$_6$O$_4$S. 2HCl.2H$_2$O.0.13 EtOAc: C, 36.18; H, 5.16; N, 15.25.

Example 68
(a) N-[(4-chloro-1-guanidino-7-isoquinolinyl)sulphonyl]-L-glutamine tert-butyl ester
(b) N-[(4-Chloro-1-guanidino-7-isoquinolinyl)sulphonyl]-L-glutamine trifluoroacetate

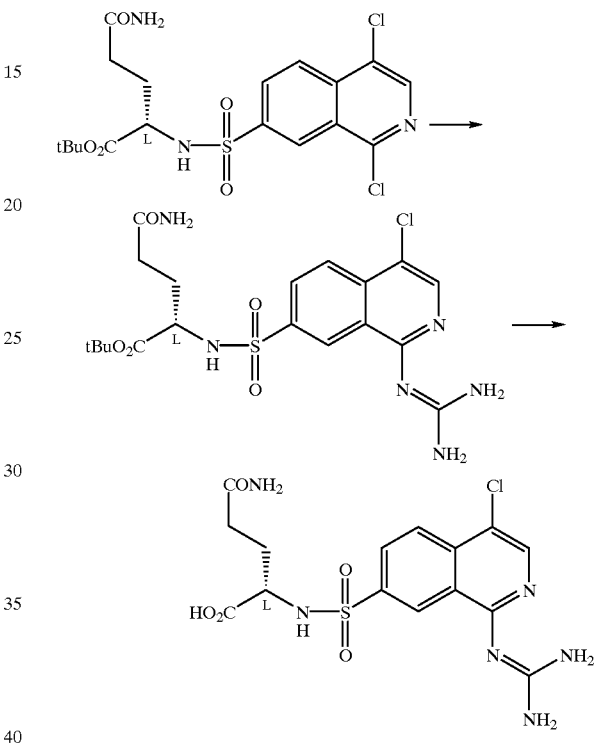

NaH (25 mg, 80% dispersion in mineral oil, 0.83 mmol) was added to a solution of guanidine hydrochloride (128 mg, 1.34 mmol) in DMSO (2 ml) and stirred at 50° C. for 1 h. N-[(1,4-Dichloro-7-isoquinolinyl)sulphonyl]-L-glutamine tert-butyl ester (150 mg, 0.32 mmol) was added and the resultant solution stirred at 100° C. for 6 h, allowed to cool and then poured into water. The aqueous mixture was extracted with EtOAc (3×30 ml) and concentrated in vacuo. The residue was purified by column chromatography upon silica gel using CH$_2$Cl$_2$-MeOH-0.880 NH$_3$ (90:10:1) as eluant to give N-[(4-chloro-1-guanidino-7-isoquinolinyl) sulphonyl]-L-glutamine tert-butyl ester (30 mg, 0.06 mmol) as a buff-coloured powder.

$^1$H (DMSO-d$_6$, 300 MHz) δ 1.0–1.2 (9H, s), 1.6–1.75 (1H, m), 1.75–1.9 (1H, m), 2.05–2.15 (2H, m), 3.26–3.8 (1H, m), 6.65–6.75 (1H, br s), 7.0–7.45 (5H, br m), 7.95–8.1 (3H, m), 8.35 (1H, d), 9.0 (1H, s) ppm.

LRMS 485 (MH$^+$).

N-[(4-Chloro-1-guanidino-7-isoquinolinyl)sulphonyl]-L-glutamine tert-butyl ester (15 mg, 0.03 mmol) was dissolved in trifluoroacetic acid (1 ml) and the resultant solution stirred at room temperature for 1 h, diluted with toluene and concentrated to a residue. Trituration with Et$_2$O gave a powder to which was added MeOH and the suspension filtered. The filtrate was concentrated and then triturated with EtOAc to give N-[(4-chloro-1-guanidino-7- isoquinolinyl)sulphonyl]-L-glutamine trifluoroacetate (9 mg, 0.02 mmol).

$^1$H (DMSO-d$_6$ +TFA-d, 300 MHz) δ 1.6–1.75 (1H, m), 1.8–2.0 (1H, m), 2.0–2.15 (2H, m), 3.8–3.9 (1H, m), 8.3 (1H, d), 8.35 (1H, d), 8.4 (1H, s), 8.8 (1H, s) ppm.

LRMS 429 (MH$^+$).

Example 69

(2R)-1-({4-Chloro-1-guanidino-7-isoquinolinyl}sulphonyl)-2-pyrrolidinecarboxamide

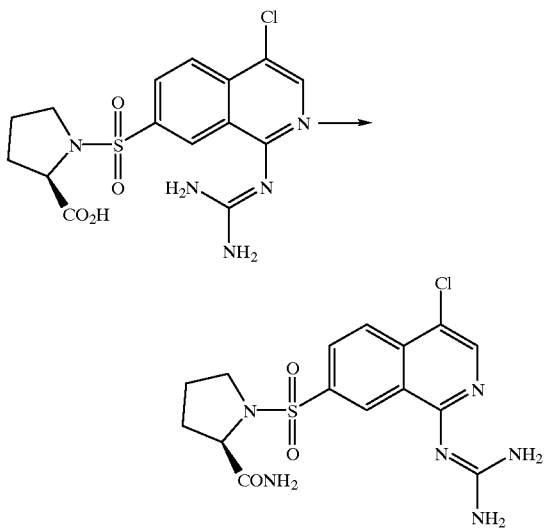

Oxalyl chloride (136 μl, 1.56 mmol) was added to a solution of N-[(4-chloro-1-guanidino-7-isoquinolinyl)sulphonyl]-D-proline (339 mg, 0.78 mmol) in CH$_2$Cl$_2$ (30 ml), followed by DMF (100 μl), and the reaction stirred at room temperature for 10 min. The mixture was evaporated in vacuo and azeotroped with toluene, to give an off-white solid. This was suspended in CH$_2$Cl$_2$ (15 ml), 0.880 NH$_3$ (760 μl, 7.8 mmol) added, and the reaction stirred at room temperature for 18 h. The mixture was partitioned between CH$_2$Cl$_2$ and water, and the layers separated. The aqueous phase was extracted with CH$_2$Cl$_2$, the combined organic solutions dried (MgSO$_4$) and evaporated in vacuo. The crude roduct was purified by column chromatography upon silica gel using an elution gradient of CH$_2$Cl$_2$-MeOH-0.880 NH$_3$ (100:0:0 to 95:5:0.1) to afford (2R)-1-({4-chloro-1-guanidino-7-isoquinolinyll}sulphonyl)-2-pyrrolidinecarboxamide (102 mg, 0.26 mmol) as a pale yellow solid.

$^1$H (d$_4$-MeOH, 400 MHz) δ 1.5–1.6 (1H, mn), 1.7–2.0 (3H, mn), 3.3–3.4 (1H, mn), 3.55–3.65 (1H, mn), 4.1–4.2 (1H, mn), 8.1–8.2 (3H, mn), 9.15 (1H, s) ppm.

LRMS 397 (MH$^+$), 419 (MNa)$^+$.

Anal. Found: C, 44.05; H, 4.42; N, 20.14. Calc for C$_{15}$H$_{17}$ClN$_6$O$_3$S+0.15CH$_2$Cl$_2$: C, 44.43; H, 4.26; N, 20.52.

Example 70
(2R)-1-({4-Chloro-1-guanidino-7-isoquinolinyl}sulphonyl)-N-(2-hydroxyethyl)-2-pyrrolidinecarboxamide.

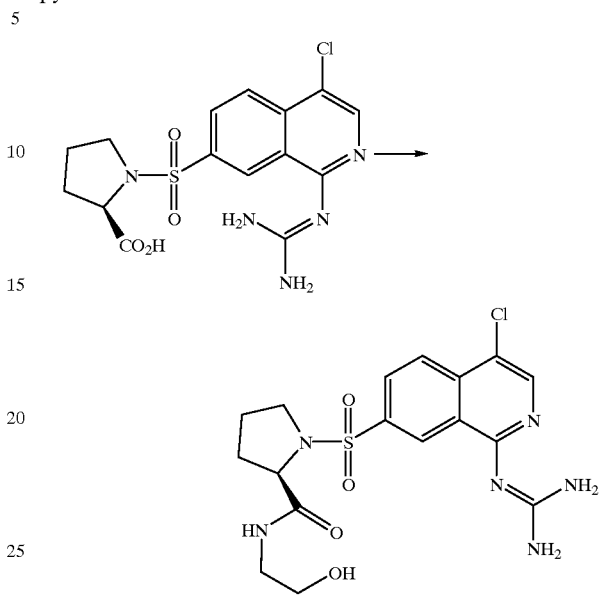

Oxalyl chloride (40 μl, 0.46 mmol) was added to a solution of N-[(4-chloro-1-guanidino-7-isoquinolinyl)sulphonyl]-D-proline (100 mg, 0.23 mmol) in CH$_2$Cl$_2$ (10 ml), followed by DMF (1 drop), and the reaction stirred at room temperature for 30 min. The mixture was evaporated in vacuo and azeotroped with toluene. The residue was dissolved in CH$_2$Cl$_2$ (5 ml), and added to a solution of ethanolamine (17 μl, 0.28 mmol) in CH$_2$Cl$_2$ (5 ml), the reaction stirred at room temperature for 2 h, then concentrated in vacuo. The crude product was purified by column chromatography upon silica gel using an elution gradient of CH$_2$Cl$_2$-MeOH-0.880 NH$_3$ (95:5:0.5 to 90:10:1) to afford (2R)-1-({4-chloro-1-guanidino-7-isoquinolinyl}sulphonyl)-N-(2-hydroxyethyl)-2-pyrrolidinecarboxamide (65 mg, 0.147 mmol) as a yellow foam.

$^1$H (DMSO-d$_6$, 300 MHz) δ 1.45–1.8 (4H, m), 3.15 (3H, m), 3.35–3.55 (3H, m), 4.1 (1H, m), 4.65 (1H, m), 7.9 (1H, m), 8.0 (1H, d), 8.15 (2H, m), 9.1 (1H, s) ppm.

LRMS 441, 443 (MH$^+$)

Anal. Found: C, 43.96; H, 4.89; H, 17.47. Calc. for C$_{17}$H$_{21}$ClN$_6$O$_4$S.0.4CH$_2$Cl$_2$: C, 44.01; H, 4.63; N, 17.70%.

Example 71
(a) tert-butyl (2R)-1-({4-chloro-1-guanidino-7-isoquinolinyl}sulphonyl)-2-piperidinecarboxylate
(b) (2R)-1-(14-Chloro-1-guanidino-7-isoquinolinyl}sulphonyl)-2-piperidinecarboxylic acid hydrochloride

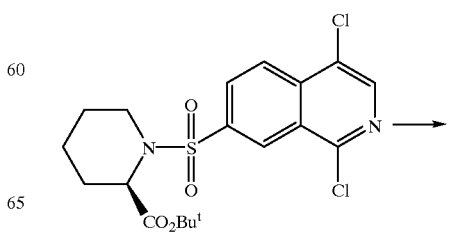

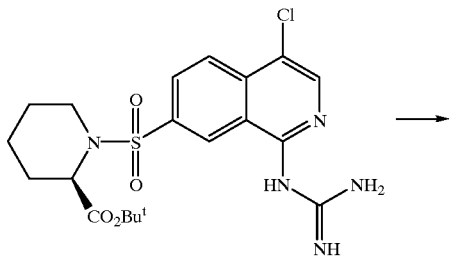

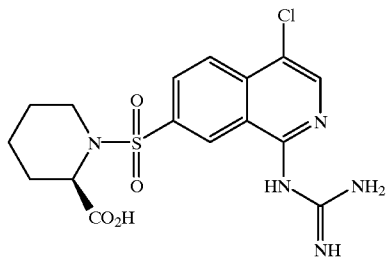

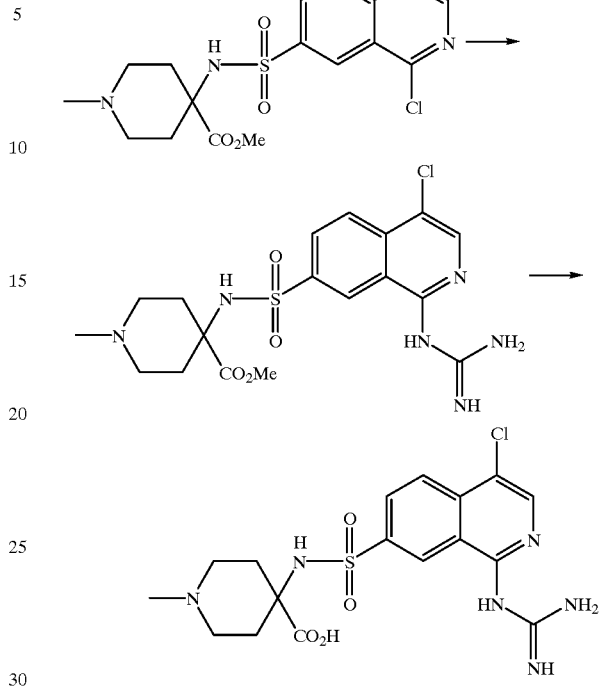

Guanidine hydrochloride (128 mg, 1.34 mmol) was added to a solution of NaH (32 mg, 80% dispersion in mineral oil, 1.07 mmol) in DME (5 ml), and the mixture stirred at 60° C., for 30 min. tert-Butyl (2R)-1-[(1,4-dichloro-7-isoquinolinyl)sulphonyl]-2-piperidinecarboxylate (150 mg, 0.34 mmol) was added and the reaction heated under reflux for 7 h, and stirred for a further 18 h at room temperature. The mixture was diluted with EtOAc, washed with water, brine, dried (MgSO$_4$), and evaporated in vacuo. The residual yellow gum was purified by column chromatography upon silica gel using CH$_2$Cl$_2$-MeOH-0.880 NH$_3$ (97:3:0.3) as eluant to give tert-butyl (2R)-1-({4-chloro-1-guanidino-7-isoquinolinyl}sulphonyl)-2-piperidinecarboxylate, as a yellow solid (126 mg, 0.27 mmol).

mp 157–158° C.

$^1$H (CDCl$_3$, 400 MHz) δ 1.3 (9H, s), 1.4 (1H, m), 1.6–1.8 (4H, m), 2.15 (1H, m), 3.3 (1, m), 3.85 (1H, m), 4.75 (1H, m), 8.0 (1H, d), 8.1 (1H, d), 8.15 (1H, s), 9.2 (1H, s) ppm.

LRMS 468 (MH$^+$)

Anal. Found: C, 51.23; H, 5.68; N, 14.51. Calc. for C$_{20}$H$_{26}$ClN$_5$O$_4$S: C, 51.33; H, 5.60; N, 14.97%.

A solution of tert-butyl (2R)-1-({4-chloro-1-guanidino-7-isoquinolinyl}sulphonyl)-2-piperidinecarboxylate (50 mg, 0.107 mmol) in EtOAc saturated with HCl (10 ml), was stirred at room temperature for 2 h. The solution was concentrated in vacuo, and azeotroped several times with CH$_2$Cl$_2$, to give (2R)-1-({4-chloro-1-guanidino-7-isoquinolinyl}sulphonyl)-2-piperidinecarboxylic acid hydrochloride (37 mg, 0.083 mmol) as a white solid.

mp dec>220° C.

$^1$H (CD$_3$OD, 400 MHz) δ 1.35 (1H, m), 1.5 (1H, m), 1.65–1.8 (3H, m), 2.2 (1H, m), 3.2–3.3 (2H, m), 3.95 (1H, m), 8.3 (1H, d), 8.45 (2H, m), 8.9 (1H, s) ppm. LRMS 412,414 (MH$^+$)

Example 72

(a) Methyl 4-[({4-chloro-1-guanidino-7-isoquinolinyl}sulphonyl)amino]-1-methyl-4-piperidinecarboxylate (b) 4-[({4-Chloro-1-guanidino-7-isoquinolinyl}sulphonyl)amino]-1-methyl-4-piperidinecarboxylic acid hydrochloride Guanidine hydrochloride (270 mg, 2.83 mmol) was added to a solution of NaH (65 mg, 80% dispersion in mineral oil, 2.16 mmol) in DMSO (6 ml), and the solution stirred at 60° C. for 30 min. Methyl 4-{[(1,4-dichloro-7-isoquinolinyl)sulphonyl]amino}-1-methyl-4-piperidinecarboxylate (300 mg, 0.7 mmol) was added and the reaction stirred at 80° C. for 5 h.

Additional NaH (30 mg, 1 mmol), and guanidine hydrochloride (135 mg, 1.4 mmol) in DMSO (1 ml) were added, and the reaction heated for a further 2½ h. The cooled mixture was poured into water, and extracted with EtOAc. The combined organic extracts were washed with brine, dried (Na$_2$SO$_4$) and evaporated in vacuo. The residual yellow solid was purified by column chromatography upon silica gel using an elution gradient of CH$_2$Cl$_2$-MeOH-0.880 NH$_3$ (95:5:0.5 to 90:10:1) to afford methyl 4-[({4-chloro-1-guanidino-7-isoquinolinyl}sulphonyl)amino]-1-methyl-4-piperidinecarboxylate (232 mg, 0.51 mmol).

mp dec>205° C.

$^1$H (CD$_3$OD, 400 MHz) δ 2.05 (4H, m), 2.15 (3H, s), 2.25 (2H, m), 2.4 (2H, m), 3.4 (3H, s), 8.05–8.15 (3H, m), 9.1 (1H, s) ppm.

LRMS 455 (MH$^+$)

Anal. Found: C, 47.17; H, 5.02; N, 17.96. Calc. for C$_{18}$H$_{23}$ClN$_6$O$_4$S.0.25H$_2$O: C, 47.06; H, 5.16; N, 18.29%.

A solution of methyl 4-[({4-chloro-1-guanidino-7-isoquinolinyl}sulphonyl)amino]-1-methyl-4-piperidinecarboxylate (100 mg, 0.22 mmol) in aqueous NaOH (2 ml, 2M, 4 mmol) and MeOH (5 ml) was stirred at 60° C. for 42 h. The cooled solution was neutralised using 2M HCl, and the mixture concentrated in vacuo, until precipitation occurred. The solid was filtered, dried and dissolved in concentrated HCl, and the solution evaporated in vacuo. The resulting solid was triturated with Et$_2$O, then i-PrOH, and dried under vacuum, to give 4-[({4-chloro-1-guanidino-7-isoquinolinyl}sulphonyl)amino]-1-methyl-4-piperidinecarboxylic acid hydrochloride (18 mg, 0.035 mmol).

¹H (DMSO-d₆, 400 MHz) δ 2.1 (2H, m), 2.3 (2H, m), 2.7 (3H, s), 2.8–3.0 (2H, m), 3.3 (2H, m), 8.25–8.75 (7H, m), 9.1 (1H, s) ppm.
LRMS 441 (MH⁺)

Example 73
(a) tert-butyl N-[(1-guanidino-7-isoquinolinyl)sulphonyl]-D-prolinecarboxylate
(b) N-[(1-Guanidino-7-isoquinolinyl)sulphonyl]-D-proline hydrochloride

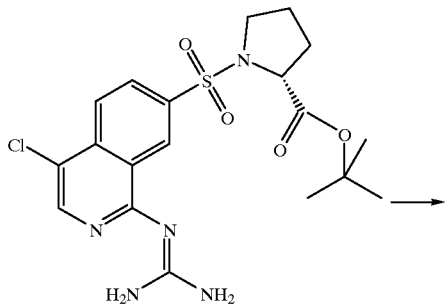

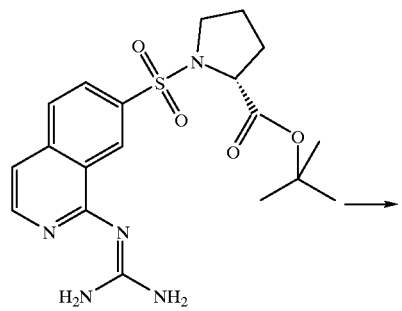

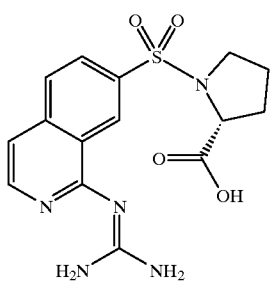

A mixture of tert-butyl N-[(4-chloro-1-guanidino-7-isoquinolinyl)sulphonyl]-D-prolinecarboxylate (200 mg, 0,44 mmol) and 5% palladium on charcoal (150 mg) in EtOH (30 ml) was hydrogenated at 50 psi and 50° C. for 24 h. The cooled mixture was filtered through Arbocel®, and the filter pad washed well with EtOH. The combined filtrates were concentrated in vacuo and the residue purified by column chromatography upon silica gel using an elution gradient of CH₂Cl₂-MeOH-0.880 NH₃ (97:3:0.3 to 95:5:0.5) to afford tert-butyl N-[(1-guanidino-7-isoquinolinyl) sulphonyl]-D-prolinecarboxylate (143 mg, 0.34 mmol) as an off-white solid.

¹H (CDCl₃, 400 MHz) δ 1.45 (9H, s), 1.75 (1H, m), 1.95 (3H, m), 3.4 (1H, m), 3.55 (1H, m), 4.3 (1H, m), 7.1 (1H, d), 7.75 (1H, d), 8.0 (1H, d), 8.15 (1H, d), 9.25 (1H, s) ppm.
LRMS 420 (MH⁺)

A solution of tert-butyl N-[(1-guanidino-7-isoquinolinyl) sulphonyl]-D-prolinecarboxylate (130 mg, 0.31 mmol) in EtOAc saturated with HCl (7 ml) was stirred at room temperature for 1 h. The reaction mixture was evaporated in vacuo and azeotroped with CH₂Cl₂, to give N-[(1-guanidino-7-isoquinolinyl)sulphonyl]-D-proline hydrochloride (118 mg, 0.295 mmol) as a white solid.
mp dec>250° C.

¹H (DMSO-d₆, 400 MHz) δ 1.6 (1H, m), 1.75–1.95 (3H, m), 3.2 (1H, m), 3.4 (1H, m), 4.4 (1H, m), 7.7 (1H, m), 8.2 (2H, m), 8.3 (1H, m), 9.05 (1H, s) ppm.
LRMS 364 (MH⁺)

Example 74
1-[({4-Chloro-1-guanidino-7-isoquinolinyl}sulphonyl) amino]-N-methyl-N-[2-(methylamino)ethyl] cyclopentanecarboxamide hydrochloride

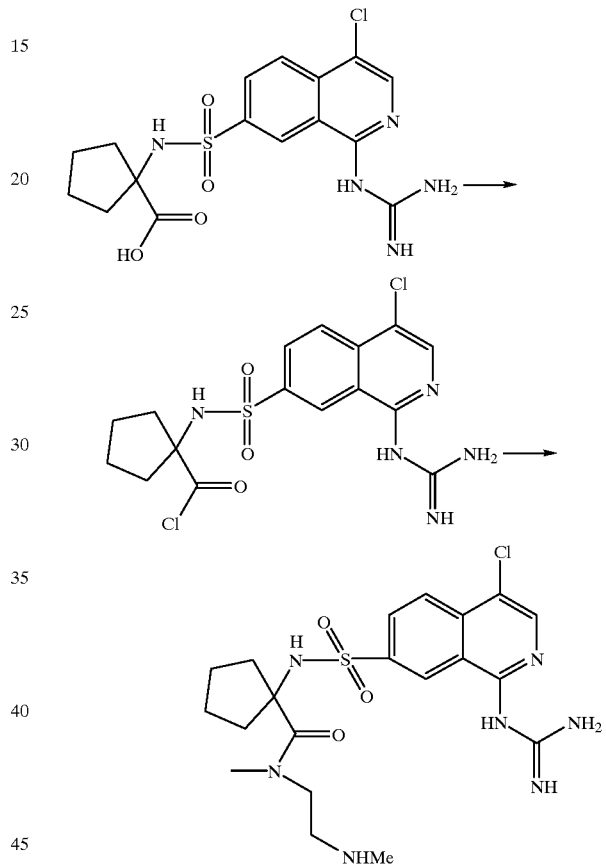

DMF (5 drops) was added to a suspension of 1-{[(1-guanidino-4-chloro-7-isoquinolinyl)sulphonyl] amino}cyclopentanecarboxylic acid hydrochloride (1.1 g, 2.46 mmol) in CH₂Cl₂ (100 ml), followed by oxalyl chloride (319 μl, 3.68 mmol), and the reaction stirred at room temperature for 45 min. Additional oxalyl chloride (106 μl, 1.23 mmol) was added, and stirring continued for a further 30 min. The mixture was evaporated in vacuo, triturated with CH₂Cl₂ and the residue then dissolved in CH₂Cl₂ (100 ml). This solution of acid chloride (10 ml) was added to a solution of N,N'-dimethylethylenediamine (500 μl, 4.7 mmol) in CH₂Cl₂ (20 ml) and the resultant solution stirred at room temperature for 1 h. After evaporation to dryness, the residue was partitioned between water and CH₂Cl₂, the aqueous layer separated and extracted with EtOAc. The combined organic extracts were dried (Na₂SO₄), evaporated to a gum and purified by column chromatography upon silica gel eluting with CH₂Cl₂-MeOH-0.880 NH₃ (90:10:1) as eluant, to give an oil. This was dissolved in EtOAc, treated with ethereal HCl (1N), and the white precipitate, filtered and triturated with Et₂O, i-Pr₂O, and EtOH to yield the title compound (28 mg, 0.058 mmol).

mp 206° C. (foams).

¹H (DMSO-d₆, 400 MHz) δ 1.35 (4H, m), 1.7 (2H, m), 2.0 (2H, m), 2.6 (3H, s), 3.05 (2H, m), 3.2 (3H, s), 3.4 (2H, m), 3.5 (2H, m), 8.35 (1H, d), 8.4 (1H, d), 8.45 (1H, s), 8.6–8.8 (4H, m), 9.2 (1H, s) ppm.

LRMS 482, 484 (MH⁺).

Example 75
1-[({4-Chloro-1-guanidino-7-isoquinolinyl}sulphonyl) amino]-N-(2-hydroxyethyl)-N-methylcyclopentanecarboxamide hydrochloride

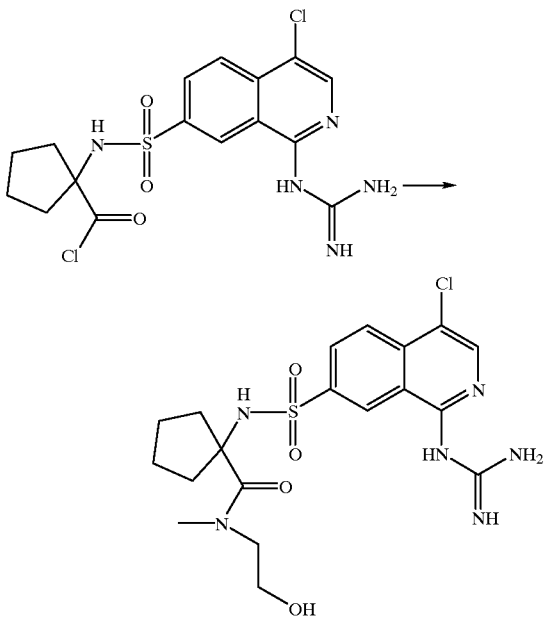

A suspension of 1-{[(4-chloro-1-guanidino-7-isoquinolinyl) sulphonyl]amino}cyclopentanecarbonyl chloride (110 mg, 0.245 mmol) in CH₂Cl₂ (10 ml) (prepared as described in example 76) was added over a minute to a solution of N-methylethanolamine (500 μl, 6.25 mmol) in CH₂Cl₂ (10 ml), and the resulting yellow solution stirred at room temperature for 72 h. The reaction mixture was evaporated in vacuo and the residue purified by column chromatography upon silica gel using CH₂Cl₂-MeOH-0.880 NH₃ (90:10:1) as eluant to give a clear gum. This was dissolved in EtOAc, ethereal HCl (1N) added, the mixture evaporated in vacuo and triturated with EtOAc. The resulting solid was filtered and dried under vacuum at 50° C. to give 1-[({4-chloro-1-guanidino-7-isoquinolinyl}sulphonyl)amino]-N-(2-hydroxyethyl)-N-methylcyclopentanecarboxamide hydrochloride.

¹H (DMSO-d₆, 400 MHz) δ 1.4 (4H, m), 1.8 (2H, m), 2.0 (2H, m), 2.6 (1H, m), 3.05–3.2 (4H, m), 3.35–3.6 (4H, m), 8.3 (1H, d), 8.4 (1H, d), 8.45 (1H, s), 8.55 (4H, m), 9.0 (1H, s), 11.0 (1H, s) ppm.

LRMS 468, 471 (MH⁺)

Anal. Found: C, 41.87; H. 5.55; N. 15.40. Calc. for C₁₉H₂₅ClN₆O₄S.HCl.2H₂O: C, 42.15; H. 5.58; N. 15.52%.

Example 76
1-[({4-Chloro-1-guanidino-7-isoquinolinyl}sulphonyl) amino]-N-(2-methoxyethyl)cyclopentanecarboxamide hydrochloride

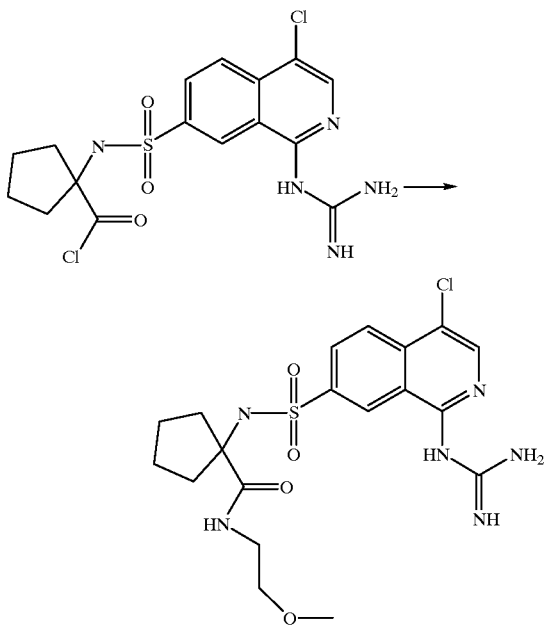

1-[({4-Chloro-1-guanidino-7-isoquinolinyl}sulphonyl) amino]-N-(2-methoxyethyl)cyclopentanecarboxamide was prepared from 2-methoxyethylamine and 1-{[(4-chloro-1-guanidino-7-isoquinolinyl)sulphonyl] amino}cyclopentanecarbonyl chloride, following the same procedure described in example 76. This product was treated with ethereal HCl (1N) and the mixture evaporated in vacuo. The residual solid was dissolved in EtOH, water (1 drop) added, the solution concentrated in vacuo until precipitation occured, and the resulting solid filtered, washed with Et₂O, and dried under vacuum, at 50° C., to afford 1-[({4-chloro-1-guanidino-7-isoquinolinyl}sulphonyl)amino]-N-(2-methoxyethyl)cyclopentanecarboxamide hydrochloride (35 mg, 28%).

¹H (DMSO-d₆, 300 MHz) δ 1.3–1.5 (4H, m), 1.9 (4H, m), 2.95 (2H, m), 3.2 (5H, m), 7.55 (1H, t), 8.2 (1H, s), 8.35 (2H, m), 8.45 (1H, s), 8.6 (4H, m), 9.1 (1H, s) ppm.

LRMS 469, 471 (MH⁺)

Anal. Found: C, 43.33; H, 5.38; N, 15.82. Calc. for C₁₉H₂₅ClN₆O₄S.HCl.1.2H₂O: C, 43.30; H, 5.43; N, 15.95%.

Example 77

(a) N-(2-tert-butyl aminoethylcarbamate)-1-[({4-chloro-1-guanidino-7-isoquinolinyl}sulphonyl)amino] cyclopentanecarboxamide (b) N-(2-Aminoethyl)-1-[({4-chloro-1-guanidino-7-isoquinolinyl}sulphonyl)amino]cyclopentane-carboxamide dihydrochloride

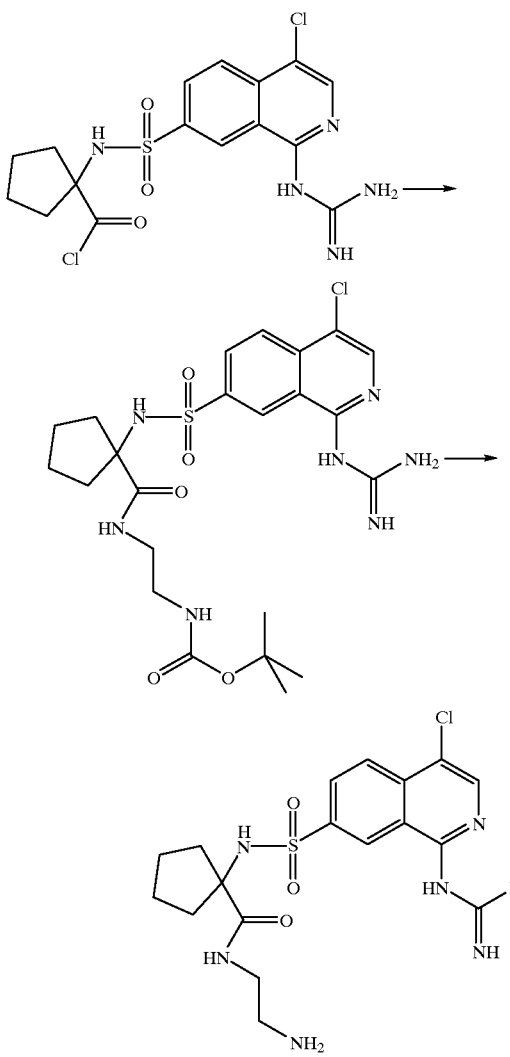

A suspension of 1-{[(4-chloro-1-guanidino-7-isoquinolinyl) sulphonyl]amino}cyclopentanecarbonyl chloride (220 mg, 0.49 mmol) was added to a solution of tert-butoxy 2-aminoethylcarbamate (250 mg, 1.56 mmol) in $CH_2Cl_2$ (10 ml), and the reaction stirred at room temperature for 18 h. The mixture was evaporated in vacuo and the residue purified by column chromatography upon silica gel using $CH_2Cl_2$-MeOH-0.880 $NH_3$(90:10:1) as eluant to give a yellow oil. This product was crystallised from MeOH-i-$Pr_2O$ to afford N-(2-tert-butyl aminoethylcarbamate)-1-[({4-chloro-1-guanidino-7-isoquinolinyl}sulphonyl)amino] cyclopentanecarboxamide (27 mg, 0.05 mmol) as a pale yellow solid.

$^1H$ ($CDCl_3$, 300 MHz) δ 1.3 (1H, m), 1.4 (2H, m), 1.8 (2H, m), 1.9 (2H, m), 2.45 (2H, m), 3.05 (4H, m), 5.65 (1H, m), 6.8 (4H, m), 7.1 (1H, m), 7.2 (1H, m), 7.9 (3H, m), 9.1 (1H, s) ppm.

LRMS 576 ($MNa^+$)

A solution of N-(2-tert-butyl aminoethylcarbamate)-1-[({4-chloro-1-guanidino-7-isoquinolinyl}sulphonyl)amino] cyclopentanecarboxamide (20 mg, 0.036 mmol) in ethereal HCl (1 ml, 1N) was stirred at room temperature for 2 h. The reaction mixture was diluted with MeOH, concentrated in vacuo, and the residue triturated with $Et_2O$, then i-$Pr_2O$, and dried, to give N-(2-aminoethyl)-1-[({4-chloro-1-guanidino-7-isoquinolinyl}sulphonyl)amino] cyclopentanecarboxamide dihydrochloride (16 mg, 0.30 mmol) as an off-white powder $^1H$ (DMSO-$d_6$, 400 MHz) δ 1.6 (4H, m), 1.85 (2H, m), 1.9 (2H, m), 2.8 (2H, m), 3.2 (2H, m), 5.4 (1H, br s), 7.9 (2H, br s), 8.05 (1H, m), 8.2 (1H, s), 8.4 (1H, m), 8.45 (1H, s), 8.55–8.75 (4H, m), 9.25 (1H, s) ppm.

LRMS 454 ($MH^+$)

Example 78

4-Chloro-1-guanidino-N-[1-(morpholinocarbonyl) cyclopentyl]-7-isoquinolinesulphonamide hydrochloride

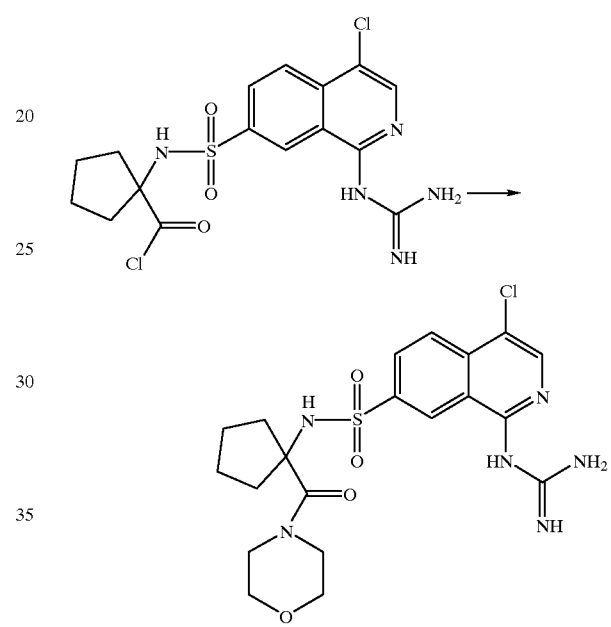

The title compound was prepared from 1-{[(4-chloro-1-guanidino-7-isoquinolinyl)sulphonyl] amino}cyclopentanecarbonyl chloride, and morpholine, following a similar procedure to that described in example 74.

$^1H$ (DMSO-$d_6$, 300 MHz) δ 1.35 (4H, m), 1.7 (2H, m), 2.0 (2H, m), 3.4–3.65 (8H, m), 8.35–8.65 (8H, m), 8.95 (1H, s) ppm.

LRMS 480, 482 ($MH^+$)

Example 79

4-Chloro-1-guanidino-N-{1-[(4-methylpiperazino) carbonyl]cyclopentyl}-7-isoquinolinesulphonamide dihydrochloride

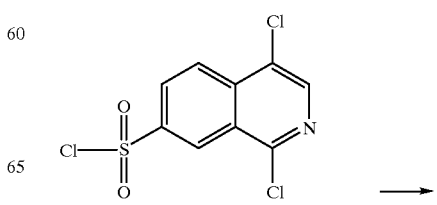

-continued

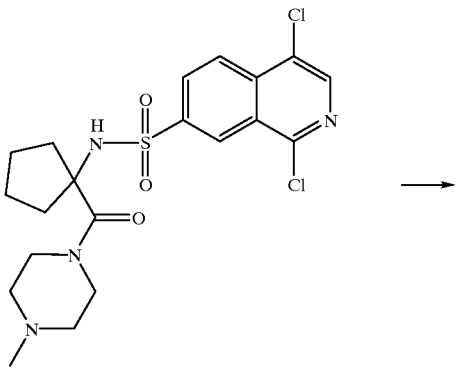

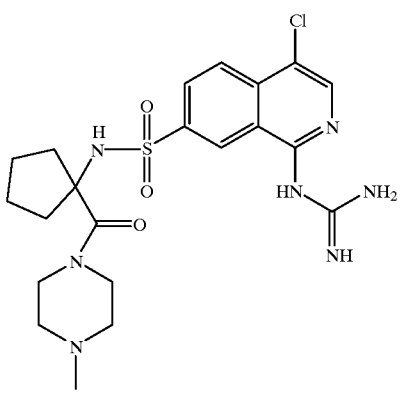

Triethylamine (1.36 ml, 10.0 mmol) was added to a solution of (1-aminocyclopentyl)(4-methyl-1-piperazinyl) methanone dihydrochloride (567 mg, 2.0 mmol) and 1,4-dichloro-7-isoquinolinesulphonyl chloride (592 mg, 2.0 mmol) in $CH_2Cl_2$ (25 ml), and the reaction stirred at room temperature for 18 h. The mixture was concentrated in vacuo and the residue partitioned between EtOAc and water, and the layers separated. The organic phase was washed with water, extracted with HCl (2N), and these combined acidic extracts washed with EtOAc, and re-basified using $Na_2CO_3$. This aqueous solution was extracted with EtOAc, the combined organic extracts washed with brine, dried ($Na_2SO_4$) and evaporated in vacuo to give a foam. This was crystallised from $CH_2Cl_2$-i-$Pr_2O$ to afford 1,4-dichloro-N-{1-[(4-methyl-1-piperazinyl)carbonyl]cyclopentyl}-7-isoquinolinesulphonamide (153 mg, 0.33 mmol) as a solid.

$^1$H ($CDCl_3$, 300 MHz) δ 1.5–1.75 (6H, m), 2.25–2.45 (9H, m), 3.6 (4H, m), 5.1 (1H, s), 8.25 (1H, d), 8.35 (1H, d), 8.5 (1H, s), 8.9 (1H, s) ppm.

Anal. Found: C, 49.12; H, 5.02; N, 1.06. Calc. for $C_{20}H_{24}Cl_2N_4O_3S.0.3CH_2Cl_2$: C, 49.07; H, 4.99; N, 11.28%.

NaH (22 mg, 80% dispersion in mineral oil, 0.73 mmol) was added to a solution of guanidine hydrochloride (142 mg, 1.49 mmol) in DMSO (2 ml), and the solution stirred at 50° C. for 30 min. 1,4-Dichloro-N-{1-[(4-methyl-1-piperazinyl)carbonyl]cyclopentyl}-7-isoquinolinesulphonamide (140 mg, 0.28 mmol) was added and the reaction stirred at 90° C. for 5 h. The cooled reaction was poured into water, the mixture extracted with EtOAc, and the combined extracts washed with brine, dried ($Na_2SO_4$) and evaporated in vacuo. The residual yellow foam was dissolved in i-PrOH, ethereal HCl (1N) was added, the solution evaporated in vacuo and the product suspended in ethanol. This mixture was filtered, the filtrate cooled in an ice-bath, and the resulting solid filtered, washed with EtOH, and dried, to give 4-chloro-1-guanidino-N-{1-[(4-methyl-1-piperazinyl) carbonyl]cyclopentyl}-7-isoquinolinesulphonamide dihydrochloride (68 mg, 0.12 mmol).

$^1$H (DMSO-$d_6$, 300 MHz) δ 1.35 (4H, m), 1.7 (2H, m), 2.0 (2H, m), 2.75 (3H, s), 3.0 (2H, m), 3.25–3.45 (4H, m), 4.4 (2H, m), 8.3 (1H, d), 8.4 (1H, d), 8.45 (1H, s), 8.6 (4H, m), 8.7 (1H, s), 9.1 (1H, s), 11.15 (2H, br s) ppm.

LRMS 494, 496 (MH$^+$)

Example 80

(a) N-[(4-chloro-1-guanidino-7-isoquinolinyl)sulphonyl]-N-(methyl)cycloleucine ethyl ester (b) N-[(4-Chloro-1-guanidino-7-isoquinolinyl)sulphonyl]-N-(methyl)cycloleucine hydrochloride

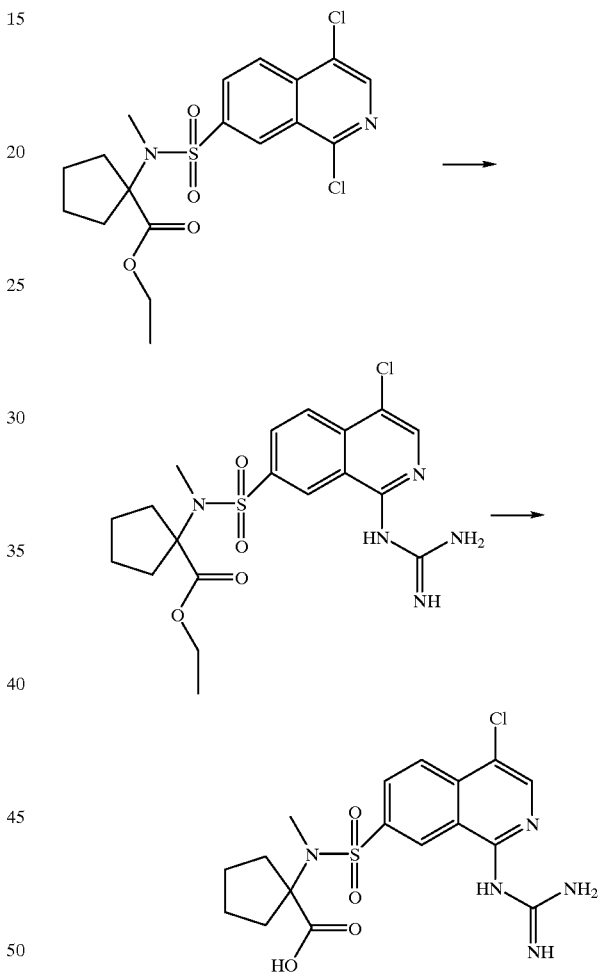

NaH (31 mg, 80% dispersion in mineral oil, 1.04 mmol) was added to a solution of guanidine hydrochloride (164 mg, 1.67 mmol) in DMSO (4 ml), and the solution heated at 50° C. for 1 h. N-[(1,4-Dichloro-7-isoquinolinyl)sulphonyl]-N-(methyl)cycloleucine ethyl ester (180 mg, 0.42 mmol) in DMSO (2 ml) was added, and the reaction heated at 80° C. for 3 h. The cooled reaction mixture was poured into water, and extracted with EtOAc. The combined organic extracts were washed with brine, dried (MgSO$_4$), and evaporated in vacuo. The residual yellow oil was purified by column chromatography upon silica gel using $CH_2Cl_2$-MeOH-0.880 NH$_3$ (90:10:1) as eluant, and recrystallised from EtOAc to afford N-[(4-chloro-1-guanidino-7-isoquinolinyl) sulphonyl]-N-(methyl)cycloleucine ethyl ester (105 mg, 0.23 mmol) as a yellow solid.

mp 186–188° C.

$^1$H (DMSO-d$_6$, 400 MHz) δ 1.1 (3H, t), 1.55 (4H, m), 2.0 (2H, m), 2.2 (2H, m), 2.95 (3H, s), 4.0 (2H, q), 7.2–7.4 (4H, br s), 8.05 (2H, m), 8.15 (1H, s), 9.1 (1H, s) ppm.

LRMS 454, 456 (MH$^+$)

Anal. Found: C, 50.04; H, 5.38; N, 15.31. Calc. for C$_{19}$H$_{24}$ClN$_5$O$_4$S.0.2H$_2$O: C, 49.88; H, 5.38; N, 15.31%.

A solution of N-[(4-chloro-1-guanidino-7-isoquinolinyl)sulphonyl]-N-(methyl)cycloleucine ethyl ester (80 mg, 0.176 mmol) in NaOH (1 ml, 2N) and MeOH (10 ml) was stirred at 70° C. for 18 h. The cooled mixture was neutralised using HCl (2N), and the MeOH was removed in vacuo. The resulting precipitate was filtered off, washed with water and re-dissolved in concentrated HCl. This solution was evaporated in vacuo, azeotroped with toluene, the residue dissolved in EtOH and filtered. The filtrate was evaporated in vacuo and the resulting solid recrystallised from i-PrOH, to give N-[(4-chloro-1-guanidino-7-isoquinolinyl)sulphonyl]-N-(methyl)cycloleucine hydrochloride (18 mg, 0.039 mmol) as a yellow solid.

mp 225° C. (dec.).

$^1$H (DMSO-d$_6$ +TFA-d, 400 MHz) δ 1.4–1.6 (4H, m), 1.95–2.0 (2H, m), 2.15–2.25 (2H, m), 3.0 (3H, s), 8.3 (1H, d), 8.35 (1H, d), 8.45 (1H, s), 8.95 (1H, s) ppm.

LRMS 426, 428 (MH$^+$).

Anal. Found: C, 41.50; H, 4.79; N, 13.82. Calc for C$_{17}$H$_{20}$ClN$_5$O$_4$S.HCl.1.8H$_2$O: C, 41.27; H, 5.01; N, 14.15.

Example 81

(a) N-[(4-Bromo-1-guanidino-7-isoquinolinyl)sulphonyl]-D-proline tert-butyl ester hydrochloride (b) N-[(4-Bromo-1-guanidino-7-isoquinolinyl)sulphonyl]-D-proline hydrochloride

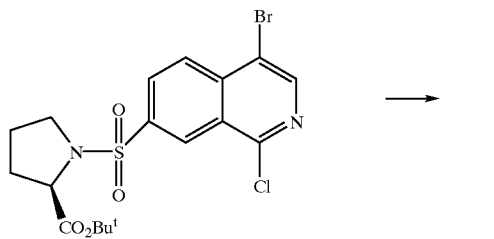

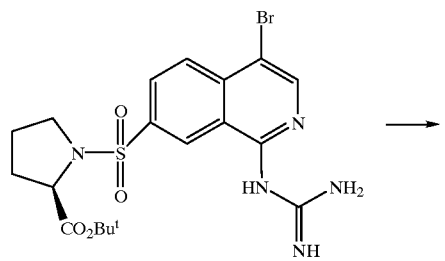

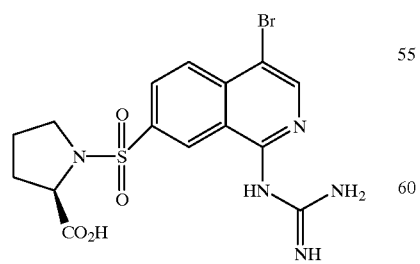

NaH (48 mg, 80% disperson in mineral oil, 1.6 mmol) was added to a solution of guanidine hydrochloride (233 mg, 2.43 mmol) in DMSO (8 ml) and the solution stirred at room temperature for 30 min. N-[(4-Bromo-1-chloro-7-isoquinolinyl)sulphonyl]-D-proline tert-butyl ester (290 mg, 0.61 mmol), was added and the reaction stirred at 60° C. for 2 h, and allowed to cool to room temperature overnight. The mixture was poured into water, and extracted with EtOAc. The combined organic extracts were washed with brine, dried (MgSO$_4$) and evaporated in vacuo. The residual yellow oil was purified by column chromatography upon silica gel using CH$_2$Cl$_2$-MeOH-0.880 NH$_3$ (97.5:2.5:0.25) as eluant, to give a yellow foam. This was dissolved in Et$_2$O, treated with ethereal HCl, the mixture evaporated in vacuo and the residue triturated with Et$_2$O to give N-[(4-bromo-1-guanidino-7-isoquinolinyl)sulphonyl]-D-proline tert-butyl ester hydrochloride (166 mg, 0.31 mmol) as a white solid.

mp. 203° C.

$^1$H (DMSO-d$_6$, 300 MHz) δ 1.4 (9H, s), 1.65 (1H, m), 1.8 (2H, m), 2.0 (1H, m), 3.35 (1H, m), 3.45 (1H, m), 8.35 (2H, m), 8.5–8.8 (5H, m), 9.1 (1H, s), 11.4 (1H, s) ppm.

LRMS 497, 499 (MH$^+$)

Anal. Found: C, 41.96: H, 4.65; N, 12.65. Calc. for C$_{19}$H$_{24}$BrN$_5$O$_4$S.HCl.90.5H$_2$O: C, 41.96:; 4.82; N, 12.88%.

N-[(4-Bromo-1-guanidino-7-isoquinolinyl)sulphonyl]-D-proline tert-butyl ester hydrochloride (150 mg, 0.28 mmol) was treated with an ice-cold solution of HCl in EtOAc (20 ml), and the reaction allowed to warm to room temperature, and stirred for 4 h. The solution was concentrated in vacuo and the crude product purified by column chromatography upon silica gel using CH$_2$Cl$_2$-MeOH-0.880 NH$_3$ (90:10:1) as eluant. The product was treated with ethereal HCl, the resulting precipitate filtered, washed with Et$_2$O and dried to afford N-[(4-bromo-1-guanidino-7-isoquinolinyl)sulphonyl]-D-proline hydrochloride (75 mg, 0.156 mmol) as a white powder.

$^1$H (DMSO-d$_6$, 300 MHz) δ 1.6 (1H, m), 1.7–2.0 (3H, m), 3.2–3.45 (2H, m), 4.4 (1H, m), 8.3 (2H, m), 8.5–8.85 (5H, m), 9.15 (1H, s) ppm.

LRMS 443 (MH$^+$)

Anal. Found: C, 35.56; H, 3.54; N, 13.52. Calc. for C$_{15}$H$_{16}$BrN$_5$O$_4$S.HCl.1.5H$_2$O: C, 35.62: H, 3.99; N, 13.85%.

Example 82

(2R)-1-({4-Chloro-1-guanidino-7-isoquinolinyl}sulphonyl)-N-[2-(dimethylamino)ethyl]-2-pyrrolidinecarboxamide

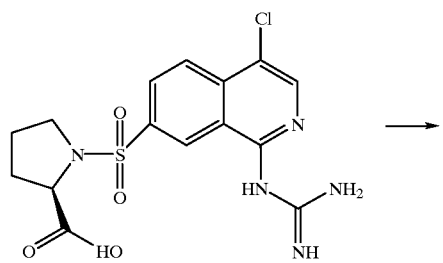

107
-continued

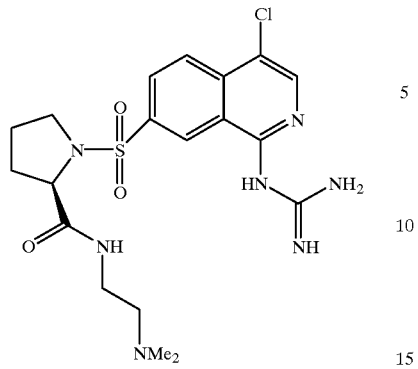

N-[(4-Chloro-1-guanidino-7-isoquinolinyl)sulphonyl]-L-proline hydrochloride (300 mg, 0.69 -mmol) was suspended in a solution of DMF (5 drops) and $CH_2Cl_2$ (15 ml), and oxalyl chloride (150 µl, 1.72 mmol) added dropwise. The reaction was stirred at room temperature for 3 h, then concentrated in vacuo and azeotroped with toluene. The residue was dissolved in $CH_2Cl_2$ (15 ml), N-(2-aminoethyl)-N,N-dimethylamine (1 ml, 0.9 mmol) added and the reaction stirred at room temperature for 2 h. The mixture was evaporated in vacuo, the residue partitioned between EtOAc and $Na_2CO_3$ solution, the layers separated, and the organic phase washed with brine, dried ($Na_2SO_4$) and evaporated in vacuo. The residual yellow solid was purified by column chromatography upon silica gel using an elution gradient of $CH_2Cl_2$-MeOH-0.880 $NH_3$ (95:5:0.5 to 90:10:1) to give (2R)-1-({4-chloro-1-guanidino-7-isoquinolinyl}sulphonyl)-N-[2-(dimethylamino)ethyl]-2-pyrrolidinecarboxamide (195 mg, 0.42 mmol) as a yellow solid.

$^1$H (DMSO-d$_6$, 400 MHz) δ 1.55 (1H, m), 1.65 (1H, m), 1.7 (2H, m), 2.15 (6H, s), 2.25 (2H, t), 3.2 (3H, m), 3.5 (1H, m), 4.1 (1H, dd), 7.2–7.4 (4H, br s), 7.8 (1H, m), 8.0 (1H,d),8.15 (2H, m), 9.1 (1H, s) ppm.

Anal. Found: C, 47.67; H. 5.61; N. 20.31. Calc. for $C_{19}H_{26}ClN_7O_3S.0.5H_2O$: C, 47.84; H. 5.71; N. 20.56%.

Example 83

1-{({4-Chloro-1-guanidino-7-isoquinolinyl}sulphonyl)]2-(dimethylamino)ethyl]amino}-N-(2-hydroxyethyl)-N-methylcyclopentanecarboxamide dihydrochloride

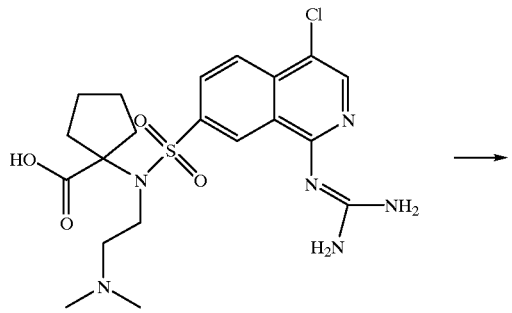

108
-continued

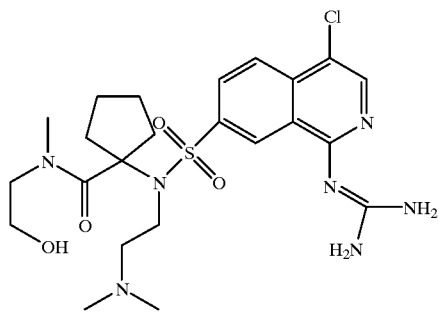

N-[(4-chloro-1-guanidino-7-isoquinolinyl)sulphonyl]-N-[2-(dimethylamino)ethyl]cycloleucine dihydrochloride (170 mg, 0.31 mmmol) was dissolved in DMF (10 µl) and $CH_2Cl_2$ (15 ml). Oxalyl chloride (100 µl, 1.15 mmol) was added and the mixture stirred at room temperature for 3 h. The solvent was removed in vacuo, replaced with fresh $CH_2Cl_2$, N-methylethanolamine (230 µl, 2.86 mmol) in $CH_2Cl_2$ (10 ml) added, and the reaction stirred for 2 h. The solvent was removed in vacuo and the resultant gum extracted with $Et_2O$ and EtOAc. These combined organic extracts were concentrated in vacuo, and the crude product purified by column chromatography upon silica gel eluting with $CH_2C_2$-MeOH-0.880 $NH_3$ (90:10:1). The resulting yellow oil was dissolved in EtOAc, and acidified with ethereal HCl (1N) to give the title compound as a cream solid (17 mg, 0.03 mmol).

$^1$H (DMSO-d$_6$+TFA-d, 300 MHz) δ 1.55 (4H, m), 2.0 (2H, m), 2.4 (2H, m), 2.6 (3H, s), 2.9 (6H, s), 3.35 (2H, m), 3.5 (3H, m), 3.95 (2H, m), 4.3 (2H, t), 8.4 (3H, m), 8.5 (1H, s), 9.35 (1H, s) ppm.

LRMS 540, 542 (MH$^+$).

Example 84

(a) Ethyl N-[(4-bromo-1-guanidino-7-isoquinolinyl) sulphonyl]-N-[2-(dimethylamino)ethyl]-cycloleucine dihydrochloride (b) N-({4-Bromo-1-guanidino-7-isoquinolinyl}sulphonyl)-N-[2-(dimethylamino)ethyl]cycloleucine dihydrochloride

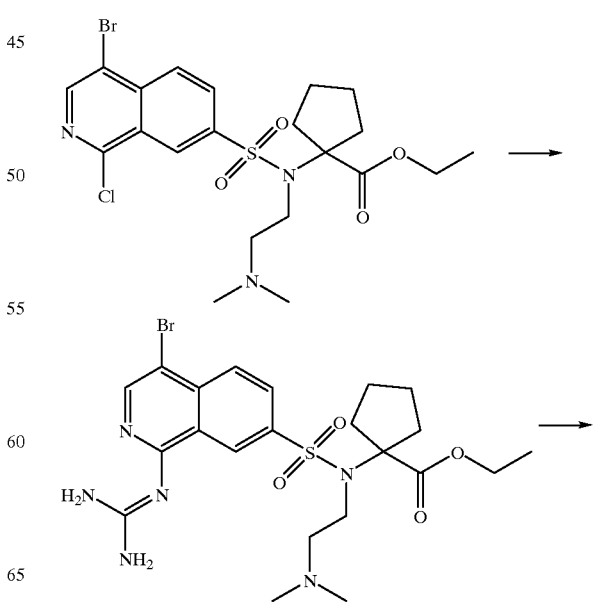

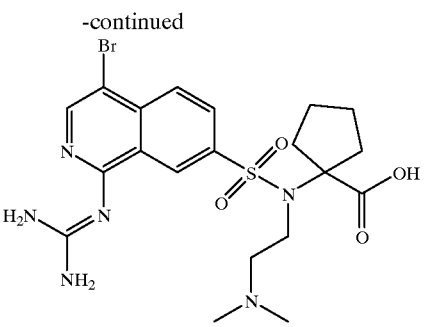

A mixture of NaH (28 mg, 80% in mineral oil, 0.93 mmol) and guanidine hydrochloride (126 mg, 1.32 mmol) in dry DMSO (3 ml) was heated at 50° C. for 30 min. N-[(4-Bromo-1-chloro-7-isoquinolinyl)sulphonyl]-N-[2-(dimethylamino)ethyl]cycloleucine hydrochloride (150 mg, 0.26 mmol) was added and the mixture heated to 90° C. for 1 h, cooled, poured into water and extracted with EtOAc (3×). The combined organic extracts were washed with water and brine, dried ($Na_2SO_4$) and concentrated in vacuo to a yellow gum. After column chromatography on silica gel eluting with $CH_2Cl_2$-MeOH-0.880 $NH_3$ (95:5:0.5), the residue was dissolved in EtOAc and acidified with ethereal HCl (1N) to afford a white precipitate. This was filtered, dried and recrystallised from EtOH to give a white solid (20 mg, 0.04 mmol). Concentration of the mother liquors afforded a second crop (95 mg, 0.17 mmol) of ethyl N-[(4-bromo-1-guanidino-7-isoquinolinyl)sulphonyl]-N-[2-(dimethylamino)ethyl]cycloleucine dihydrochloride.

$^1$H (DMSO-$d_6$, 300 MHz) δ 1.15 (3H, t), 1.6 (4H, m), 2.0 (2H, m), 2.3 (2H, m), 2.9 (6H, s), 3.5 (2H, m), 3.95 (2H, m), 4.0 (2H, q), 8.34 (2H, s), 8.6 (1H, s), 9.4 (1H, s), 11.6 (1H, br s) ppm.

LRMS 555, 557 (MH$^+$).

Anal. Found: C, 39.67; H, 5.61; N, 12.51. Calc. for $C_{22}H_3BrN_6O_4S.2HCl.2H_2O$: C, 39.77; H, 5.61; N, 12.65%.

Ethyl N-[(4-Bromo-1-guanidino-7-isoquinolinyl)sulphonyl]-N-[2-(dimethylamino)ethyl]cycloleucine dihydrochloride (95 mg, 0.17 mmol) in EtOH (3 ml) was treated with NaOH (4N, 8 ml) and the solution stirred at 60° C. for 5 h and allowed to stand for 60 h at room temperature. The reaction mixture was acidified using 2N HCl, concentrated in vacuo and the residue azeotroped with i-PrOH to give an off-white solid. This was extracted into MeOH, the solution evaporated in vacuo and the residue purified by column chromatography upon silica gel using $CH_2Cl_2$-MeOH-0.880 $NH_3$ (80:20:5) as eluant. The product was suspended in EtOAc, treated with ethereal HCl, the mixture evaporated in vacuo and the product triturated with EtOAc to afford N-({4-bromo-1-guanidino-7-isoquinolinyl}sulphonyl)-N-[2-(dimethylamino)ethyl]cycloleucine dihydrochloride (15 mg, 0.027 mmol) as a pale yellow solid.

$^1$H (DMSO-$d_6$, 300 MHz) δ 1.45–1.6 (4H, m), 1.95 (2H, m), 2.2 (2H, m), 2.6 (6H, s), 3.1 (2H, m), 3.7 (2H, t), 7.35–7.6 (4H, br s), 8.0 (1H, d), 8.15 (1H, d), 8.25 (1H, s), 9.15 (1H, s) ppm.

LRMS 527, 529 (MH$^+$)

Anal. Found: C, 41.31; H, 5.35; N, 14.14. Calc. for $C_{20}H_{27}BrN_6O_4S.HCl.H_2O$: C, 41.27; H, 5.19; N, 14.44%.

Example 85

(a) Ethyl 3-{[(4-chloro-1-guanidino-7-isoquinolinyl)sulphonyl]amino}-2,2-dimethylpropanoate hydrochloride
(b) N-({4-Chloro-)-guanidino-7-isoquinolinyl}sulphonyl)-2,2-dimethyl-β-alanine hydrochloride

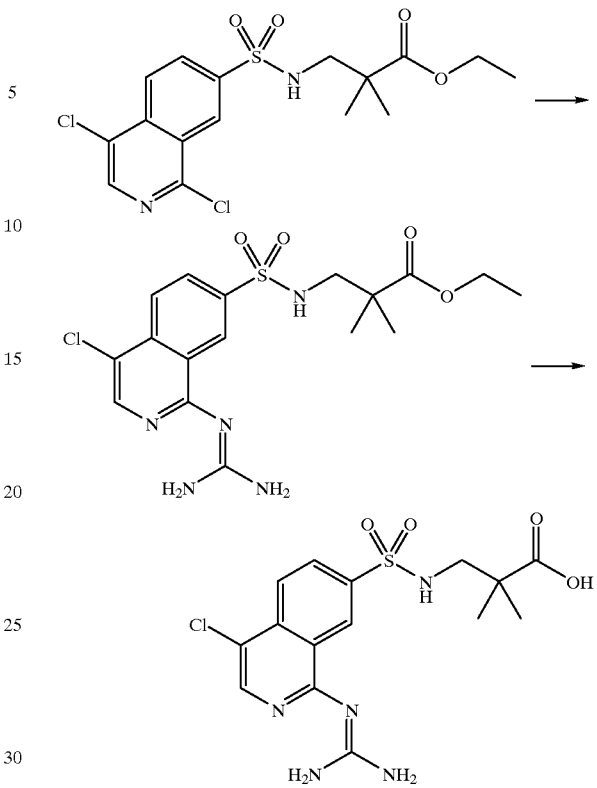

Ethyl 3-{[(4-chloro-1-guanidino-7-isoquinolinyl)sulphonyl]amino}-2,2-dimethylpropanoate hydrochloride was prepared (29%) as a white solid, from ethyl 3-{[(1,4-dichloro-7-isoquinolinyl)sulphonyl]amino}-2,2-dimethylpropanoate, following a similar procedure to that described in example 83.

mp. 183–187° C.

$^1$H (DMSO-$d_6$, 300 MHz) δ 1.1 (6H, s), 1.15 (3H, t), 2.95 (2H, d), 4.0 (2H, q), 7.95 (1H, t), 8.35 (1H, m), 8.4 (1H, m), 8.45 (1H, s), 8.5–8.65 (3H, br s), 9.1 (1H, s), 11.2 (1H, s).

LRMS 428 (MH$^+$)

Anal. Found: C, 43.99; H, 5.01; N, 14.69. Calc. for $C_{17}H_{22}ClN_5O_4S.HCl$: C, 43.97; H, 4.99; N, 15.08%.

A solution of ethyl 3-{[(4-chloro-1-guanidino-7-isoquinolinyl)sulphonyl]amino}-2,2-dimethylpropanoate hydrochloride (28 mg, 0.06 mmol) in NaOH solution (2N, 0.5 ml), and MeOH (1 ml), was stirred at 75° C. for 24 h. The cooled mixture was acidified to pH 6 using HCl (2N), concentrated in vacuo to remove the MeOH, and the resulting precipitate filtered, washed with water and dried. The solid was suspended in a MeOH/EtOAc solution, ethereal HCl added, and the mixture evaporated in vacuo to afford N-({4-chloro-1-guanidino-7-isoquinolinyl}sulphonyl)-2,2-dimethyl-β-alanine hydrochloride as a white solid (22 mg, 0.05 mmol).

mp. Dec>304° C.

$^1$H (DMSO-$d_6$, 300 MHz) δ 1.05 (6H, s), 2.9 (2H, d), 7.9 (1H, t), 8.3–8.6 (6H, m), 9.05 (1H, s) ppm.

Example 86

(a) 1-[({4-Chloro-1-guanidino-7-isoquinolinyl}sulphonyl)amino]-N,N-dimethylcyclopentanecarboxamide
(b) 1-{[(4-Chloro-1-guanidino-7-isoquinolinyl)sulphonyl][2-(tetrahydro-2H-pyran-2-yloxy)ethyl]amino}-N-N-dimethylcyclopentanecarboxamide (c) 1-[({4-Chloro-1-guanidino-7-isoquinolinyl}sulphonyl)(2-hydroxyethyl)amino]-N,N-dimethylcyclopentanecarboxamide hydrochloride

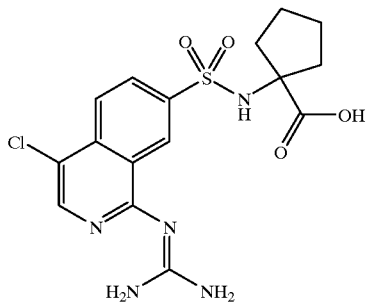

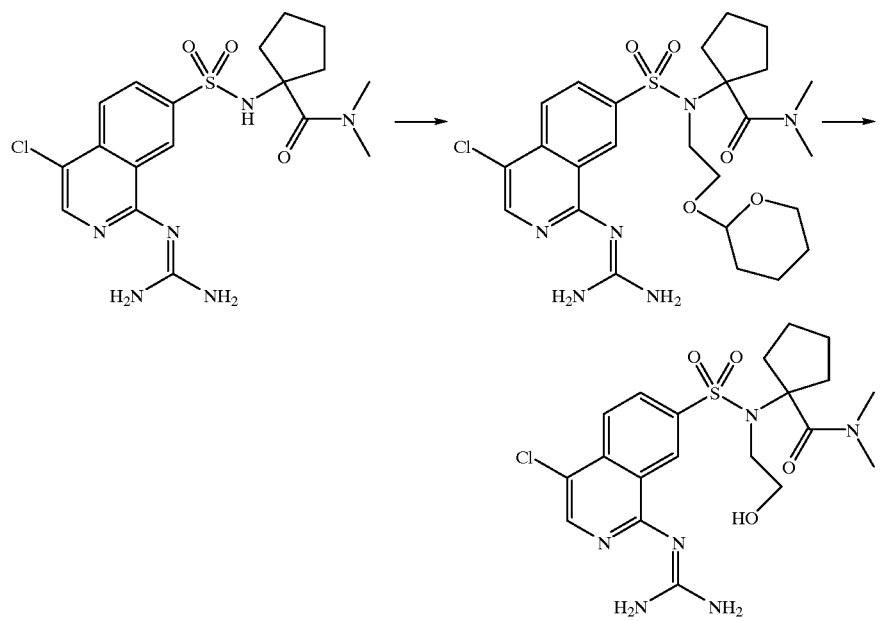

Oxalyl chloride (3.5 ml, 4.0 mmol) was added to a suspension of N-({4-chloro-1-guanidino-7-isoquinolinyl}sulphonyl)cycloleucine hydrochloride (870 mg, 1.94 mmol) in $CH_2Cl_2$ (100 ml), followed by DMF (5 drops), and the reaction stirred at room temperature for 2 h. The solution was concentrated in vacuo and azeotroped with toluene to give a yellow gum. This was dissolved in $CH_2Cl_2$ (100 ml), the solution cooled to −20° C., and cooled N,N-dimethylamine (10 ml) added. The reaction was allowed to warm to room temperature with stirring, over 30 min, then concentrated in vacuo, and the residue azeotroped with toluene. The crude product was purified by column chromatography upon silica gel using $CH_2Cl_2$-MeOH-0.880 $NH_3$ (95:5:0.5) as eluant, and crystallised from MeOH to afford to afford 1-[({4-chloro-1-guanidino-7-isoquinolinyl}sulphonyl)amino]-N,N-dimethylcyclopentanecarboxamide (302 mg, 0.69 mmol) as a yellow solid. mp. 264–268° C.

$^1$H (DMSO-$d_6$, 400 MHz) δ 1.35 (4H, m), 2.0 (2H, m), 2.2 (2H, m), 3.1 (6H, s), 8.35 (2H, m), 8.4–8.7 (2H, m), 9.1 (1H, s) ppm.

LRMS 439, 441 ($MH^+$)

Anal. Found: C, 49.07; H, 5.27; N, 18.51. Calc. for $C_{18}H_{23}ClN_6O_3S.0.3H_2O$: C, 48.66; H, 5.35; N, 18.91%.

$K_2CO_3$ (113 mg, 0.82 mmol) was added to a solution of 1-[({4-chloro-1-guanidino-7-isoquinolinyl}sulphonyl)amino]-N,N-dimethylcyclopentanecarboxamide (150 mg, 0.34 mmol) in DMF (2.5 ml), and the mixture heated to 75° C. 2-(2-Bromoethoxy)tetrahydro-2H-pyran (J.C.S. 1948; 4187) (150 mg, 0.72 mmol) and sodium iodide (3 mg) were then added and the reaction stirred at 75° C. for 3 days. The cooled reaction mixture was poured into water, and extracted with EtOAc. The combined organic extracts were washed with brine, dried ($Na_2SO_4$) and evaporated in vacuo. The residual yellow oil was purified by column chromatography upon silica gel using EtOAc as eluant, and triturated with a hexane-EtOAc (20:1) solution, to give 1-{[(4-chloro-1-guanidino-7-isoquinolinyl)sulphonyl][2-(tetrahydro-2H-pyran-2-yloxy)ethyl]amino}-N-N-dimethylcyclopentanecarboxamide (56 mg, 0.099 mmol).

$^1$H (CDCl$_3$, 400 MHz) δ 1.45–1.85 (?H, m), 2.9–3.2 (6H, m), 3.35–3.6 (4H, m), 3.95 (2H, m), 4.1 (1H, m), 4.65 (1H, s), 8.1 (3H, m), 9.25 (1H, s) ppm. Ethereal HCl was added dropwise to a solution of 1-{[(4-chloro-1-guanidino-7-isoquinolinyl)sulphonyl][2-(tetrahydro-2H-pyran-2-yloxy)ethyl]amino}-N-N-dimethylcyclopentanecarboxamide (37 mg, 0.065 mmol) in EtOAc (1.5 ml), until no further precipitation occurred. The resulting suspension was stirred at room temperature for 20 min, and then evaporated in vacuo. The residue was purified by column chromatography upon silica gel using $CH_2Cl_2$-MeOH-0.880 $NH_3$ (95:5:0.5)

as eluant, and azeotroped with toluene. This product was dissolved in a MeOH—CH$_2$Cl$_2$ solution, ethereal HCl added (5 ml), and the mixture evaporated in vacuo, and triturated with Et$_2$O to afford 1-[({4-chloro-1-guanidino-7-isoquinolinyl}sulphonyl)(2-hydroxyethyl)amino]-N,N-dimethylcyclopentanecarboxamide hydrochloride (9 mg, 0.017 mmol) as a cream/white solid.

$^1$H (DMSO-d$_6$+TFA-d, 300 MHz) δ 1.25–1.45 (4H, m), 1.7 (2H, m), 2.25 (2H, m), 2.8–3.0 (6H, m), 3.3 (2H, m), 3.7 (2H, t), 8.35 (1H, d), 8.4 (1H, d), 8.5 (1H, s), 8.6 (1H, br s), 9.0 (1H, s) ppm.

LRMS 483 (MH$^+$)

Example 87

(a) Ethyl 1-{[(4-chloro-1-guanidino-7-isoquinolinyl)sulphonyl][2-(tetrahydro-2H-pyran-2-yloxy)ethyl]amino}cyclopentanecarboxylate (b) 1-{[(4-Chloro-1-guanidino-7-isoquinolinyl)sulphonyl][2-(tetrahydro-2H-pyran-2-yloxy)ethyl]amino}cyclopentanecarboxylic acid (c) N''-{4-Chloro-7-[(10-oxo-9-oxa-6-azaspiro [4.5]dec-6-yl)sulphonyl]-1-isoquinolinyl}guanidine hydrochloride 20 min. Ethyl 1-{[(1,4-dichloro-7-isoquinolinyl)sulphonyl][2-(tetrahydro-2H-pyran-2-yloxy)ethyl]amino}cyclopentanecarboxylate (330 mg, 0.6 mmol) was added and the reaction stirred at 70° C. for 2½ h. The cooled reaction was poured into water, extracted with EtOAc, and the combined organic extracts washed with brine, dried (MgSO$_4$) and evaporated in vacuo. The residual yellow gum was purified by column chromatography upon silica gel using CH$_2$Cl$_2$-MeOH-0.880 NH$_3$ (95:5:0.5) as eluant to give ethyl 1-{[(4-chloro-1-guanidino-7-isoquinolinyl)sulphonyl][2-(tetrahydro-2H-pyran-2-yloxy)ethyl]amino}cyclopentanecarboxylate as an orange oil.

$^1$H (CDCl$_3$, 400 MHz) δ 1.25 (3H, t), 1.45–1.75 (14H, m), 2.1 (2H, m), 2.35 (2H, m), 3.5 (1H, m), 3.75–3.9 (4H, m), 4.0 (1H, m), 4.2 (2H, q), 4.61 (1H, s), 8.05–8.15 (3H, m), 9.25 (1H, s) ppm.

LRMS 568 (M+)

A solution of ethyl 1-{[(4-chloro-1-guanidino-7-isoquinolinyl)sulphonyl][2-(tetrahydro-2H-pyran-2-yloxy)ethyl]amino}cyclopentanecarboxylate in MeOH (5 ml), was heated to 75° C., NaOH solution (1 ml, 2N, 2 mmol) added, and the reaction stirred at 50° C. for 48 h. The cooled

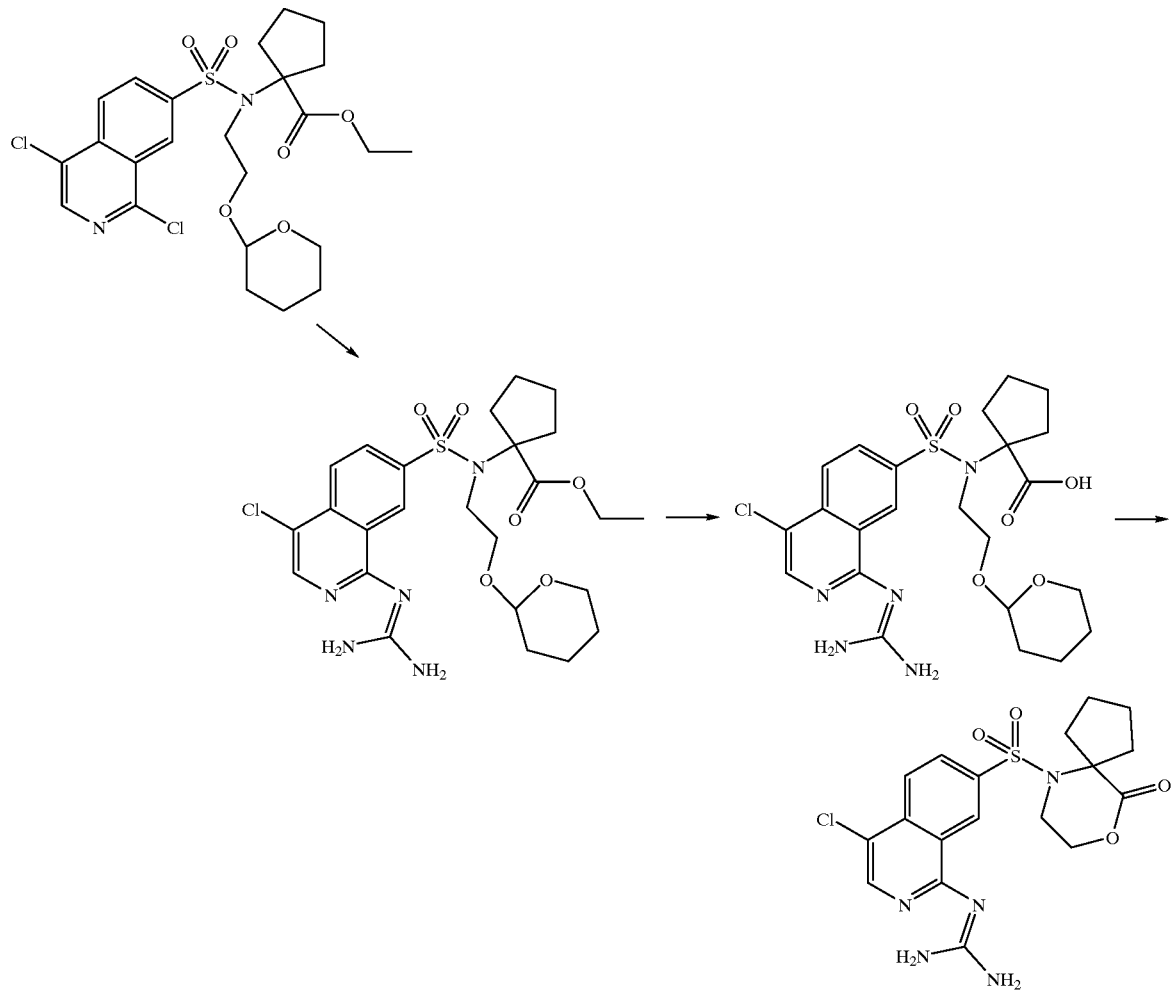

NaH (45 mg, 80% dispersion in mineral oil, 1.5 mmol) was added to a solution of guanidine hydrochloride (231 mg, 2.4 mmol) in DMSO (5 ml), and the solution stirred at 50° C. for reaction mixture was concentrated in vacuo, to remove the MeOH, and the remaining aqueous solution acidifed to pH 6 using 1N HCl. The resulting precipitate was filtered, washed with water, and the filtrate extracted with EtOAc. The combined organic extracts were dried (MgSO$_4$), and evaporated in vacuo to give 1-{[(4-chloro-1-guanidino-7-isoquinolinyl)sulphonyl][2-(tetrahydro-2H-pyran-2-yloxy)ethyl]amino}cyclopentanecarboxylic acid (9 mg, 0.017 mmol) as a pale yellow solid.

$^1$H (CDCl$_3$, 300 MHz) δ 1.4 (4H, m), 1.55 (4H, m), 2.0 (2H, m), 2.2 (2H, m), 3.35 (3H, m), 3.45–3.75 (5H, m), 4.5 (1H, m), 8.0 (1H, d), 8.15 (2H, m), 9.15 (1H, s) ppm.

Anal. Found: C, 49.50; H, 5.50; N, 12.26. Calc. for C$_{23}$H$_{30}$ClN$_5$O$_6$S.H$_2$O: C, 49.50; H, 5.78; N, 12.55%.

1-{[(4-Chloro-1-guanidino-7-isoquinolinyl)sulphonyl][2-(tetrahydro-2H-pyran-2-yloxy)ethyl]amino}cyclopentanecarboxylic acid (20 mg, 0.037 mmol) was dissolved in EtOAc (20 ml), ethereal HCl (10 ml) added, and the reaction stirred at room temperature for 18 h. The resulting precipitate was filtered, washed with EtOAc and dried under vacuum to give N''-{4-Chloro-7-[(10-oxo-9-oxa-6-azaspiro[4.5]dec-6-yl)sulphonyl]-1-isoquinolinyl}guanidine hydrochloride (17 mg, 0.36 mmol).

$^1$H (CDCl$_3$, 300 MHz) δ 1.6–1.8 (4H, m), 2.25 (4H, m), 3.95 (2H, t), 4.4 (2H, t), 8.35 (2H, m), 8.45 (1H, s), 9.25 (1H, s), 11.5 (1H, s) ppm.

LRMS 437 (M$^+$)

Anal. Found: C, 44.04; H, 4.58; N, 14.17. Calc. for, C$_{18}$H$_{20}$ClN$_5$O$_4$S.HCl.H$_2$O: C, 43.91; H, 4.71; N, 14.22%.

Example 88

(a) N-[(4-chloro-1-guanidino-7-isoquinolinyl)methyl]cycloleucine methyl ester
(b) N-({4-Chloro-1-guanidino-7-isoquinolinyl}methyl)cycloleucine dihydrochloride

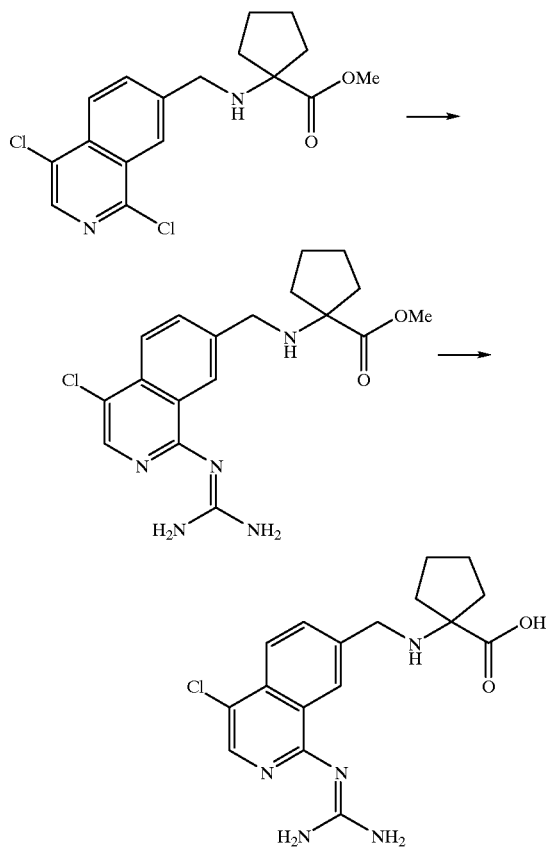

NaH (52 mg, 80% dispersion in mineral oil, 1.73 mmol) was added to a slurry of guanidine hydrochloride (265 mg, 2.77 mmol) in DMSO (2.5 ml) and the mixture heated to 50° C. for 20 mins. N-[(1,4-Dichloro-7-isoquinolinyl)methyl]cycloleucine methyl ester (245 mg, 0.69 mmol) in DMSO (2.5 ml) was added and after heating at 90° C. for 4½ h, the solution was poured into water (50 ml). The mixture was extracted with EtOAc (2×), the combined organic extracts washed with water, brine and then dried (Na$_2$SO$_4$). The residue was purified by column chromatography upon silica gel eluting with CH$_2$Cl$_2$-MeOH -0.880 NH$_3$ (90:10:1) to give a yellow solid. This was dissolved in a CH$_2$Cl$_2$-MeOH solution and acidified with ethereal HCl (1N), concentrated in vacuo and the crude product recrystallised from EtOH to give N-[(4-chloro-1-guanidino-7-isoquinolinyl)methyl]cycloleucine methyl ester (30 mg, 0.08 mmol) as a cream solid.

mp. 271–275° C.

$^1$H (DMSO-d$_6$, 300 MHz) δ 1.25 (3H, t), 1.75 (2H, m), 1.9 (2H, m), 2.1–2.3 (4H, m), 4.25 (2H, q), 4.35 (2H, m), 8.25 (3H, m), 8.4 (1H, s), 9.3 (1H, s), 11.7 (1H, s) ppm.

LRMS 390 (MH$^+$)

Anal. Found: C, 49.09; H, 5.74; N, 14.71. Calc. For C$_{19}$H$_{24}$ClN$_5$O$_2$.2HCl.0.2H$_2$O: C, 48.93; H, 5.71; N, 15.02%.

N-[(4-Chloro-1-guanidino-7-isoquinolinyl)methyl]cycloleucine methyl ester (100 mg, 0.27 mmol) was dissolved in methanol (4 ml) at 50° C., NaOH (2N, 1 ml) was added, and the reaction mixture heated for 2 days at 50° C. The cooled mixture was basified to pH 6 with NaOH (2N) to give a precipitate which was filtered off and washed with water. The solid was dissolved in MeOH/EtOAc, acidified with ethereal HCl (1N) and triturated with i-Pr$_2$O to give the title compound (b) as a pale yellow solid (10 mg, 0.03 mmol).

mp 281–289° C.

$^1$H (DMSO-d$_6$+TFA-d, 300 MHz) δ 1.8 (2H, m), 1.85 (2H, m), 2.15 (2H, m), 2.25 (2H, m), 4.4 (2H, s), 8.2 (1H, d), 8.3 (1H, d), 8.4 (1H, s), 9.15 (1H, s) ppm.

LRMS 362 (MH$^+$).

PREPARATIONS

Preparation 1:
7-Bromo-1,4-dichloroisoquinoline

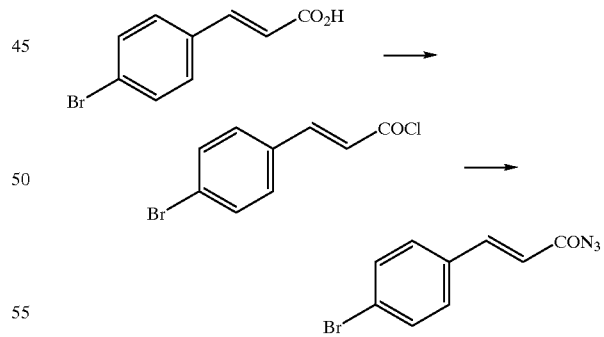

A solution of 4-bromocinnamic acid (5.03 g, 22.2 mmol) in SOCl$_2$ (15 mL) was stirred at 23° C. for 16 h, and then heated at reflux for a further 2 h. The solvents were evaporated in vacuo and the residue azeotroped with PhMe (×3) to yield 4-bromocinnamoyl chloride (22 mmol) as an orange-brown solid.

$^1$H NMR (CDCl$_3$, 300 MHz) δ 6.65 (1H, d), 7.4 (2H, d), 7.6 (2H, d), 7.8 (1H, d) ppm.

A solution of NaN$_3$ (2.2 g, 33.8 mmol) in water (7.5 mL) was added dropwise over 5 min to a stirred solution of 4-bromocinnamoyl chloride (22 mmol) in acetone (22 mL) at −10° C. The heterogeneous mixture was stirred at 0° C. for 1 h and diluted with water (25 mL). The precipitate was collected by filtration and dried in vacuo over $P_2O_5$ to give 4-bromocinnamoyl azide (5.22 g, 20.7 mmol) as a golden-coloured solid.

$^1$H NMR (CDCl$_3$, 300 MHz) δ 6.4 (1H, d), 7.4 (2H, d), 7.5 (2H, d), 7.65 (1H, d) ppm.

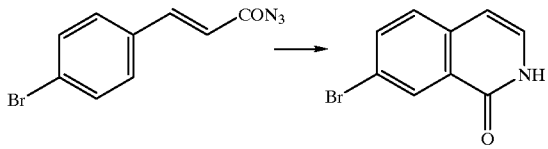

A warm solution of 4-bromocinnamoyl azide (5.22 g, 20.7 mmol) in Ph$_2$O (25 mL) was added dropwise over 15 min to stirred Ph$_2$O (10 mL) at 270° C. [CAUTION: Potentially explosive—use a blast screen.] The mixture was heated at 270° C. for 1.5 h, cooled to 23° C. and then poured into hexanes (400 mL). The precipitate was collected by filtration, with hexanes (2×100 mL) rinsing, and purified by column chromatography upon silica gel using hexanes-EtOAc (6:4 to 0:100) as eluant to give 7-bromo-1(2H)-isoquinolone (1.64 g, 7.3 mmol) as a white solid.

$^1$H NMR (DMSO-d$_6$, 300 MHz) δ 6.55 (1H, d), 7.25–7.15 (1H, m), 7.6 (1H, d), 7.8 (1H, d), 8.25 (1H, s), 11.4 (1H, br s) ppm.

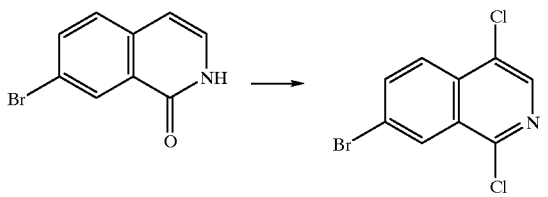

A mixture of 7-bromo-1(2H)-isoquinolone (1.28 g, 5.69 mmol) and PCl$_5$ (2.04 g, 9.80 mmol) was heated at 140° C. for 5 h. The cooled mixture was quenched with ice (50 g) and 0.880NH$_3$ was added until alkaline by litmus paper. The aqueous mixture was extracted with CH$_2$Cl$_2$ (3×50 mL) and the combined organic phases were dried (MgSO$_4$) and evaporated in vacuo. The residue was purified by column chromatography upon silica gel using hexanes-EtOAc (97:3 to 95:5) as eluant to give 7-bromo-1,4-dichloroisoquinoline (1.13 g, 4.08 mmol) as a white solid.

mp 133.5–135° C.

$^1$H (CDCl$_3$, 300 MHz) δ 7.9 (1H, d), 8.1 (1H, d), 8.35 (1H, s), 8.5 (1H, s).

LRMS 276, 278 (MH$^+$).

Anal. Found: C, 39.04; H, 1.32; N, 5.06. Calc for C$_9$H$_4$BrCl$_2$N: C, 39.03; H, 1.46; N, 5.06.

Preparation 2:
t-Butyl 2-aminobenzoate

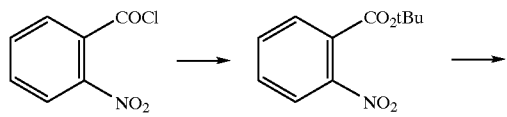

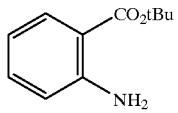

A mixture of 2-nitrobenzoyl chloride (15 mL, 110 mmol) and t-BuOH (100 mL) were heated at reflux for 3 h. The cooled mixture was poured onto ice-water, basified with Na$_2$CO$_3$ and extracted with CH$_2$Cl$_2$ (×2). The combined organic extracts were washed with brine, the solvents evaporated in vacuo and the residue was purified by column chromatography upon silica gel using hexanes-EtOAc (95:5) as eluant to give t-butyl 2-nitrobenzoate (4.9 g, 22 mmol) as a yellow oil.

$^1$H (CDCl$_3$, 300 MHz) δ 1.6 (9H, s), 7.5 (1H, dd), 7.6 (1H, dd), 7.7 (1H, d), 7.8 (1H, d) ppm.

LRMS 240 (MNH$_4^+$).

A solution of t-butyl 2-nitrobenzoate (4.9 g, 22 mmol) in EtOH (160 mL) was stirred with 10% palladium-carbon (700 mg) under an atmosphere of H2 (60 psi) at 23° C. After 4 h, the mixture was filtered and evaporated in vacuo to give t-butyl 2-aminobenzoate (4.0 g, 20.7 mmol) as a yellow oil.

$^1$H (CDCl$_3$, 300 MHz) δ 1.6 (9H, s), 5.6–5.8 (2H, br s), 6.6 (1H, dd), 6.6 (1H, d), 7.2 (1H, dd), 7.8 (1H, d) ppm.

LRMS 194 (MH$^+$).

Preparation 3:
t-Butyl 2-{[(1,4-dichloro-7-isoquinolinyl)sulphonyl]amino}benzoate

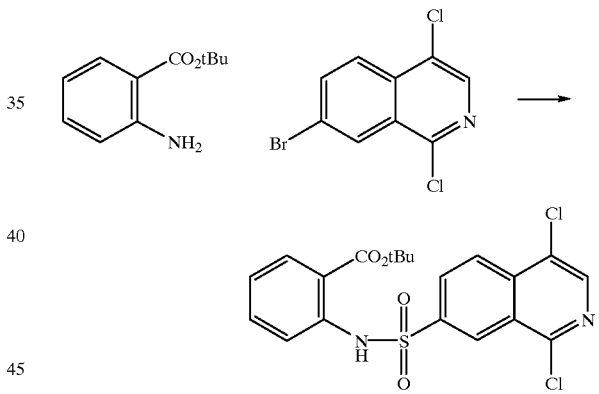

n-Butyllithium (0.88 mL, 2.5 M in hexanes, 2.2 mmol) was added dropwise to a stirred solution of 7-bromo-1,4-dichloroisoquinoline (570 mg, 2.0 mmol) in THF-Et$_2$O (10 mL, 1:1) under N$_2$ at −78° C. After 5 min, the mixture was added to a solution of SO$_2$Cl$_2$ (0.35 mL, 4.35 mmol) in hexane (10 mL) at −78° C. under N$_2$, and the mixture was slowly warmed to 23° C. and then stirred for 4.5 h. The solvents were evaporated in vacuo, azeotroping with CH$_2$Cl$_2$ and PhMe, the residue was suspended in CH$_2$Cl$_2$ (12 mL) containing NEt$_3$ (1.15 mL, 8.25 mmol) and t-butyl 2-aminobenzoate (520 mg, 2.7 mmol) was added. The mixture was stirred at room temperature for 3 d and then heated at reflux for 6 h. The cooled mixture was diluted with CH$_2$Cl$_2$, washed with aqueous HCl (2 M), brine, and then evaporated in vacuo. The residue was purified by column chromatography upon silica gel using hexanes-EtOAc (97:3 to 95:5) as eluant to give, initially, 1,4,7-trichloroisoquinoline (200 mg) followed by t-butyl 2-{[(1,4-dichloro-7-isoquinolinyl)sulphonyl]amino}benzoate (120 mg, 0.26 mmol) as a yellow resin.

¹H (CDCl₃, 400 MHz) δ 1.5 (9H, s), 7.05 (1H, dd), 7.5 (1H, dd), 7.7 (1H, d), 7.8 (1H, d), 8.2 (1H, d), 8.3 (1H, d), 8.4 (1H, s), 8.8 (1H, s), 10.0 (1H, s) ppm.

LRMS 454 (MH⁺).

Preparation 4:

t-Butyl 3-aminobenzoate

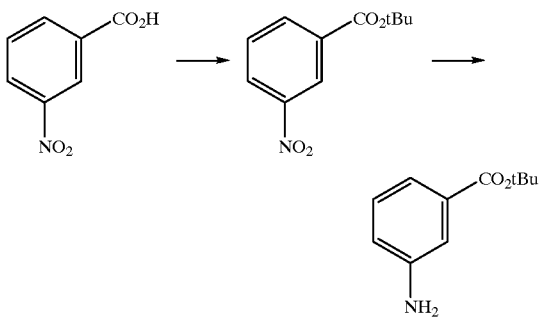

A mixture of 3-nitrobenzoic acid (5 g, 30 mmol), di-tert-butyl dicarbonate (20 g, 92 mmol), and DMAP (0.84 g, 6.9 mmol) in THF (60 mL) was stirred at 23° C. for 2 d. The mixture was poured onto ice-water, basified with Na₂CO₃ and extracted with CH₂Cl₂ (×3). The combined organic extracts were washed with brine, the solvents evaporated in vacuo and the residue was purified by column chromatography upon silica gel using hexanes-EtOAc (95:5) as eluant to give t-butyl 3-nitrobenzoate (5.4 g, 24 mmol) as a colourless oil.

¹H (CDCl₃, 400 MHz) δ 1.4 (9H, s), 7.6 (1H, dd), 8.3 (1H, d), 8.4 (1H, d), 8.8 (1H, s) ppm. A solution of t-butyl 3-nitrobenzoate (5.8 g, 26 mmol) in EtOH (260 mL) was stirred with 10% palladium-carbon (1.0 g) under an atmosphere of H₂ (60 psi) at 23° C. After 4 h, the mixture was filtered and evaporated in vacuo to give t-butyl 3-aminobenzoate (4.0 g, 20.7 mmol) as a white solid.

¹H (CDCl₃, 400 MHz) δ 1.6 (9H, s), 3.6–3.9 (2H, br s), 6.8 (1H, d), 7.2 (1H, dd), 7.3 (1H, s), 7.4 (1H, d) ppm.

LRMS 194 (MH⁺), 387 (M₂H⁺).

Preparation 5:

t-Butyl 3-{[(1,4-dichloro-7-isoquinolinyl)sulphonyl]amino}benzoate

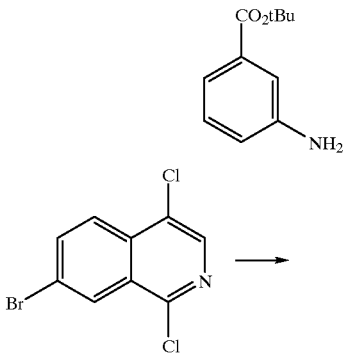

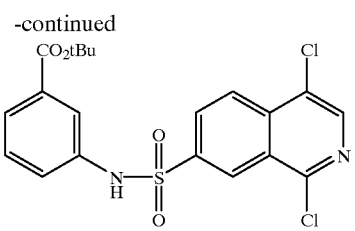

n-Butyllithium (0.88 mL, 2.5 M in hexanes, 2.2 mmol) was added dropwise to a stirred solution of 7-bromo-1,4-dichloroisoquinoline (570 mg, 2.0 mmol) in THF-Et₂O (10 mL, 1:1) under N₂ at −78° C. After 5 min, the mixture was added to a solution of SO₂Cl₂ (0.35 mL, 4.35 mmol) in hexane (10 mL) at −78° C. under N₂, and the mixture was slowly warmed to 23° C. and then stirred for 4.5 h. The solvents were evaporated in vacuo, azeotroping with PhMe, the residue was suspended in CH₂Cl₂ (12 mL) and t-butyl 3-aminobenzoate (520 mg, 2.7 mmol) followed by NEt₃ (1.15 mL, 8.25 mmol) were added. The mixture was stirred at room temperature for 4 d and evaporated in vacuo. The residue was purified by column chromatography upon silica gel using hexanes-EtOAc (90:10 to 50:50) as eluant to give, initially, 1,4,7-trichloroisoquinoline (150 mg) followed by t-butyl 2-{[(1,4-dichloro-7-isoquinolinyl)sulphonyl]amino}benzoate (289 mg, 0.63 mmol) as a brown solid which was used without further purification.

¹H (CDCl₃, 400 MHz) selected data: δ 1.5 (9H, s), 7.20–7.25 (1H, m), 7.3–7.45 (1H, m), 7.5 (1H, dd), 7.6 (1H, s), 8.45 (1H, d), 8.5 (1H, d), 8.6 (1H, s), 8.9 (1H, s) ppm.

LRMS 454 (MH⁺).

Preparation 6:

1,4-Dichloro-7-isoquinolinesulphonyl chloride

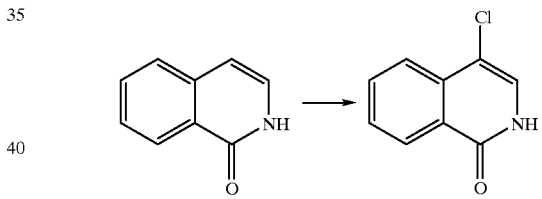

A solution of N-chlorosuccinimide (9.66 g, 72 mmol) in MeCN (80 mL) was added dropwise to a stirred solution of 1-(2H)-isoquinolone (10 g, 69 mmol) in MeCN (250 mL) which was being heated under reflux. The mixture was heated under reflux for an additional 1.5 h and then cooled to room temperature. The resulting precipitate was collected by filtration, with MeCN rinsing, and then dried in vacuo to give 4-chloro-1(2H)-isoquinolone (11.3 g, 62.9 mmol) as a pale pink solid.

¹H (DMSO-d₆, 300 MHz) δ 7.5 (1H, s), 7.6 (1H, dd), 7.8–7.9 (2H, m), 8.25 (1H, d), 11.5 (1H, br s), ppm.

LRMS 180, 182 (MH⁺), 359, 361, 363 (M₂H⁺).

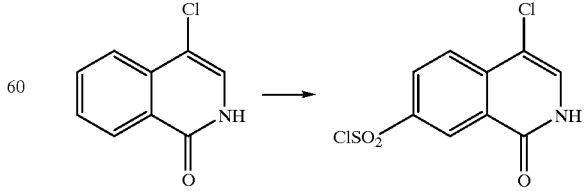

4-Chloro-1-(2H)-isoquinolone (20.62 g, 115 mmol) was added portionwise to stirred chlorosulphonic acid (61 mL, 918 mmol) at 0° C. The mixture was heated at 100° C. for 3.5 d and then cooled to room temperature. The reaction mixture was added in small portions onto ice-water [CAUTION] and the resulting precipitate was collected by filtration. The solid was washed with water, triturated with MeCN and then dried in vacuo to give 4-chloro-1-oxo-1,2-dihydro-7-isoquinolinesulphonyl chloride (18.75 g, 67.4 mmol) as a cream solid.

$^1$H (DMSO-d$_6$, 400 MHz) δ 7.45 (1H, s), 7.8 (1H, d), 8.0 (1H, d), 8.5 (1H, s), 11.5 (1H, br s) ppm.

Anal. Found: C, 39.37; H, 2.09; N, 4.94. Calc for C$_9$H$_5$Cl$_2$NO$_3$S: C, 38.87; H, 1.81; N, 5.04.

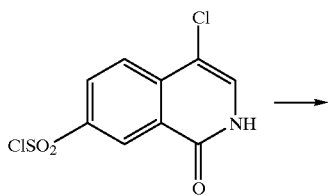

POCl$_3$ (9.65 mL, 103.5 mmol) was added to a stirred suspension of 4-chloro-1-oxo-1,2-dihydro-7-isoquinolinesulphonyl chloride (22.1 g, 79.6 mmol) in MeCN (500 mL) at room temperature and the mixture was then heated at reflux for 15 h. On cooling, the MeCN solution was decanted from the insoluble sludge and evaporated in vacuo. The residue was extracted with hot EtOAc and evaporated to leave a solid which was stirred with Et$_2$O (1.2 L) at room temperature overnight. The ethereal solution was decanted from the insoluble material and evaporated in vacuo to give 1,4-dichloro-7-isoquinolinesulphonyl chloride (20 g, 67 mmol) as a pale yellow solid.

$^1$H (DMSO-d$_6$, 400 MHz) δ 8.2 (2H, s), 8.5 (1H, s), 8.55 (1H, s) ppm.

Anal. Found: C, 37.19; H, 1.34; N, 4.77. Calc for C$_9$H$_4$Cl$_3$NO$_2$S: C, 36.45; H, 1.36; N, 4.72.

Preparation 7:
Methyl 3-{[(1,4-dichloro-7-isoquinolinyl)sulphonyl]amino}-4-methoxybenzoate

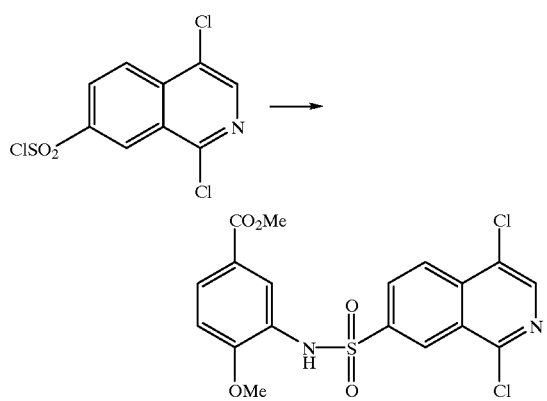

Methyl 3-amino-4-methoxybenzoate (212 mg, 1.17 mmol) was added to a stirred solution of 1,4-dichloro-7-isoquinolinesulphonyl chloride (342 mg, 1.15 mmol) in CH$_2$Cl$_2$ (10 mL) containing 2,6-lutidine (0.135 mL, 1.16 mmol) under N$_2$ at 0° C. After 5 min, the mixture was warmed to room temperature and stirred for 22 h. The solvents were evaporated in vacuo and the residue was suspended in EtOAc (50 mL), and then washed with water, brine, dried (MgSO$_4$) and evaporated in vacuo. The residue was purified by column chromatography upon silica gel using hexanes-EtOAc (80:20 to 20:80) as eluant to give methyl 3-{[(1,4-dichloro-7-isoquinolinyl)sulphonyl]amino}-4-methoxybenzoate (365 mg, 0.83 mmol) as an off-white solid.

$^1$H (CDCl$_3$, 300 MHz) δ 3.7 (3H, s), 3.9 (3H, s), 6.75 (1H, d), 7.2 (1H, s), 7.8 (1H, dd), 8.15 (1H, dd), 8.25 (1H, s), 8.3 (1H, d), 8.5 (s, 1H), 8.85 (1H, s) ppm.

LRMS 441 (MH$^+$), 458 (MNH$_4^+$).

Preparation 8:
N-[(1,4-Dichloro-7-isoquinolinyl)sulphonyl]glycine t-butyl ester

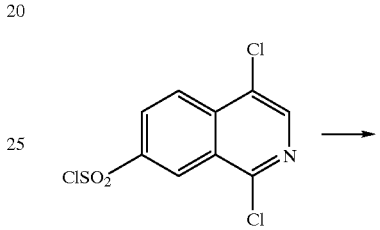

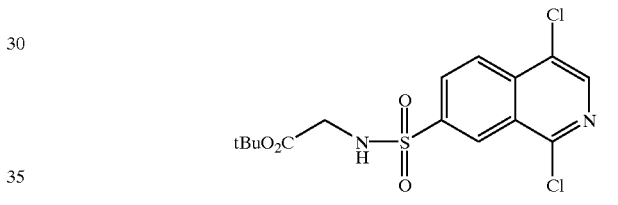

NEt$_3$ (0.59 mL, 4.24 mmol) was added to a stirred solution of glycine t-butyl ester hydrochloride (340 mg, 2.02 mmol) and 1,4-dichloro-7-isoquinolinesulphonyl chloride (500 mg, 1.68 mmol) in CH$_2$Cl$_2$ (25 mL) under N$_2$ and the mixture was stirred at room temperature for 18 h. The mixture was diluted with CH$_2$Cl$_2$ (25 mL), washed with dilute HCl (×2, 1 M), saturated aqueous NaHCO$_3$, brine, dried (MgSO$_4$) and evaporated in vacuo. The solid was triturated with EtOAc, collected by filtration and dried to give N-[(1,4-dichloro-7-isoquinolinyl)sulphonyl]glycine t-butyl ester (435 mg, 1.11 mmol) as a white solid.

mp 194–196° C.

$^1$H (CDCl$_3$, 300 MHz) δ 1.3 (9H, s), 3.8 (2H, d), 5.3 (1H, br t), 8.25 (1H, d), 8.4 (1H, d), 8.5 (1H, s), 8.9 (1H, s) ppm.

LRMS 391 (MH$^+$), 408, 410 (MNH$_4^+$).

Anal. Found: C, 45.58; H, 4.03; N, 7.03. Calc for C$_{15}$H$_{16}$Cl$_2$N$_2$O$_4$S: C, 46.04; H, 4.12; N, 7.16.

Preparation 9:
N-[(1,4-Dichloro-7-isoquinolinyl)sulphonyl]-β-alanine t-butyl ester

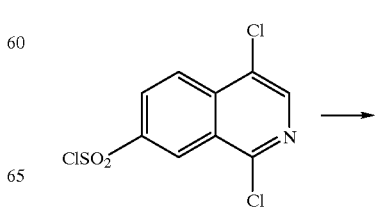

-continued

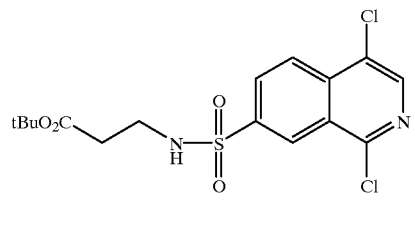

NEt₃ (0.60 mL, 4.3 mmol) was added to a stirred solution of ,alanine t-butyl ester hydrochloride (331 mg, 1.82 mmol) and 1,4-dichloro-7-isoquinolinesulphonyl chloride (510 mg, 1.72 mmol) in $CH_2Cl_2$ (10 mL) under $N_2$ and the mixture was stirred at room temperature for 22 h. The mixture was diluted with $CH_2Cl_2$ (50 mL), washed with half saturated brine, dried ($MgSO_4$) and evaporated in vacuo. The residue was purified by column chromatography upon silica gel using pentane-EtOAc (90:10 to 60:40) as eluant to give N-[(1,4-dichloro-7-isoquinolinyl)sulphonyl]-β-alanine t-butyl ester (580 mg, 1.43 mmol) as a white solid.

$^1H$ (CDCl₃, 300 MHz) δ 1.4 (9H, s), 2.5 (2H, t), 3.25 (2H, dt), 5.5 (1H, br t), 8.25 (1H, d), 8.4 (1H, d), 8.5 (1H, s), 8.9 (1H, s) ppm.

LRMS 405, 407 (MH⁺), 422 (MNH₄⁺).

Anal. Found: C, 47.41; H, 4.46; N, 6.80. Calc for $C_{16}H_{18}Cl_2N_2O_4S$: C, 47.42; H, 4.48; N, 6.91.

Preparation 10:
N-[(1,4-Dichloro-7-isoquinolinyl)sulphonyl]-N-methylglycine t-butyl ester

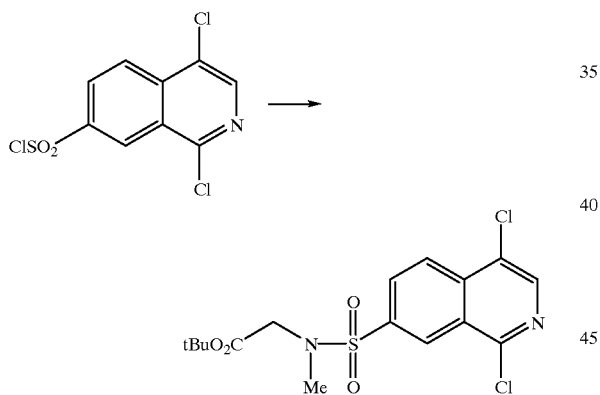

N-Methylglycine t-butyl ester hydrochloride (264 mg, 1.45 mmol) was added to a stirred solution of 1,4-dichloro-7-isoquinolinesulphonyl chloride (376 mg, 1.27 mmol) in $CH_2Cl_2$ (25 mL) containing NEt₃ (0.44 mL, 3.16 mmol) under $N_2$ at 0° C., and the mixture was then stirred at room temperature for 22 h. The solvents were evaporated in vacuo, the residue dissolved in EtOAc (50 mL), washed with water, brine, dried ($MgSO_4$) and evaporated in vacuo. The residue was purified by column chromatography upon silica gel using pentanes-EtOAc (80:20) as eluant to give N-[(1,4-dichloro-7-isoquinolinyl)sulphonyl]-N-methylglycine t-butyl ester (485 mg, 1.20 mmol) as a white solid.

$^1H$ (CDCl₃, 300 MHz) δ 1.35 (9H, s), 3.0 (3H, s), 4.05 (2H, d), 8.2 (1H, d), 8.35 (1H, d), 8.5 (1H, s), 8.85 (1H, s) ppm.

LRMS 709 (M₂H⁺).

Anal. Found: C, 47.37; H, 4.43; N, 6.79. Calc for $C_{16}H_{18}Cl_2N_2O_4S$: C, 47.42; H, 4.48; N, 6.91.

Preparation 11:
N-Phenylglycine t-butyl ester

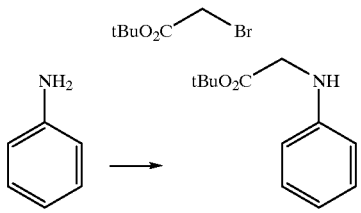

t-Butyl chloroacetate (10 g, 66.3 mmol) was added dropwise to a stirred solution of aniline (11.3 g, 120 mmol) in NEt₃ (10 mL), and the mixture was stirred at to room temperature for 24 h and then at 60° C. for 18 h. The cooled mixture was diluted with Et₂O (100 mL), filtered with Et₂O rinsing, and the filtrate was then washed with water, brine, dried ($MgSO_4$) and evaporated in vacuo. The residue was purified by column chromatography upon silica gel using hexanes-EtOAc (98:2 to 92:8) as eluant to give N-phenylglycine t-butyl ester (6.56 g, 31.6 mmol) as an oil.

$^1H$ (CDCl₃, 400 MHz) δ 1.5 (9H, s), 3.8 (2H, s), 4.45 (1H, br s), 6.6 (2H, d), 6.7 (1H, t), 7.2 (2H, dd) ppm.

LRMS 208 (MH⁺), 415 (M₂H⁺).

Preparation 12:
N-[(1,4-Dichloro-7-isoquinolinyl)sulphonyl]-N-phenylglycine t-butyl ester

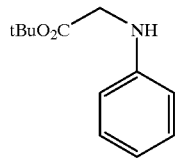

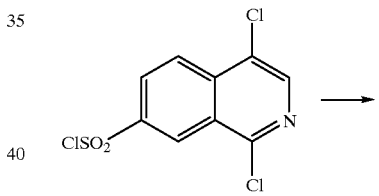

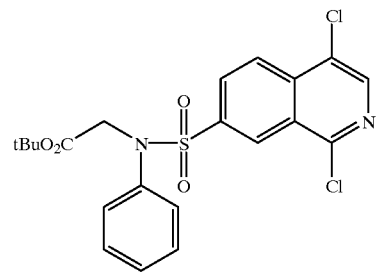

1,4-Dichloro-7-isoquinolinesulphonyl chloride (300 mg, 1.01 mmol) was added to a stirred solution of N-phenylglycine t-butyl ester (228 mg, 1.10 mmol) in $CH_2Cl_2$ (5.0 mL) containing NEt₃ (0.35 mL, 2.5 mmol) under $N_2$ at room temperature, and the mixture stirred for 5 d. The mixture was diluted with $CH_2Cl_2$ (50 mL), washed with dilute HCl (20 mL, 1 M), saturated aqueous NaHCO₃, dried ($MgSO_4$) and evaporated in vacuo. The residue was purified by column chromatography upon silica gel using hexanes-EtOAc (90:10 to 60:40) as eluant to give N-[(1,4-dichloro-7-isoquinolinyl)sulphonyl]-N-phenylglycine t-butyl ester (485 mg, 1.20 mmol) as a white solid.

$^1H$ (CDCl₃, 300 MHz) 5 1.4 (9H, s), 4.4 (2H, d), 7.2–7.4 (5H, m), 8.05 (1H, d), 8.3 (1H, d), 8.45 (1H, s), 8.7 (1H, s) ppm.

LRMS 467 (MH⁺).

Preparation 13:

N-(Cyclopentylmethyl)-N-[(1,4-dichloro-7-isoquinolinyl)sulphonyl]glycine t-butyl ester

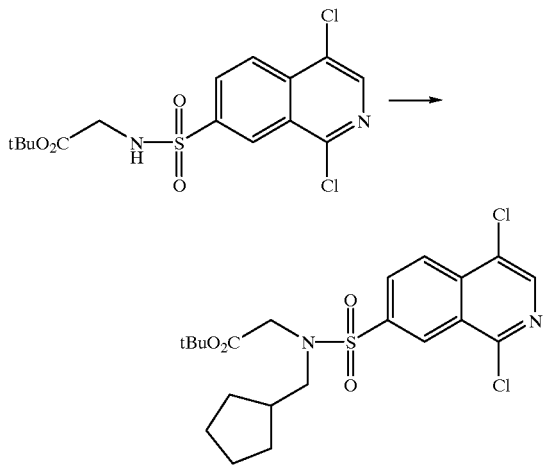

PPh$_3$ (243 mg, 1.5 mmol) and then a solution of DEAD (236 µL, 1.5 mmol) in THF (2 mL) were added to a stirred solution of N-[(1,4-dichloro-7-isoquinolinyl)sulphonyl]glycine t-butyl ester (391 mg, 1.00 mmol) and cyclopentanemethanol (130 µL, 1.2 mmol) in THF (3 mL) under N$_2$ at 0° C., and the mixture was stirred at room temperature for 18 h. An additional portion of cyclopentanemethanol (1.2 mmol), PPh$_3$ (1.5 mmol), and DEAD (1.5 mmol) were added and the mixture stirred at room temerature for a further 2 d. The solvents were evaporated in vacuo and the residue was purified by column chromatography upon silica gel using pentane-EtOAc (100:0 to 95:5) as eluant to give N-(cyclopentylmethyl)-N-[(1,4-dichloro-7-isoquinolinyl)sulphonyl]glycine t-butyl ester (144 mg, 0.30 mmol) as a white solid.

$^1$H (CDCl$_3$, 400 MHz) δ 1.15–1.4 (3H, m), 1.3 (9H, s), 1.5–1.7 (3H, m), 1.7–1.8 (2H, m), 2.1 (1H, m), 3.25 (2H, d), 4.1 (2H, s), 8.25 (1H, d), 8.35 (1H, d), 8.5 (1H, s), 8.85 (1H, s) ppm.

LRMS 473 (MH$^+$), 490, 492 (MNH$_4^+$).

Anal. Found: C, 53.23; H, 5.58; N, 5.86. Calc for C$_{21}$H$_{26}$Cl$_2$N$_2$O$_4$S: C, 53.28; H, 5.54; N, 5.92.

Preparation 14:

N-(Cyclohexylmethyl)-N-[(1,4-dichloro-7-isoquinolinyl)sulphonyl]glycine t-butyl ester

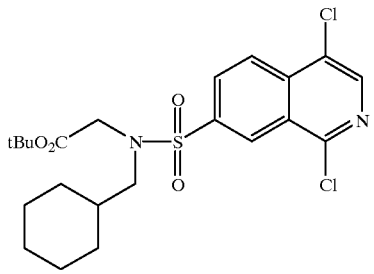

Cyclohexylmethyl bromide (209 µL, 1.5 mmol) was added to a stirred solution of N-[(1,4-dichloro-7-isoquinolinyl)sulphonyl]glycine t-butyl ester (391 mg, 1.00 mmol) and anhydrous K$_2$CO$_3$ (276 mg, 2.0 mmol) in DMF (5 mL) under N$_2$ at 23° C. The mixture was stirred for 2 h and then heated at 50–60° C. for 6 h. The cooled mixture was diluted with EtOAc (200 mL), washed with water (250 mL), dried (MgSO$_4$), and the solvents were evaporated in vacuo. The residue was purified by column chromatography upon silica gel using pentane-EtOAc (100:0 to 95:5) as eluant to give N-(cyclohexylmethyl)-N-[(1,4-dichloro-7-isoquinolinyl)sulphonyl]glycine t-butyl ester (320 mg, 0.66 mmol).

$^1$H (CDCl$_3$, 400 MHz) δ 1.15–1.3 (3H, m), 1.3 (9H, s), 1.5–1.8 (8H, m), 3.15 (2H, d), 4.05 (2H, s), 8.2 (1H, d), 8.35 (1H, d), 8.45 (1H, s), 8.85 (1H, s) ppm.

LRMS 487 (MH$^+$), 504, 506, 508 (MNH$_4^+$).

Preparation 15:

N-Berzylglycine t-butyl ester

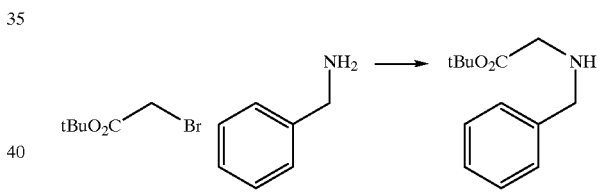

A solution of t-butyl bromoacetate (1.5 mL, 10.1 mmol) in CH$_2$Cl$_2$ (10 mL) was added dropwise to a stirred solution of benzylamine (10.9 mL, 100 mmol) in CH$_2$Cl$_2$ (40 mL) at 0° C., the mixture was stirred for 1 h and then warmed to room temperature and stirred for an additional 3 d. The mixture was washed with water (3×50 mL), dilute HCl (1 N) and the combined aqueous washings were extracted with Et$_2$O. The organic phase was washed with saturated aqueous NaHCO$_3$, dried (Na$_2$SO$_4$) and evaporated in vacuo. The residue was dissolved in Et$_2$O, treated with a solution of HCl in ether (0.5 M) and the resulting precipitate was collected and dissolved in EtOAc. This solution was filtered through hyflo, and partially evaporated in vacuo to give a thick slurry. The solid was collected by filtration, washed with Et$_2$O and then dried to give N-benzylglycine t-butyl ester hydrochloride (1.03 g, 4.00 mmol) as a white solid.

$^1$H (CDCl$_3$, 300 MHz) δ 1.4 (9H, s), 3.5 (2H, s), 4.4 (2H, s), 7.3–7.4 (3H, m), 7.55–7.65 (2H, m), 10.2–10.3 (2H, br s).

LRMS 222, (MH$^+$), 443 (M$_2$H$^+$).

Preparation 16:

N-[(1,4-Dichloro-7-isoquinolinyl)sulphonyl]-N-benzylglycine t-butyl ester

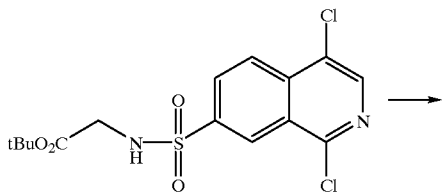

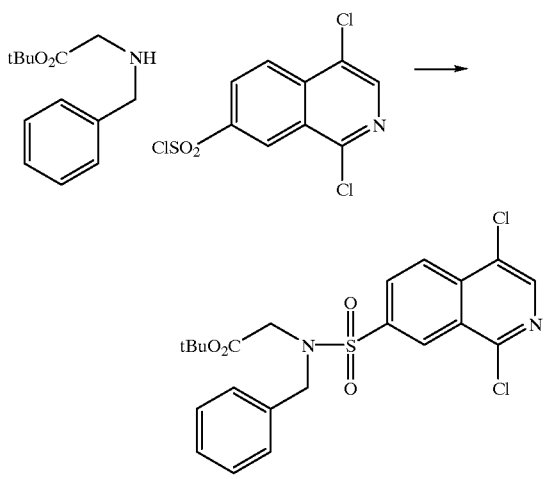

1,4-Dichloro-7-isoquinolinesulphonyl chloride (300 mg, 1.01 mmol) was added to a stirred solution of N-benzylglycine t-butyl ester (310 mg, 1.20 mmol) in CH$_2$Cl$_2$ (20 mL) containing NEt$_3$ (0.35 mL, 2.5 mmol) under N$_2$ and the mixture was stirred at room temperature for 3 d. The mixture was diluted with CH$_2$Cl$_2$ and washed with dilute HCl (2 M), saturated aqueous NaHCO$_3$, brine, dried (Na$_2$SO$_4$) then and evaporated in vacuo. The residue was purified by column chromatography upon silica gel using hexanes-EtOAc (90:10) as eluant to give N-[(1,4-dichloro-7-isoquinolinyl)sulphonyl]-N-benzylglycine t-butyl ester (290 mg, 0.60 mmol) as an off-white solid.

mp 134–136° C.

$^1$H (CDCl$_3$, 400 MHz) δ 1.3 (9H, s), 3.9 (2H, s), 4.55 (2H, s), 7.25–7.4 (5H, m), 8.25 (1H, d), 8.4 (1H, d), 8.5 (1H, s), 8.9 (1H, s) ppm.

LRMS 481 (MH$^+$), 498 (MNH$_4^+$).

Anal. Found: C, 54.52; H, 4.50; N, 5.77. Calc for C$_{22}$H$_{22}$Cl$_2$N$_2$O$_4$S: C, 54.89; H, 4.61; N, 5.82.

Preparation 17:
N-(2-Methylbenzyl)glycine t-butyl ester

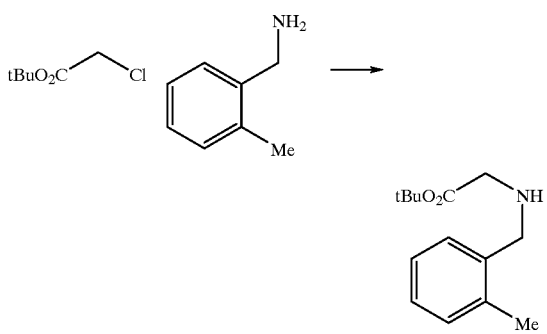

t-Butyl chloroacetate (2.13 g, 14.1 mmol) was added to a stirred solution of 2-methylbenzylamine (1.71 g, 14.1 mmol) in CH$_2$Cl$_2$ (20 mL) containing NEt$_3$ (2.95 mL, 21.2 mmol) under N$_2$ and the mixture was stirred at room temperature for 17 h. The solvents were evaporated in vacuo, the residue suspended in EtOAc and and washed with water, brine, dried (MgSO$_4$) then and evaporated in vacuo. The residue was purified by column chromatography upon silica gel using pentanes-EtOAc (95:5 to 80:20) as eluant to give N-(2-methylbenzyl)glycine t-butyl ester (1.29 g, 5.48 mmol).

$^1$H (CDCl$_3$, 300 MHz) δ 1.5 (9H, s), 2.35 (3H, s), 3.3 (2H, s), 3.8 (2H, s), 7.1–7.2 (3H, m), 7.25–7.3 (1H, m) ppm.

LRMS 236 (MH$^+$), 471 (M$_2$H$^+$).

Preparation 18:
N-[(1,4-Dichloro-7-isoquinolinyl)sulphonyl]-N-(2-methylbenzyl)glycine 1-butyl ester

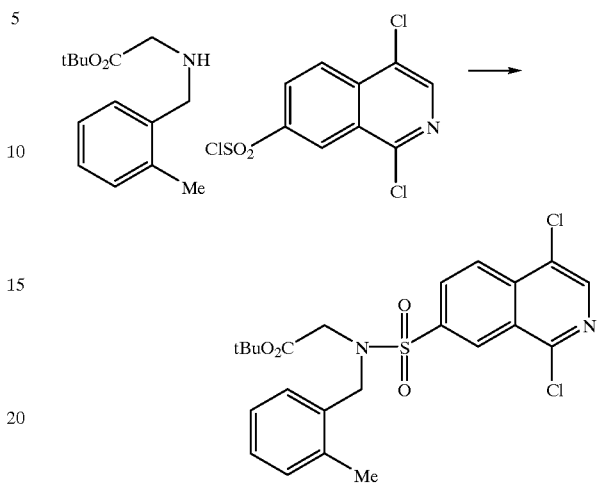

1,4-Dichloro-7-isoquinolinesulphonyl chloride (400 mg, 1.35 mmol) was added to a stirred solution of N-(2-methylbenzyl)glycine t-butyl ester (380 mg, 1.61 mmol) in CH$_2$Cl$_2$ (20 mL) containing NEt$_3$ (0.28 mL, 2.5 mmol) under N$_2$ and the mixture was stirred at room temperature for 18 h. The mixture was diluted with CH$_2$Cl$_2$ and washed with dilute HCl (2 M), saturated aqueous NaHCO$_3$, brine, dried (MgSO$_4$) then and evaporated in vacuo. The residue was purified by column chromatography upon silica gel using pentane-EtOAc (100:0 to 90:10) as eluant to give N-[(1,4-dichloro-7-isoquinolinyl)sulphonyl]-N-(2-methylbenzyl)glycine t-butyl ester (480 mg, 0.97 mmol) as a white solid.

mp 96–98° C.

$^1$H (CDCl$_3$, 400 MHz) δ 1.25 (9H, s), 2.3 (3H, s), 3.9 (2H, s), 4.6 (2H, s), 7.1–7.25 (4H, m), 8.3 (1H, d), 8.4 (1H, d), 8.5 (1H, s), 8.9 (1H, s) ppm.

LRMS 495 (MH$^+$), 512 (MNH$_4^+$).

Anal. Found: C, 55.70; H, 4.86; N, 5.63. Calc for C$_{23}$H$_{24}$Cl$_2$N$_2$O$_4$S: C, 55.76; H, 4.88; N, 5.65.

Preparation 19:
N-(2-Methoxybenzyl)glycine t-butyl ester

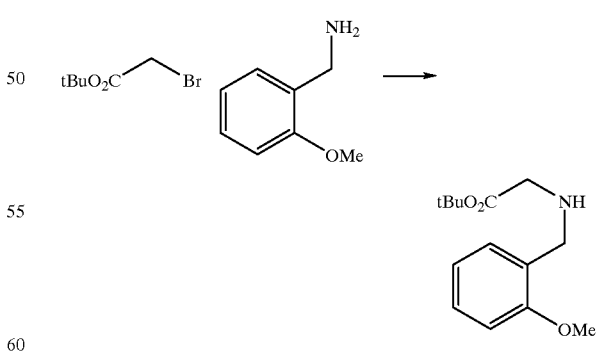

A solution of t-butyl bromooacetate (1.5 mL, 10.2 mmol) in CH$_2$Cl$_2$ (30 mL) was added to a stirred solution of 2-methoxybenzylamine (6.88 g, 50.2 mmol) in CH$_2$Cl$_2$ (70 mL) under N$_2$ at 0° C., and the mixture was then stirred at room temperature for 1 h. The mixture was thoroughly washed with dilute HCl (30 mL, 1 M) and the separated aqueous phase was extracted with in CH₂Cl₂. The combined organic extracts were washed with saturated NaHCO₃, brine, dried (Na₂SO₄) then and evaporated in vacuo. The residue was purified by column chromatography upon silica gel using in CH₂Cl₂-MeOH (99:1 to 95:5) as eluant to give N-(2-methoxybenzyl)glycine t-butyl ester (0.90 g, 3.58 mmol) as a pale yellow oil.

¹H (CDCl₃, 400 MHz) δ 1.25 (9H, s), 2.0 (1H, br s), 3.3 (2H, s), 3.8 (2H, s), 3.85 (3H, s), 6.85 (1H, d), 6.9 (1H, dd), 7.2–7.3 (2H, m) ppm.

LRMS 252 (MH⁺), 503 (M₂H⁺), 525 (M₂Na⁺).

Anal. Found: C, 66.52; H, 8.54; N, 5.54. Calc for C₁₄H₂₁NO₃: C, 66.91; H, 8.42; N, 5.57.

Preparation 20:

N-[(1,4-Dichloro-7-isoquinolinyl)sulphonyl]-N-(2-methoxybenzyl)glycine t-butyl ester

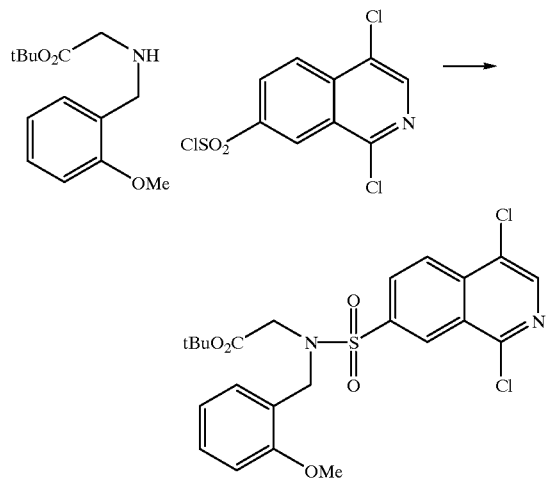

1,4-Dichloro-7-isoquinolinesulphonyl chloride (500 mg, 1.69 mmol) was added to a stirred solution of N-(2-methoxybenzyl)glycine t-butyl ester (508 mg, 2.02 mmol) in CH₂Cl₂ (30 mL) containing NEt₃ (0.35 mL, 2.5 mmol) under N₂ and the mixture was stirred at room temperature for 21 h. The mixture was diluted with CH₂Cl₂ and washed with dilute HCl (2 M), saturated aqueous NaHCO₃, brine, dried (Na₂SO₄) then and evaporated in vacuo. The residue was purified by column chromatography upon silica gel using hexane-EtOAc (95:5 to 90:10) as eluant and then triturated with hexane-i-Pr₂O to give N-[(1,4-dichloro-7-isoquinolinyl)sulphonyl]-N-(2-methoxybenzyl)glycine t-butyl ester (501 mg, 1.02 mmol) as a yellow solid.

mp 106–108° C.

¹H (CDCl₃, 400 MHz) δ 1.3 (9H, s), 3.7 (3H, s), 4.0 (2H, s), 4.6 (2H, s), 6.8 (1H, d), 6.9 (1H, dd), 7.2 (1H, dd), 7.3 (1H, d), 8.2 (1H, d), 8.3 (1H, d), 8.45 (1H, s), 8.8 (1H, s) ppm.

LRMS 511, 513 (MH⁺), 528 (MNH₄⁺).

Anal. Found: C, 54.09; H, 4.78; N, 5.33. Calc for C₂₃H₂₄Cl₂N₂O₅S: C, 54.01; H, 4.73; N, 5.48.

Preparation 21:

N-(3-Methoxybenzyl)glycine t-butyl ester

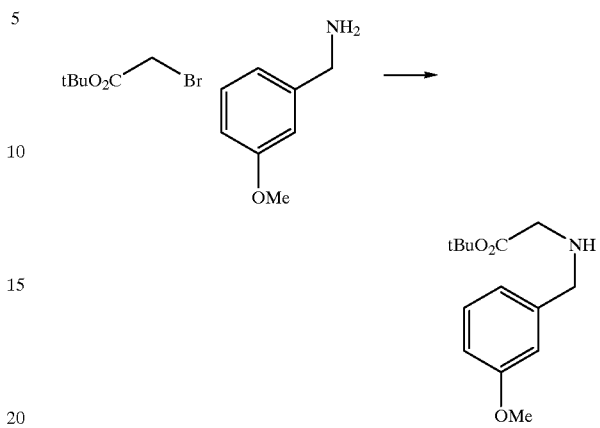

A solution of t-butyl bromoacetate (1.5 mL, 10.1 mmol) in CH₂Cl₂ (30 mL) was added dropwise to a stirred solution of 3-methoxybenzylamine (6.86 g, 50 mmol) in CH₂Cl₂ (20 mL) at 0° C., and the mixture was then warmed to room temperature and stirred for 1.5 h. Dilute HCl (30 mL, 1 M) was added and the mixture stirred for 15 min. The aqueous phase was extracted with CH₂Cl₂ and the combined organic extracts were washed with water, brine, saturated aqueous NaHCO₃, dried (MgSO₄) then and evaporated in vacuo. The residue was purified by column chromatography upon silica gel using CH₂Cl₂-MeOH (99:1 to 90:10) as eluant to give the required amine as a colourless oil. Treatment with a solution of HCl in ether (1 M) gave N-(3-methoxybenzyl)glycine t-butyl ester hydrochloride (0.83 g, 2.88 mmol) as a white solid.

mp 141–142° C.

¹H (CDCl₃, 300 MHz) δ 1.45 (9H, s), 3.5 (2H, s), 3.85 (3H, s), 4.35 (2H, s), 6.9 (1H, d), 7.1 (1H, d), 7.3 (1H, s), 7.3–7.35 (1H, m), 10.3 (2H, br s) ppm.

LRMS 252 (MH⁺), 503 (M₂H⁺).

Anal. Found: C, 58.37; H, 7.75; N, 4.83. Calc for C₁₄H₂₁NO₃.HCl: C, 58.43; H, 7.71; N, 4.87.

Preparation 22:

N-[(1,4-Dichloro-7-isoquinolinyl)sulphonyl]-N-(3-methoxybenzyl)glycine t-butyl ester

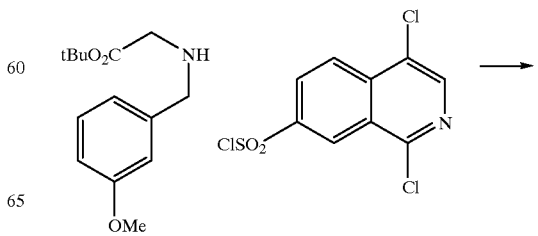

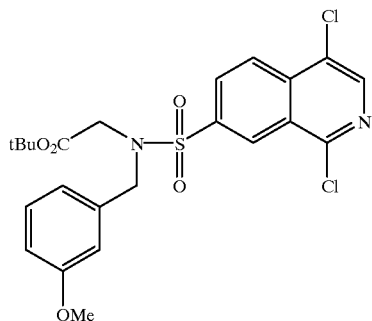

NEt₃ (0.59 mL, 4.24 mmol) and then 1,4-dichloro-7-isoquinolinesulphonyl chloride (500 mg, 1.68 mmol) were added to a stirred solution of N-(3-methoxybenzyl)glycine t-butyl ester hydrochloride (582 mg, 2.02 mmol) in $CH_2Cl_2$ (25 mL) under $N_2$ and the mixture was stirred at room temperature for 18 h. The mixture was diluted with $CH_2Cl_2$ (25 mL), washed with dilute HCl (×2, 1 M), saturated aqueous $NaHCO_3$, brine, dried ($MgSO_4$) and evaporated in vacuo. The residue was extracted with i-$Pr_2O$ which gave a precipitate on standing. The white solid was collected by filtration and dried to give N-[(1,4-dichloro-7-isoquinolinyl)sulphonyl]-N-(3-methoxybenzyl)glycine t-butyl ester (262 mg, 0.51 mmol). A second batch (165 mg, 0.32 mmol) was obtained by evaporation of the mother liquors and purification of the residue by column chromatography upon silica gel using hexane-EtOAc (80:20).

mp 129–131° C.

¹H ($CDCl_3$, 300 MHz) δ 1.3 (9H, s), 3.75 (3H, s), 3.9 (2H, s), 4.55 (2H, s), 6.8–6.9 (2H, m), 6.85 (1H, s), 7.25 (1H, m), 8.3 (1H, d), 8.4 (1H, d), 8.5 (1H, s), 8.9 (1H, s) ppm.

LRMS 511 (MH⁺), 528 ($MNH_4^+$).

Anal. Found: C, 54.03; H, 4.79; N, 5.34. Calc for $C_{23}H_{24}Cl_2N_2O_5S$: C, 54.01; H, 4.73; N, 5.48.

Preparation 23:
N-[(1,4-Dichloro-7-isoquinolinyl)sulphonyl]-N-(3-chlorobenzyl)glycine t-butyl ester

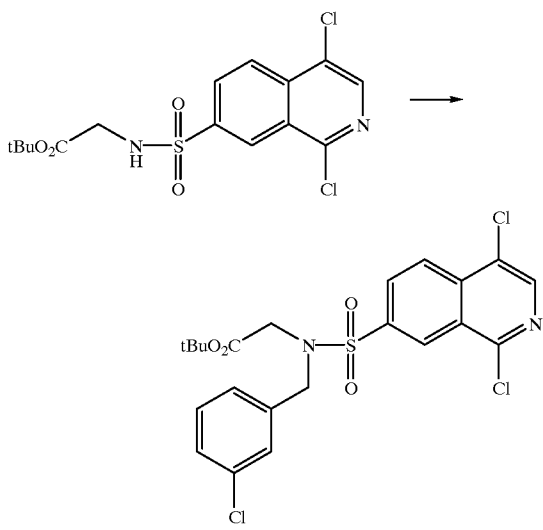

3-Chlorobenzyl chloride (0.063 mL, 0.50 mmol) was added to a stirred solution of N-[(1,4-dichloro-7-isoquinolinyl)sulphonyl]glycine t-butyl ester (195.5 mg, 0.50 mmol) in DMF (5 mL) containing $K_2CO_3$ (83 mg, 0.60 mmol) and the mixture was stirred at room temperature for 18 h. The mixture was diluted with water (50 mL), extracted with $Et_2O$ (3×30 mL) and with EtOAc (3×30 mL), and the combined organic extracts were then washed with water, brine, dried ($Na_2SO_4$) and evaporated in vacuo. The solid was triturated with hexanes, collected by filtration and dried to give N-[(1,4-dichloro-7-isoquinolinyl)sulphonyl]-N-(3-chlorobenzyl)glycine t-butyl ester (212 mg, 0.41 mmol) as a pale yellow solid.

mp 141–143° C.

¹H ($CDCl_3$, 400 MHz) δ 1.3 (9H, s), 3.95 (2H, d), 4.5 (2H, s), 7.15–7.3 (4H, m), 8.25 (1H, d), 8.35 (1H, d), 8.5 (1H, s), 8.85 (1H, s) ppm.

LRMS 515, 517 (MH⁺), 532, 534 ($MNH_4^+$).

Anal. Found: C, 51.14; H. 4.14; N, 5.31. Calc for $C_{22}H_{21}Cl_3N_2O_4S$: C, 51.22; H, 4.10; N, 5.43.

Preparation 24:
N-(4-Methoxybenzyl)glycine t-butyl ester

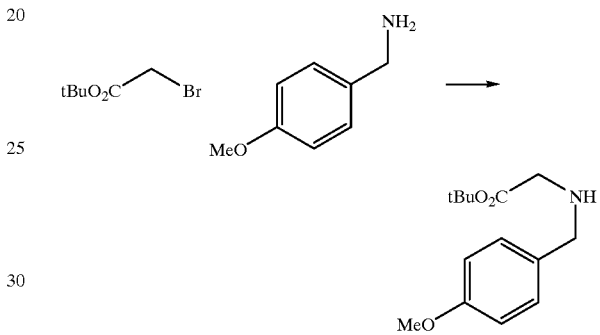

A solution of t-butyl bromoacetate (1.5 mL, 10.2 mmol) in $CH_2Cl_2$ (30 mL) was added dropwise to a stirred solution of 4-methoxybenzylamine (6.89 g, 50.2 mmol) in $CH_2Cl_2$ (70 mL) at 0° C., and the mixture was then warmed to room temperature and stirred for 1 h. Dilute HCl (30 mL, 1 M) was added and the mixture stirred for 10 min. The aqueous phase was extracted with $CH_2Cl_2$ and the combined organic extracts were washed with saturated aqueous $NaHCO_3$, brine, dried ($Na_2SO_4$) then and evaporated in vacuo. The residue was purified by column chromatography upon silica gel using $CH_2Cl_2$-MeOH (99:1 to 90:10) as eluant to give the required amine as a colourless oil. Treatment with a solution of HCl in ether (1 M) followed by trituration with $Et_2O$ gave N-(4-methoxybenzyl)glycine t-butyl ester hydrochloride (148 mg, 0.51 mmol) as an orange solid.

mp 133–134° C.

¹H ($CDCl_3$, 400 MHz) δ 1.45 (9H, s), 3.5 (2H, s), 3.8 (3H, s), 4.3 (2H, s), 6.9 (2H, d), 7.5 (2H, d), 10.2 (2H, br s) ppm.

LRMS 252 (MH⁺), 503 ($M_2H^+$), 525 ($M_2Na^+$).

Anal. Found: C, 58.08; H, 7.71; N, 4.80. Calc for $C_{14}H_{21}NO_3 \cdot HCl$: C, 58.42; H, 7.71; N, 4.87.

Preparation 25:
N-[(1,4-Dichloro-7-isoquinolinyl)sulphonyl]-N-(4-methoxybenzyl)glycine t-butyl ester

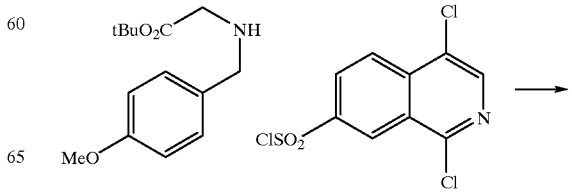

133
-continued

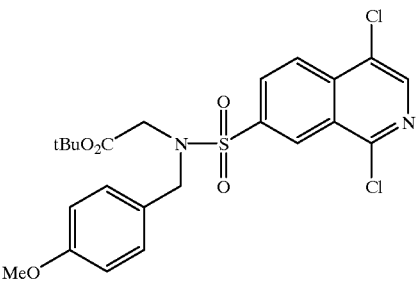

NEt₃ (0.25 mL, 1.78 mmol) and then 1,4-dichloro-7-isoquinolinesulphonyl chloride (210 mg, 0.71 mmol) were added to a stirred solution of N-(4-methoxybenzyl)glycine t-butyl ester hydrochloride (245 mg, 0.85 mmol) in $CH_2Cl_2$ (20 mL) under $N_2$ and the mixture was stirred at room temperature for 18 h. The mixture was diluted with $CH_2Cl_2$, washed with dilute HCl (2 M), saturated aqueous $NaHCO_3$, brine, dried ($Na_2SO_4$) and evaporated in vacuo. The residue was purified by column chromatography upon silica gel using hexane-EtOAc (95:5 to 90:10) as eluant and then triturated with hexane-i-$Pr_2O$ to give N-[(1,4-dichloro-7-isoquinolinyl)sulphonyl]-N-(4-methoxybenzyl)glycine t-butyl ester (160 mg, 0.31 mmol) as a white solid.

mp 117–118° C.

$^1$H (CDCl₃, 300 MHz) δ 1.3 (9H, s), 3.8 (3H, s), 3.9 (2H, s), 4.5 (2H, s), 6.85 (2H, d), 7.2 (2H, d), 8.3 (1H, d), 8.35 (1H, d), 8.5 (1H, s), 8.9 (1H, s) ppm.

LRMS 511 (MH⁺), 528 ($MNH_4^+$).

Anal. Found: C, 53.90; H, 4.59; N, 5.34. Calc for $C_{23}H_{24}Cl_2N_2O_5S$: C, 54.01; H, 4.73; N, 5.48.

Preparation 26:

N-[(1,4-Dichloro-7-isoquinolinyl)sulphonyl]-N-(2-pyridylmethyl)glycine t-butyl ester

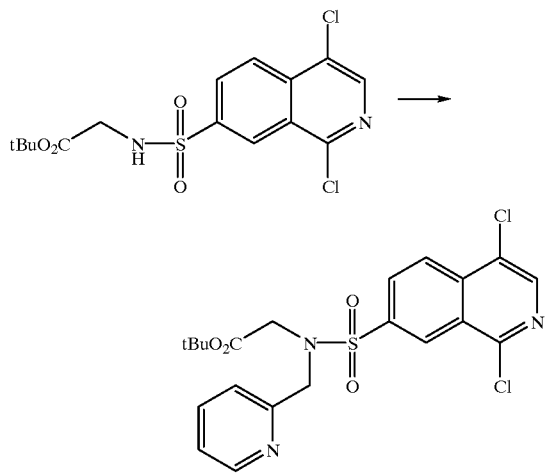

2-(Chloromethyl)pyridine hydrochloride (246 mg, 1.5 mmol) was added to a stirred solution of N-[(1,4-dichloro-7-isoquinolinyl)sulphonyl]glycine t-butyl ester (391 mg, 1.0 mmol) and anhydrous $K_2CO_3$ (415 mg, 3.0 mmol) in DMF (5 mL) under $N_2$ at 23° C. and the mixture was stirred for 18 h. The cooled mixture was azeotroped with xylene, diluted with EtOAc, washed with water, and the organic extracts were then dried ($MgSO_4$) and evaporated in vacuo. The residue was purified by column chromatography upon silica gel using pentane-EtOAc (100:0 to 50:50) as eluant to give N-[(1,4-dichloro-7-isoquinolinyl)sulphonyl]-N-(2-pyridylmethyl)glycine t-butyl ester (400 mg, 0.83 mmol) as a white solid.

134

$^1$H (CDCl₃, 400 MHz) δ 1.3 (9H, s), 4.1 (2H, s), 4.7 (2H, s), 7.1 (1H, m), 7.5 (1H, d), 7.7 (1H, dd), 8.25 (1H, d), 8.35 (1H, d), 8.45 (1H, m), 8.5 (1H, s), 8.9 (1H, s) ppm.

LRMS 482, 484 (MH⁺).

Preparation 27:

N-[(1,4-Dichloro-7-isoquinolinyl)sulphonyl]-N-(3-pyridylmethyl)glycine t-butyl ester

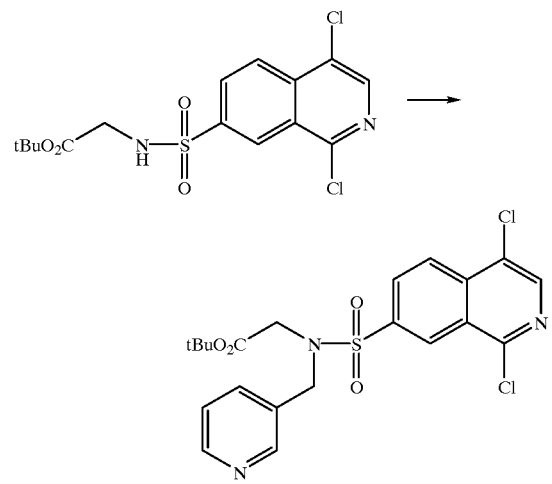

3-(Chloromethyl)pyridine hydrochloride (246 mg, 1.5 mmol) was added to a stirred solution of N-[(1,4-dichloro-7-isoquinolinyl)sulphonyl]glycine t-butyl ester (391 mg, 1.0 mmol) and anhydrous $K_2CO_3$ (416 mg, 3.0 mmol) in DMF (5 mL) under $N_2$ at 23° C. and the mixture was stirred for 18 h. The cooled mixture was azeotroped with xylene, diluted with EtOAc, washed with water, and the organic extracts were then dried ($MgSO_4$) and evaporated in vacuo. The residue was purified by column chromatography upon silica gel using pentane-EtOAc (100:0 to 50:50) as eluant to give N-[(1,4-dichloro-7-isoquinolinyl)sulphonyl]-N-(3-pyridylmethyl)glycine t-butyl ester (400 mg, 0.83 mmol) as a white solid.

$^1$H (CDCl₃, 400 MHz) δ 1.3 (9H, s), 4.1 (2H, d), 4.7 (2H, s), 7.1 (1H, m), 7.5 (1H, d), 7.7 (1H, dd), 8.25 (1H, d), 8.35 (1H, d), 8.45 (1H, m), 8.5 (1H, s), 8.9 (1H, s) ppm.

LRMS 482, 484 (MH⁺).

Preparation 28:

N-[(1,4-Dichloro-7-isoquinolinyl)sulphonyl]-N-(4-pyridylmethyl)glycine t-butyl ester

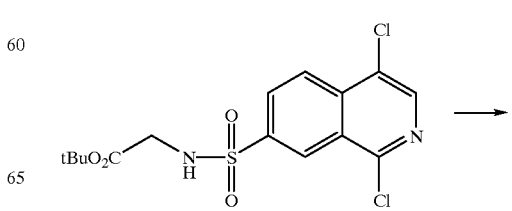

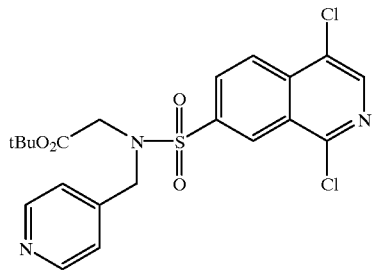

4-(Chloromethyl)pyridine hydrochloride (246 mg, 1.5 mmol) was added to a stirred solution of N-[(1,4-dichloro-7-isoquinolinyl)sulphonyl]glycine t-butyl ester (391 mg, 1.0 mmol) and anhydrous K$_2$CO$_3$ (416 mg, 3.0 mmol) in DMF (5 mL) under N$_2$ at 23° C. and the mixture was stirred for 18 h. The cooled mixture was azeotroped with xylene, diluted with EtOAc, washed with water, and the organic extracts were then dried (MgSO$_4$) and evaporated in vacuo. The residue was purified by column chromatography upon silica gel using pentane-EtOAc (100:0 to 50:50) as eluant to give N-[(1,4-dichloro-7-isoquinolinyl)sulphonyl]-N-(4-pyridylmethyl)glycine t-butyl ester (397 mg, 0.82 mmol) as a white solid.

$^1$H (CDCl$_3$, 400 MHz) δ 1.3 (9H, s), 4.0 (2H, d), 4.6 (2H, s), 7.3 (2H, d), 8.25 (1H, dd), 8.4 (1H, d), 8.5 (1H, s), 8.6 (2H, d), 8.9 (1H, d) ppm.

LRMS 482, 484 (MH$^+$).

Preparation 29:

N-[(1R)-1-Phenylethyl)]glycine t-butyl ester

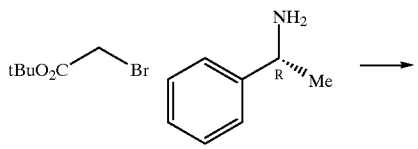

A solution of t-butyl bromoacetate (5.0 g, 25.6 mmol) in CH$_2$Cl$_2$ (5 mL) was added dropwise to a stirred solution of (+)-(R)-α-methylbenzylamine (4.65 g, 38.5 mmol) in CH$_2$Cl$_2$ (40 mL) at 0° C., and the mixture was then warmed to room temperature and stirred for 18 h. The mixture was diluted with CH$_2$Cl$_2$, washed with water, with dilute HCl (1 M) and then dried (MgSO$_4$). The solvents were evaporated in vacuo to give N-[(1R)-1-phenylethyl)]glycine t-butyl ester (3.15 g, 13.4 mmol) as a white powder.

mp 193–197° C.

$^1$H (CDCl$_3$, 300 MHz) δ 1.4 (9H, s), 1.95 (3H, d), 3.3 (1H, d), 3.6 (1H, d), 4.6 (1H, q), 5.3 (1H, s), 7.3–7.45 (3H, m), 7.5–7.65 (2H, m).

LRMS 236 (MH$^+$).

Preparation 30:

N-[(1,4-Dichloro-7-isoquinolinyl)sulphonyl]-N-[(1R)-1-phenylethyl)]glycine t-butyl ester

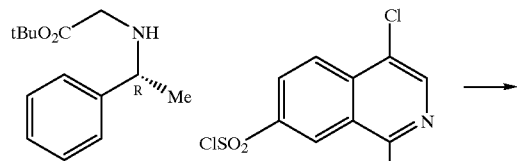

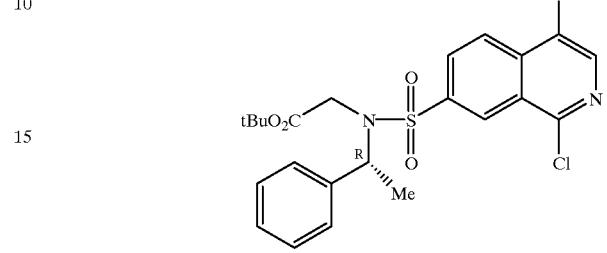

A mixture of NEt$_3$ (0.59 mL, 4.21 mmol), 1,4-dichloro-7-isoquinolinesulphonyl chloride (500 mg, 1.69 mmol) and N-[(1R)-1-phenylethyl)]glycine t-butyl ester (476 mg, 2.02 mmol) in CH$_2$Cl$_2$ (8 mL) were stirred under N$_2$ at room temperature for 18 h. The mixture was diluted with CH$_2$Cl$_2$ (50 mL), washed with dilute HCl (2 M), saturated aqueous NaHCO$_3$, brine, dried (Na$_2$SO$_4$) and evaporated in vacuo. The residue was purified by column chromatography upon silica gel using pentane-EtOAc (90:10) as eluant to give N-[(1,4-dichloro-7-isoquinolinyl)sulphonyl]-N-[(1R)-1-phenylethyl)]glycine t-butyl ester (490 mg, 0.99 mmol) as a colourless oil.

$^1$H (CDCl$_3$, 300 MHz) δ 1.3 (9H, s), 1.4 (3H, d), 3.9 (1H, d), 4.1 (1H, d), 5.15 (1H, q), 7.1–7.25 (5H, m), 8.4 (1H, d), 8.5 (1H, d), 8.65 (1H, s), 8.7 (1H, d) ppm.

LRMS 495 (MH$^+$), 512 (MNH$_4^+$).

Preparation 31:

N-[(1S)-1-Phenylethyl)]glycine t-butyl ester

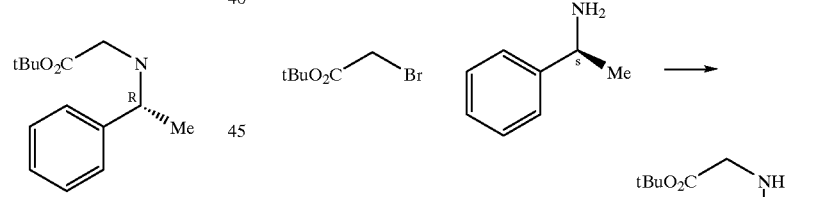

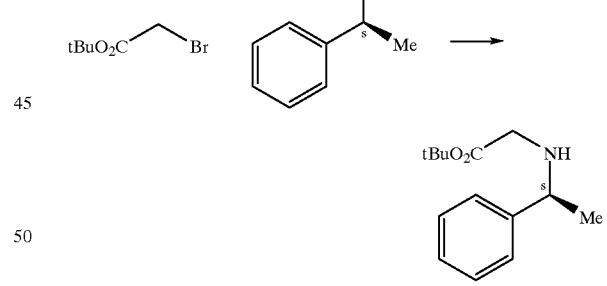

A solution of t-butyl bromoacetate (5.0 g, 25.6 mmol) in CH$_2$Cl$_2$ (5 mL) was added dropwise to a stirred solution of (−)-(S)-α-methylbenzylamine (4.65 g, 38.5 mmol) in CH$_2$Cl$_2$ (40 mL) at 0° C., and the mixture was then warmed to room temperature and stirred for 18 h. The mixture was diluted with CH$_2$Cl$_2$, washed with water, with dilute HCl (1 M) and then dried (MgSO$_4$). The solvents were evaporated in vacuo to give N-[(1S)-1-phenylethyl)]glycine t-butyl ester (2.02 g, 8.6 mmol) as a white powder.

mp 197–202° C.

$^1$H (CDCl$_3$, 300 MHz) δ 1.4 (9H, s), 1.9 (3H, d), 3.3 (1H, d), 3.55 (1H, d), 4.5 (1H, q), 5.3 (1H, s), 7.3–7.45 (3H, m), 7.5–7.6 (2H, m) ppm.

LRMS 236 (MH$^+$).

Preparation 32:
N-[(1,4-Dichloro-7-isoquinolinyl)sulphonyl]-N-[(1S)-1-phenylethyl)]glycine t-butyl ester

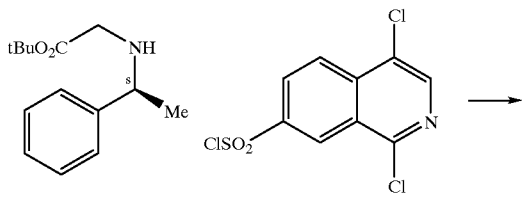

A mixture of NEt₃ (0.59 mL, 4.21 mmol), 1,4-dichloro-7-isoquinolinesulphonyl chloride (500 mg, 1.69 mmol) and N-[(1S)-1-phenylethyl)]glycine t-butyl ester (476 mg, 2.02 mmol) in CH$_2$Cl$_2$ (8 mL) were stirred under N$_2$ at room temperature for 24 h. The mixture was diluted with CH$_2$Cl$_2$ (50 mL), washed with dilute HCl (2 M), saturated aqueous NaHCO$_3$, brine, dried (Na$_2$SO$_4$) and evaporated in vacuo. The residue was purified by column chromatography upon silica gel using pentane-EtOAc (90:10) as eluant to give N-[(1,4-dichloro-7-isoquinolinyl)sulphonyl]-N-[(1S)-1-phenylethyl)]glycine t-butyl ester (420 mg, 0.85 mmol) as a colourless oil.

$^1$H (CDCl$_3$, 300 MHz) δ 1.3 (9H, s), 1.4 (3H, d), 3.9 (1H, d), 4.1 (1H, d), 5.15 (1H, q), 7.1–7.25 (5H, m), 8.4 (1H, d), 8.5 (1H, d), 8.65 (1H, s), 8.7 (1H, d) ppm.

LRMS 495 (MH$^+$), 512 (MNH$_4^+$).

Preparation 33:
N-Benzyl-L-alanine t-butyl ester

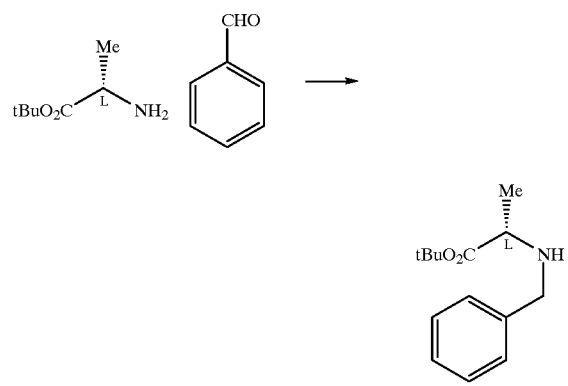

Benzaldehyde (2.69 mL, 26.4 mmol) was added to a stirred slurry of L-alanine t-butyl ester (4.0 g, 22.0 mmol) and NEt$_3$ (3.07 mL, 22.0 mmol) in CH$_2$Cl$_2$ (70 mL) at 23° C. and the mixture was stirred for 10 min. NaBH(OAc)$_3$(6.44 g, 30.4 mmol) was added portionwise and the mixture stirred at 23° C. for 24 h. The mixture was washed with water, dried (MgSO$_4$) and the solvents were evaporated in vacuo. The residue was purified by column chromatography upon silica gel using CH$_2$Cl$_2$-MeOH (99:1 to 95:5) as eluant to give to give N-benzyl-L-alanine t-butyl ester (3.97 g, 16.9 mmol) as a colourless oil.

$^1$H (CDCl$_3$, 300 MHz) δ 1.3 (3H, d), 1.5 (9H, s), 2.1 (1H, s), 3.25 (1H, q), 3.7 (1H, d), 3.8 (1H, d), 7.2–7.4 (5H, m) ppm.

LRMS 236 (MH$^+$), 258 (MNa$^+$).

Preparation 34:
N-Benzyl-N-[(1,4-dichloro-7-isoquinolinyl)sulphonyl]-L-alanine t-butyl ester

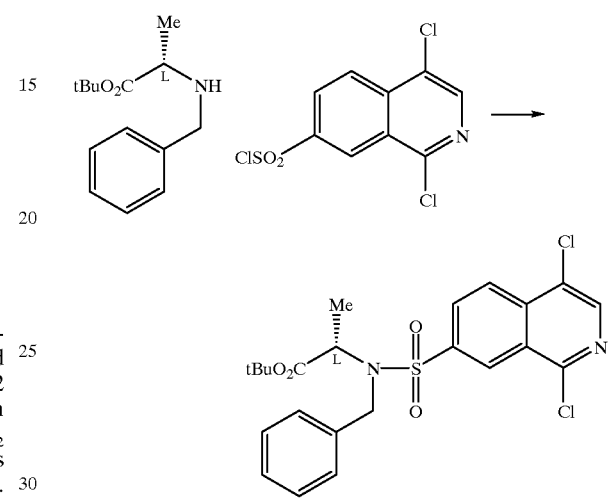

A solution of 1,4-dichloro-7-isoquinolinesulphonyl chloride (600 mg, 2.02 mmol) in CH$_2$Cl$_2$ (3 mL) was added to a stirred solution of N-benzyl-L-alanine t-butyl ester (571 mg, 2.43 mmol) and NEt$_3$ (0.70 mL, 5.06 mmol) in CH$_2$Cl$_2$ (3 mL) and the mixture was stirred at room temperature for 24 h. The mixture was diluted with CH$_2$Cl$_2$ (50 mL), washed with dilute HCl (2 M), saturated aqueous NaHCO$_3$, brine, dried (Na$_2$SO$_4$) and evaporated in vacuo. The residue was purified by column chromatography upon silica gel using pentane-EtOAc (95:5 to 85:15) as eluant to give N-benzyl-N-[(1,4-dichloro-7-isoquinolinyl)sulphonyl]-L-alanine t-butyl ester (470 mg, 0.95 mmol) as a colourless solid.

mp 92–96° C.

$^1$H (CDCl$_3$, 300 MHz) δ 1.3 (9H, s), 1.35 (3H, d), 4.4 (1H, d), 4.7 (1H, q), 4.8 (1H, d), 7.1–7.3 (3H, m), 7.3–7.4 (2H, m), 8.15 (1H, d), 8.3 (1H, d), 8.45 (1H, s), 8.7 (1H, s) ppm.

LRMS 495 (MH$^+$).

Preparation 35:
N-[(1,4-Dichloro-7-isoquinolinyl)sulphonyl]-L-alanine t-butyl ester

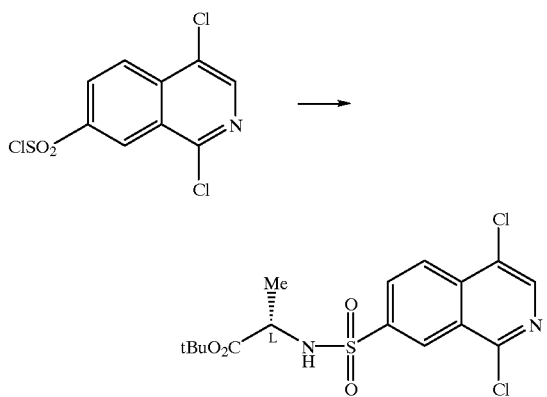

A solution of 1,4-dichloro-7-isoquinolinesulphonyl chloride (500 mg, 1.69 mmol) in CH$_2$Cl$_2$ (3 mL) was added to a stirred solution of L-alanine t-butyl ester (322 mg, 1.77 mmol) and NEt$_3$ (0.82 mL, 5.9 mmol) in CH$_2$Cl$_2$ (6 mL) and the mixture was stirred at 23° C. for 17 h. The mixture was diluted with CH$_2$Cl$_2$, washed with dilute HCl (2 M), saturated aqueous NaHCO$_3$, brine, dried (MgSO$_4$) and evaporated in vacuo. The residue was purified by column chromatography upon silica gel using pentane-EtOAc (90:10 to 50:50) as eluant to give N-[(1,4-dichloro-7-isoquinolinyl)sulphonyl]-L-alanine t-butyl ester (500 mg, 1.23 mmol) as a white powder.

mp 115–119° C.

$^1$H (CDCl$_3$, 300 MHz) δ 1.2 (9H, s), 1.4 (3H, d), 4.0 (1H, dq), 5.4 (1H, d), 8.25 (1H, d), 8.4 (1H, d), 8.5 (1H, s), 8.9 (1H, s) ppm.

LRMS 405 (MH$^+$).

Anal. Found: C, 47.57; H, 4.39; N, 6.72. Calc for C$_{16}$H$_{18}$Cl$_2$N$_2$O$_4$S: C, 47.42; H, 4.48; N, 6.91.

Preparation 36:
N-[(1,4-Dichloro-7-isoquinolinyl)sulphonyl]-D-alanine methyl ester

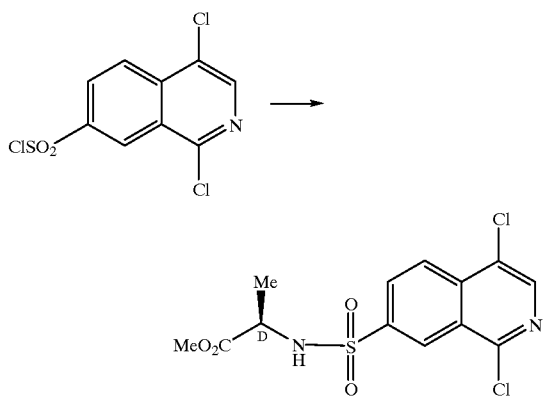

A solution of 1,4-dichloro-7-isoquinolinesulphonyl chloride (500 mg, 1.69 mmol) in CH$_2$Cl$_2$ (3 mL) was added to a stirred solution of D-alanine methyl ester (247 mg, 1.77 mmol) and NEt$_3$ (0.82 mL, 5.9 mmol) in CH$_2$Cl$_2$ (6 mL) and the mixture was stirred at 23° C. for 16 h. The mixture was diluted with CH$_2$Cl$_2$, washed with dilute HCl (2 M), saturated aqueous NaHCO$_3$, brine, dried (MgSO$_4$) and evaporated in vacuo. The residue was purified by column chromatography upon silica gel using pentane-EtOAc (90:10 to 50:50) as eluant to give N-[1,4-dichloro-7-isoquinolinyl) sulphonyl]-D-alanine methyl ester (420 mg, 1.16 mmol) as a white powder.

mp 150–152° C.

$^1$H (CDCl$_3$, 300 MHz) δ 1.45 (3H, d), 3.55 (3H, s), 4.15 (1H, dq), 5.4 (1H, d), 8.2 (1H, d), 8.4 (1H, d), 8.5 (1H, s), 8.9 (1H, s) ppm.

LRMS 363, 365 (MH$^+$).

Anal. Found: C, 42.97; H, 3.29; N, 7.42. Calc for C$_{13}$H$_{12}$Cl$_2$N$_2$O$_4$S: C, 42.99; H, 3.33; N, 7.71.

Preparation 37:
N-[(1,4-Dichloro-7-isoquinolinyl)sulphonyl]-L-valine t-butyl ester

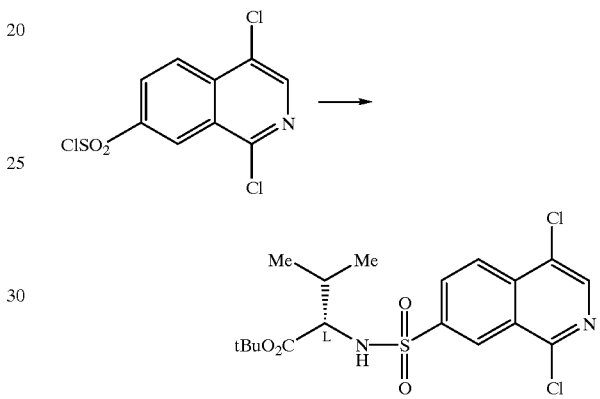

NEt$_3$ (0.59 mL, 4.2 mmol) was added to a stirred mixture of 1,4-dichloro-7-isoquinolinesulphonyl chloride (500 mg, 1.69 mmol) and L-valine t-butyl ester (354 mg, 1.69 mmol) and in CH$_2$Cl$_2$ (25 mL) and the mixture was stirred at 23° C. for 3 d. The mixture was washed with dilute HCl (2×20 mL, 1 M), saturated aqueous NaHCO$_3$, brine, dried (MgSO$_4$) and evaporated in vacuo. The residue was extracted with hexane, which crystallised on standing, to give N-[(1,4-dichloro-7-isoquinolinyl)sulphonyl]-L-valine t-butyl ester (463 mg, 1.07 mmol) as a white solid.

mp 127–129° C.

$^1$H (CDCl$_3$, 300 MHz) δ 0.9 (3H, d), 1.0 (3H, d), 1.1 (9H, s), 2.0–2.2 (1H, m), 3.8 (1H, dd), 5.25 (1H, d), 8.2 (1H, d), 8.35 (1H, d), 8.5 (1H, s), 8.9 (1H, s) ppm.

LRMS 433, 435 (MH$^+$), 450, 452 (MNH$_4^+$).

Anal. Found: C, 49.86; H, 5.13; N, 6.40. Calc for C$_{18}$H$_{22}$Cl$_2$N$_2$O$_4$S: C, 49.89; H, 5.18; N, 6.46.

Preparation 38:
N-[(1,4-Dichloro-7-isoquinolinyl)sulphonyl]-D-valine t-butyl ester

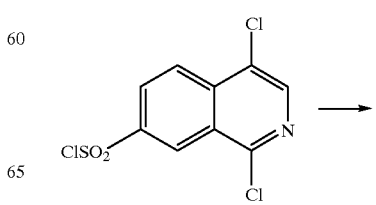

-continued

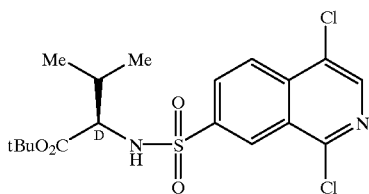

D-Valine t-butyl ester has been prepared previously, see: Shepel, E. N.; Iodanov, S.; Ryabova, I. D.; Miroshnikov, A. I.; Ivanov, V. T.; Ovchinnikov, Yu A. *Bioorg. Khim.* 1972, 2, 581–593.

D-Valine t-butyl ester (354 mg, 1.69 mmol) and then $NEt_3$ (0.59 mL, 4.2 mmol) were added to a stirred solution of 1,4-dichloro-7-isoquinolinesulphonyl chloride (500 mg, 1.69 mmol) and in $CH_2Cl_2$ (20 mL) and the mixture was stirred at 23° C. for 16 h. The mixture was diluted with $CH_2Cl_2$ (50 mL), washed with saturated aqueous $NaHCO_3$, water, aqueous citric acid (1 M), water, brine, dried ($MgSO_4$) and evaporated in vacuo. The residue was dissolved in i-$Pr_2O$ and hexane was added which gave a precipitate. The solvents were evaporated in vacuo and the solid was triturated with hexane to give N-[(1,4-dichloro-7-isoquinolinyl)sulphonyl]-D-valine t-butyl ester (532 mg, 1.22 mmol) as a white solid. An analytical sample was obtained by recrystallisation from hexane.

mp 117–119° C.

$^1$H (CDCl$_3$, 400 MHz) δ 0.9 (3H, d), 1.0 (3H, d), 1.1 (9H, s), 2.0–2.2 (1H, m), 3.8 (1H, dd), 5.3 (1H, d), 8.2 (1H, d), 8.35 (1H, d), 8.5 (1H, s), 8.9 (1H, s) ppm.

LRMS 433, 435 (MH$^+$).

Anal. Found: C, 49.99; H, 5.28; N, 6.34. Calc for $C_{18}H_{22}Cl_2N_2O_4S$: C, 49.89; H, 5.12; N, 6.46.

Preparation 39:
N-[(1,4-Dichloro-7-isoquinolinyl)sulphonyl]-D-tert-leucine t-butyl ester

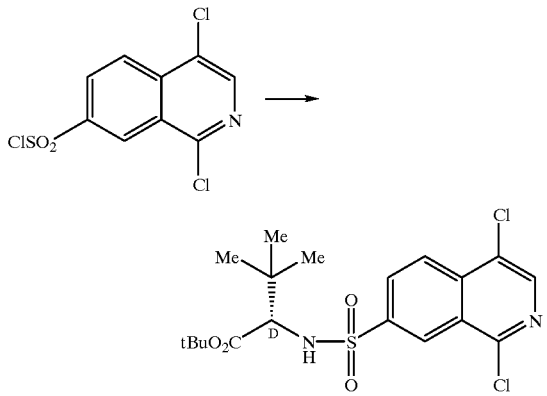

A mixture of D-tert-leucine t-butyl ester hydrochloride (250 mg, 1.12 mmol), $NEt_3$ (0.40 mL, 2.87 mmol) and 1,4-dichloro-7-isoquinolinesulphonyl chloride (330 mg, 1.11 mmol) in $CH_2Cl_2$ (20 mL) was stirred at 23° C. for 16 h. The mixture was diluted with $CH_2Cl_2$ (50 mL), washed with water, aqueous citric acid (1 M), water, saturated aqueous $NaHCO_3$, brine, dried ($MgSO_4$) and evaporated in vacuo. The residue was purified by column chromatography upon silica gel using hexane-EtOAc (90:10) as eluant to give N-[(1,4-dichloro-7-isoquinolinyl)sulphonyl]-D-tert-leucine t-butyl ester (250 mg, 0.56 mmol) as a white foam.

mp 140–142° C.

$^1$H (CDCl$_3$, 400 MHz) δ 1.0 (9H, s), 1.05 (9H, s), 3.6 (1H, d), 5.35 (1H, d), 8.2 (1H, d), 8.35 (1H, d), 8.45 (1H, s), 8.85 (1H, s).

LRMS 447, 449, 451 (MH$^+$).

Anal. Found: C, 51.03; H, 5.41; N, 6.13. Calc for $C_{19}H_{24}Cl_2N_2O_4S$: C, 51.01; H, 5.41; N, 6.26.

Preparation 40:
N-[(1,4-Dichloro-7-isoquinolinyl)sulphonyl]-L-phenylalanine t-butyl ester

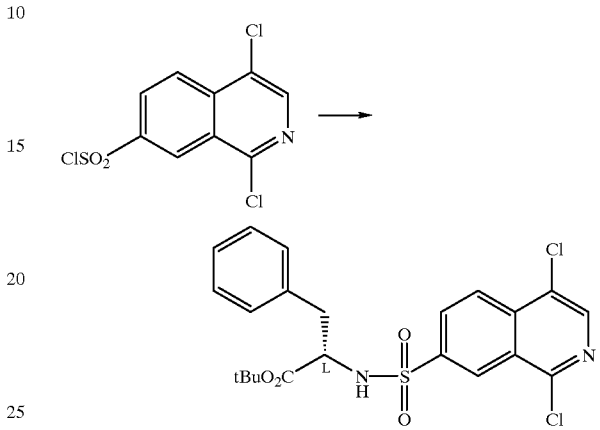

A mixture of L-phenylalanine t-butyl ester (352 mg, 1.37 mmol), $NEt_3$ (0.41 mL, 2.97 mmol) and 1,4-dichloro-7-isoquinolinesulphonyl chloride (399 mg, 1.35 mmol) in $CH_2Cl_2$ (10 mL) was stirred at 23° C. for 20 h. The solvents were evaporated in vacuo and the residue suspended in EtOAc. This solution was washed with water, brine, dried ($MgSO_4$) and evaporated in vacuo. The residue was purified by column chromatography upon silica gel using pentane-EtOAc (90:10 to 70:30) as eluant to give N-[(1,4-dichloro-7-isoquinolinyl)sulphonyl]-L-phenylalanine t-butyl ester (450 mg, 0.94 mmol) as a white crystallised foam.

$^1$H (CDCl$_3$, 300 MHz) δ 1.2 (9H, s), 2.95 (1H, dd), 3.1 (1H, dd), 4.1 (1H, m), 5.3 (1H, d), 7.0–7.2 (5H, m), 8.1 (1H, d), 8.25 (1H, d), 8.5 (1H, s), 8.75 (1H, d) ppm.

LRMS 481 (MH$^+$), 498 (MNH$_4^+$).

Preparation 41:
N-(Benzyloxycarbonyl)-O-methyl-D-serine t-butyl ester

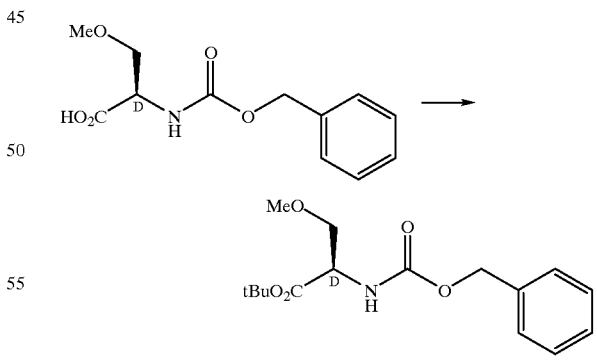

Condensed isobutylene gas (35 mL) was added to a solution of N-(benzyloxycarbonyl)-O-methyl-D-serine dicyclohexlamine salt (2.5 g, 5.76 mmol) in $CH_2Cl_2$ (35 mL) at −78° C. in a steel bomb. Conc. $H_2SO_4$ (0.5 mL) was added, the vessel was sealed and the mixture allowed to warm to 23° C. [CAUTION: Pressure]. The mixture was stirred at 23° C. for 6 d, the vessel was vented and excess isobutylene was allowed to evaporate. The mixture then poured into aqueous NaHCO₃ (30 mL, 10%), extracted with CH₂Cl₂ (3×30 mL), and the combined organic extracts were dried (Na₂SO₄) and evaporated in vacuo. The residue was purified by column chromatography upon silica gel using hexane-EtOAc (80:20) as eluant to give N-(benzyloxycarbonyl)-O-methyl-D-serine t-butyl ester (1.2 g, 3.88 mmol) as a colorless oil.

¹H (CDCl₃, 400 MHz) δ 1.45 (9H, s), 3.35 (3H, s), 3.6 (1H, dd), 3.75 (1H, dd), 4.35 (1H, br d), 5.1 (2H, s), 5.6 (1H, br d), 8.4–8.9 (5H, m) ppm.

LRMS 310 (MH⁺), 327 (MNH₄⁺).

Preparation 42:
O-Methyl-D-serine t-butyl ester

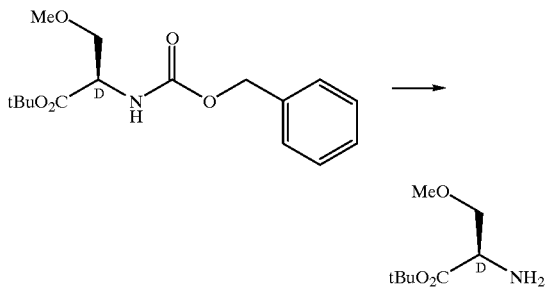

A solution of N-(benzyloxycarbonyl)-O-methyl-D-serine t-butyl ester (1.15 g, 3.72 mmol) in MeOH (20 mL) was hydrogenated over 10% Pd/C (150 mg) under an atmosphere of Hz (15 psi) at 23° C. for 18 h. The mixture was filtered and the filtrate evaporated in vacuo. The residue was dissolved in Et₂O, a solution of HCl in Et₂O (1 M) was added, the solvents were evaporated in vacuo to give a white solid and this material was triturated with hexane to give O-methyl-D-serine t-butyl ester hydrochloride (0.62 g, 2.90 mmol).

mp 167–169° C. (dec).

¹H (CDCl₃, 400 MHz) δ 1.5 (9H, s), 1.8–2.2 (1H, br s), 3.4 (3H, s), 3.9 (1H, dd), 4.0 (1H, dd), 4.2 (1H, t), 8.4–8.9 (3H, br s) ppm. LRMS 176 (MH⁺).

Anal. Found: C, 45.26; H, 8.59; N, 6.39. Calc for C₈H₁₇NO₃.HCl: C, 45.39; H, 8.57; N, 6.62.

Preparation 43:
N-[(1,4-Dichloro-7-isoquinolinyl)sulphonyl]-O-methyl-D-serine t-butyl ester

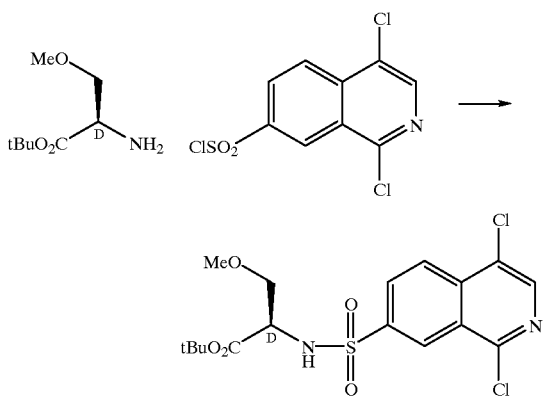

A mixture of O-methyl-D-serine t-butyl ester hydrochloride (300 mg, 1.42 mmol), NEt₃ (0.50 mL, 3.6 mmol) and 1,4-dichloro-7-isoquinolinesulphonyl chloride (420 mg, 1.42 mmol) in CH₂Cl₂ (20 mL) was stirred at 23° C. for 3 d. The mixture was diluted with CH₂Cl₂ (30 mL), washed with water, aqueous citric acid (1 M), water, saturated aqueous NaHCO₃, brine, dried (MgSO₄) and evaporated in vacuo. The residue was purified by column chromatography upon silica gel using hexane-EtOAc (80:20) as eluant to give N-[(1,4-dichloro-7-isoquinolinyl)sulphonyl]-O-methyl-D-serine t-butyl ester (356 mg, 0.82 mmol) as a white solid.

mp 135–137° C.

¹H(CDCl₃, 400 MHz) δ 1.25 (9H, s), 3.3 (3H, s), 3.6 (1H, dd), 3.7 (1H, dd), 4.1 (1H, br s), 5.6 (1H, br d), 8.25 (1H, d), 8.35 (1H, d), 8.5 (1H, s), 8.9 (1H, s) ppm.

LRMS 435, 437 (MH⁺), 452, 454 (MNH₄⁺).

Anal. Found: C, 47.04; H, 4.62; N, 6.42. Calc for C₁₇H₂₀Cl₂N₂O₅S: C, 46.90; H, 4.63; N, 6.44.

Preparation 44:
N-[(1,4-Dichloro-7-isoquinolinyl)sulphonyl]-D-aspartic acid di-t-butyl ester

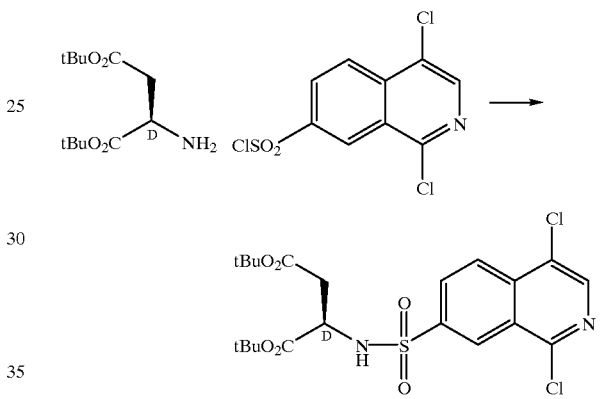

A mixture of D-aspartic acid di-t-butyl ester (462 mg, 1.64 mmol), NEt₃ (0.50 mL, 3.6 mmol) and 1,4-dichloro-7-isoquinolinesulphonyl chloride (400 mg, 1.35 mmol) in CH₂Cl₂ (30 mL) was stirred at 23° C. for 18 h. The mixture was diluted with CH₂Cl₂ (30 mL), washed with dilute HCl (2 M), saturated aqueous NaHCO₃, brine, dried (MgSO₄) and evaporated in vacuo to give N-[(1,4-dichloro-7-isoquinolinyl)sulphonyl]-D-aspartic acid di-t-butyl ester (520 mg, 1.03 mmol) as a white solid.

mp 106–110° C.

¹H (CDCl₃, 400 MHz) δ 1.2 (9H, s), 1.4 (9H, s), 2.7–2.8 (1H, dd), 2.8–2.9 (1H, dd), 4.15 (1H, m), 8.2 (1H, d), 8.4 (1H, d), 8.5 (1H, s), 8.9 (1H, s) ppm.

LRMS 507 (MH⁺).

Preparation 45:
N-[(1,4-Dichloro-7-isoquinolinyl)sulphonyl]-L-proline t-butyl ester

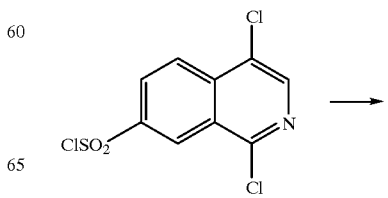

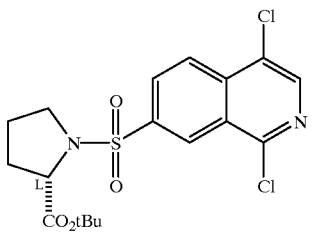

A mixture of L-proline t-butyl ester hydrochloride (335 mg, 1.61 mmol), NEt₃ (0.53 mL, 3.78 mmol) and 1,4-dichloro-7-isoquinolinesulphonyl chloride (449 mg, 1.51 mmol) in CH₂Cl₂ (10 mL) was stirred at 23° C. for 20 h. The solvents were evaporated in vacuo and the residue suspended in EtOAc. This solution was washed with water, brine, dried (MgSO₄) and evaporated in vacuo. The residue was purified by column chromatography upon silica gel using pentane-EtOAc (90:10 to 70:30) as eluant to give N-[(1,4-dichloro-7-isoquinolinyl)sulphonyl]-L-proline t-butyl ester (543 mg, 1.26 mmol) as a white solid.

¹H (CDCl₃, 300 MHz) δ 1.45 (9H, s), 1.8–2.1 (3H, m), 2.1–2.3 (1H, m), 3.4–3.6 (2H, m), 4.4 (1H, dd), 8.3 (1H, d), 8.4 (1H, d), 8.5 (1H, s), 8.9 (1H, d) ppm.

LRMS 431 (MH⁺), 448, 450 (MNH₄⁺).

Anal. Found: C, 50.09; H, 4.62; N, 6.37. Calc for C₁₈H₂₀Cl₂N₂O₄S: C, 50.12; H, 4.67; N, 6.49.

Preparation 46:

N-[(1,4-Dichloro-7-isoquinolinyl)sulphonyl]-D-proline t-butyl ester

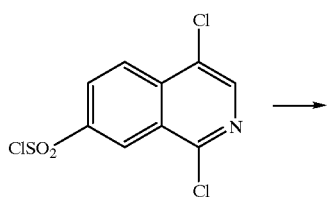

A mixture of D-proline t-butyl ester hydrochloride (340 mg, 1.64 mmol), NEt₃ (0.50 mL, 3.6 mmol) and 1,4-dichloro-7-isoquinolinesulphonyl chloride (400 mg, 1.35 mmol) in CH₂Cl₂ (30 mL) was stirred at 23° C. for 20 h. The mixture was diluted with CH₂Cl₂ (50 mL), washed with dilute HCl (2 M), saturated aqueous NaHCO₃, brine, dried (MgSO₄) and evaporated in vacuo to give N-[(1,4-dichloro-7-isoquinolinyl)sulphonyl]-D-proline t-butyl ester (550 mg, 1.28 mmol) as a white solid.

mp 80–82° C.

¹H (CDCl₃, 400 MHz) δ 1.4 (9H, s), 1.9–2.0 (3H, m), 2.2 (1H, m), 3.4–3.6 (2H, m), 4.4 (1H, m), 8.3 (1H, d), 8.4 (1H, d), 8.5 (1H, s), 8.9 (1H, s) ppm.

LRMS 431 (MH⁺), 448 (MNH₄⁺).

Anal. Found: C, 49.76; H, 4.75; N, 6.39. Calc for C₁₈H₂₀Cl₂N₂O₄S: C, 50.12; H, 4.67; N, 6.49.

Preparation 47:

1,4-Dichloro-7-{[(2R)-(hydroxymethyl)-1-pyrrolidinyl]sulphonyl}isoquinoline

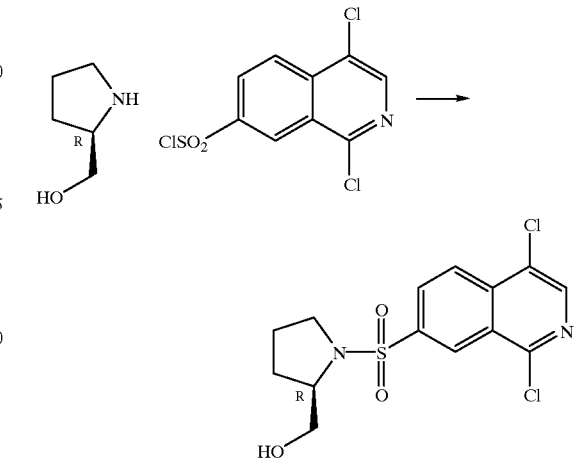

A mixture of (R)-2-pyrrolidinemethanol (1.1 mL, 11.0 mmol), NEt₃ (1.5 mL, 20 mmol) and 1,4-dichloro-7-isoquinolinesulphonyl chloride (3.0 g, 10 mmol) in CH₂Cl₂ (50 mL) was stirred at 23° C. for 30 min. The mixture was diluted with CH₂Cl₂ (50 mL), washed with aqueous citric acid (1 N), water, brine, dried (MgSO₄) and evaporated in vacuo to give 1,4-dichloro-7-{[(2R)-(hydroxymethyl)-1-pyrrolidinyl]sulphonyl}isoquinoline (4.0 g, 11 mmol) as a white solid.

mp 167.5–168.5° C.

¹H (CDCl₃, 400 MHz) δ 1.5–1.55 (1H, m), 1.6–2.0 (3H, m), 2.5 (1H, br t), 3.3–3.4 (1H, m), 3.5–3.6 (1H, m), 3.7–3.8 (3H, m), 8.25 (1H, d), 8.4 (1H, d), 8.5 (1H, s), 8.9 (1H, s) ppm.

LRMS 361, 363 (MH⁺), 378 (MNH₄⁺), 383 (MNa⁺).

Anal. Found: C, 46.65; H, 3.91; N, 7.61. Calc for C₁₄H₁₄Cl₂N₂O₃S: C, 46.55; H, 3.91; N, 7.75.

Preparation 48:

Methyl 2-{[(1,4-dichloro-7-isoquinolinyl)sulphonyl]amino}isobutyrate

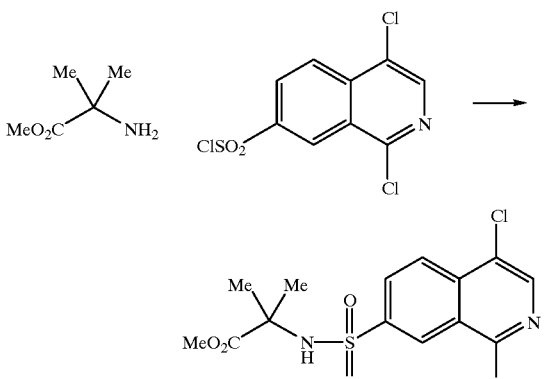

A mixture of methyl 2-aminoisobutyrate (310 mg, 2.02 mmol), NEt₃ (0.70 mL, 5.05 mmol) and 1,4-dichloro-7-isoquinolinesulphonyl chloride (500 mg, 1.69 mmol) in CH₂Cl₂ (30 mL) was stirred at 23° C. for 17 h. The mixture was diluted with CH$_2$Cl$_2$ (50 mL), washed with dilute HCl (2 M), saturated aqueous NaHCO$_3$, brine, dried (Na$_2$SO$_4$) and evaporated in vacuo The residue was purified by column chromatography upon silica gel using hexane-EtOAc (70:30) as eluant to give methyl 2-{[(1,4-dichloro-7-isoquinolinyl)sulphonyl]amino}isobutyrate (210 mg, 0.56 mmol) as a white solid.

mp 159.5–161° C.

$^1$H (CDCl$_3$, 400 MHz) δ 1.5 (6H, s), 3.7 (3H, s), 5.55 (1H, s), 8.25 (1H, d), 8.35 (1H, d), 8.5 (1H, s), 8.9 (1H, s) ppm.

LRMS 377 (MH$^+$).

Anal. Found: C, 44.24; H, 3.72; N, 7.29. Calc for C$_{14}$H$_{14}$Cl$_2$N$_2$O$_4$S: C, 44.57; H, 3.74; N, 7.43.

Preparation 49:

2-{[(1,4-Dichloro-7-isoquinolinyl)sulphonyl]amino}-2-methylpropanamide

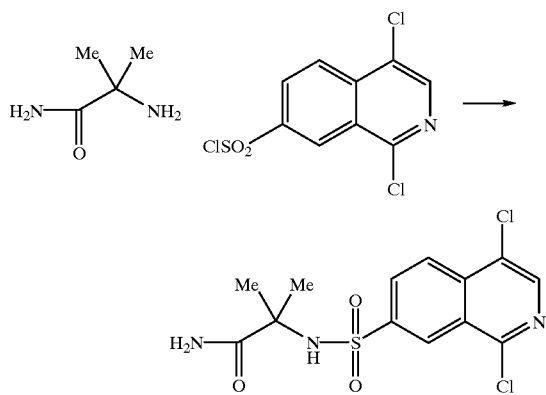

A mixture of 2-amino-2-methylpropanamide (200 mg, 1.96 mmol), NEt$_3$ (0.69 mL, 5.0 mmol) and 1,4-dichloro-7-isoquinolinesulphonyl chloride (580 mg, 1.96 mmol) in CH$_2$Cl$_2$ (20 mL) was stirred at 23° C. for 17 h. The mixture was diluted with CH$_2$Cl$_2$ (50 mL), washed with water, aqueous citric acid (1 N), water, brine, dried (MgSO$_4$) and evaporated in vacuo The residue was purified by column chromatography upon silica gel using CH$_2$Cl$_2$-MeOH-0.880NH$_3$ (90:10:1) as eluant to give 2-{[(1,4-dichloro-7-isoquinolinyl)sulphonyl]amino}-2-methylpropanamide (228 mg, 0.62 mmol) as a white solid.

mp 220–222° C.

$^1$H (d$_4$-MeOH, 400 MHz) δ 1.4 (6H, s), 3.3 (2H, s), 8.4 (1H, dd), 8.45 (1H, d), 8.55 (1H, d), 8.9 (1H, s).

LRMS 362, 364 (MH$^+$), 379, 381 (MNH$_4^+$).

Anal. Found: C, 42.81; H, 3.70; N, 11.15. Calc for C$_{13}$H$_{13}$Cl$_2$N$_3$O$_3$S.0.25H$_2$O: C, 42.58; H, 3.71; N, 11.46.

Preparation 50:

Ethyl 1-aminocyclobutanecarboxylate

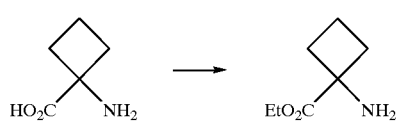

A solution 1-aminocyclobutanecarboxylic acid (500 mg, 4.34 mmol) in EtOH (10 mL) was saturated with HCl gas, and the mixture was stirred at 23° C. for 4 d. The solvents were vaporated in vacuo, azeotroping with PhMe and CH$_2$Cl$_2$, to give ethyl 1-aminocyclobutanecarboxylate hydrochloride (754 mg, 4.20 mmol) as an off-white solid.

$^1$H (DMSO-d$_6$, 300 MHz) δ 1.25 (3H, t), 1.9–2.1 (2H, m), 2.3–2.5 (4H, m), 4.2 (2H, q), 8.8 (2H, br s) ppm.

LRMS 2 87 (M$_2$H$^+$).

Preparation 51:

Ethyl 1-{[(1,4-dichloro-7-isoquinolinyl)sulphonyl]amino}cyclobutanecarboxylate

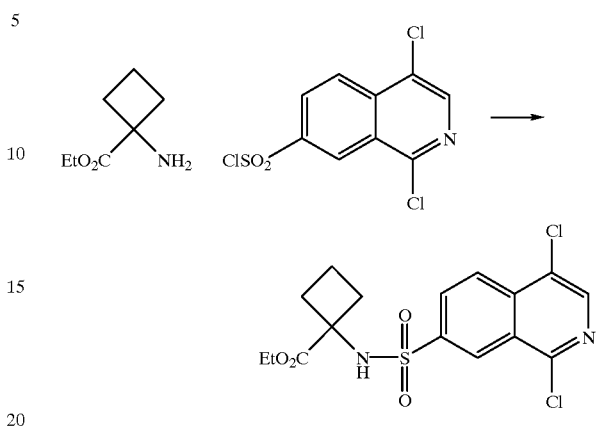

A mixture of ethyl 1-aminocyclobutanecarboxylate hydrochloride (382 mg, 2.12 mmol), NEt$_3$ (1.04 mL, 7.43 mmol) and 1,4-dichloro-7-isoquinolinesulphonyl chloride (630 mg, 2.12 mmol) in CH$_2$Cl$_2$ (8 mL) was stirred at 23° C. for 18 h. The mixture was diluted with CH$_2$Cl$_2$, washed with dilute HCl (2 M), saturated aqueous NaHCO$_3$, brine, dried (MgSO$_4$) and evaporated in vacuo. The residue was purified by column chromatography upon silica gel using pentane-EtOAc (90:10 to 80:20) as eluant to give ethyl 1-{[(1,4-dichloro-7-isoquinolinyl)sulphonyl]amino}cyclobutanecarboxylate (480 mg, 1.19 mmol) as a white powder.

mp 123–125° C.

$^1$H (CDCl$_3$, 300 MHz) δ 1.2 (3H, t), 1.9–2.1 (2H, m), 2.4–2.6 (4H, m), 4.0 (2H, q), 5.5 (1H, br s), 8.25 (1H, d), 8.4 (1H, d), 8.5 (1H, s), 8.9 (1H, s) ppm.

LRMS 403, 405 (MH$^+$), 420 (MNH$_4^+$).

Preparation 52:

Cycloleucine ethyl ester

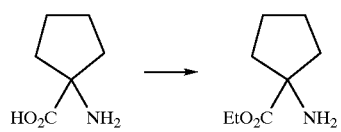

A solution of cycloleucine (8.94 g, 69.2 mmol) in EtOH (100 mL) was saturated with HCl gas, and the mixture was stirred at 23° C. for 2 d. The solvents were evaporated in vacuo, the residue was dissolved in water (200 mL) and the solution basified with solid NaHCO$_3$. The aqueous solution was extracted with EtOAc (3×100 mL) and the combined extracts were washed with brine, dried (MgSO$_4$) and evaporated in vacuo. The residue was dissolved in hexane-Et$_2$O (1:1) and a solution of HCl in Et$_2$O-dioxane (0.5 M, 1:1) was added which gave a precipitate. This off-white solid was collected by filtration and dried to give cycloleucine ethyl ester hydrochloride (6.57 g, 33.9 mmol).

$^1$H (d$_6$-DMSO, 400 MHz) δ 1.2 (3H, t), 1.6–1.8 (2H, m), 1.8–2.0 (4H, m), 2.05–2.15 (2H, m), 4.15 (2H, q), 8.6–8.7 (3H, br s) ppm.

Preparation 53:
N-[(1,4-Dichloro-7-isoquinolinyl)sulphonyl]cycloleucine ethyl ester

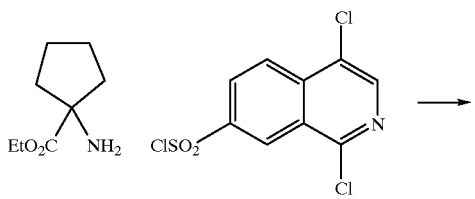

A mixture of cycloleucine ethyl ester hydrochloride (5.56 g, 28.7 mmol), NEt$_3$ (9.9 mL, 72 mmol) and 1,4-dichloro-7-isoquinolinesulphonyl chloride (7.10 g, 24.0 mmol) in CH$_2$Cl$_2$ (480 mL) was stirred at 23° C. for 3 d. The mixture was diluted with CH$_2$Cl$_2$, washed with dilute HCl (2 M), saturated aqueous NaHCO$_3$, brine, dried (Na$_2$SO$_4$) and evaporated in vacuo. The residue was purified by column chromatography upon silica gel using pentane-EtOAc (80:20 to 70:30) as eluant to give N-[(1,4-dichloro-7-isoquinolinyl)sulphonyl]cycloleucine ethyl ester (6.36 g, 15.2 mmol) as a white solid.
mp 127–129° C.
$^1$H (CDCl$_3$, 400 MHz) 3 1.2 (3H, t), 1.6–1.8 (4H, m), 1.9–2.0 (2H, m), 2.1–2.2 (2H, m), 4.1 (2H, q), 5.25 (1H, s), 8.25 (1H, d), 8.35 (1H, d), 8.5 (1H, s), 8.9 (1H, s) ppm.
LRMS 417,419 (MH$^+$).
Anal. Found: C, 48.57; H, 4.35; N, 6.58. Calc for C$_{17}$H$_{18}$Cl$_2$N$_3$O$_4$S: C, 48.93; H, 4.35; N, 6.71.

Preparation 54:
1,4-Dichloro-N-[1-(hydroxymethyl)cyclopentyl]-7-isoquinolinesulphonamide

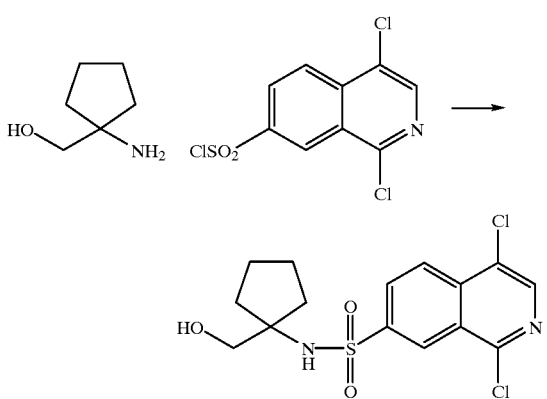

A mixture of 1-amino-1-cyclopentylmethanol (559 mg, 4.86 mmol), NEt$_3$ (0.85 mL, 6.0 mmol) and 1,4-dichloro-7-isoquinolinesulphonyl chloride (1.2 g, 4.05 mmol) in CH$_2$Cl$_2$ (80 mL) was stirred at 23° C. for 16 h. The mixture was diluted with CH$_2$Cl$_2$ (50 mL), washed with dilute HCl (2 M), saturated aqueous NaHCO$_3$, brine, dried (Na$_2$SO$_4$) and evaporated in vacuo. The residue was purified by column chromatography upon silica gel using CH$_2$Cl$_2$-MeOH-0.880NH$_3$ (95:5:0.5) as eluant, followed by trituration with Et$_2$O, to give to give 1,4-dichloro-N-[1-(hydroxymethyl)cyclopentyl]-7-isoquinolinesulphonamide (0.62 g, 1.65 mmol) as a white solid.
mp 148–150° C.
$^1$H (CDCl$_3$, 400 MHz) δ 1.5–1.6 (4H, m), 1.6–1.7 (2H, m), 1.7–1.8 (2H, m), 2.2 (1H, br t), 3.65 2H, d), 5.1 (1H, s), 8.3 (1H, d), 8.35 (1H, d), 8.5 (1H, s), 8.9 (1H, s) ppm.
LRMS 375 (MH$^+$).

Preparation 55:
N-[(1,4-Dichloro-7-isoquinolinyl)sulphonyl]-N-[2-(dimethylamino)ethyl]cycloleucine ethyl ester

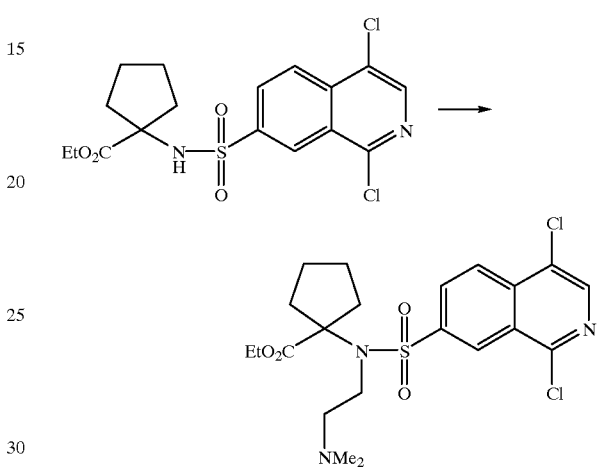

2-(Dimethylamino)ethyl chloride (140 mg, 1.3 mmol) was added to a stirred solution of N-[(1,4-dichloro-7-isoquinolinyl)sulphonyl]cycloleucine ethyl ester (200 mg, 0.48 mmol) and anhydrous K$_2$CO$_3$ (80 mg, 0.58 mmol) in DMF (4 mL) under N$_2$ at 23° C. and the mixture was stirred for 21 h. The cooled mixture was diluted with EtOAc, washed with water, dried (Na$_2$SO$_4$), and the solvents were evaporated in vacuo. The residue was dissolved in Et$_2$O and a solution of HCl in Et$_2$O (1 M) was added which gave a precipitate. This off-white solid was collected by filtration and dried to give to give N-[(1,4-dichloro-7-isoquinolinyl)sulphonyl]-N-[2-(dimethylamino)ethyl]cycloleucine ethyl ester (170 mg, 0.32 mmol).
mp 238–240° C.
$^1$H (DMSO-d$_6$, 300 MHz) δ 1.15 (3H, t), 1.55–1.7 (4H, m), 2.0–2.1 (2H, m), 2.2–2.35 (2H, m), 2.8 (6H, s), 3.35–3.45 (2H, m), 3.75–3.85 (2H, m), 4.0 (2H, q), 8.45 (1H, d), 8.5 (1H, d), 8.7 (1H, s), 8.7 (1H, s) ppm.
LRMS 488, 490 (MH$^+$).
Anal. Found: C, 47.53; H, 5.37; N, 7.96. Calc for C$_2$H$_{27}$Cl$_2$N$_3$O$_4$S.0.25H$_2$O: C, 47.65; H, 5.43; N, 7.94.

Preparation 56:
Methyl 1-{[(1,4-dichloro-7-isoquinolinyl)sulphonyl]amino}cyclohexanecarboxylate

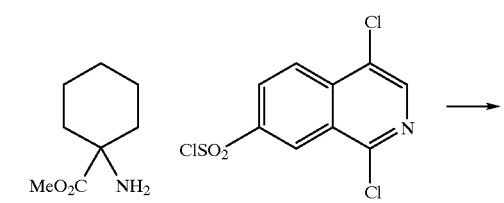

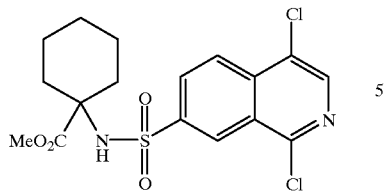

Methyl 1-aminocyclohexanecarboxylate has been prepared previously, see: Didier, E.; Horwell, D. C.; Pritchard, M. C. *Tetrahedron*, 1992, 48, 8471–8490.

A mixture of methyl 1-aminocyclohexanecarboxylate (325 mg, 1.68 mmol), NEt₃ (0.49 mL, 3.5 mmol) and 1,4-dichloro-7-isoquinolinesulphonyl chloride (415 mg, 1.40 mmol) in CH₂Cl₂ (30 mL) was stirred at 23° C. for 16 h. The mixture was diluted with CH₂Cl₂, washed with dilute HCl (2 M), saturated aqueous NaHCO₃, brine, dried (Na₂SO₄) and evaporated in vacuo. The residue was purified by column chromatography upon silica gel using hexane-EtOAc (80:20 to 70:30) as eluant, followed by trituration with i-Pr₂O, to give to give methyl 1-{[(1,4-dichloro-7-isoquinolinyl)sulphonyl]amino}-cyclohexanecarboxylate (132 mg, 0.32 mmol) as a white solid.

mp 185–186° C.

$^1$H (CDCl₃, 300 MHz) δ 1.2–1.5 (6H, m), 1.8–2.0 (4H, m), 3.6 (3H, s), 4.95 (1H, s), 8.25 (1H, d), 8.4 (1H, d), 8.5 (1H, s), 8.9 (1H, s) ppm.

LRMS 418 (MH⁺).

Anal. Found: C, 48.94; H, 4.43; N, 6.42. Calc for C₁₇H₁₈Cl₂N₂O₄S: C, 48.93; H, 4.35; N, 6.71.

Preparation 57:

Methyl 4-aminotetrahydro-2H-pyran-4-carboxylate

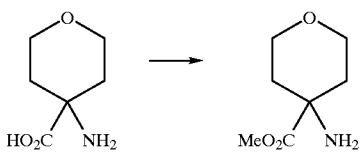

4-Aminotetrahydro-2H-pyran-4-carboxylic acid has been prepared previously, see: Palacin, S.; Chin, D. N.; Simanek, E. E.; MacDonald, J. C.; Whitesides, G. M.; McBride, M. T.; Palmore, G. J. *Am. Chem. Soc.*, 1997, 119, 11807–11816.

A solution 4-aminotetrahydro-2H-pyran-4-carboxylic acid (0.50 g, 3.4 mmol) in MeOH (10 mL) was saturated with HCl gas at 0–5° C., and the mixture was then heated at reflux for 3.5 h. The solvents were evaporated in vacuo, the residue was dissolved in saturated aqueous NaHCO₃ and the aqueous solution was extracted with CH₂Cl₂ (2×50 mL). The combined extracts were dried (MgSO₄) and evaporated in vacuo to give methyl 4-aminotetrahydro-2H-pyran-4-carboxylate (410 mg, 2.58 mmol).

$^1$H (CDCl₃, 300 MHz) δ 1.4–1.6 (4H, m), 2.05–2.2 (2H, m), 3.6–3.7 (2H, m), 3.75 (3H, s), 3.8–3.9 (2H, m) ppm.

LRMS 160 (MH⁺).

Preparation 58:

Methyl 4-{[(1,4-dichloro-7-isoquinolinyl)sulphonyl]amino}tetrahydro-2H-pyran-4-carboxylate

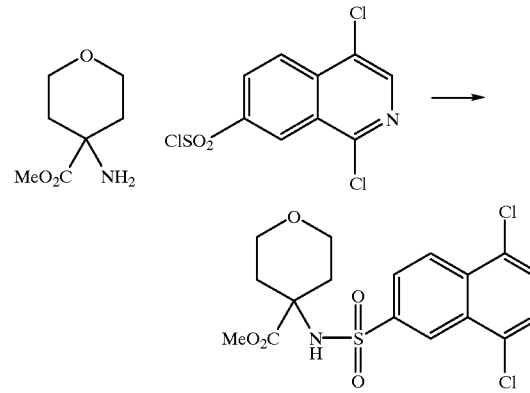

A mixture of methyl 4-aminotetrahydro-2H-pyran-4-carboxylate (400 mg, 2.51 mmol), NEt₃ (0.44 mL, 3.14 mmol) and 1,4-dichloro-7-isoquinolinesulphonyl chloride (621 mg, 2.09 mmol) in CH₂Cl₂ (30 mL) was stirred at 23° C. for 20 h. The mixture was diluted with CH₂Cl₂, washed with dilute HCl (2 M), saturated aqueous NaHCO₃, brine, dried (Na₂SO₄) and evaporated in vacuo. The residue was purified by column chromatography upon silica gel using hexane-EtOAc (80:20) and then CH₂Cl₂-MeOH-0.880NH₃ (95:5:0.5) as eluant, followed by trituration with i-Pr₂O, to give to give methyl 4-{[(1,4-dichloro-7-isoquinolinyl)sulphonyl]amino}tetrahydro-2H-pyran-4-carboxylate (197 mg, 0.47 mmol) as a white solid.

mp 168–170° C.

$^1$H (CDCl₃, 400 MHz) δ 1.8–1.95 (2H, m), 2.1–2.2 (2H, m), 3.5 (3H, s), 3.5–3.7 (4H, m), 5.4 (1H, s), 8.25 (1H, d), 8.4 (1H, d), 8.5 (1H, s), 8.9 (1H, s) ppm.

LRMS 419 (MH⁺).

Anal. Found: C, 45.97; H, 3.85; N, 6.36. Calc for C₁₆H₁₆Cl₂N₂O₅S: C, 45.83; H, 3.85; N, 6.68.

Preparation 59:

t-Butyl (±)-cis-2-{[(1,4-dichloro-7-isoquinolinyl)sulphonyl]amino}cyclohexanecarboxylate

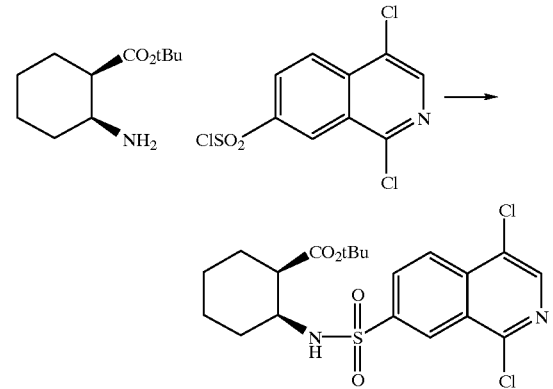

t-Butyl (±)-cis-2-aminocyclohexanecarboxylate has been prepared previously, see: Xie, J.; Soleilhac, J. M.; Renwart, N.; Peyroux, J.; Roques, B. P.; Fournie-Zaluski, M. C. *Int. J. Pept. Protein Res* 1989, 34, 246–255.

A mixture of t-butyl (±)-cis-2-aminocyclohexanecarboxylate hydrochloride (282 mg, 1.20 mmol), NEt₃(0.33 mL, 2.37 mmol) and 1,4-dichloro-7-isoquinolinesulphonyl chloride (282 mg, 0.95 mmol) in CH₂Cl₂ (10 mL) was stirred at 23° C. for 1 h. The solvents were evaporated in vacuo and the residue suspended in EtOAc (100 mL). This solution was washed with dilute HCl (10 mL, 1 M), water, dried (MgSO₄) and evaporated in vacuo to give t-butyl (±)-cis-2-{[(1,4-dichloro-7-isoquinolinyl)sulphonyllamino}cyclohexanecarboxylate (395 mg, 0.86 mmol) as a white solid.

$^1$H (CDCl₃, 300 MHz) δ 1.1–1.8 (16H, m), 1.95–2.1 (1H, m), 2.5–2.6 (1H, m), 3.4–3.55 (1H, m), 6.1 (1H, d), 8.25 (1H, d), 8.35 (1H, d), 8.45 (1H, s), 8.9 (1H, s).

LRMS 459, 461 (MH⁺).

Anal. Found: C, 51.99; H, 5.28; N, 6.01. Calc for C₂₀H₂₄Cl₂N₂O₄S: C, 52.29; H, 5.27; N, 6.10.

Preparation 60:

Ethyl (±)-cis-2-{[(1,4-dichloro-7-isoquinolinyl)sulphonyl]amino}cyclohexanecarboxylate

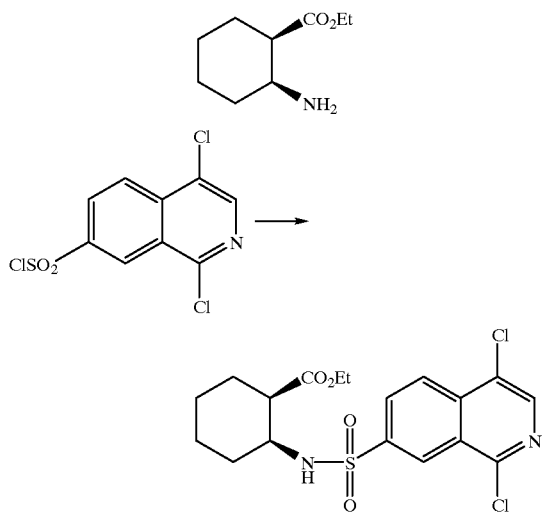

A mixture of ethyl (±)-cis-2-aminocyclohexanecarboxylate hydrochloride (251 mg, 1.20 mmol), NEt₃ (0.33 mL, 2.4 mmol) and 1,4-dichloro-7-isoquinolinesulphonyl chloride (296 mg, 1.00 mmol) in CH₂Cl₂ (10 mL) were stirred at 23° C. for 1 h. The mixture was diluted with CH₂Cl₂ (100 mL), washed with dilute HCl (30 mL, 1 M), water, dried (MgSO₄) and evaporated in vacuo to give ethyl (±)-cis-2-{[(1,4-dichloro-7-isoquinolinyl)sulphonyl]amino}cyclohexanecarboxylate (385 mg, 0.89 mmol) as a white solid.

$^1$H (CDCl₃, 400 MHz) δ 1.2 (3H, t), 1.2–1.4 (3H, m), 1.4–1.7 (3H, m), 1.75–1.85 (1H, m), 2.0–2.1 (1H, m), 2.65 (1H, q), 3.5–3.6 (1H, m), 3.95–4.0 (1H, m), 4.05–4.15 (1H, m), 5.9 (1H, d), 8.2 (1H, d), 8.35 (1H, d), 8.5 (1H, s), 8.9 (1H, s).

LRMS 431, 433 (MH⁺).

Anal. Found: C, 50.45; H, 4.79; N, 6.31. Calc for C₁₈H₂₀Cl₂N₂O₄S: C, 50.12; H, 4.67; N, 6.49.

Preparation 61:

t-Butyl cis-4-{[(1,4-dichloro-7-isoquinolinyl)sulphonyl]amino}cyclohexanecarboxylate

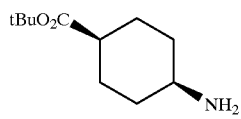

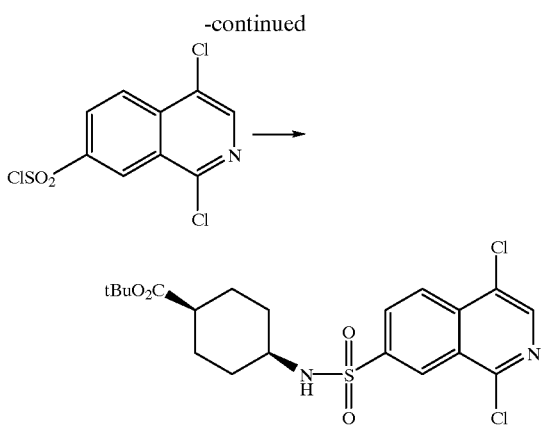

t-Butyl cis-4-aminocyclohexanecarboxylate has been prepared previously, see: Barnish, I. T.; James, K.; Terrett, N. K.; Danilewicz, J. C.; Samuels, G. M. R.; Wythes, M. J. Eur. Patent, 1988, EP 274234.

A mixture of t-butyl cis-4-aminocyclohexanecarboxylate (282 mg, 1.20 mmol), NEt₃ (0.33 mL, 2.37 mmol) and 1,4-dichloro-7-isoquinolinesulphonyl chloride (296 mg, 1.00 mmol) in CH₂Cl₂ (10 mL) was stirred at 0° C. for 1 h. The mixture was diluted with CH₂Cl₂ (150 mL), was washed with dilute HCl (30 mL, 1 M), water, dried (MgSO₄) and evaporated in vacuo. The residue was purified by column chromatography upon silica gel using pentane-EtOAc (100:0 to 75:25) to give t-butyl cis-4-{[(1,4-dichloro-7-isoquinolinyl)sulphonyl]amino}cyclohexanecarboxylate (360 mg, 0.78 mmol) as a white solid.

$^1$H (CDCl₃, 400 MHz) δ 1.4 (9H, s), 1.5–1.65 (6H, m), 1.75–1.85 (2H, m), 2.3 (1H, m), 3.45 (1H, m), 4.75 (1H, d), 8.25 (1H, d), 8.4 (1H, d), 8.5 (1H, s), 8.9 (1H, s) ppm.

LRMS 459, 461 (MH⁺), 476 (MNH₄⁺).

Anal. Found: C, 52.34; H, 5.28; N, 5.98. Calc for C₂₀H₂₄Cl₂N₂O₄S: C, 52.29; H, 5.27; N, 6.10.

Preparation 62:

Ethyl trans-4-{[(1,4-dichloro-7-isoquinolinyl)sulphonyl]amino}cyclohexanecarboxylate

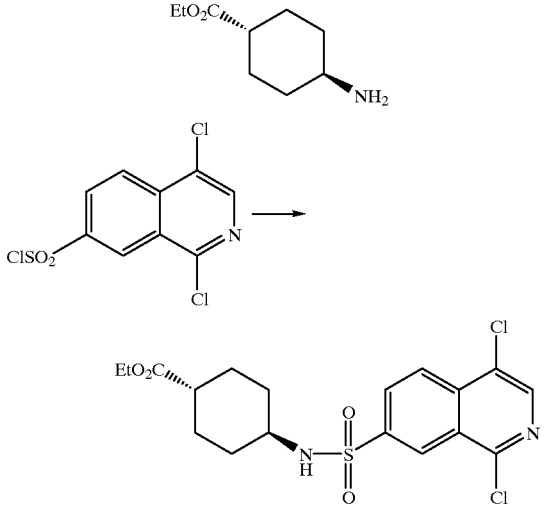

Ethyl trans-4-aminocyclohexanecarboxylate has been prepared previously, see: Skaric, V.; Kovacevic, M.; Skaric, D. J. Chem. Soc., Perkin Trans.] 1976, 1199–1201.

A mixture of ethyl trans-4-aminocyclohexanecarboxylate (168 mg, 0.81 mmol), NEt₃ (0.22 mL, 1.6 mmol) and 1,4-dichloro-7-isoquinolinesulphonyl chloride (200 mg, 0.67 mmol) in CH₂Cl₂ (8 mL) was stirred at 0° C. for 1 h. The mixture was diluted with CH₂Cl₂ (100 mL), was washed with dilute HCl (50 mL, 1 M), water, dried (MgSO₄) and evaporated in vacuo to give ethyl trans-4-{[(1,4-dichloro-7-isoquinolinyl)sulphonyl]amino}cyclohexanecarboxylate (232 mg, 0.54 mmol) as a white solid.

¹H (CDCl₃, 400 MHz) δ 1.15–1.3 (5H, m), 1.4–1.55 (2H, m), 1.9–2.0 (4H, m), 2.1–2.2 (1H, m), 3.2–3.3 (1H, m), 4.1 (2H, t), 4.55 (1H, d), 8.25 (1H, d), 8.35 (1H, d), 8.5 (1H, s), 8.9 (1H, s)

LRMS 431 (MH⁺).

Preparation 63:

1,4-Dichloro-7-isoquinolinecarbonyl chloride

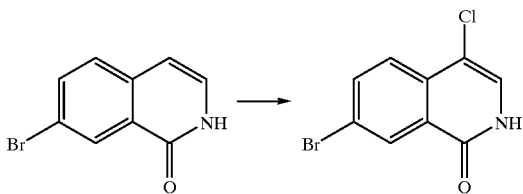

A solution of N-chlorosuccinimide (4.13 g, 31 mmol) in MeCN (50 mL) was added dropwise to a stirred solution of 7-bromo-1-(2H)-isoquinolone (6.6 g, 29.5 mmol) in MeCN (150 mL) which was heating under reflux. The mixture was heated under reflux for an additional 3 h and then cooled to room temperature. The resulting precipitate was collected by filtration, with MeCN rinsing, and then dried in vacuo to give 7-bromo-4-chloro-1(2h)-isoquinolone (6.72 g, 26.0 mmol) as a white solid.

mp 241–243° C.

¹H (DMSO-d₆, 300 MHz) δ 7.5 (1H, s), 7.73 (1H, d), 7.8 (1H, dd), 8.3 (1H, s) ppm.

LRMS 259 (MH⁺), 517 (M₂H⁺).

Anal. Found: C, 41.69; H, 1.90; N, 5.37. Calc for C₉H₅BrClNO: C, 41.80; H, 1.95; N, 5.42.

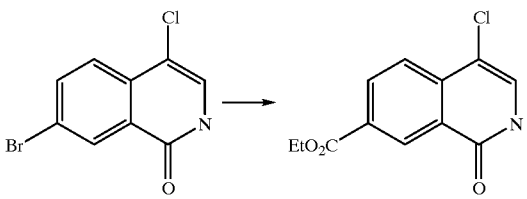

A mixture of 7-bromo-4-chloro-1(2H)-isoquinolone (1.0 g, 3.87 mmol) and bis(triphenylphosphine) palladium (II) chloride (100 mg, 0.14 mmol) in EtOH (15 mL) and NEt₃ (2 mL) was heated to 100° C. in a pressure vessel under an atmosphere of CO (100 psi) for 48 h. After cooling and venting the vessel, the catalyst was removed by filtration, and the filtrate was evaporated in vacuo. The residue was purified by column chromatography upon silica gel using hexane-EtOAc (50:50) as eluant, and then by crystallisation from i-Pr₂O. This material was combined with CH₂Cl₂ washings of the catalyst residues to give ethyl 4-chloro-1-oxo-1,2-dihydro-7-isoquinolinecarboxylate (743 mg, 2.95 mmol) as a white solid.

mp 184–186° C.

¹H (CDCl₃, 300 MHz) δ 1.45 (2H, t), 4.45 (2H, q), 7.4 (1H, s), 7.95 (1H, d), 8.4 (1H, d), 9.05 (1H, s) ppm.

LRMS 252 (MH⁺), 269 (MNH₄⁺), 503 (M₂H⁺).

Anal. Found: C, 57.02; H, 3.99; N, 5.53. Calc for C₁₂H₁₀ClNO₃: C, 57.27; H, 4.01; N, 5.57.

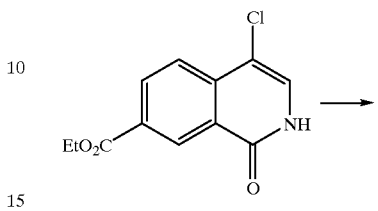

Ethyl 4-chloro-1-oxo-1,2-dihydro-7-isoquinolinecarboxylate (500 mg, 1.99 mmol) was warmed in POCl₃ (3 mL) until a clear solution formed, and was then allowed to stand at 23° C. for 18 h. The reaction mixture was poured into warm water, extracted with EtOAc (3×20 mL), and the combined organic extracts washed with water and saturated brine, dried (MgSO₄), and evaporated in vacuo. The residue was purified by column chromatography upon silica gel using hexane-EtOAc (90:10) as eluant followed by crystallisation from i-Pr₂O to give ethyl 1,4-dichloro-7-isoquinolinecarboxylate (377 mg, 1.40 mmol) as a pale pink solid.

mp 92–94° C.

¹H (CDCl₃, 300 MHz) δ 1.45 (2H, t), 4.45 (2H, q), 8.25 (1H, d), 8.4–8.45 (2H, m), 9.05 (1H, s) ppm.

LRMS 270 (MH⁺).

Anal. Found: C, 53.27; H, 3.48; N, 5.14. Calc for C₁₂H₉Cl₂NO₂: C, 53.36; H, 3.36; N, 5.19.

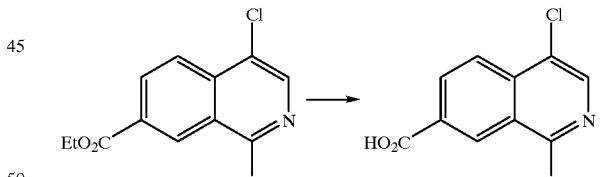

Ethyl 1,4-dichloro-7-isoquinolinecarboxylate (500 mg, 1.85 mmol) in THF (2 mL) was treated with an aqueous solution of NaOH (3.7 mL, 1 M) and EtOH (few drops) added to give a single phase mixture. After stirring at room temperature overnight, HCl (3.7 mL, 1 M) was added to give a thick slurry which was filtered off, washed with water, and crystallised from i-PrOH. The fluffy white crystalline solid was triturated with hexane and dried to afford 1,4-dichloro-7-isoquinolinecarboxylic acid (240 mg, 0.99 mmol).

mp 226–228° C.

¹H (DMSO-d₆, 300 MHz) δ 8.3 (1H, d), 8.4 (1H, d), 8.55 (1H, s), 8.8 (1H, s) ppm.

LRMS 242 (MH⁺).

Anal. Found: C, 49.59; H, 2.08; N, 5.74. Calc for C₁₀H₅Cl₂NO₂: C, 49.62; H, 2.08; N, 5.78.

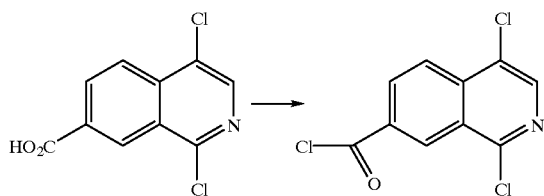

Oxalyl chloride (144 μL, 1.65 mmol) was added to a suspension of 1,4-dichloro-7-isoquinolinecarboxylic acid (200 mg, 0.83 mmol) at room temperature in $CH_2Cl_2$ (10 mL), followed by DMF (1 drop). After 30 min the resultant clear solution was evaporated in vacuo to afford 1,4-dichloro-7-isoquinolinecarbonyl chloride which was used without further purification.

Preparation 64:

N-[(1,4-Dichloro-7-isoquinolinyl)carbonyl]glycine t-butyl ester

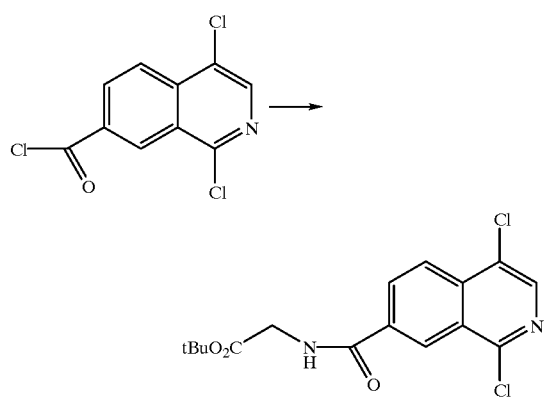

A solution of 1,4-dichloro-7-isoquinolinecarbonyl chloride (213 mg, 0.8 mmol) in $CH_2Cl_2$ (10 mL) was added to a stirred suspension of glycine t-butyl ester hydrochloride (166 mg, 0.99 mmol) and $NEt_3$ (253 μL, 1.82 mmol) in $CH_2Cl_2$ (5 mL). The reaction mixture was stirred at room temperature overnight, quenched with a drop of water and then evapourated in vacuo. The residue was purified by column chromatography upon silica gel using hexane-EtOAc (70:30) as eluant to give N-[(1,4-dichloro-7-isoquinolinyl)carbonyl]glycine t-butyl ester (140 mg, 0.39 mmol). An analytical sample was prepared by crystallisation from i-$Pr_2$O-$CH_2Cl_2$.

mp 162–164° C.

$^1$H (CDCl$_3$, 300 MHz) δ 1.5 (9H, s), 4.15–4.2 (2H, m), 6.9 (1H, s), 8.25–8.3 (2H, m), 8.4 (1H, s), 8.75 (1H, s) ppm.

LRMS 355 (MH$^+$).

Anal. Found: C, 53.98; H, 4.36; N, 7.83. Calc for $C_{16}H_{16}Cl_2N_2O_3$: C, 54.10; H, 4.54; N, 7.89.

Preparation 65:
N-[(1,4-Dichloro-7-isoquinolinyl)carbonyl]-β-alanine t-butyl ester

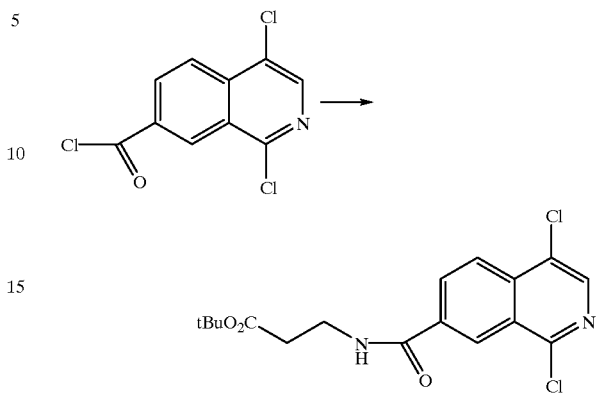

A solution of 1,4-dichloro-7-isoquinolinecarbonyl chloride (450 mg, 1.7 mmol) in $CH_2Cl_2$ (20 mL) was added to a stirred solution of 13-alanine t-butyl ester hydrochloride (376 mg, 2.07 mmol) and $NEt_3$ (530 μL, 3.81 mmol) in $CH_2Cl_2$ (10 mL) and the mixture was stirred at room temperature for 3 h. The mixture was washed with HCl (2×30mL, 1 M), aqueous $NaHCO_3$ (10%, 30 mL), dried ($Na_2SO_4$), and evaporated in vacuo. The residue was crystallised from i-$Pr_2$O to give N-[(1,4-dichloro-7-isoquinolinyl)carbonyl]-β-alanine t-butyl ester (440 mg, 1.19 mmol) as a white solid.

mp 131–133° C.

$^1$H (CDCl$_3$, 400 MHz) δ 1.5 (9H, s), 2.6 (2H, t), 3.7–3.8 (2H, m), 7.15 (1H, br s), 8.2–8.3 (2H, m), 8.4 (1H, s), 8.65 (1H, s) ppm.

LRMS 369 (MH$^+$), 740 ($M_2H^+$).

Anal. Found: C, 55.11; H, 4.88; N, 7.48. Calc for $C_{17}H_{18}Cl_2N_2O_3$: C, 55.29; H, 4.91; N, 7.59.

Preparation 66:
N-[(1,4-Dichloro-7-isoquinolinyl)carbonyl]cycloleucine ethyl ester

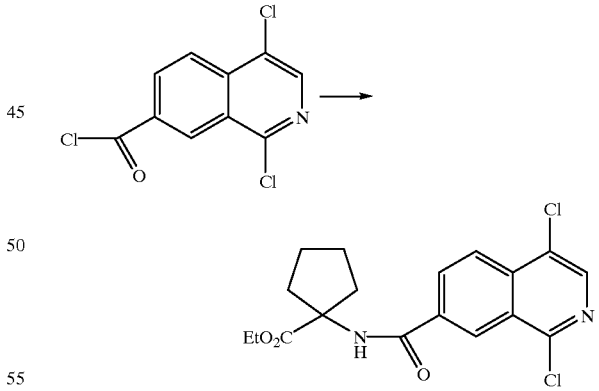

A solution of 1,4-dichloro-7-isoquinolinecarbonyl chloride (270 mg, 1.04 mmol) in $CH_2Cl_2$ (12 mL) was added to a stirred solution of cycloleucine ethyl ester hydrochloride (300 mg, 1.55 mmol) and $NEt_3$ (415 μL, 2.98 mmol) in $CH_2Cl_2$ (20 mL) and the mixture was stirred at room temperature for 1 h. The mixture was washed with dilute HCl (2 M), aqueous $NaHCO_3$ (10%), dried ($Na_2SO_4$), and evaporated in vacuo. The residue was crystallised from i-$Pr_2$O to give N-[(1,4-dichloro-7-isoquinolinyl)carbonyl] cycloleucine ethyl ester (372 mg, 0.98 mmol) as a white solid.

mp 178–180° C.

$^1$H (CDCl$_3$, 300 MHz) δ 1.3 (3H, t), 1.8–2.05 (4H, m), 2.1–2.3 (2H, m), 2.3–2.45 (2H, m), 4.25 (2H, q), 6.95 (1H, br s), 8.2–8.25 (2H, m), 8.4 (1H, s), 8.7(1H, s) ppm.

LRMS 382 (MH$^+$), 398 (MNH$_4^+$), 763 (M$_2$H$^+$).

Anal. Found: C, 56.71; H, 4.77; N, 7.27. Calc for C$_{18}$H$_{18}$Cl$_2$N$_2$O$_3$: C, 56.70; H, 4.76; N, 7.35.

Preparation 67:

N-[(1,4-Dichloro-7-isoquinolinyl)carbonyl]-DL-phenylglycine t-butyl ester

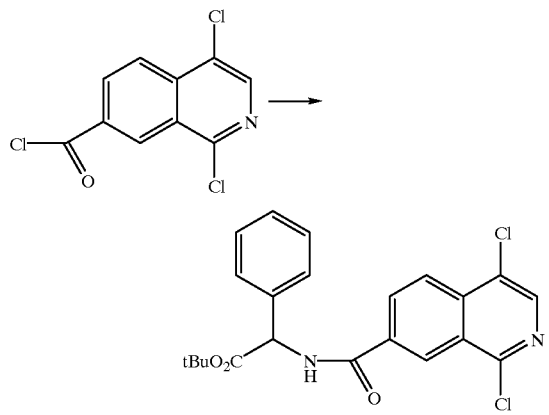

A solution of 1,4-dichloro-7-isoquinolinecarbonyl chloride (450 mg, 1.73 mmol) in CH$_2$Cl$_2$ (20 mL) was added to a stirred solution of DL-phenylglycine t-butyl ester hydrochloride (505 mg, 2.07 mmol) and NEt$_3$ (530 μL, 3.81 mmol) in CH$_2$Cl$_2$ (30 mL) and the mixture was stirred at room temperature for 3 h. The mixture was washed with dilute HCl (2×30 mL, 1 M), aqueous NaHCO$_3$ (10%), dried (Na$_2$SO$_4$), and evaporated in vacuo to give N-[(1,4-dichloro-7-isoquinolinyl)carbonyl]-DL-phenylglycine t-butyl ester (600 mg, 1.39 mmol) as a waxy solid. An analytical sample was prepared by the slow evaporation of a solution in CH$_2$Cl$_2$ to give a fluffy white solid.

mp 146–149° C.

$^1$H (CDCl$_3$, 300 MHz) δ 1.5 (9H, s), 5.7 (1H, d), 7.3–7.5 (6H, m), 8.2–8.3 (2H, m), 8.4 (1H, s), 8.8 (1H, s) ppm.

LRMS 431 (MH$^+$), 861 (M$_2$H$^+$).

Anal. Found: C, 60.57; H, 4.76; N, 6.42. Calc for C$_{22}$H$_{20}$Cl$_2$N$_2$O$_3$.0.25H$_2$O: C, 60.63; H, 4.74; N, 6.43

Preparation 68:

N-[(1,4-Dichloro-7-isoquinolinyl)carbonyl]-L-phenylglycine t-butyl ester

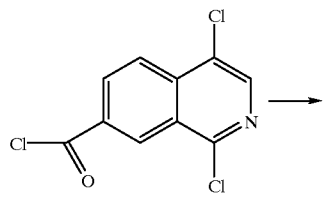

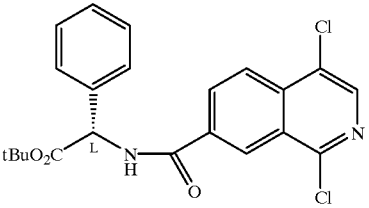

A solution of 1,4-dichloro-7-isoquinolinecarbonyl chloride (148 mg, 0.57 mmol) in CH$_2$Cl$_2$ (6 mL) was added to a stirred solution of S-(+)-phenylglycine t-butyl ester hydrochloride (138 mg, 0.57 mmol) and NEt$_3$ (200 μL, 1.44 mmol) in CH$_2$Cl$_2$ (5 mL), and the mixture was stirred at room temperature overnight. The mixture was diluted with CH$_2$Cl$_2$ (25 mL), washed with dilute HCl (0.5 M), aqueous NaHCO$_3$ (10%), brine, dried (Na$_2$SO$_4$), and evaporated in vacuo to give N-[(1,4-dichloro-7-isoquinolinyl)carbonyl]-L-phenylglycine t-butyl ester (218 mg, 0.51 mmol) as a gum. An analytical sample was prepared by trituration with hexane yielding a solid.

mp 173–175° C.

$^1$H (CDCl$_3$, 300 MHz) δ 1.45 (9H, s), 5.7 (1H, d), 7.3–7.5 (6H, m), 8.25 (2H, s), 8.4 (1H, s), 8.8 (1H, s) ppm.

LRMS 431 (MH$^+$), 448 (MNH$_4^+$), 861 (M$_2$H$^+$), 883 (M$_2$Na$^+$).

Anal. Found: C, 58.83; H, 4.88; N, 5.90. Calc for C$_{22}$H$_{20}$Cl$_2$N$_2$O$_3$.H$_2$O: C, 58.80; H, 4.93; N, 6.23

Preparation 69:

N-[(1,4-Dichloro-7-isoquinolinyl)carbonyl]-D-phenylglycine t-butyl ester

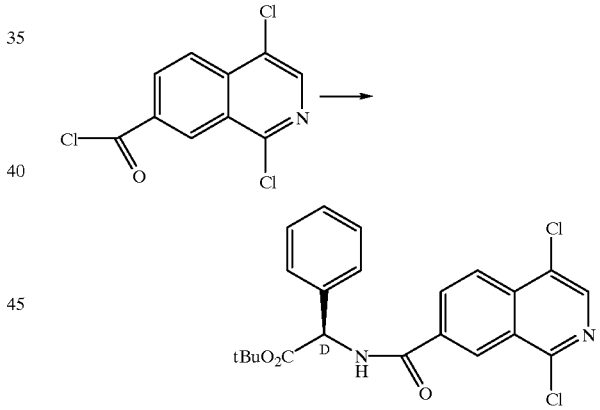

A solution of 1,4-dichloro-7-isoquinolinecarbonyl chloride (148 mg, 0.57 mmol) in CH$_2$Cl$_2$ (6 mL) was added to a stirred solution of R-(+)-phenylglycine t-butyl ester hydrochloride (138 mg, 0.57 mmol) and NEt$_3$ (200 μL, 1.44 mmol) in CH$_2$Cl$_2$ (5 mL), and the mixture was stirred at room temperature overnight. The mixture was diluted with CH$_2$Cl$_2$ (25 mL), washed with dilute HCl (0.5 M), aqueous NaHCO$_3$ (10%), brine, dried (Na$_2$SO$_4$), and evaporated in vacuo. Trituration of the residue with hexane gave N-[(1,4-dichloro-7-isoquinolinyl)carbonyl]-D-phenylglycine t-butyl ester (203 mg, 0.47 mmol) as a white solid.

$^1$H (CDCl$_3$, 300 MHz) δ 1.4 (9H, s), 5.7 (1H, d), 7.3–7.5 (6H, m), 8.25 (2H, s), 8.4 (1H, s), 8.8 (1H, s) ppm.

LRMS 431 (MH$^+$), 448 (MNH$_4^+$), 861 (M$_2$H$^+$), 883 (M$_2$Na$^+$).

Anal. Found: C, 61.17; H. 4.70; N, 6.37. Calc for C$_{22}$H$_{20}$Cl$_2$N$_2$O$_3$: C, 61.26; H, 4.67; N, 6.50

Preparation 70:
N-[(1,4-Dichloro-7-isoquinolinyl)carbonyl]-DL-valine t-butyl ester

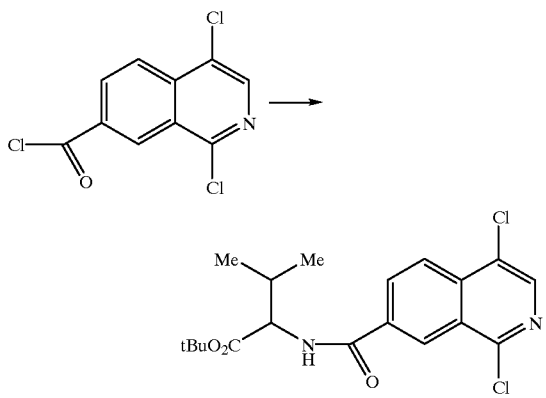

A solution of 1,4-dichloro-7-isoquinolinecarbonyl chloride (450 mg, 1.73 mmol) in $CH_2Cl_2$ (20 mL) was added to a stirred solution of DL-valine t-butyl ester hydrochloride (435 mg, 2.07 mmol) and $NEt_3$ (530 µL, 3.81 mmol) in $CH_2Cl_2$ (10 mL) and the mixture was stirred at room temperature for 3 h. The mixture was washed with dilute HCl (1 M), aqueous $NaHCO_3$ (10%), dried ($Na_2SO_4$), and evaporated in vacuo. The residue was crystallised with i-$Pr_2O$ to give N-[(1,4-dichloro-7-isoquinolinyl)carbonyl]-DL-valine t-butyl ester (390 mg, 0.98 mmol) as a white solid.

$^1$H ($CDCl_3$, 400 MHz) δ 1.0–1.05 (6H, m), 1.5 (9H, s), 2.3–2.4 (1H, m), 4.7–4.8 (1H, m), 6.85 (1H, d), 8.25–8.3 (2H, m), 8.4 (1H, s), 8.75 (1H, s) ppm.

LRMS 397 ($MH^+$), 793 ($M_2H^+$).

Anal. Found: C, 57.20; H, 5.53; N, 6.99. Calc for $C_{19}H_{22}Cl_2N_2O_3$: C, 57.44; H, 5.58; N, 7.05.

Preparation 71:
N-[(1,4-Dichloro-7-isoquinolinyl)carbonyl]-DL-proline t-butyl ester

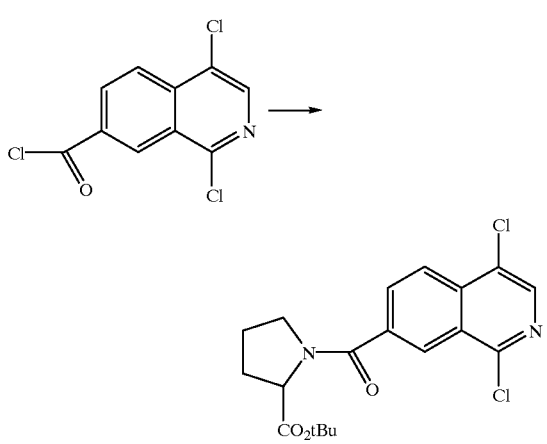

DL-Proline t-butyl ester hydrochloride (320 mg, 1.54 mmol) and then $NEt_3$ (513 µL, 3.69 mmol) were added to a stirred solution of 1,4-dichloro-7-isoquinolinecarbonyl chloride (270 mg, 1.04 mmol) in $CH_2Cl_2$ (32 mL) and the cloudy solution was then stirred at room temperature for 4 h. The mixture was diluted with $CH_2Cl_2$ (20 mL), washed with dilute HCl (1 M), saturated brine, dried ($Na_2SO_4$), and evaporated in vacuo. The residue was crystallised with i-$Pr_2O$ to give N-[(1,4-dichloro-7-isoquinolinyl)carbonyl]-DL-proline t-butyl ester (395 mg, 1.00 mmol) as a white solid.

mp 144–146° C.

$^1$H ($CDCl_3$, 300 MHz) shows a 3:1 mixture of rotamers δ 1.15 (¼ of 9H, s), 1.55 (¾ of 9H, s), 1.8–2.15 (3H, m), 2.2–2.4 (1H, m), 3.45–3.9 (2H, m), 4.2–4.3 (¼ of 1H, m), 4.6–4.7 (¾ of 1H, m), 7.9 (¼ of 1H, d), 8.05 (¾ of 1H, d), 8.2–8.3 (1H, m), 8.4 (1H, s), 8.55 (1H, s) ppm.

LRMS 395 ($MH^+$), 789 ($M_2H^+$).

Anal. Found: C, 57.79; H, 5.11 ; N, 6.97. Calc for $C_{19}H_{20}Cl_2N_2O_3$: C, 57.73; H, 5.10; N, 7.09.

Preparation 72:
N-[(1,4-Dichloro-7-isoquinolinyl)carbonyl]-DL-phenylalanine t-butyl ester

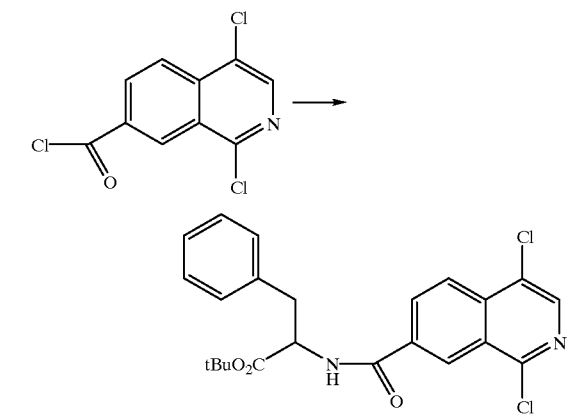

A mixture of $NEt_3$ (330 µL, 2.37 mmol), DL-phenylalanine t-butyl ester hydrochloride (293 mg, 1.14 mmol) and 1,4-dichloro-7-isoquinolinecarbonyl chloride (247 mg, 0.95 mmol) in $CH_2Cl_2$ (20 mL) was stirred at room temperature for 18 h. The solvents were evaporated in vacuo and the residue partioned between dilute HCl (1M) and EtOAc. The organic phase was washed with brine, dried ($Na_2SO_4$) and evaporated in vacuo. The residue was crystallised with i-$Pr_2O$ to give N-[(1,4-dichloro-7-isoquinolinyl)carbonyl]-DL-phenylalanine t-butyl ester (384 mg, 0.86 mmol) as a white solid.

mp 156–157° C.

$^1$H ($CDCl_3$, 300 MHz) δ 1.5 (9H, s), 3.2–3.3 (2H, m), 5.0 (1H, dt), 6.8 (1H, d), 7.2–7.49 (5H, m), 8.2 (1H, d), 8.25 (1H, d), 8.4 (1H, s), 8.6 (1H, s) ppm.

LRMS 445 ($MH^+$).

Anal. Found: C, 62.02; H, 4.98; N, 6.28. Calc for $C_{23}H_{22}Cl_2N_2O_3$: C, 62.03; H, 4.98; N, 6.29.

Preparation 73:
N-[(1,4-Dichloro-7-isoquinolinyl)carbonyl]-DL-leucine t-butyl ester

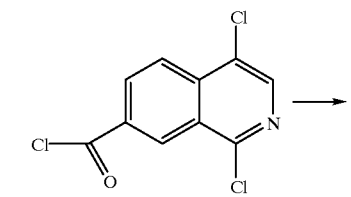

-continued

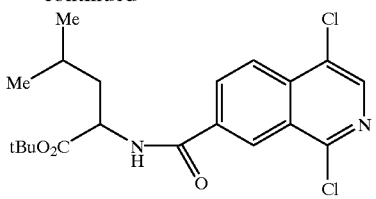

A solution of 1,4-dichloro-7-isoquinolinecarbonyl chloride (247 mg, 0.95 mmol) in $CH_2Cl_2$ (10 mL) was added to a solution of DL-leucine 1-butyl ester hydrochloride (255 mg, 1.14 mmol) and $NEt_3$ (330 µL, 2.37 mmol) in $CH_2Cl_2$ (10 mL) and the mixture was stirred at room temperature overnight. The solvents were evaporated in vacuo and the residue was partioned between dilute HCl (1 M) and EtOAc. The organic phase was washed with brine, dried ($Na_2SO_4$) and evaporated in vacuo. The residue was crystallised with i-$Pr_2O$ to give N-[(1,4-dichloro-7-isoquinolinyl)carbonyl]-DL-leucine t-butyl ester (285 mg, 0.69 mmol).

mp 183–184° C.

$^1H$ (CDCl$_3$, 300 MHz) δ 1.0–1.1 (6H, m), 1.5 (9H, s), 1.65–1.85 (3H, m), 4.75–4.85 (1H, m), 6.8 (1H, d), 8.2 (2H, s), 8.4 (1H, s), 8.7 (1H, s) ppm.

LRMS 411 (MH$^+$).

Anal. Found: C, 58.39; H, 5.84; N, 6.76. Calc for $C_{20}H_{24}Cl_2N_2O_3$: C, 58.40; H, 5.88; N, 6.81.

Preparation 74:
1-Butyl DL-3-{[(1,4-dichloro-7-isoquinolinyl)carbonyl]amino}-3-phenylpropanoate

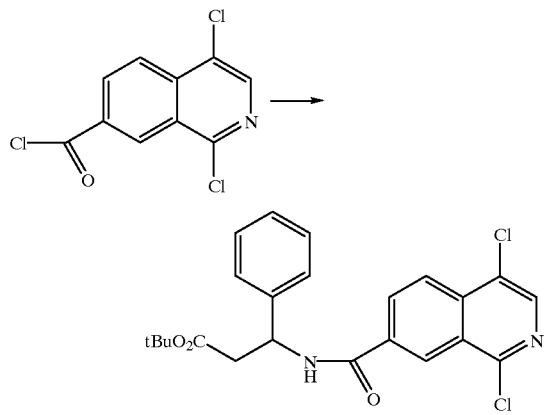

A solution of 1,4-dichloro-7-isoquinolinecarbonyl chloride (247 mg, 0.95 mmol) in $CH_2Cl_2$ (10 mL) was added to a solution of DL-3-amino-3-phenylpropionic acid t-butyl ester (252 mg, 1.14 mmol) and $NEt_3$ (260 µL, 1.87 mmol) in $CH_2Cl_2$ (10 mL) and the mixture was stirred at room temperature overnight. The solvents were evaporated in vacuo and the residue was partioned between dilute HCl (1 M) and EtOAc. The organic phase was washed with brine, dried ($Na_2SO_4$) and evaporated in vacuo to give t-butyl DL-3-{[(1,4-dichloro-7-isoquinolinyl)carbonyl]amino}-3-phenylpropanoate (323 mg, 0.73 mmol). An analytical sample was prepared by crystallisation with i-$Pr_2O$-hexane to yield a white powder.

mp 153–155° C.

$^1H$ (CDCl$_3$, 300 MHz) δ 1.4 (9H, m), 2.9–3.05 (2H, m), 5.6 (1H, dt), 7.2–7.4 (5H, m), 7.9 (1H, d), 8.2 (2H, s), 8.4 (1H, s), 8.7 (1H, s) ppm.

LRMS 445 (MH$^+$).

Anal. Found: C, 61.99; H, 5.07; N, 6.15. Calc for $C_{23}H_{22}Cl_2N_2O_3$: C, 62.03; H, 4.98; N, 6.29.

Preparation 75:
N-[(1,4-Dichloro-7-isoquinolinyl)carbonyl]-DL-aspartic acid α,β-di-t-butyl ester

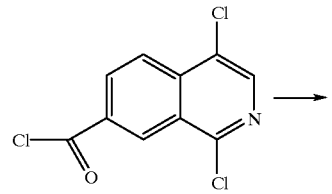

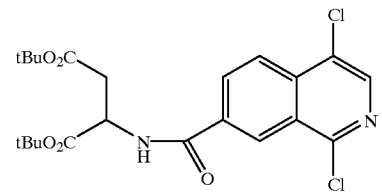

A solution of 1,4-dichloro-7-isoquinolinecarbonyl chloride (247 mg, 0.95 mmol) in $CH_2Cl_2$ (10 mL) was added to a solution of aspartic acid α,β-di-t-butyl ester hydrochloride (321 mg, 1.14 mmol) and $NEt_3$ (330 µL, 2.37 mmol) in $CH_2Cl_2$ (10 mL) and the mixture was stirred at room temperature overnight. The mixture was diluted with $CH_2Cl_2$ (30 mL), washed with dilute HCl (3×30 mL, 1 M), saturated aqueous $Na_2CO_3$, brine, dried ($MgSO_4$) and evaporated in vacuo. The residue was crystallised from hexane to give, in two crops, N-[(1,4-dichloro-7-isoquinolinyl)carbonyl]-DL-aspartic acid α,β-di-t-butyl ester (298+88 mg, 0.63+0.19 mmol) as a fluffy white solid.

mp 112–114° C.

$^1H$ (CDCl$_3$, 300 MHz) δ 1.45 (9H, m), 1.55 (9H, m), 2.9 (1H, dd), 3.05 (1H, dd), 4.9–5.0 (1H, m), 7.45 (1H, d), 8.25–8.35 (2H, m), 8.45 (1H, s), 8.75 (1H, s) ppm.

LRMS 469 (MH$^+$), 491 (MNa$^+$), 959 (M$_2$Na$^+$).

Anal. Found: C, 56.20; H, 5.57; N, 5.88. Calc for $C_{22}H_{26}Cl_2N_2O_5$: C, 56.29; H, 5.58; N, 5.97.

Preparation 76:
O-t-Butyl-N-[(1,4-dichloro-7-isoquinolinyl)carbonyl]-DL-serine t-butyl ester

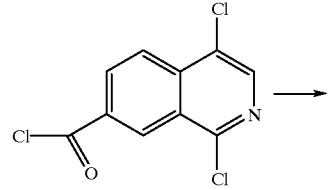

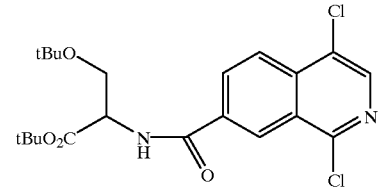

A solution of 1,4-dichloro-7-isoquinolinecarbonyl chloride (247 mg, 0.95 mmol) in $CH_2Cl_2$ (10 mL) was added to a solution of O-t-butyl-DL-serine t-butyl ester hydrochloride (288 mg, 1.14 mmol) and $NEt_3$ (330 µL, 2.37 mmol) in $CH_2Cl_2$ (10 mL) and the mixture was stirred at room temperature for 3 h. The mixture was diluted with CH₂Cl₂ (30 mL), washed with HCl (1 M), saturated aqueous Na₂CO₃, saturated brine, dried (Na₂SO₄) and evaporated in vacuo. The residue was crystallised from hexane to give 0-t-butyl-N-[(1,4-dichloro-7-isoquinolinyl)carbonyl]-DL-serine t-butyl ester (378 mg, 0.86 mmol) as a white solid.

mp 116–117° C.

¹H (CDCl₃, 300 MHz) δ 1.1 (9H, m), 1.5 (9H, m), 3.7 (1H, dd), 3.9 (1H, dd), 4.8–4.9 (1H, m), 7.15 (1H, d), 8.25–8.35 (2H, m), 8.4 (1H, s), 8.75 (1H, s) ppm.

LRMS 441 (MH⁺), 881 (M₂H⁺), 903 (M₂Na⁺).

Anal. Found: C, 57.15; H, 5.94; N, 6.27. Calc for C₂₁H₂₆Cl₂N₂O₄: C, 57.15; H, 5.94; N, 6.35.

Preparation 77:
N-[(1,4-Dichloro-7-isoquinolinyl)carbonyl]-DL-α-cyclopentylglycine t-butyl ester

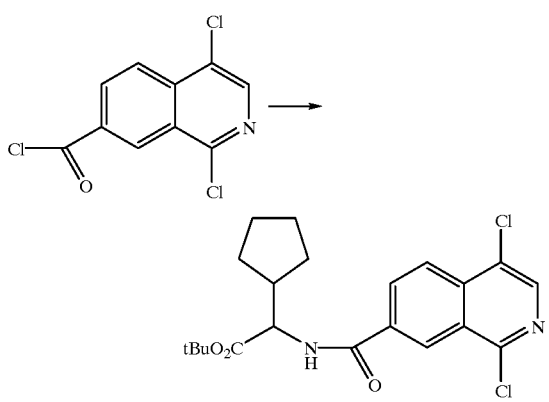

A solution of 1,4-dichloro-7-isoquinolinecarbonyl chloride (148 mg, 0.57 mmol) in CH₂Cl₂ (6 mL) was added to a solution of DL-α-cyclopentylglycine t-butyl ester hydrochloride (134 mg, 0.57 mmol) and NEt₃ (200 μL, 1.44 mmol) in CH₂Cl₂ (5 mL) and the mixture was stirred at room temperature overnight. The reaction mixture was diluted with CH₂Cl₂ (25 mL), washed with dilute HCl (0.5 M), saturated aqueous Na₂CO₃, brine, dried (Na₂SO₄) and evaporated in vacuo. The residue was crystallised from i-Pr₂O-hexane to give N-[(1,4-dichloro-7-isoquinolinyl) carbonyl]-DL-ca-cyclopentylglycine t-butyl ester (198 mg, 0.47 mmol) as a white solid.

¹H (CDCl₃, 300 MHz) δ 1.4–1.9 (17H, m), 2.3–2.5 (1H, m), 4.8 (1H, dd), 6.85 (1H, d), 8.2–8.3 (2H, m), 8.4 (1H, s), 8.7 (1H, s) ppm.

LRMS 423 (MH⁺), 440 (MNH₄⁺), 445 (MNa⁺), 845 (M₂H⁺), 867 (M₂Na⁺).

Anal. Found: C, 59.56; H, 5.72; N, 6.57. Calc for C₂₁H₂₄Cl₂N₂O₃: C, 59.58; H, 5.72; N, 6.62.

Preparation 78:
N-Benzyl-N-[(1,4-dichloro-7-isoquinolinyl)carbonyl] glycine t-butyl ester

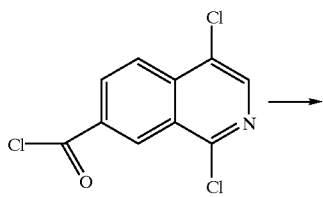

-continued

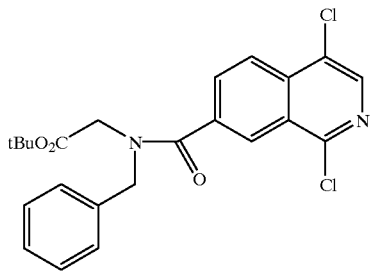

Oxalyl chloride (95 μl, 1.09 mmol) and then DMF (2 drops) were added to a stirred suspension of 1,4-dichloro-7-isoquinolinecarboxylic acid (130 mg, 0.54 mmol) in CH₂Cl₂ (10 mL), and the mixture was stirred for 30 min. to give a clear solution of the corresponding acid chloride. The solvents were evaporated in vacuo and the residue redissolved in CH₂Cl₂ (10 mL). N-Benzylglycine t-butyl ester hydrochloride (152 mg, 0.59 mmol) and NEt₃ (200 μL, 1.44 mmol) were added and the mixture stirred at room temperature overnight. The solvents were evaporated in vacuo, and the residue was partioned between Et₂O and dilute HCl (1 M). The organic phase was washed with dilute HCl (1 M), aqueous Na₂CO₃ (10%, 20 mL), saturated brine, dried (Na₂SO₄), and evaporated in vacuo. The residue was extracted with hot hexane, and the organic solution was decanted from the insoluble material. The organic solution was evaporated in vacuo and the residue purified by column chromatography upon silica gel using hexane-EtOAc (80:20) as eluant to give N-benzyl-N-[(1,4-dichloro-7-isoquinolinyl)carbonyl]glycine t-butyl ester (130 mg, 0.29 mmol) as an oil.

¹H (CDCl₃, 400 MHz) shows a 1:2 mixture of rotamers δ 1.4 (⅓ of 9H, s), 1.5 (⅔ of 9H, s), 3.75 (⅓ of 2H, s), 4.1 (⅔ of 2H, s), 4.6 (⅔ of 2H, s), 4.85 (⅓ of 2H, s), 7.2–7.45 (5H, m), 7.9–8.05 (1H, m), 8.2–8.5 (3H, m) ppm.

LRMS 445 (MH⁺), 467 (MNa⁺), 889 (M₂H⁺), 911 (M₂Na⁺).

Preparation 79:
7-(Chloromethyl)-1,4-dichloro-isoquinoline

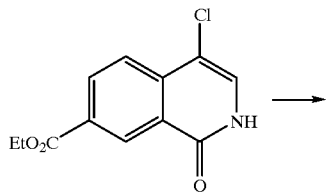

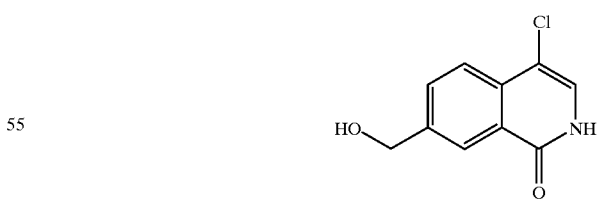

LiBH₄ (530 mg, 24.3 mmol) was added portionwise to a stirred solution of ethyl 4-chloro-1-oxo-1,2-dihydro-7-isoquinolinecarboxylate (3.06 g, 12.2 mmol) in THF (100 mL) and the mixture was stirred at room temperature for 1 h. The heterogeneous mixture was quenched with dilute HCl (2 M), and extracted with CH₂Cl₇ (2×100 mL) and EtOAc (5×100 mL). The remaining solid was taken up in hot EtOH, and allowed to cool to yield a white fluffy solid. This solid was combined with the combined organic extracts, evaporated in vacuo and crystallised with EtOH to give 4-chloro-7-(hydroxymethyl)-1(2H)-isoquinolone (2.19 g, 10.49 mmol) as a white solid.

mp 266–268° C.

$^1$H (DMSO-$d_6$, 300 MHz) δ 4.6 (2H, d), 5.4 (1H, t), 7.4 (1H, s), 7.7–7.8 (2H, m), 8.2 (1H, s) ppm.

LRMS 210 (MH$^+$), 419 (M$_2$H$^+$).

Anal. Found: C, 57.11; H, 3.81; N, 6.54. Calc for $C_{10}H_8ClNO_2$: C, 57.29; H, 3.85; N, 6.68.

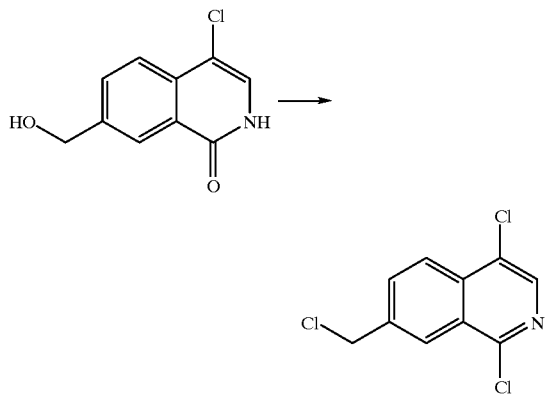

A solution of 4-chloro-7-(hydroxymethyl)-1(2H)-isoquinolone (1.00 g, 4.77 mmol) in POCl$_3$ was stirred at 50° C. for 19 h. The reaction mixture was cooled in an ice-bath, quenched by the dropwise addition of dilute HCl (1 M) (reaction temperature <30° C.) and then partioned between water and EtOAc. The aqueous phase was reextracted with EtOAc and the combined organic extracts were dried (Na$_2$SO$_4$) and evaporated in vacuo. The residue was purified by column chromatography upon silica gel using hexane-EtOAc (80:20) as eluant to give 7-(chloromethyl)-1,4-dichloroisoquinoline (870 mg, 3.53 mmol).

mp 139–141° C.

$^1$H (CDCl$_3$, 400 MHz) δ 4.8 (2H, s), 7.9 (1H, d), 8.1 (1H, d), 8.3–8.4 (2H, m) ppm.

LRMS 241 [$C_{11}H_9Cl_2ON.H^+$; product of MeO (from MeOH) substitution of Cl]

Preparation 80:

N-[(1,4-Dichloro-7-isoquinolinyl)methyl]-N-methyl-DL-phenylglycine t-butyl ester

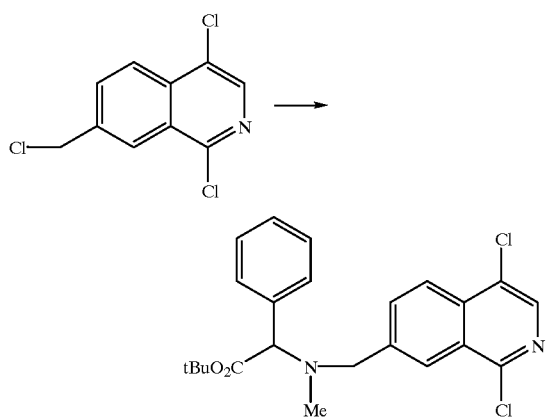

7-(Chloromethyl)-1,4-dichloroisoquinoline (230 mg, 0.93 mmol) was added to a solution of N-methyl-DL-phenylglycine t-butyl ester (248 mg, 0.96 mmol) and NEt$_3$ (187 μL, 1.34 mmol) in CH$_2$Cl$_2$ (5 mL), and the mixture heated at reflux for 15 h. [TLC indicated incomplete reaction]. The solvent was evaporated in vacuo, THF (30 mL) and NEt$_3$ (100 μL, 0.72 mmol) were added, and the mixture heated at reflux for 24 h. Although the reaction was still incomplete, the solvent was evaporated in vacuo, and the residue purified by column chromatography upon silica gel using hexane-Et$_2$O (98:2) as eluant to give N-[(1,4-dichloro- 7-isoquinolinyl)methyl]-N-methyl-DL-phenylglycine 1-butyl ester (120 mg, 0.28 mmol) as a colourless oil.

The corresponding dihydrochloride salt was prepared as follows: a solution of the amine in hexane was stirred with a solution of HCl in Et$_2$O (0.5 M). The resulting white precipitate was collected by filtration and dried.

mp 120–122° C.

$^1$H (CDCl$_3$, 400 MHz) δ 1.5 (9H, s), 2.25 (3H, s), 3.8 (1H, d), 3.9 (1H, d), 4.3 (1H, s), 7.3–7.4 (3H, m), 7.45–7.5 (2H, m), 7.95 (1H, d), 8.15 (1H, d), 8.2 (1H, s), 8.3 (1H, s) ppm.

LRMS 432 (MH$^+$).

Anal. Found: C, 56.62; H, 5.58; N, 5.63. Calc for $C_{23}H_{24}Cl_2N_2O_2.HCl.H_2O$: C, 56.86; H, 5.60; N, 5.77.

Preparation 81:

N-Benzyl-N-[(1,4-dichloro-7-isoquinolinyl)methyl]glycine t-butyl ester

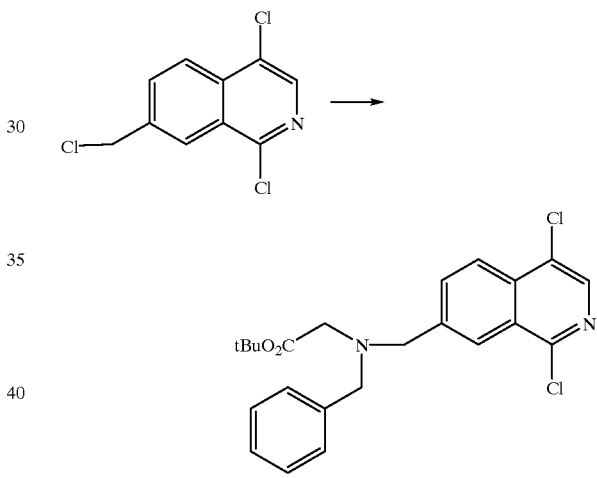

7-(Chloromethyl)-1,4-dichloroisoquinoline (378 mg, 1.53 mmol) was added to a stirred solution of N-benzyl glycine t-butyl ester (340 mg, 1.53 mmol) and NEt$_3$ (256 μL, 1.84 mmol) in THF (20 mL) and the mixture heated at reflux for 18 h. The solvent was evaporated in vacuo and the residue was purified by column chromatography upon silica gel using hexane-EtOAc (95:5 to 90:10) as eluant to give N-benzyl-N-[(1,4-dichloro-7-isoquinolinyl)methyl]glycine t-butyl ester (245 mg, 0.57 mmol).

The corresponding dihydrochloride salt was prepared as follows: a solution of the amine in Et$_2$O was stirred with a solution of HCl in dioxane (0.5 M). The resulting white precipitate was collected by filtration and dried.

mp 140–143° C.

$^1$H (CDCl$_3$, 400 MHz) δ 1.4 (9H, s), 3.3 (2H, s), 4.6 (2H, s), 4.8 (2H, s), 7.4–7.45 (3H, m), 7.75–7.8 (2H, m), 8.35 (1H, d), 8.4 (1H, s), 8.45 (1H, s), 8.8 (1H, d) ppm.

LRMS 433 (MH$^+$).

Anal. Found: C, 58.91; H, 5.38; N, 5.90. Calc for $C_{23}H_{24}Cl_2N_2O_2.HCl$: C, 59.05; H, 5.39; N, 5.99.

Preparation 82:

Nα-[(1,4-Dichloro-7-isoquinolinyl)sulphonyl]-Nε-tert-butyloxycarbonyl-L-lysine tert-butyl ester

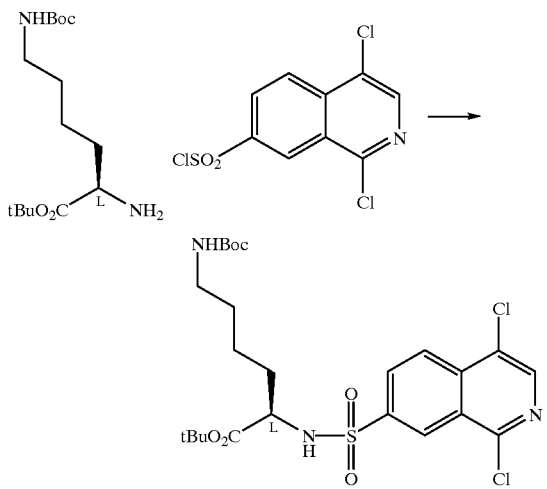

A solution of 1,4-dichloro-7-isoquinolinylsulphonyl chloride (250 mg, 0.84 mmol), Nε-tert-butyloxycarbonyl-L-lysine tert-butyl ester hydrochloride (286 mg, 0.84 mmol) and triethylamine (235 μl, 1.69 mmol) in CH₂Cl₂ (25 ml) was stirred at 23° C. for 3h. The reaction mixture was washed with water (2×20 ml), dried (MgSO₄) and concentrated in vacuo to a residue which upon trituration with hexane and then i-Pr₂O gave Nα-[(1,4-dichloro-7-isoquinolinyl)sulphonyl]-Nε-tert-butyloxycarbonyl-L-lysine tert-butyl ester as a white powder (270 mg, 0.48 mmol).

¹H (CDCl₃, 300 MHz) δ 1.1 (9H, s), 1.35–1.5 (13H, m), 1.6–1.85 (2H, m), 3.0–3.2 (2H, m), 3.8–3.95 (1H, m), 4.45–4.6 (1H, br m), 5.35 (1H, d), 8.2 (1H, dd), 8.35 (1H, d), 8.45 (1H, s), 8.8 (1H, d) ppm.

LRMS 562 (MH⁺), 584 (MNa⁺).

Anal. Found: C, 51.04; H, 5.96; N, 7.42. Calc for C₂₄H₃₃Cl₂N₃O₆S: C, 51.24; H, 5.91; N, 7.47.

Preparation 83:
Nα-[(1,4-Dichloro-7-isoquinolinyl)sulphonyl]-Nε-tert-butyloxycarbonyl-D-lysine tert-butyl ester

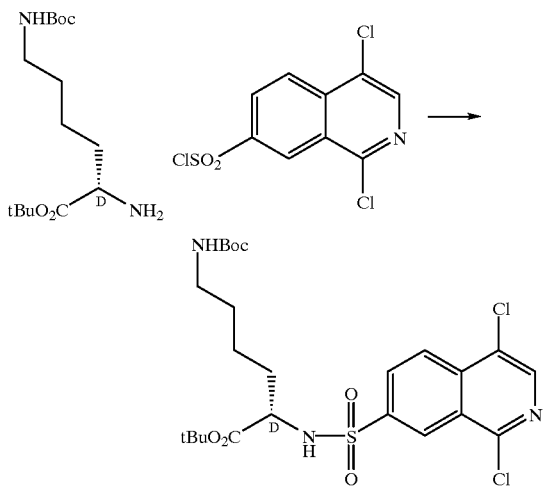

A solution of 1,4-dichloro-7-isoquinolinylsulphonyl chloride (250 mg, 0.84 mmol), NE-tert-butyloxycarbonyl-D-lysine tert-butyl ester hydrochloride (286 mg, 0.84 mmol) and triethylamine (235 μl, 1.69 mmol) in CH₂Cl₂ (25 ml) was stirred at 23° C. for 18 h. The reaction mixture was concentrated in vacuo and the residue purified by column chromatography upon silica gel using hexane-EtOAc (70:30) as eluant. Crystallisation from i-Pr₂O gave N-[(1,4-dichloro-7-isoquinolinyl)sulphonyl]-N,-t-butyloxycarbonyl-D-lysine tert-butyl ester (285 mg, 0.51 mmol).

¹H (CDCl₃, 400 MHz) δ 1.15 (9H, s), 1.2–1.55 (13H, m), 1.55–1.8 (2H, m), 3.05–3.15 (2H, m), 3.85–3.9 (1H, m), 4.5–4.6 (1H, m), 5.4 (1H, br d), 8.2 (1H, d), 8.35 (1H, d), 8.45 (1H, s), 8.8 (1H, s) ppm.

LRMS 584 (MNa⁺).

Anal. Found: C, 51.18; H, 5.89; N, 7.33. Calc for C₂₄H₃₃Cl₂N₃O₆S: C, 51.24; H, 5.91; N, 7.47.

Preparation 84:
N-[(1,4-Dichloro-7-isoquinolinyl)sulphonyl]-L-glutamine tert-butyl ester

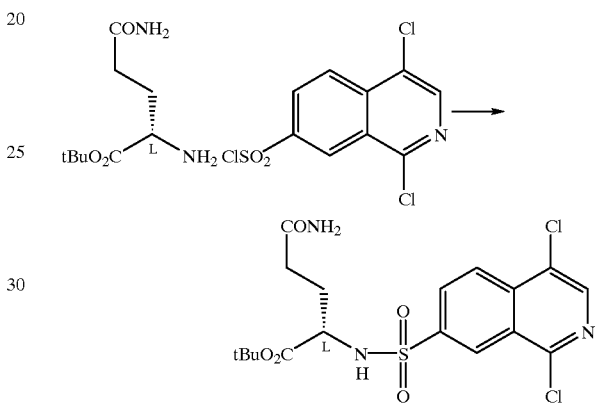

A solution of 1,4-dichloro-7-isoquinolinyl sulphonylchloride (250 mg, 0.84 mmol), L-glutamine tert-butyl ester hydrochloride (201 mg, 0.84 mmol) and triethylamine (235 μl, 1.69 mmol) in CH₂Cl₂ (25 ml) was stirred at 23° C. for 18 h. The reaction mixture was washed with water (2×20 ml) and the solvent removed in vacuo to give N-[(1,4-dichloro-7-isoquinolinyl)sulphonyl]-L-glutamine tert-butyl ester (309 mg, 0.67 mmol). An analytical sample was obtained following crystallisation from EtOAc.

¹H (CDCl₃, 300 MHz) δ 1.05–1.15 (9H, s), 1.8–1.95 (1H, m), 2.1–2.25 (1H, m), 2.35–2.55 (2H, m), 3.9–4.0 (1H, m), 5.4–5.6 (1H, br s), 5.6–5.8 (1H, br s), 5.85 (1H, d), 8.2 (1H, d), 8.35 (1H, d), 8.5 (1H, s), 8.8 (1H, s) ppm.

LRMS 462 (MH⁺), 479 (MNH₄⁺).

Anal. Found: C, 46.66; H, 4.54; N, 8.96. Calc for C₁₈H₂₁Cl₂N₃O₅S: C, 46.75; H, 4.58; N, 9.09.

Preparation 85:
N-[(1,4-Dichloro-7-isoquinolinyl)sulphonyl]-cyclopentylamin

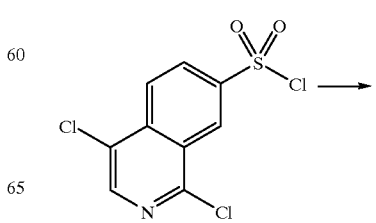

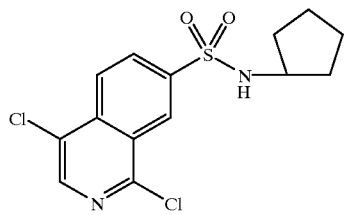

1,4-Dichloro-7-isoquinolinylsulphonyl chloride (250 mg, 0.84 mmol) was added to a solution of cyclopentylamine (100 μl, 1.0 mmol) and triethylamine (170 μl, 1.22 mmol) in $CH_2Cl_2$ (15 ml), and the reaction stirred at room temperature for 18 h. The solution was diluted with $CH_2Cl_2$, washed with 2M hydrochloric acid, saturated aqueous $Na_2CO_3$ solution and then brine. This solution was dried ($MgSO_4$), and evaporated in vacuo, to give N-[(1,4-dichloro-7-isoquinolinyl)sulphonyl]-cyclopentylamine (250 mg, 0.72 mmol) as a white crystalline solid.

$^1$H (CDCl$_3$, 300 MHz) δ 1.4 (2H, m), 1.5–1.7 (4H, m), 1.85 (2H, m), 3.75 (1H, m), 4.6 (1H, d), 8.25 (1H, d), 8.4 (1H, d), 8.5 (1H, s), 8.95 (1H, s) ppm.

LRMS 346 (MH$^+$)

Anal. Found: C, 48.68; H, 4.02; N, 7.97. Calc. for $C_{14}H_{14}Cl_2N_2O_2S$: C, 48.71; H, 4.09; N, 8.11%.

Preparation 86:
1,4-Dichloro-7-(1-pyrrolidinylsulphonyl)isoquinoline

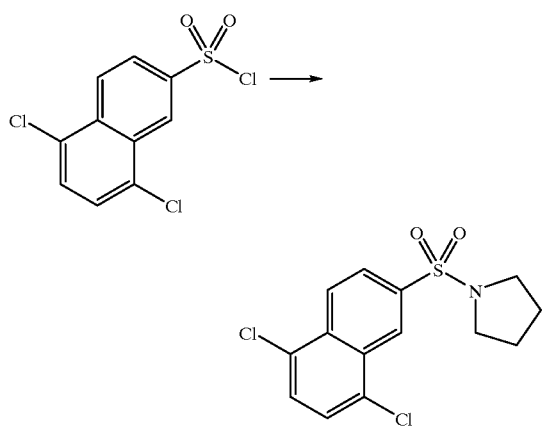

Pyrrolidine (96 mg, 1.35 mmol) was added to a solution of 1,4-dichloro-7-isoquinolinylsulphonyl chloride (20 mg, 0.67 mmol) in $CH_2Cl_2$ (5 ml), and the reaction stirred at room temperature for 72 h. The mixture was concentrated in vacuo, and the residual solid triturated with water, filtered and dried. The crude product was purified by column chromatography upon silica gel using EtOAc-hexane (50:50) as eluant, and recrystallised from i-Pr$_2$O, to give 1,4-dichloro-7-(1-pyrrolidinylsulphonyl)isoquinoline (67 mg, 0.20 mmol) as a white solid, $^1$H (CDCl$_3$, 300 MHz) δ 1.8 (4H, m), 3.35 (4H, m), 8.25 (1H, d), 8.4 (1H, d), 8.5 (1H, s), 8.85 (1H, s) ppm.

LRMS : 331, 333 (MH$^+$)

Anal. Found: C, 47.23; H, 3.60; N, 8.32. Calc. for $C_{13}H_{12}N_2Cl_2O_2S$: C, 47.14; H, 3.65; N, 8.46%.

Preparation 87:
tert-Butyl (2R)-1-[(1,4-dichloro-7-isoquinolinyl)sulphonyl]-2-piperidinecarboxylate

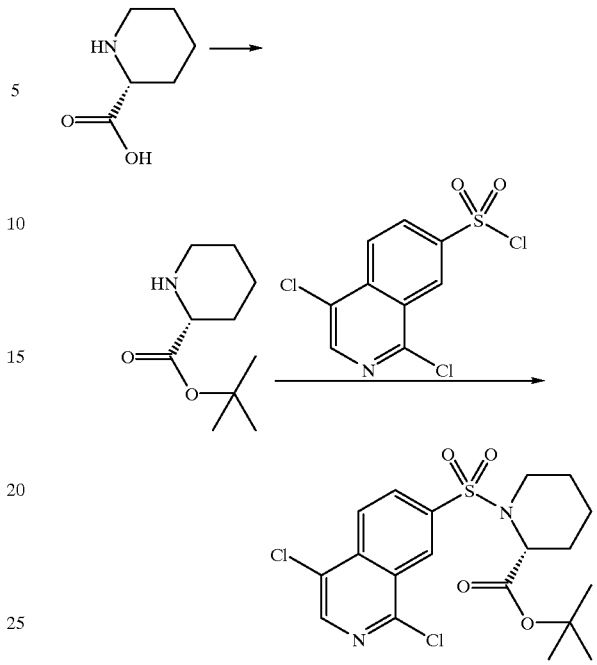

Concentrated $H_2SO_4$ (2.0 ml) was added to an ice-cold solution of $^2$-(R)-piperidine carboxylic acid (415 mg, 3.21 mmol) in dioxan (10 ml). Condensed isobutylene (40 ml) was carefully added, and the reaction stirred at room temperature in a sealed vessel for 21 h. The reaction mixture was poured into an ice-cooled solution of Et$_2$O (100 ml) and 5N NaOH (20 ml), the mixture allowed to warm to room temperature with stirring, and then diluted with water. The phases were separated, the organic layer washed with 1N NaOH, then concentrated in vacuo, to half the volume, and extracted with 2N HCl. The combined acidic extracts were basified using 1N NaOH, and extracted with CH$_2$Cl$_2$, the combined organic solutions dried (MgSO$_4$) and evaporated in vacuo to afford tert-butyl 2(R)-piperidine carboxylate (210 mg, 1.4 mmol) as an oil.

$^1$H (CDCl$_3$, 300 MHz) δ 1.4–1.6 (1H, m), 1.75 (3H, m), 1.9 (1H, m), 2.65 (1H, m), 3.1 (1H, m), 3.2 (1H, m) ppm.

LRMS 186 (MH$^+$).

1,4-Dichloro-7-isoquinolinylsulphonyl chloride (245 mg, 0.83 mmol) was added to a solution of tert-butyl 2(R)-piperidine carboxylate (153 mg, 0.83 mmol) and triethylamine (170 μl, 1.22 mmol) in CH$_2$Cl$_2$ (15 ml), and the reaction stirred at room temperature for 18 h. The solution was diluted with CH$_2$Cl$_2$, washed with 2M hydrochloric acid, saturated Na$_2$CO$_3$ solution and then brine, dried (MgSO$_4$), and evaporated in vacuo. The residual oil was purified by column chromatography upon silica gel using an elution gradient of pentane-EtOAc (100:0 to 90:10), to give tert-butyl (2R)-1-[(1,4-dichloro-7-isoquinolinyl)sulphonyl]-2-piperidinecarboxylate, (290 mg, 0.65 mmol) as a colourless film.

$^1$H (CDCl$_3$, 400 MHz) δ 1.3 (9H, s), 1.55 (2H, m), 1.7–1.85 (3H, m), 2.2 (1H, m), 3.3 (1H, dd), 3.9 (1H, dd), 4.75 (1H, d), 8.15 (1H, d), 8.35 (1H, dd), 8.45 (1H, s), 8.8 (1H, s) ppm.

LRMS 462, 464 (MNH$_4^+$)

Anal. Found: C, 50.99; H, 4.95; N, 6.10. Calc. For $C_{19}H_{22}Cl_2N_2O_4S$; C, 51.24; H, 4.98; N, 6.29%.

Preparation 88:
Methyl 4-{[(1,4-dichloro-7-isoquinolinyl)sulphonyl]amino}-1-methyl-4-piperidinecarboxylate

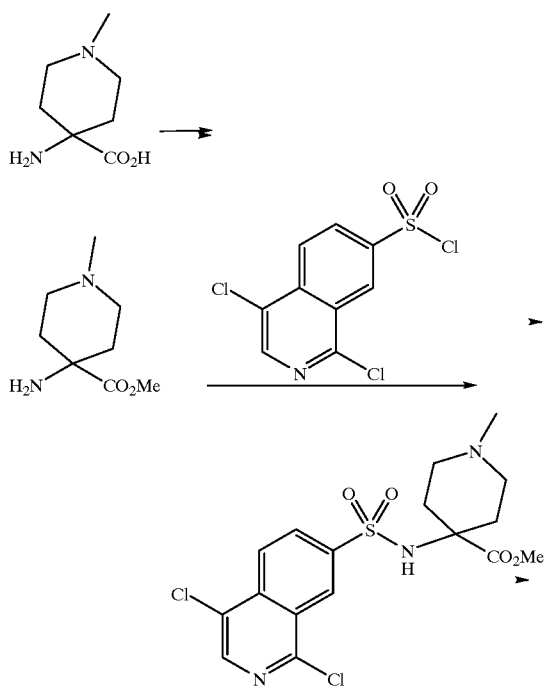

A solution of 4-amino-1-methyl-4-piperidinecarboxylic acid (4.0 g, 15.6 mmol) in methanolic HCl (100 ml) was stirred under reflux for 20 h. The cooled mixture was concentrated in vacuo and azeotroped with $CH_2Cl_2$ to give an oil. This was dissolved in ice-cold $Na_2CO_3$ solution and extracted with $CH_2Cl_2$ (2×). The combined organic extracts were -dried ($MgSO_4$) and evaporated in vacuo to afford 4-amino-1-methyl-4-piperidinecarboxylate (1.6 g, 9.3 mmol) as an oil.

$^1$H ($CDCl_3$, 400 MHz) δ 1.4–1.65 (4H, m), 2.1–2.25 (2H, m), 2.35 (3H, s), 2.4–2.55 (4H, m), 3.75 (3H, s) ppm.

LRMS 173 (MH$^+$)

1,4-Dichloro-7-isoquinolinylsulphonyl chloride (1.0 g, 3.37 mmol) was added to a solution of methyl 4-amino-1-methyl-4-piperidinecarboxylate (700 mg, 4.0 mmol) and triethylamine (700 μl, 1.0 mmol) in $CH_2Cl_2$ (60 ml), and the reaction stirred at room temperature for 18 h. The mixture was concentrated in vacuo, and the residue purified by column chromatography upon silica gel using an elution gradient of $CH_2Cl_2$-MeOH-0.880 $NH_3$ (97:3:0.3 to 95:5:0.5) to give methyl 4-{[(1,4-dichloro-7-isoquinolinyl)sulphonyl]amino}-1-methyl-4-piperidinecarboxylate (700 mg, 1.62 mmol) as a white solid.

$^1$H ($CDCl_3$, 400 MHz) δ 2.05 (2H, m), 2.25 (6H, m), 2.4 (2H, m), 2.55 (2H, m), 3.5 (3H, s), 8.25 (1H, d), 8.4 (1H, d), 8.5 (1H, s), 8.85 (1H, s) ppm.

LRMS 432, 434 (MH$^+$)

Preparation 89:
N-[(1,4-Dichloro-7-isoquinolinyl)sulphonyl]-N-(methyl)cycloleucine ethyl ester

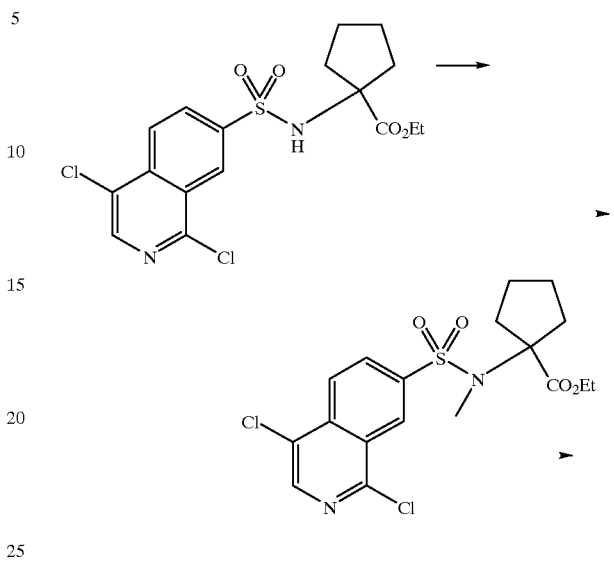

$K_2CO_3$ (238 mg, 1.73 mmol) was added to a solution of N-[(1,4-dichloro-7-isoquinolinyl)sulphonyl]-cycloleucine ethyl ester (300 mg, 0.72 mmol) in DMF (5 ml), and the mixture stirred at room temperature for 40 min. Methyl iodide (47 μl, 0.76 mmol) was added and the reaction stirred for a further 30 min. at room temperature. The mixture was poured into water, extracted with EtOAc, and the combined organic extracts washed with water, then brine, dried ($Na_2SO_4$) and evaporated in vacuo. The residual yellow solid was purified by column chromatography upon silica gel using EtOAc-hexane (20:80) as eluant to give N-[(1,4-dichloro-7-isoquinolinyl)sulphonyl]-N-(methyl)cycloleucine ethyl ester (204 mg, 0.47 mmol) as a white solid.

$^1$H ($CDCl_3$, 400 MHz) δ 1.25 (3H, t), 1.75 (4H, m), 2.1 (2H, m), 2.4 (2H, m) 3.05 (3H, s), 4.2 (2H, q), 8.25 (1H, d), 8.35 (1H, d), 8.5 (1H, s), 8.9 (1H, s) ppm.

LRMS 431,433 (MH$^+$)

Anal. Found: C, 50.12; H, 4.66; N, 6.43. Calc. for $C_{18}H_{20}Cl_2N_2O_4S$: C, 50.12; H, 4.67; N, 6.49%.

Preparation 90:
4-Bromo-1-chloro-7-isoquinolinesulphonyl chloride

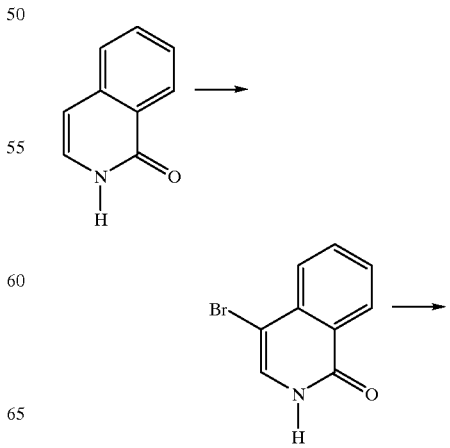

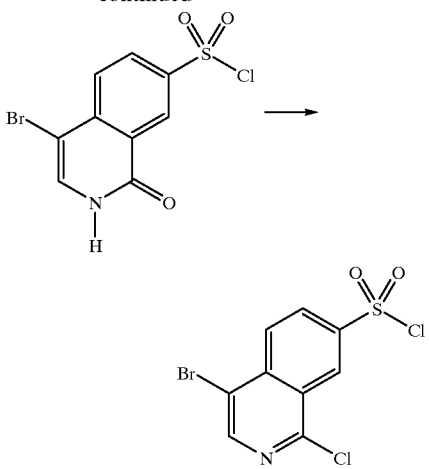

A suspension of isoquinolinol (10 g, 68.9 mmol) in MeCN (250 ml) at 50° C., was treated with N-bromosuccinimide (12.6 g, 70.8 mmol) whereupon almost complete solution occurred before a thick white precipitate was formed. After heating under reflux for 3 h, the reaction mixture was cooled in ice and the solid filtered, washed with MeCN, and dried to afford 4-bromo-1-(2H)-isoquinolone (7.6 g, 34.0 mmol).

$^1$H (DMSO-$d_6$, 300 MHz) δ 7.55 (1H, s), 7.6 (1H, m), 7.75 (1H, d), 7.85 (1H, m), 8.2 (1H, d), 11.55 (1H, br s) ppm.

LRMS 223, 225 (MH$^+$).

4-Bromo-1-(2H)-isoquinolone (7.5 g, 33.0 mmol) was added portionwise to chlorosulphonic acid (23 ml, 346 mmol) and the resultant solution heated to 100° C. for 2½ days. After cooling, the reaction mixture was poured carefully onto ice to give a white solid which was filtered, washed with water, MeCN, and Et$_2$O and air-dried to give a cream solid. 4-Bromo-1-oxo-1,2-dihydro-7-isoquinolinesulphonyl chloride (-13.5 g) was immediately used without further drying.

mp>300° C.

$^1$H (DMSO-$d_6$, MHz) δ 7.45 (1H, s), 7.7 (1H, d), 8.0 (1H, d), 8.45 (1H, s), 11.55 (1H, br s) ppm.

To a stirred solution of 4-bromo-1-oxo-1,2-dihydro-7-isoquinolinesulphonyl chloride (~13.5 g) in acetonitrile (200 ml) was added portionwise POCl$_3$ (10 ml, 110 mmol). The resultant heterogeneous mixture was heated under reflux for 24 h, allowed to cool, and the supernatant decanted from the brown oily residues and concentrated to a solid. Extraction of the solid into EtOAc gave, after solvent removal, a sticky solid which was triturated with Et$_2$O to afford the title compound (3.83 g, 11.0 mmol) as a white solid.

mp 120.5–121° C.

$^1$H (DMSO-$d_6$, 300 MHz) δ 8.2 (2H, m), 8.5 (1H, s), 8.6 (1H, s) ppm. Anal. Found: C, 31.21; H, 1.27; N, 4.08. Calc for C$_9$H$_4$BrCl$_2$NO$_2$S.0.25H$_2$O: C, 31.29; H, 1.31; N, 4.05.

Preparation 91:
N-[(4-Bromo-1-chloro-7-isoquinolinyl)sulphonyl]-D-proline tert-butyl ester

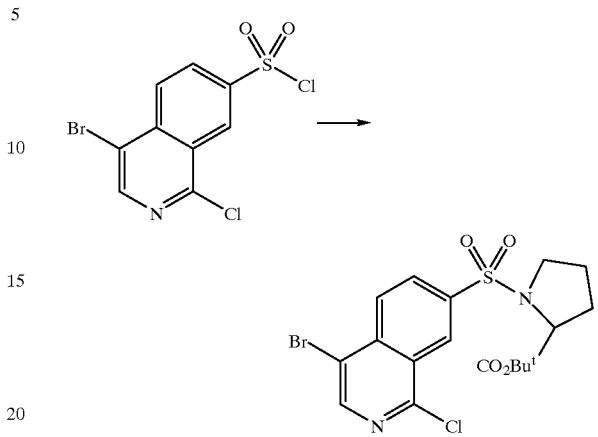

4-Bromo-1-chloro-7-isoquinolinesulphonyl chloride (400 mg, 1.17 mmol) in CH$_2$Cl$_2$ (20 ml) was treated with (D)-proline tert-butyl ester hydrochloride (250 mg, 1.20 mmol) and triethylamine (410 μl, 2.94 mmol) and stirred at room temperature for 2 h. The reaction was diluted with CH$_2$Cl$_2$, washed consecutively with water, 10% aqueous citric acid and brine, and then dried (MgSO$_4$) and concentrated in vacuo to give an off-white solid. This was purified by column chromatography upon silica gel eluting with EtOAc-hexane (16:84) to give N-[(4-bromo-1-chloro-7-isoquinolinyl)sulphonyl]-D-proline tert-butyl ester (350 mg, 0.74 mmol) as a white solid.

mp 128.5–129.5° C.

$^1$H (CDCl$_3$, 300 MHz) δ 1.1 (9H, s), 1.85–2.0 (3H, m), 2.2 (1H, m), 3.5 (2H, m), 4.4 (1H, dd), 8.3 (2H, m), 8.6 (1H, s), 8.9 (1H, s) ppm.

LRMS 475, 477 (MH$^+$).

Anal. Found: C, 45.41; H, 4.21; N, 5.83. Calc for C$_{18}$H$_{20}$BrClN$_2$O$_4$S: C, 45.44; H, 4.24; N, 5.89.

Preparation 92:
N-{[(4-Bromo-1-chloro-7-isoquinolinyl)sulphonyl]-N-[2-(dimethylamino)ethy-]cycloleucine ethyl ester hydrochloride

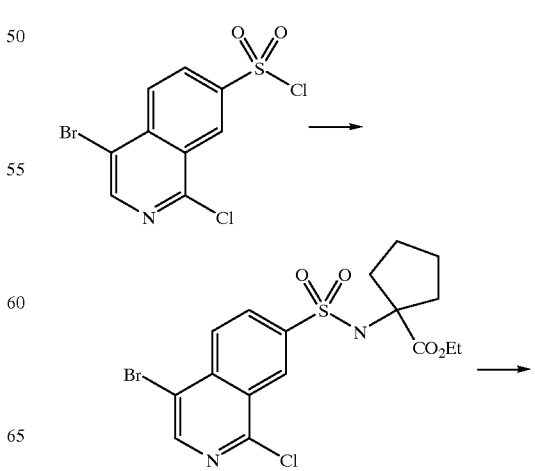

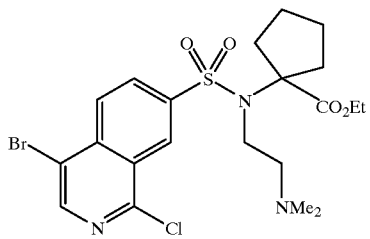

Triethylamine (1.02 ml, 7.33 mmol) was added to a solution of 4-bromo-1-chloroisoquinolinylsulphonyl chloride (1.0 g, 2.93 mmol) in $CH_2Cl_2$ (25 ml) and the reaction stirred at room temperature for 2 h. The reaction was washed consecutively with 1N HCl, $Na_2CO_3$ solution, and brine, then dried ($Na_2SO_4$) and evaporated in vacuo. The residual oil was crystallised from $CH_2Cl_2$-i-$Pr_2O$ to give N-([(4-bromo-1-chloro-7-isoquinolinyl)sulphonyl]cycloleucine ethyl ester (380 mg, 0.82 mmol) as a solid.

$^1H$ (CDCl$_3$, 300 MHz) δ 1.2 (3H, t), 1.6–1.8 (4H, m), 2.0 (2H, m), 2.15 (2H, m), 4.05 (2H, q), 8.25 (1H, d), 8.35 (1H, d), 8.6 (1H, s), 8.9 (1H, s) ppm.

LRMS 484 (MNa$^+$)

$K_2CO_3$ (157 mg, 1.14 mmol) was added to a solution of N-{[(4-bromo-1-chloro-7-isoquinolinyl)sulphonyl]cycloleucine ethyl ester (300 mg, 0.65 mmol) in DMF (5 ml), and the solution stirred for 5 min. N,N-dimethylaminoethyl chloride hydrochloride (112 mg, 0.78 mmol) was added and the reaction stirred at room temperature for 36 h. The reaction mixture was partitioned between water and EtOAc, the layers separated, and the aqueous phase extracted with EtOAc. The combined organic solutions were washed with brine, dried ($Na_2SO_4$) and evaporated in vacuo. The residue was purified by column chromatography upon silica gel using $CH_2Cl_2$-MeOH-0.880 $NH_3$ (95:5:0.5) as eluant, to give a gum. This was dissolved in an $Et_2O$-EtOAc solution, ethereal HCl added and the mixture evaporated in vacuo. The resulting solid was triturated with water, filtered and dried to give N-{[(4-bromo-1-chloro-7-isoquinolinyl)sulphonyl]-N-[2-(dimethylamino)ethyl]cycloleucine ethyl ester hydrochloride (90 mg, 0.16 mmol) as a solid.

$^1H$ (CDCl$_3$, 300 MHz) δ 1.3 (3H, t), 1.65 (2H, m), 1.8 (2H, m), 2.15 (2H, m), 2.4 (2H, m), 2.9 (6H, m), 3.6 (2H, m), 4.0 (2H, m), 4.2 (2H, q), 8.2 (1H, d), 8.4 (1H, d), 8.65 (1H, s), 8.80 (1H, s) ppm.

LRMS 534 (MH$^+$)

Anal Found: C, 44.17; H, 4.97; N, 7.24. Calc. for $C_{21}H_{27}BrClN_3O_4S.HCl$: C, 44.30; H, 4.96; N, 7.38%.

Preparation 93:
Ethyl 3-{[(1,4-dichloro-7-isoquinolinyl)sulphonyl]amino}-2,2-dimethylpropanoate hydrochloride

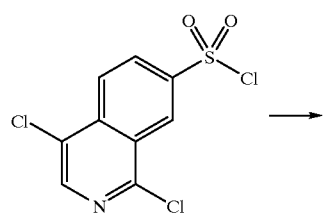

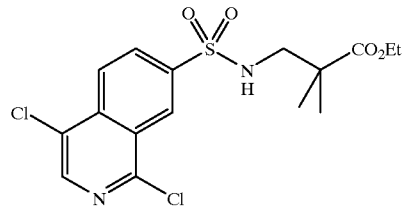

The title compound was obtained as a white solid (86%) from 1,4-dichlorosulphonyl chloride and ethyl 3-amino-2,2-dimethylpropanoate hydrochloride, following a similar procedure to that described in preparation 90.

$^1H$ (CDCl$_3$, 300 MHz) δ 1.25 (9H, m), 3.0 (2H, d), 4.1 (2H, q), 5.4 (1H, t), 8.2 (1H, d), 8.4 (1H, d), 8.5 (1H, s), 8.9 (1H, s) ppm.

LRMS 404, 406 (MH$^+$)

Anal. found: C, 47.39; H, 4.44: N, 6.73. Calc. for $C_{16}H_{18}Cl_2N_2O_4S$: C, 47.42; H, 4.48; N, 6.91%.

Preparation 94:
N-[(1,4-Dichloro-7-isoquinolinyl)sulphonyl]-N-[2-(tetrahydro-2H-pyran-2-yloxy)ethyl]cycloleucine ethyl ester

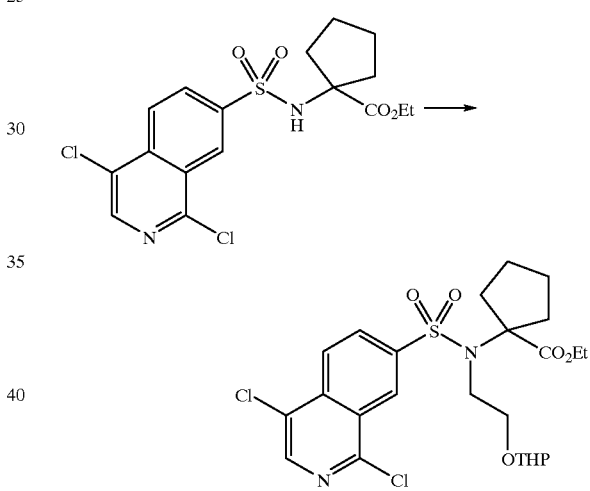

$K_2CO_3$ (238 mg, 1.73 mmol) was added to a solution of N-[(1,4-dichloro-7-isoquinolinyl)sulphonyl]cycloleucine ethyl ester (600 mg, 1.44 mmol) in DMF (10 ml), and the suspension stirred at room temperature for 30 min. A solution of 2-(2-bromoethoxy)tetrahydro-2H-pyran (J. C. S. 1948; 4187) (316 mg, 1.44 mmol) in DMF (4 ml) was added, followed by sodium iodide (10 mg), and the reaction stirred at 70° C. for 23 h. The cooled mixture was poured into water, and extracted with EtOAc. The combined organic extracts were washed with brine, dried (MgSO$_4$), and evaporated in vacuo. The residual yellow oil was purified by column chromatography upon silica gel using hexane-$Et_2O$ (75:25) as eluant, azeotroped with $CH_2Cl_2$ and dried under vacuum to afford N-[(1,4-dichloro-7-isoquinolinyl)sulphonyl]-N-[2-(tetrahydro-2H-pyran-2-yloxy)ethyl]cycloleucine ethyl ester (341 mg, 0.63 mmol) as a solid.

$^1H$ (CDCl$_3$, 400 MHz) δ 1.3 (3H, t), 1.55 (4H, m), 1.65–1.8 (6H, m), 2.15 (2H, m), 2.4 (2H, m), 3.5 (1H, m), 3.7 (3H, m), 3.8 (1H, m), 3.95 (1H, m), 4.2 (2H, q), 4.55 (1H, m), 8.35 (2H, s), 8.45 (1H, s), 8.9 (1H, s) ppm.

LRMS 545 (MH$^+$), 562 (MNH$_4^+$)

Anal. Found: C, 52.31; H, 5.58; N, 4.84. Calc. for $C_{24}H_{30}Cl_2N_2O_6S.0.3H_2O$: C, 52.33; H, 5.60; N, 5.09%.

Preparation 95:
N-[(1,4-dichloro-7-isoquinolinyl)methyl]cycloleucine methyl ester

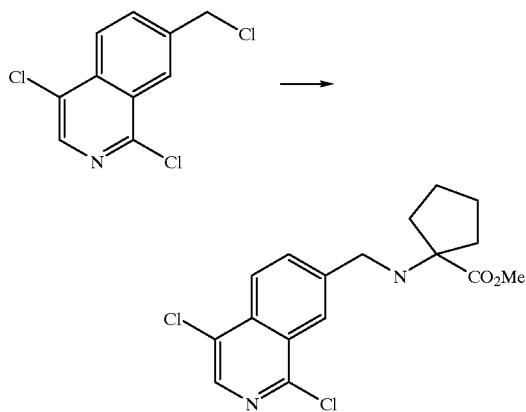

7-Chloromethyl-1,4-dichloro-isoquinoline (400 mg, 1.62 mmol) was added to a suspension of cycloleucine methyl ester (255 mg, 1.78 mmol), $K_2CO_3$ (500 mg, 3.62 mmol) and sodium iodide (15 mg) and the resultant mixture heated to 75° C. for 2½ h. After cooling, the reaction mixture was poured into water and extracted with $CH_2Cl_2$ (2×60 ml). The organic extracts were washed with water, brine, dried ($Na_2SO_4$) and concentrated in vacuo to give an oil. This was purified by column chromatography upon silica gel eluting with hexane-EtOAc (85:15) to give N-[(1,4-dichloro-7-isoquinolinyl)methyl]cycloleucine methyl ester (414 mg, 1.17 mmol) as a yellow oil.

A sample of this oil was treated with ethereal HCl, and the mixture evaporated to give the hydrochloride salt of the title compound as a white solid.

$^1$H (CDCl$_3$, 300 MHz) δ 1.4–1.8 (5H, m), 2.0 (3H, m), 3.75 (3H, s), 4.15 (2H, s), 8.25 (3H, m), 8.5 (1H, s), 10.5 (2H, br s) ppm.

Anal. found: C, 52.53; H, 4.99; N, 6.84. Calc. for $C_{17}H_{18}Cl_2N_2O_2 \cdot HCl$: C, 52.39; H, 4.91; N, 7.19%.

Preparation 96:
(1-Aminocyclopentyl)(4-methyl-1-piperazinyl)methanone dihydrochloride

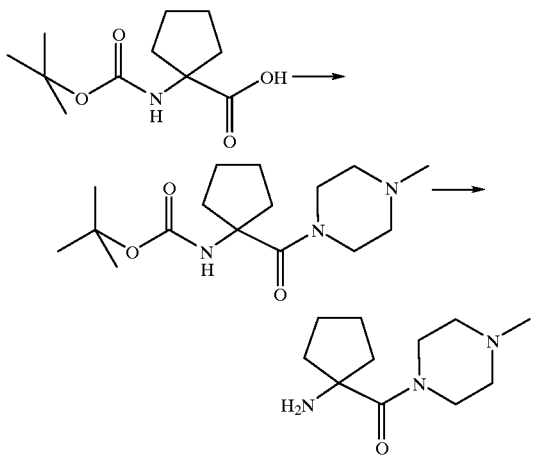

1-(3-Dimethylaminopropyl)-3-ethylcarbodiimide hydrochloride (2.49 g, 13.0 mmol) was added portionwise to a cooled (4° C.) solution of hydroxybenzotriazole hydrate (1.49 g, 11.0 mmol) and 1-[(tert-butoxycarbonyl)amino] cyclopentanecarboxylic acid (2.29 g, 10.0 mmol) in DMF (15 ml), and the mixture stirred for 30 min. N-Methylpiperazine (1.10 g, 11.0 mmol) was added, the reaction stirred for 30 min. allowed to warm to room temperature and stirring continued for a further 17 h. The reaction mixture was evaporated in vacuo, and the residual yellow oil partitioned between saturated $Na_2CO_3$ solution and EtOAc. The layers were separated, the aqueous phase extracted with EtOAc, and the combined organic solutions dried (MgSO$_4$) and concentrated in vacuo. The residual solid was pre-adsorbed onto silica gel and purified by column chromatography upon silica gel using an elution gradient of $CH_2Cl_2$-MeOH-0.880 NH$_3$(97.5:2.5:0.25 to 90:10:1) and triturated with Et$_2$O to afford tert-butyl 1-[(4-methyl-1-piperazinyl)carbonyl]cyclopentylcarbamate (2.31 g, 7.4 mmol) as a crystalline solid.

mp 171–175° C.
$^1$H (CDCl$_3$, 300 MHz) δ 1.4 (9H, s), 1.7 (6H, m), 2.25 (3H, s), 2.4 (6H, m), 3.65 (4H, m), 4.7 (1H, br s).
LRMS 312 (MH$^+$)

A suspension of tert-butyl 1-[(4-methyl-1-piperazinyl) carbonyl]cyclopentylcarbamate (2.2 g, 7.06 mmol) in EtOAc (120 ml) at 4° C. was saturated with HCl gas, and the reaction then stirred for 4 h. The mixture was azeotroped with EtOAc, then dry Et$_2$O, and dried under vacuum to afford (1-aminocyclopentyl)(4-methyl-1-piperazinyl) methanone dihydrochloride (2.1 g) as a white solid.

mp 267–270° C. (Decomp)
Anal. Found: C, 43.29; H, 7.99; N, 13.84. Calc. for $C_{11}H_{21}N_3O \cdot 2HCl \cdot H_2O$: C, 43.71; H, 8.34; N, 13.90%.
LRMS 212 (MH$^+$)

What is claimed is:
1. A compound of formula (I):

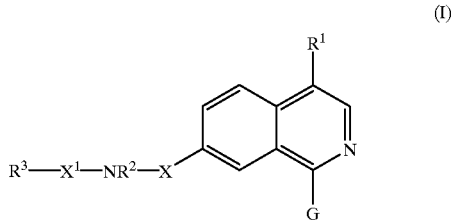

(I)

or a pharmaceutically acceptable salt thereof, wherein:
G is N=C(NH$_2$)$_2$ or NHC(=NH)NH$_2$;
R$^1$ is H or halo;
X is CO, CH$_2$ or SO$_2$;
R$^2$ is H, aryl, heteroaryl, C$_{3-7}$ cycloalkyl or C$_{1-6}$ alkyl, each of which C$_{3-7}$ cycloalkyl and C$_{1-6}$ alkyl is optionally substituted by one or more substituents independently selected from halo, aryl, het, C$_{3-7}$ cycloalkyl, C$_{5-7}$ cycloalkenyl, OH, C$_{1-6}$ alkoxy, O-het$^1$, C$_{1-3}$ alkyl, CO$_2$R$^7$, and NR$^4$R$^5$;
X$^1$ is arylene, C$_{1-6}$ alkylene optionally substituted by one or more R$^6$ group, or cyclo(C$_{4-7}$)alkylene optionally substituted by one or more R$^6$, which cyclo(C$_{4-7}$) alkylene ring can optionally contain a hetero moiety selected from O, S(O)$_p$ or NR$^7$;
or R$^2$ and X$^1$ are taken together with the N atom to which they are attached to form an azetidine, pyrrolidine, piperidine or homopiperidine ring;
R$^3$ is CO$_2$R$^7$, CH$_2$OH, CONR$^8$R$^9$ or CH$_2$NR$^8$R$^9$;
or, when X$^1$ is taken independently from R$^2$ and is methylene optionally substituted by one or more R$^6$ group, or is a 1,1-cyclo(C$_{4-7}$)alkylene optionally containing a hetero moiety selected from O, $S(O)_p$ or $NR^7$ and optionally substituted by $R^6$, then $R^2$ and $R^3$ are taken together with the N and $X^1$ groups to which they are attached, as a group of formula (IA) or (IB):

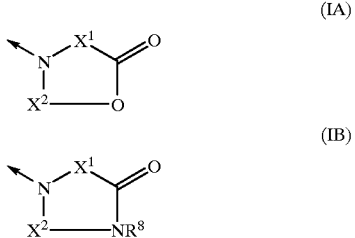

wherein $X^2$ is ethylene, n-propylene or n-butylene;

$R^4$ and $R^5$ are each independently H, aryl or $C_{1-6}$ alkyl optionally substituted by aryl;

$R^6$ is halo, OH, $C_{1-6}$ alkoxy, $C_{1-6}$ alkylthio, $C_{3-7}$ cycloalkyl, SH, aryl, $CO_2R^7$, $CONHR^8$, or $C_{1-6}$ alkyl optionally substituted by aryl, $C_{1-6}$ alkoxy, $CO_2H$, OH, $CONR^8R^9$, or $NR^8R^9$;

$R^7$ is H or $C_{1-6}$ alkyl;

$R^8$ and $R^9$ are either each independently H, or $C_{1-6}$ alkyl optionally substituted by OH, $CO_2R^7$, $C_{1-6}$ alkoxy, or $NR^4R^5$;

or $R^8$ and $R^9$ are taken together with the N atom to which they are attached to form a 4- to 7-membered ring optionally incorporating an additional hetero-group selected from O, S and $NR^7$;

p is 0, 1 or 2;

"aryl" is phenyl optionally substituted by one or more, and preferably one to three, substituents independently selected from $C_{1-6}$ alkyl, $C_{1-6}$ alkoxy, and halo;

"het" is a saturated or partly or fully unsaturated 5- to 7-membered heterocycle containing up to 3 heteroatoms independently selected from O, N and S, and which is optionally substituted by one or more, and preferably one to three, substituents independently selected from $C_{1-6}$ alkyl, $C_{1-6}$ alkoxy, $CO_2R^7$ and halo;

"heteroaryl" is a fully unsaturated 5- to 7-membered heterocycle containing up to 3 hetero-atoms independently selected from O, N and S, and which is optionally substituted by one or more, and preferably one to three, substituents independently selected from $C_{1-6}$ alkyl, $C_{1-6}$ alkoxy, $CO_2R^7$ and halo;

"$het^1$" is tetrahydropyran-2-yl (2-THP);

and "arylene" is phenylene optionally substituted by one or more, and preferably one to three, substituents independently selected from $C_{1-6}$ alkyl, $C_{1-6}$ alkoxy, $CO_2R^7$, and halo.

2. The compound or salt according to claim 1 wherein $R^1$ is halo.

3. The compound or salt according to claim 1 wherein X is $SO_2$.

4. The compound or salt according to claim 1, wherein $R^2$ is $C_{3-7}$ cycloalkyl or $C_{1-6}$ alkyl, each of which $C_{3-7}$ cycloalkyl and $C_{1-6}$ alkyl is optionally substituted by one to three substituents independently selected from halo, aryl, het, $C_{3-7}$ cycloalkyl, $C_{5-7}$ cycloalkenyl, OH, $C_{1-6}$ alkoxy, O-$het^1$, $C_{1-3}$ alkyl, $CO_2R^7$, and $NR^4R^5$.

5. The compound or salt according to claim 1 wherein $R^2$ is H, $C_{3-7}$ cycloalkyl or $C_{1-6}$ alkyl, each of which $C_{3-7}$ cycloalkyl and $C_{1-6}$ alkyl is optionally substituted by aryl, het, $C_{3-7}$ cycloalkyl, OH, $Ohet^1$, $C_{1-6}$ alkoxy, $CO_2H$, $CO_2$ ($C_{1-6}$ alkyl) or $NR^4R^5$; or $R^2$ and $X^1$ are taken together with the N atom to which they are attached to form an azetidine, pyrrolidine, piperidine or homopiperidine ring.

6. The compound of claim 1, wherein $X^1$ is $C_{1-6}$ alkylene optionally substituted by one to three $R^6$ groups, or cyclo($C_{4-7}$)alkylene optionally substituted by one to three $R^6$ groups.

7. The compound or salt according to claim 1 wherein $X^1$ is phenylene optionally substituted by one or two substituents independently selected from methoxy and halo;

or $X^1$ is $C_{1-3}$ alkylene optionally substituted by one or more groups selected from aryl and ($C_{1-6}$ alkyl optionally substituted by aryl, $C_{1-6}$ alkoxy, $CO_2H$, OH, $NH_2$ or $CONH_2$);

or $X^1$ is cyclo($C_{4-7}$)alkylene optionally containing a hetero moiety selected from O or $NR^7$, which ring is optionally substituted by $R^6$;

or $X^1$ is taken together with $R^2$ and with the N atom to which they are attached to form an azetidine, pyrrolidine, piperidine or homopiperidine ring.

8. The compound or salt according to claim 1 wherein $R^3$ is $CO_2R^7$ or $CONR^8R^9$.

9. The compound or salt according to claim 2 wherein $R^1$ is chloro or bromo.

10. The compound or salt according to claim 5 wherein $R^2$ is H; $C_{1-3}$ alkyl optionally substituted by aryl or by optionally substituted pyridyl or by $NR^4R^5$ or by HO or by $Ohet^1$; or $R^2$ and $X^1$ are taken together with the N atom to which they are attached to form an azetidine, pyrrolidine, piperidine or homopiperidine ring.

11. The compound or salt according to claim 7 wherein $X^1$ is methylene optionally substituted by one or more groups selected from aryl and ($C_{1-4}$ alkyl optionally substituted by OH, $NH_2$ or $CONH_2$);

or $X^1$ is cyclobutylene, cyclopentylene, cyclohexylene, cycloheptylene, tetrahydropyranylene, piperidinylene substituted by $R^7$;

or $X^1$ is taken together with $R^2$ and with the N atom to which they are attached to form an azetidine, pyrrolidine, piperidine or homopiperidine ring.

12. The compound or salt according to claim 8 wherein $R^3$ is $CO_2H$; $CONH_2$; $CON(CH_3)(CH_2)_2OH$; $CON(CH_3)(CH_2)_2NHCH_3$; $CO_2(C_{1-3}alkyl)$; $CONH(CH_2)_2OH$; $CONH(CH_2)_2OCH_3$; (morpholino)CO; or (4-methylpiperazino)CO.

13. The compound or salt according to claim 9 wherein $R^1$ is chloro.

14. The compound or salt according to claim 10 wherein $R^2$ is H, $CH_2CH_2N(CH_3)_2$, $CH_3$, $CH_2CH_2OH$, $CH_2CH_2O$ (2-THP), pyridinylmethyl, benzyl, or methoxybenzyl; or $R^2$ and $X^1$ are taken together with the N atom to which they are attached to form an azetidine, pyrrolidine, piperidine or homopiperidine ring linked to the $R^3$ moiety via the 2-position of said ring.

15. The compound or salt according to claim 11 wherein $X^1$ is $C(CH_3)_2$; 1,1-cyclopentylene; 4,4-tetrahydropyranylene; N-methyl-4,4-piperidinylene; $CH_2$;$CH(CH(CH_3)_2)$; $CH(CH_2)_4NH_2$; $CH(CH_2)_3NH_2$; $CH(CH_2)CONH_2$; 1,1-cyclobutylene; 1,1-cyclopentylene; 1,1-cyclohexylene; or 1,1-cycloheptylene; or $X^1$ is taken together with $R^2$ and with the N atom to which they are attached to form an azetidine, pyrrolidine, piperidine or homopiperidine ring linked to the $R^3$ moiety via the 2-position.

16. The compound or salt according to claim 12 wherein $R^3$ is $CO_2H$.

17. The compound or salt according to claim 14 wherein $R^2$ is H, $CH_2CH_2N(CH_3)_2$, $CH_3$, $CH_2CH_2OH$, or $CH_2CH_2O$ (2-THP); or $R^2$ and $X^1$ are taken together with the N atom to which they are attached to form a pyrrolidine ring linked to the $R^3$ moiety via the 2-position.

18. The compound or salt according to claim 15 wherein $X^1$ is $C(CH_3)_2$; 1,1-cyclopentylene; 4,4-tetrahydropyranylene; N-methyl-4,4-piperidinylene; or $X^1$ is taken together with $R^2$ and with the N atom to which they are attached to form an azetidine, pyrrolidine, or piperidine ring linked to the $R^3$ moiety via the 2-position.

19. The compound or salt according to claim 1 wherein X is $SO_2$ in which the $R^3$-$X^1$-$NR^2$-moiety is, where $X^1$ is taken independently from $R^2$ and is methylene optionally substituted by one or more $R^6$ group, or is a 1,1-cyclo($C_{4-7}$) alkylene optionally containing a hetero moiety selected from O, $S(O)_p$ or $NR^7$ and optionally substituted by $R^6$, and $R^2$ and $R^3$ are taken together with the N and $X^1$ groups to which they are attached, a group of formula (IA) or (IB):

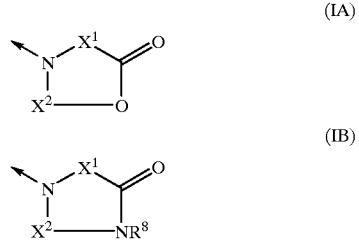

wherein $X^2$ is ethylene, n-propylene or n-butylene.

20. The compound or salt according to claim 19 wherein $X^1$ is $C(CH_3)_2$; 1,1-cyclobutylene; 1,1-cyclopentylene; 1,1-cyclohexylene; 4,4-tetrahydropyranylene; or N-methyl-4,4-piperidinylene.

21. The compound or salt according to claim 19 or 20 wherein $X^2$ is ethylene.

22. The compound or salt according to claim 1 wherein $R^1$ is chloro or bromo; X is $SO_2$;

$R^2$ is H, $CH_2CH_2N(CH_3)_2$, $CH_3$, $CH_2CH_2OH$, $CH_2CH_2O$ (2-THP), pyridinylmethyl, benzyl or methoxybenzyl; or $R^2$ and $X^1$ are taken together with the N atom to which they are attached to form an azetidine, pyrrolidine, piperidine or homopiperidine ring linked to the $R^3$ moiety via the 2-position of said ring; or $X^1$ is $C(CH_3)_2$; 1,1-cyclopentylene; 4,4-tetrahydropyranylene; N-methyl-4,4-piperidinylene; $CH_2$; $CH(CH(CH_3)_2)$; $CH(CH_2)_4NH_2$; $CH(CH_2)_3NH_2$; $CH(CH_2)CONH_2$; 1,1-cyclobutylene; 1,1-cyclopentylene; 1,1-cyclohexylene; 1,1-cycloheptylene; N-methyl-4,4-piperidinylene; or 4,4-tetrahydropyranylene; or $X^1$ is taken together with $R^2$ and with the N atom to which they are attached to form an azetidine, pyrrolidine, piperidine or homopiperidine ring linked to the $R^3$ moiety via the 2-position;

and $R^3$ is $CO_2H$, $CONH_2$, $CON(CH_3)(CH_2)_2OH$, $CON(CH_3)(CH_2)_2NHCH_3$, $CO_2(C_{1-3}alkyl)$, $CONH(CH_2)_2OH$, $CONH(CH_2)_2OCH_3$, (morpholino)CO or (4-methylpiperazino)CO.

23. The compound or salt according to claim 1 wherein $R^1$ is chloro; X is $SO_2$;

$R^2$ if taken independently, is H, $CH_2CH_2N(CH_3)_2$, $CH_3$, $CH_2CH_2OH$, or $CH_2CH_2O$(2-THP);

$X^1$ when taken independently, is $C(CH_3)_2$; 1,1-cyclopentylene; 4,4-tetrahydropyranylene; or N-methyl-4,4-piperidinylene;

or $X^1$ and $R^2$ are taken together with the N atom to which they are attached to form an azetidine, pyrrolidine, or piperidine ring linked to the $R^3$ moiety via the 2-position;

and $R^3$ is $CO_2H$.

24. A compound, or salt thereof, selected from the group consisting of:

N-[(4-chloro-1-guanidino-7-isoquinolinyl)sulphonyl]-D-proline;

2-{[(4-chloro-1-guanidino-7-isoquinolinyl)sulphionyl]amino}isobutyric acid;

1-{[(4-chloro-1-guanidino- 7-isoquinolinyl)sulphonyl]amino}cyclobutanecarboxylic acid;

N-[(4-chloro-1-guanidino-7-isoquinolinyl)sulphonyl]cycloleucine;

1-{[(4-chloro-1-guanidino-7-isoquinolinyl)sulphonyl]amino}-N-(2-hydroxyethyl)cyclopentanecarboxamine;

1-{[(4-chloro-1-guanidino-7-isoquinolinyl)sulphonyl]amino}-N-[2-(dimethylamino)ethyl]cyclopentanecarboxamine;

1-{[(4-chloro-1-guanidino-7-isoquinolinyl)sulphonyl]amino}-N-[2-(dimethylamino)ethyl]cyclopentanecarboxamine;

N-[(4-chloro-1-guanidino-7-isoquinolinyl)sulphonyl]-N-[2-(dimethylamino)ethyl]cycloleucine;

1-{[(4-chloro-1-guanidino-7-isoquinolinyl)sulphonyl]amino}cyclohexanecarboxylic acid;

4-{[(4-chloro-1-guanidino-7-isoquinolinyl)sulphonyl]amino}tetrahydro-2H-pyran-4-carboxylic acid;

tert-butyl (2R)-1-({4-chloro-1-guanidino-7-isoquinolinyl}sulphonyl)-2-piperidinecarboxylate;

(2R)-1-({4-chloro-1-guanidino-7-isoquinolinyl}sulphonyl)-2-piperidinecarboxylic acid;

1-[({4-chloro-1-guanidino-7-isoquinolinyl}sulphonyl)amino]-N-(2-hydroxyethyl)-N-methylcyclopentanecarboxamide;

1-[({4-chloro-1-guanidino-7-isoquinolinyl}sulphonyl)amino]-N-(2-methoxyethyl)cyclopentanecarboxamide;

4-chloro-1-guanidino-N-[1-(morpholinocarbonyl)cyclopentyl]-7-isoquinolinesulphonamide;

4-chloro-1-guainidino-N-{-1[(4-methylpiperazino)carbonyl]cyclopentyl}-7-isoquinolinesulphonamide;

N-({4-bromo-1-guanidino-7-isoquinolinyl}sulphonyl)-N-[2-(dimethylamino)ethyl]cycloleucine;

1-{[(4-chloro-1-guanidino-7-isoquinolinyl)sulphonyl][2-(tetrahydro-2H-pyran-2-yloxy)ethyl]amino}cyclopentanecarboxylic acid; and N"-{4-chloro-7-[(1-oxo-9-oxa-6-azaspiro[4.5]dec-6-yl)sulphonyl]-1-isoquinolinyl}guanidine;

and the pharmaceutically acceptable salts thereof.

25. A pharmaceutical composition comprising a compound or salt according to claim 1 and a pharmaceutically acceptable adjuvant, diluent or carrier.

26. A method of treating a condition mediated by uPA which comprises administering to a person in need of such treatment an effective amount of a compound or salt according to claim 1.

27. A process for making a compound of formula (I) or salt thereof according to claim 1, which comprises reacting the corresponding 1-aminoisoquinoline derivative (II):

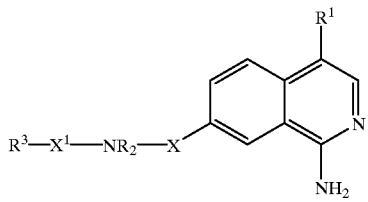

(II)

with cyanamide (NH$_2$CN) or a reagent which acts as a "NHC$^+$=NH" synthon, wherein R$^1$, R$^2$, R$^3$, X and X$^1$ are as defined in claim 1.

28. A process for making a compound of formula (I) or salt thereof according to claim 1, which comprises reacting the corresponding 1-aminoisoquinoline derivative (II):

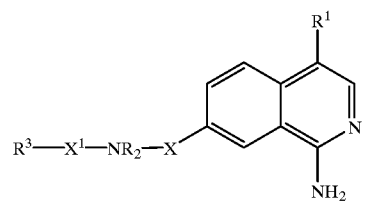

(II)

wherein R$^1$, R$^2$, R$^3$, X and X$^1$ are as defined in claim 1, with a reagent which acts as a protected amidine(2+) synthon (III):

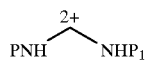

(III)

to give an intermediate of formula (IV):

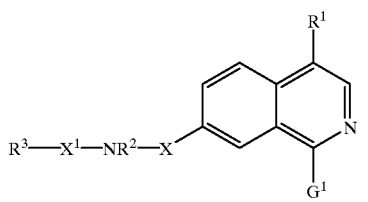

(IV)

wherein G$^1$ is a protected guanidine moiety N=C(NHP)(NHP$_1$) or tautomer thereof, and wherein P and P$_1$ are nitrogen-protecting groups, and deprotecting the intermediate of formula (IV) to give the compound of formula (I) or a salt thereof.

29. The process of claim 28, wherein the nitrogen-protecting groups are selected from t-butoxycarbonyl, benzyl, and benzyloxycarbonyl.

30. A process for making a compound of formula (I) or salt thereof according to claim 1, which comprises reacting the corresponding compound of formula (V):

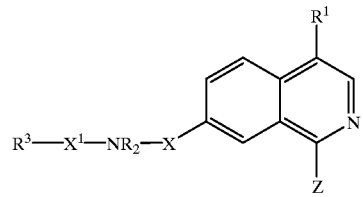

(V)

wherein R$^1$, R$^2$, R$^3$, X and X$^1$ are as defined in claim 1, and Z is a suitable leaving group, with the free base of guanidine under conditions such that the leaving group is displaced.

31. The process of claim 30, wherein the leaving group is selected from the group consisting of Cl, Br, and OPh.

32. A compound of formula (II):

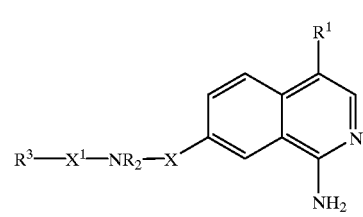

(II)

wherein R$^1$, R$^2$, R$^3$, X and X$^1$ are as defined in claim 1, or salt thereof.

33. A compound of formula (IV):

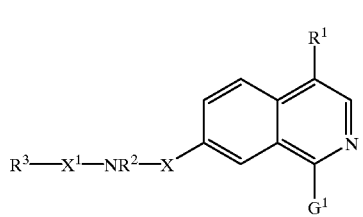

(IV)

where R$^1$, R$^2$, R$^3$, X and X$^1$ are as defined in claim 1, and G$^1$ is a protected guanidine moiety N=C(NHP)(NHP$_1$) or tautomer thereof, where P and P$_1$ are nitrogen-protecting groups.

34. A compound of formula (V):

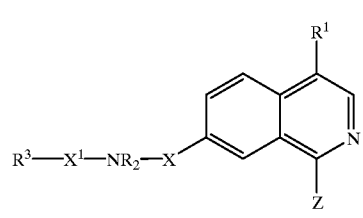

(V)

where R$^1$, R$^2$, R$^3$, X and X$^1$ are as defined in claim 1, and Z is a leaving group.

* * * * *

UNITED STATES PATENT AND TRADEMARK OFFICE
CERTIFICATE OF CORRECTION

PATENT NO. : 6,093,731
DATED : July 25, 2000
INVENTOR(S) : Roger Peter Dickinson et al.

It is certified that error appears in the above-identified patent and that said Letters Patent is hereby corrected as shown below:

On the first page, left column, the patent should list Pfizer Inc. of 235 East 42$^{nd}$ Street, New York, N.Y. 10017, United States of America, as the assignee of the patent.

Signed and Sealed this

Seventeenth Day of April, 2001

Attest:

NICHOLAS P. GODICI

Attesting Officer

Acting Director of the United States Patent and Trademark Office